US009163091B2

(12) United States Patent
Sabbadini et al.

(10) Patent No.: US 9,163,091 B2
(45) Date of Patent: *Oct. 20, 2015

(54) COMPOSITIONS AND METHODS FOR BINDING LYSOPHOSPHATIDIC ACID

(75) Inventors: Roger A. Sabbadini, Lakeside, CA (US); William A. Garland, San Clemente, CA (US); Genevieve Hansen, San Diego, CA (US); James Stephen Swaney, Carlsbad, CA (US); Rosalia Matteo, Chula Vista, CA (US); Gordon Mills, Houston, TX (US); Jonathan Michael Wojciak, Encinitas, CA (US)

(73) Assignee: Lpath, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/406,874

(22) Filed: Mar. 18, 2009
(Under 37 CFR 1.47)

(65) Prior Publication Data
US 2010/0034814 A1    Feb. 11, 2010

Related U.S. Application Data

(63) Continuation-in-part of application No. 12/129,109, filed on May 29, 2008, now Pat. No. 8,158,124.

(60) Provisional application No. 60/940,964, filed on May 30, 2007.

(51) Int. Cl.
*G01N 33/92* (2006.01)
*C07K 16/30* (2006.01)
*C07K 16/18* (2006.01)
*A61K 39/00* (2006.01)
*C12Q 1/68* (2006.01)

(52) U.S. Cl.
CPC ............ *C07K 16/3076* (2013.01); *C07K 16/18* (2013.01); *G01N 33/92* (2013.01); *A61K 2039/505* (2013.01); *C07K 2316/96* (2013.01); *C07K 2317/24* (2013.01); *C07K 2317/56* (2013.01); *C07K 2317/565* (2013.01); *C07K 2317/73* (2013.01); *C07K 2317/92* (2013.01); *C12Q 1/6883* (2013.01); *C12Q 1/6886* (2013.01)

(58) Field of Classification Search
CPC ..................................................... G01N 33/92
USPC ....................................................... 435/7.92
See application file for complete search history.

(56) References Cited

U.S. PATENT DOCUMENTS

| | | |
|---|---|---|
| 3,773,919 A | 11/1973 | Boswell et al. |
| 4,179,337 A | 12/1979 | Davis et al. |
| 4,275,149 A | 6/1981 | Litman et al. |
| 4,301,144 A | 11/1981 | Iwashita et al. |
| 4,318,980 A | 3/1982 | Boguslaski et al. |
| RE30,985 E | 6/1982 | Cartaya |
| 4,376,110 A | 3/1983 | David et al. |
| 4,485,045 A | 11/1984 | Regen |
| 4,496,689 A | 1/1985 | Mitra |
| 4,544,545 A | 10/1985 | Ryan et al. |
| 4,560,655 A | 12/1985 | Baker |
| 4,640,835 A | 2/1987 | Shimizu et al. |
| 4,657,866 A | 4/1987 | Kumar |
| 4,670,417 A | 6/1987 | Iwasaki et al. |
| 4,676,980 A | 6/1987 | Segal et al. |
| 4,737,456 A | 4/1988 | Weng et al. |
| 4,767,704 A | 8/1988 | Cleveland et al. |
| 4,791,192 A | 12/1988 | Nakagawa et al. |
| 4,816,397 A | 3/1989 | Boss et al. |
| 4,816,567 A | 3/1989 | Cabilly et al. |
| 4,927,762 A | 5/1990 | Darfler |
| 5,013,556 A | 5/1991 | Woodle et al. |
| 5,122,469 A | 6/1992 | Mather et al. |
| 5,204,244 A | 4/1993 | Fell et al. |
| 5,225,539 A | 7/1993 | Winter |
| 5,229,275 A | 7/1993 | Goroff |
| 5,530,101 A | 6/1996 | Queen et al. |
| 5,534,615 A | 7/1996 | Baker et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,589,369 A | 12/1996 | Seidman et al. |
| 5,591,669 A | 1/1997 | Krimpenfort et al. |
| 5,624,821 A | 4/1997 | Winter et al. |
| 5,693,761 A | 12/1997 | Queen et al. |

(Continued)

FOREIGN PATENT DOCUMENTS

EP    0183070 B1    10/1985
EP    0244234 B2    4/1987

(Continued)

OTHER PUBLICATIONS

Ikeda et al., Biological Am. J. Physiol. Gastrointest. Liver Physiol., 2000, G304-G310, 279(2).
Inoue et al., Nat. Med., 2004, 712-718, 10(7).
Jakobovits et al., Nature, 1993, 255-258, 362(6417).
Jakobovits et al., Proc. Natl. Acad. Sci. USA, 1993, 2551-2555, 90(6).
Jalink et al., Cell Growth Differ., 1993, 247-255, 4(4).
Janeway et al., Immunobiology, Fifth Edition, 2001, Garland Publishing (Electronic Table of Contents Only).

(Continued)

*Primary Examiner* — Lynn Bristol
(74) *Attorney, Agent, or Firm* — Acuity Law Group, P.C.; Daniel M. Chambers

(57) ABSTRACT

Compositions and methods for making and using anti-LPA agents, for example, monoclonal antibodies, are described. Variable domain and complementarity determining region amino acid sequences of several monoclonal antibodies against LPA are disclosed, as is a consensus anti-LPA monoclonal antibody variable domain sequence.

6 Claims, 9 Drawing Sheets

(56) References Cited

U.S. PATENT DOCUMENTS

| | | | |
|---|---|---|---|
| 5,693,762 | A | 12/1997 | Queen et al. |
| 5,714,350 | A | 2/1998 | Co et al. |
| 5,777,085 | A | 7/1998 | Co et al. |
| 5,834,597 | A | 11/1998 | Tso et al. |
| 5,861,155 | A | 1/1999 | Lin |
| 5,882,644 | A | 3/1999 | Chang et al. |
| 5,932,448 | A | 8/1999 | Tso et al. |
| 6,013,256 | A | 1/2000 | Light et al. |
| 6,129,914 | A | 10/2000 | Weiner et al. |
| 6,180,370 | B1 | 1/2001 | Queen et al. |
| 6,210,671 | B1 | 4/2001 | Co |
| 6,248,553 | B1 | 6/2001 | Small et al. |
| 6,255,063 | B1 | 7/2001 | Small et al. |
| 6,329,511 | B1 | 12/2001 | Vasquez et al. |
| 6,350,861 | B1 | 2/2002 | Co et al. |
| 6,407,213 | B1 | 6/2002 | Carter et al. |
| 6,479,284 | B1 | 11/2002 | Marasco et al. |
| 6,500,931 | B1 | 12/2002 | Tempest et al. |
| 6,548,640 | B1 | 4/2003 | Winter |
| 6,639,055 | B1 | 10/2003 | Carter et al. |
| 8,796,429 | B2 * | 8/2014 | Sabbadini et al. ............ 530/403 |
| 2005/0255102 | A1 | 11/2005 | Violette et al. |
| 2006/0228299 | A1 | 10/2006 | Thorpe et al. |
| 2011/0076267 | A1 | 3/2011 | Sabbadini et al. |

FOREIGN PATENT DOCUMENTS

| | | | |
|---|---|---|---|
| EP | 0402226 | A1 | 6/1990 |
| EP | 0404097 | B1 | 6/1990 |
| EP | 0125023 | B1 | 6/1991 |
| EP | 0519596 | A1 | 12/1992 |
| EP | 0120694 | B1 | 7/1993 |
| EP | 0194276 | B1 | 8/1993 |
| EP | 0239400 | B1 | 8/1994 |
| WO | 86/01533 | A1 | 3/1986 |
| WO | 87/00195 | A1 | 1/1987 |
| WO | 90/03430 | A1 | 4/1990 |
| WO | 93/11161 | A1 | 6/1993 |
| WO | 96/27011 | A1 | 9/1996 |
| WO | 96/32478 | A1 | 10/1996 |
| WO | 2004/003019 | A2 | 1/2004 |
| WO | WO 2004053459 | * | 6/2004 |
| WO | WO 2005064332 | * | 7/2005 |
| WO | 2006/105062 | A2 | 10/2006 |
| WO | 2007/053447 | A2 | 5/2007 |
| WO | 2007/140431 | A2 | 12/2007 |
| WO | 2007/140433 | A2 | 12/2007 |
| WO | 2007/140434 | A2 | 12/2007 |

OTHER PUBLICATIONS

Jang et al., Mol. Immunol., 1998, 1207-1217, 35(18).
Jones et al., Nature, 1986, 522-525, 321(6069).
Kingsbury et al., Nat. Neurosci., 2003, 1292-1299, 6(12).
Kobayashi et al., Protein Eng., 1999, 879-884, 12(10).
Kohler et al., Nature, 1975, 495-497, 256(5517).
Kostelny et al., J. Immunol., 1992, 1547-1553, 148(5).
Kozbor et al., J. Immunol., 1984, 3001-3005, 133(6).
Kumar et al., J. Biol. Chem., 2000, 35129-35136, 275(45).
Lee et al., Am. J. Physiol. Cell Physiol., 2000, C612-C618, 278(3).
Lee et al., Clin. Cancer Res., 2006, 6351-6358, 12(21).
Lefranc, Nucleic Acids Res., 2003, 307-310, 31(1).
Lindmark et al., J. Immunol. Methods, 1983, 1-13, 62(1).
Maccallum et al., J. Mol., Biol., 1996, 732-745, 262(5).
Marks et al., J. Mol. Biol., 1991, 581-597, 222(3).
Martin et al., J. Biol. Chem., 1982, 286-288, 257(1).
Martin et al., J. Mol. Biol., 1996, 800-815, 263(5).
Mather, Biol. Reprod., 1980, 243-251, 23(1).
Mather et al., Annals N.Y. Acad. Sci., 1982, 44-68, 383.
Morais et al. Mem. Inst. Oswaldo Cruz, 2006, 353-354, 101(Suppl. I).
Morea et al., Methods, 2000, 267-279, 20(3).
Morimoto et al., J. Biochem. Biophys. Methods, 1992, 107-117, 24(1-2).
Morrison et al., Proc. Natl. Acad. Sci. USA, 1984, 6851-6855, 81(21).
Mueller et al., Nat. Rev. Drug Discov., 2005, 387-398, 4(5).
Munson et al., Anal. Biochem., 1980, 220-239, 107(1).
Neuberger et al., Nature, 1984, 604-608, 312(5995).
O'Sullivan et al., Methods Enzymol., 1981, 147-166, 73(Pt B).
Pradere et al., Biochim. Biophys. Acta, 2007, 93-102, 1771(1).
Pradere et al., J. Am. Soc. Nephrol., 2007, 3110-3118, 18(12).
Pradere et al., Biochim. Biophys. Acta, 2008, 582-587, 1781(9).
Presta, Curr. Opin. Struct. Biol., 1992, 593-596, 2(4).
Pyne et al., Biochem. J., 2000, 385-402, 349(Pt. 2).
Queen et al., Proc. Natl. Acad. Sci. USA, 1989, 10029-10033, 86(24).
Ramakers et al., Exp. Cell Res., 1998, 252-262, 245(2).
Ramer et al. J. Neurosci., 2004, 10796-10805, 24(48).
Reichmann et al., Nature, 1988, 323-329, 332(6162).
Remington's Pharmaceutical Sciences 16th edition (1980).
01 27/2012 43 Ren et al., Cancer Res., 2006, 3006-3014, 66(6).
Scotton et al., Chest, 2007, 1311-1321, 132(4).
Shalaby et al., J. Exp. Med., 1992, 217-225, 175(1).
Smith-Gill et al., J. Immunol., 1987, 4135-4144, 139(12).
Song et al., Biochem. Biophys. Res. Comm., 2000, 390-394, 268(2).
Sun et al., J. Mol. Cell. Cardiol., 1996, 851-858, 28(5).
Sun et al., Cardiovasc. Res., 2000, 250-256, 46(2).
Tager et al., Proc. Am. Thorac. Soc., 2008, 363, 5(3):363.
Tigyi et al., J. Biol. Chem., 1992, 21360-21367, 267(30).
Tokumura et al., Life Sci., 2007, 1641-1649, 80(18).
Tomasek et al., Nat. Rev. Mol. Cell Biol., 2002, 349-363, 3(5).
Tutt et al., J. Immunol., 1991, 60-69, 147(1).
Urlaub et al., Proc. Natl. Acad. Sci. USA, 1980, 4216-4220, 77(7).
Vajdos et al., J. Mol. Biol., 2002, 415-428, 320(2).
Virag et al., Am. J. Pathol., 2003, 2433-2440, 163(6).
Ward et al., Nature, 1989, 544-546, 341(6242).
Watterson et al., Wound Repair Regen., 2007, 607-616, 15(5).
Weiner et al., J. Neurosci., 2001, 7069-7078, 21(18).
Wu et al., J. Mol. Biol., 1999, 151-162, 294(1).
Yuan et al., Nat. Cell Biol., 2003, 38-45, 5(1).
Zapata et al., Protein Eng., 1995, 1057-1062, 8(10).
Anliker et al., Semin.Cell Dev. Biol., 2004, 457-465 15(5):457-465.
Ashcroft et al., J. Clin Pathol., 1988, 467-470 41(4).
Barekzi et al., Prostaglandins Leukot. Essent. Fatty Acids, 2006, 357-363, 74(6).
Barnes et al., Anal. Biochem., 1980, 255-270, 102(2).
Berge et al., J. Pharm. Sci., 1977, 1-19, 66(1).
Boucher et al., Diabetologia, 2005, 569-577, 48(3).
Brennan et al., Science, 1985, 81-83, 229(4708).
Brorson et al., J. Immunol., 1999, 6694-6701, 163(12).
Brummell et al., Biochemistry, 1993, 1180-1187, 32(4) (Abstract Only).
Burks et al., Pro. Natl. Acad. Sci., 1997, 412-417, 94(2).
Carter et al., Biotechnology (N.Y)., 1992, 163-167, 10(2).
Casset et al., BBRC, 2003, 198-205, 307(1).
Champe et al., J. Biol. Chem., 1995, 1388-1394, 270(3).
Chen et al., J. Mol. Bio., 1999, 865-881, 293(4).
Chen et al., Bioorg. Med. Chem. Lett., 2000, 1691-1693, 10(15).
Chen et al., Febs Lett., 2006, 4737-4745, 580(19).
Chothia et al., J. Mol. Biol., 1985, 651-663, 186(3).
Chothia et al., J. Mol. Biol., 1987, 901-917, 196(4).
Chun et al, Curr. Pharm. Des., 2006, 161-171, 12(2).
Clackson et al., Nature, 1991, 624-628, 352(6336).
Coligen et al., Current Protocols in Immunology, 1991, vol. 1 and 2, Wiley-Interscience, New York, N.Y., Pubs.
Colman, Res. Immunol., 1994, 33-36, 145(1).
Coloma et al., J. Immunol. Methods, 1992, 89-104, 152(1).
Coronella et al., Nucleic Acids Res., 2000, E85, 28(20).
Cunningham et al., Science, 1989, 1081-1085, 244(4908).
Dattamajumdaret al., Immunogenetics, 1996, 141-151, 43(3).
Davaille et al., J. Biol. Chem., 2000, 34268-34633, 275(44).
De Pascalis et al., J. Immunol., 2002, 3076-3084, 169(6).
Deutschman et al., Am. Heart J., 2003, 62-68, 146(1).
Dufner, Trends Biotechnol., 2006, 523-529, 24(11).
Eppstein et al., Proc. Natl. Acad. Sci. USA, 1985, 3688-3692, 82(11).

(56) References Cited

OTHER PUBLICATIONS

Fang et al., Ann. NY Acad. Sci., 2000, 188-208, 905.
Ferry et al., J. Biol. Chem., 2003, 18162-18169, 278(20).
Folkman, J. Nat. Cancer Inst., 2001, 734-735, 93(10).
Foote et al., J. Mol. Biol., 1992, 487-499, 224(2).
Fujita et al., Neurochem. Int., 2007, 351-355, 50(2).
Fukushima et al., Dev Biol., 2000, 6-18, 228(1).
Fukushima et al., Neurochem. Int., 2007, 302-307, 50(2).
Gardell et al., Trends Mol. Med., 2006, 65-75, 12(2).
Georas et al., Clin. Exp. Allergy, 2007, 311-322, 37(3).
Graham et al., J. Gen. Virol., 1977, 59-72, 36(1).
Gruber et al., J. Immunol., 1994, 5368-5374, 152(11).
Guss et al., EMBO J., 1986, 1567-1575, 5(7).
Ham et al., Methods Enzymol., 1979, 44-93, 58.
Hama, et al., J. Biol. Chem., 2004, 17634-17639, 279(17).
Hinz, J. Invest. Dermatol., 2007, 526-537, 127(3).
Hollinger et al., Proc. Natl. Acad. Sci. USA, 1993, 6444-6448, 90(14).
Holm et al., Mol. Immunol., 2007, 1075-1084, 44(6).
Hoogenboom et al., J. Mol. Biol., 1992, 381-388, 227(2).
Hwang et al., Proc. Natl. Acad. Sci. USA, 1980, 4030-4034, 77(7).
Gussow et al., Methods Enzymol., 1991, 99-121, 203.
Mariuzza et al., Ann. Rev. Biophys. Biophys. Chem., 1987, 139-159, 16.
Winkler et al., J. Immunol., 2000, 4505-4514, 165(8).
Matted et al., Proc. Am. Assoc. Cancer Res., 2007, 971, #4101, 48.
Mills et al., Nat. Rev. Cancer, 2003, 582-591, 3(8).
Argiles, Cancer-associated malnutrition, Eur. J. Oncol. Nurs., 2005, S39-S50, 9(Suppl. 2).
Bas et al., Collagen Antibody-Induced Arthritis Evokes Persistent Pain With Spinal Glial Involvement and Transient Prostaglandin Dependency, Arthritis Rheum., 2012, 3886-3896, 64(12).
Rantapaa-Dahlqvist et al., Antibodies Against Cyclic Citrullinated Peptide and IgA Rheumatoid Factor Predict the Development of Rheumatoid Arthrities, Arthritis Rheum., 2003, 2741-2749, 48(10).
Rostrom, Metabolic syndrome in rheumatoid arthritis: case control study, BMC Musculoskelet. Disord., 2013, 147, 14.
Su et al., Novel anti-lysophosphatidic acid antibody reverses arthritis-induced mechanical hypersensitivity and associated upregulation of P2X3, galanin and GFAP, Neuroscience, 2012, Program# 179.07/ GG15 (Presentation Abstract Only).

* cited by examiner

Synthesis of Typical Thiolated S1P-Related Antigen

Synthesis of Typical Thiolated S1P-Related Antigen (Continued)

Synthesis of Typical Thiolated S1P-Related Antigen (Continued)

Synthesis of Typical Protected Thiolated Fatty Acid

Synthesis of Typical Thiolated Fatty Acid

Synthesis of Typical Thiolated LPA Hapten

Synthesis of Typical Thiolated LPA Hapten (Continued)

```
                                                              CDR H1
B58_Vh    1  QVQLQQSGAELVRPGTSVRVSCKASGDAFTN-YLIEWVKQRPGQGL  45
3A6_Vh    1  QVQLQQSGAELVRPGTSVRLSCKASGDAFTN-YLIEWVKQRPGQGL  45
B7_Vh     1  QVQLQQSGAELVRPGTSVRVSCKASGYGFIN-YLIEWIKQRPGQGL  45
B3_Vh     1  QVKLQQSGPELVRPGTSVRVSCTASGDAFTN-YLIEWVKQRPGQGL  45
A63_Vh    1  DIQLQESGPGLVRPSQSLSLTCSVTGFSITSGYYWTWIRQFPGNKL  46

CDR H2
B58_Vh   46  EWIGLIIPGTGYTNYNENFKGKATLTADKSSSTAYMQLSSLTSEDS  91
3A6_Vh   46  EWIGLIIPGTGYTNYNENFKGKATLTADKSSSTAYMQLSSLTSEDS  91
B7_Vh    46  EWIGLINPGSDYTNYNENFKGKATLTADKSSSTAYMHLSSLTSEDS  91
B3_Vh    46  EWIGLIYPDSGYINYNENFKGKATLTADKSSSTAYMQLSSLTSEDS  91
A63_Vh   47  EWVAYIGYD-GSNDSNPSLKNRISITRDTSKNQFFLKNSVTTEDT  91

CDR H3
B58_Vh   92  AVYFCARRFGYYGSSNYFDYWGQGTTLTVSS  122
3A6_Vh   92  AVYFCARRFGYYGSGYYFDYWGQGTTLTVSS  122
B7_Vh    92  AVYFCARRFGYYGSGNYFDYWGQGTTLTVSS  122
B3_Vh    92  AVYFCARRFAYYGSGYYFDYWGQGTTLTVSS  122
A63_Vh   92  ATYYCARAMLRRG----FDYWGQGTTLTVSS  118
```

Figure 4A

```
                                                    CDR L1
B58_Vk    1  DVVMTQTPLSLPVSLGDQASISCRSSQSLVHSNGNTYLHW  40
3A6_Vk    1  DVVMTQTPLSLPVSLGDQASISCRSSQSLVHSNGNTYLHW  40
B3_Vk     1  DVVMTQTPLSLPVSLGDQASISCRSSQSLLKTNGNTYLHW  40
B7_Vk     1  DVVMTQTPLSLPVSLGDQASISCTSGQSLVHINGNTYLHW  40
A63_Vk    1  QIVLTQSPAIMSASPGEKVTMTCSASSSLS------YMHW  34

CDR L2
B58_Vk   41  YLQKPGQSPKLLIYKVSNRFSGVPDRFSGSGPGTDFTLKI  80
3A6_Vk   41  YLQKPGQSPKLLIYKVSNRFSGVPDRFSGSGPGTDFTLKI  80
B3_Vk    41  YLQKPGQSPKLLIFKVSNRFSGVPDRFSGSGSGTDFTLKI  80
B7_Vk    41  YLQKPGQSPKLLIYKVSNLFSGVPDRFSGSGSGTDFTLKI  80
A63_Vk   35  YQQKPGTSPKRWIYDTSKLASGVPARFSGSGSGTSYSLTI  74

CDR L3
B58_Vk   81  SRVEAEDLGIYFCSQSTHFPPFTFGTGTKLEIK        112
3A6_Vk   81  SRVEAEDLGVYFCSQSTHFPFTFGTGTKLEIK         112
B3_Vk    81  SRVEAEDLGVYFCSQSTHFPFTFGTGTKLEIK         112
B7_Vk    81  SRVEAEDLGVYFCSQSTHFPFTFGTGTKLEIK         112
A63_Vk   75  SSMEAEDAATYYCHRRS--SYTFGGGTKLEIK         104
```

Figure 4B

COMPOSITIONS AND METHODS FOR BINDING LYSOPHOSPHATIDIC ACID

This application is a continuation-in-part of application Ser. No. 12/129,109, filed 29 May 2008, which in turn claims the benefit of and priority to provisional application Ser. No. 60/940,964, filed 30 May 2007, both of which are commonly owned with the instant application and are herein incorporated by reference in their entirety and for all purposes.

TECHNICAL FIELD

The present invention relates to agents that bind lysophosphatidic acid (LPA) and its variants, particularly to monoclonal antibodies, antibody fragments, and antibody derivatives specifically reactive to LPA under physiological conditions. Such agents can be used in the treatment and/or prevention of various diseases or disorders through the delivery of pharmaceutical compositions that contain such agents.

LPA is a bioactive lipid mediating multiple cellular responses including proliferation, differentiation, angiogenesis, motility, and protection from apoptosis in a variety of cell types.

LPA is involved in the establishment and progression of cancer by providing a pro-growth tumor microenvironment and promoting angiogenesis. In addition, LPA has been implicated in fibrosis, ocular diseases such as macular degeneration, and pain-related disorders. Therefore, an antibody-based approach to the neutralization of LPA offers the potential to increase the arsenal of current therapies for these indications.

The inventors have invented a family of high-affinity, specific monoclonal antibodies to LPA, one of which is known as Lpathomab or LT3000. The efficacy of Lpathomab in various animal models of cancer, fibrosis, and ocular disorders highlights the utility of this class of anti-LPA antibodies (and molecules derived therefrom), for example, in the treatment of malignancies, angiogenesis, and fibrosis-related disorders.

BACKGROUND OF THE INVENTION

1. Introduction

The following description includes information that may be useful in understanding the present invention. It is not an admission that any of the information provided herein, or any publication specifically or implicitly referenced herein, is prior art, or even particularly relevant, to the presently claimed invention.

2. Background

A. Bioactive Signaling Lipids

Certain lipids and their derivatives are now recognized as important targets for medical research, not as just simple structural elements in cell membranes or as a source of energy for β-oxidation, glycolysis or other metabolic processes. In particular, certain lipids function as signaling mediators important in animal and human disease. Although most of the lipids of the plasma membrane play an exclusively structural role, a small proportion of them are involved in relaying extracellular stimuli into cells. These lipids are referred to as "bioactive lipids" or, alternatively, "bioactive signaling lipids." "Lipid signaling" refers to any of a number of cellular signal transduction pathways that use cell membrane lipids as second messengers, as well as referring to direct interaction of a lipid signaling molecule with its own specific receptor. Lipid signaling pathways are activated by a variety of extracellular stimuli, ranging from growth factors to inflammatory cytokines, and regulate cell fate decisions such as apoptosis, differentiation and proliferation. Research into bioactive lipid signaling is an area of intense scientific investigation as more and more bioactive lipids are identified and their actions characterized.

Examples of bioactive lipids include the eicosanoids (including the cannabinoids, leukotrienes, prostaglandins, lipoxins, epoxyeicosatrienoic acids, and isoeicosanoids), non-eicosanoid cannabinoid mediators, phospholipids and their derivatives such as phosphatidic acid (PA) and phosphatidylglycerol (PG), platelet activating factor (PAF) and cardiolipins as well as lysophospholipids such as lysophosphatidyl choline (LPC) and various lysophosphatidic acids (LPA). Bioactive signaling lipids also include the sphingolipids such as sphingomyelin, ceramide, ceramide-1-phosphate, sphingosine, sphingosylphosphoryl choline, sphinganine, sphinganine-1-phosphate (dihydro-S1P) and sphingosine-1-phosphate. Sphingolipids and their derivatives represent a group of extracellular and intracellular signaling molecules with pleiotropic effects on important cellular processes. Other examples of bioactive signaling lipids include phosphatidylinositol (PI), phosphatidylethanolamine (PEA), diacylglyceride (DG), sulfatides, gangliosides, and cerebrosides.

1. Lysolipids

Lysophospholipids (LPLs), also known as lysolipids, are low molecular weight (typically less than about 500 dalton) lipids that contain a single hydrocarbon backbone and a polar head group containing a phosphate group. Some lysolipids are bioactive signaling lipids. Two particular examples of medically important bioactive lysolipids are LPA (glycerol backbone) and S1P (sphingoid backbone). The structures of selected LPAs, S1P, and dihydro S1P are presented below.

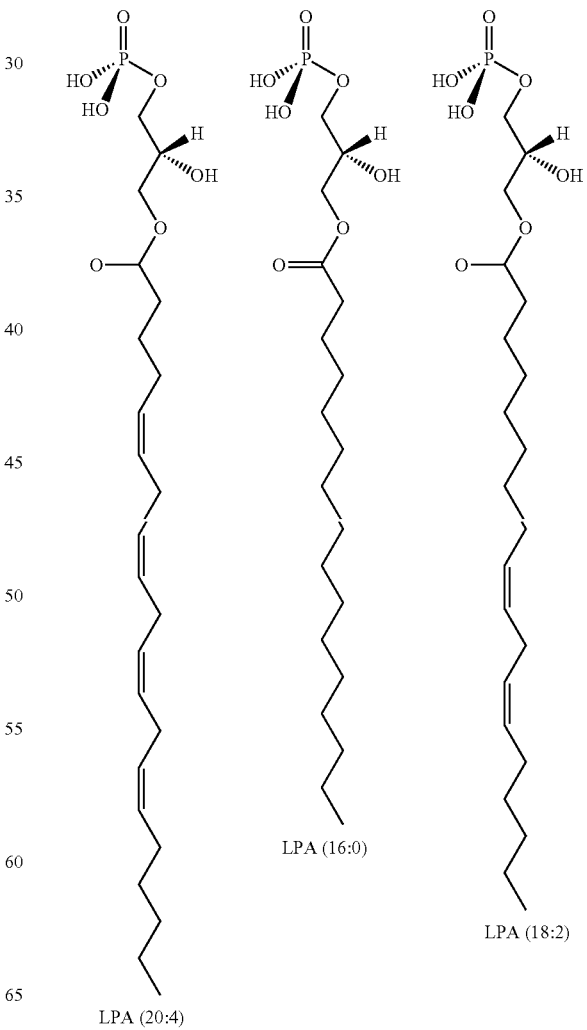

LPA (16:0)

LPA (18:2)

LPA (20:4)

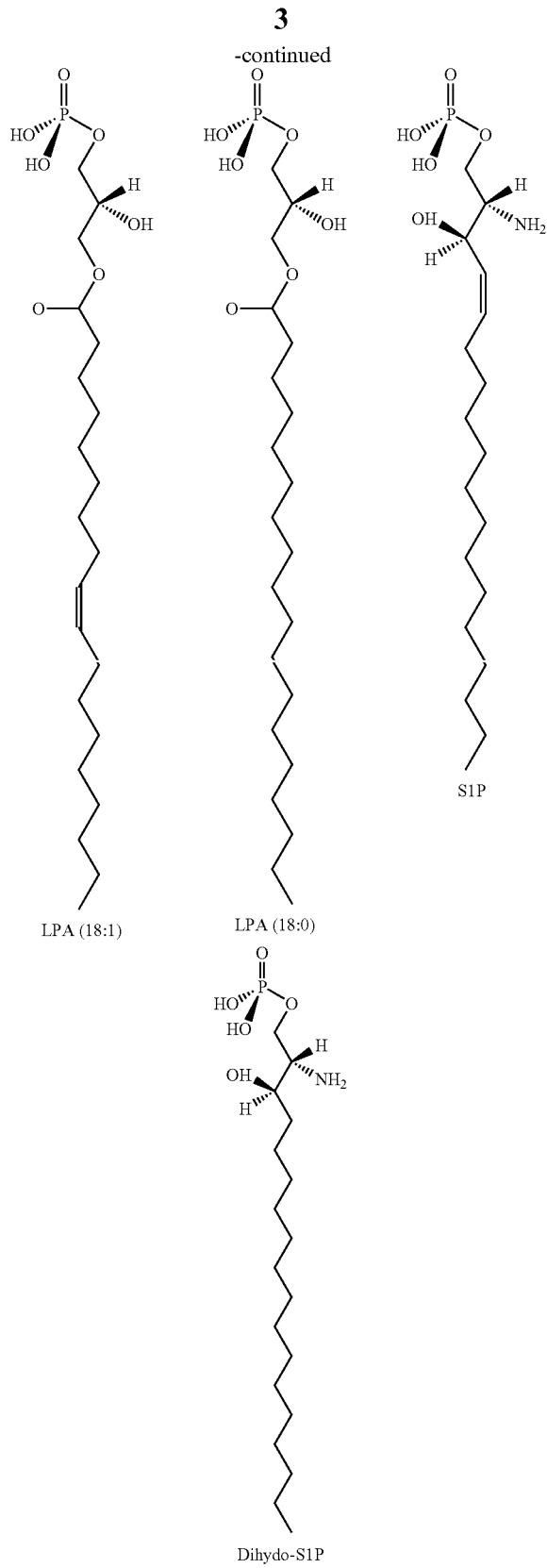

The structural backbone of LPA is derived from glycerol-based phospholipids such as phosphatidylcholine (PC) or phosphatidic acid (PA). In the case of lysosphingolipids such as S1P, the fatty acid of the ceramide backbone is missing.

The structural backbone of S1P, dihydro S1P (DHS1P), and sphingosylphosphorylcholine (SPC) is based on sphingosine, which is derived from sphingomyelin.

LPA and S1P regulate various cellular signaling pathways by binding to the same class of multiple transmembrane domain G protein-coupled (GPCR) receptors. The S1P receptors are designated as S1P1, S1P2, S1P3, S1P4 and S1P5 (formerly EDG-1, EDG-5/AGR16, EDG-3, EDG-6 and EDG-8) and the LPA receptors designated as LPA1, LPA2, LPA3 (formerly, EDG-2, EDG-4, and EDG-7). A fourth LPA receptor of this family has been identified for LPA (LPA4), and other putative receptors for these lysophospholipids have also been reported.

LPA and S1P have been shown to play a role in the immune response through modulation of immune-related cells such as T- and B-lymphocytes. These lipids promote T-cell migration to sites of immune response and regulate proliferation of T cells as well as secretion of various cytokines. In particular, S1P is thought to control egress of lymphocytes into the peripheral circulation. Thus agents which bind LPA and S1P are believed to be useful in methods for decreasing an undesired, excessive or aberrant immune response, and for treating diseases and conditions, including certain hematological cancers and autoimmune disorders that are associated with an undesired, excessive or aberrant involvement of lymphocytes and or an aberrant immune response.

a. Lysophosphatic Acid (LPA)

Lysophosphatidic acid (mono-acylglycerol-3-phosphate, <500 Dalton) consists of a single hydrocarbon backbone and a polar head group containing a phosphate group. LPA is not a single molecular entity but a collection of endogenous structural variants with fatty acids of varied lengths and degrees of saturation. Thus, when used herein, "LPA" refers to the set of bioactive LPA variants, unless stated otherwise. Biologically relevant variants of LPA include 18:2, 18:1, 18:0, 16:0 and 20:4. LPA species with both saturated fatty acids (16:0 and 18:0) and unsaturated fatty acids (16:1, 18:1, 18:2, and 20:4) have been detected in serum and plasma. The 16:0, 18:1, 18:2 and 20:4 LPA isoforms are the predominant species in blood. Significant levels (>1 µM) of bioactive LPA are detectable in various body fluids, including serum, saliva, follicular fluid and malignant effusions.

The present invention provides among its aspects anti-LPA agents that are useful for treating or preventing hyperproliferative disorders and various other disorders, as described in greater detail below. In particular, certain embodiments of the invention is drawn to antibodies targeted to LPA including but not limited to 18:2, 18:1, 18:0, 16:0, and 20:4 variants of LPA.

LPA has long been known as precursors of phospholipid biosynthesis in both eukaryotic and prokaryotic cells, but LPA has emerged only recently as a signaling molecule that are rapidly produced and released by activated cells, notably platelets, to influence target cells by acting on specific cell-surface receptor. Besides being synthesized and processed to more complex phospholipids in the endoplasmic reticulum, LPA can be generated through the hydrolysis of pre-existing phospholipids following cell activation; for example, the sn-2 position is commonly missing a fatty acid residue due to de-acylation, leaving only the sn-3 hydroxyl esterified to a fatty acid. Moreover, a key enzyme in the production of LPA, autotaxin (lysoPLD/NPP2), may be the product of an oncogene, as many tumor types up-regulate autotaxin. The concentrations of LPA in human plasma and serum have been reported, including determinations made using sensitive and specific LC/MS procedures. For example, in freshly prepared human serum allowed to sit at 25° C. for one hour, LPA concentrations have been estimated to be approximately 1.2 mM, with the LPA analogs 16:0, 18:1, 18:2, and 20:4 being the predominant species. Similarly, in freshly prepared human plasma allowed to sit at 25° C. for one hour, LPA concentrations have been estimated to be approximately 0.7 mM, with 18:1 and 18:2 LPA being the predominant species.

LPA mediates its biological functions predominantly by binding to a class of multiple transmembrane G protein-coupled receptors (GPCR). Five LPA-specific GPCRs, termed LPA1-5, have been identified to date; they show both overlapping and distinct signaling properties and tissue expression. The LPA1-3 receptors belong to the so-called EDG subfamily (EGD2/LPA1, EDG4/LPA2, and EDG7/LPA3) of GPCRs with 50% sequence similarity to each other. Their closest relative is the cannabinoid CB1 receptor, which binds the bioactive lipids 2-arachidonoyl-glycerol (2-AG) and arachidonoyl-ethanolamine. Two newly identified LPA receptors, termed LPA4 (formerly GPR23/p2y9) and LPA5 (formerly GPR92) are more closely related to the P2Y nucleotide receptors. In addition, LPA recognizes the intracellular receptor, PPRgamma.

LPA1 is expressed in a wide range of tissues and organs whereas LPA2 and LPA3 show more restricted expression profile. However, LPA2 and LPA3 expressions were shown to be increased in ovarian and colon cancers and inflammation, suggesting that the main role of LPA2 and LPA3 is in pathophysiological conditions.

The role of these receptors has been in part elucidated by receptor knockout studies in mice. LPA1-deficient mice show partial postnatal lethality due to a suckling defect resulting from impaired olfaction. LPA1-deficient mice are also protected from lung fibrosis in response to bleomycin-induced lung injury. Furthermore, mice lacking the LPA1 receptor gene lose the nerve injury-induced neuropathic pain behaviors and phenomena.

In contrast, mice lacking LPA2 receptors appear to be normal. LPA3 receptor knockout mice have reduced litter size due to delayed blastocyst implantation and altered embryo spacing, and LPA3-deficient uteri show reduced cyclooxygenase-2 (COX-2) expression and prostaglandin synthesis; while exogenous administration of PGE2 into LPA3-deficient female mice has been reported to rescue the implantation defect.

LPAs influence a wide range of biological responses, including induction of cell proliferation, stimulation of cell migration and neurite retraction, gap junction closure, and even slime mold chemotaxis. The body of knowledge about the biology of LPA continues to grow as more and more cellular systems are tested for LPA responsiveness. The major physiological and pathophysiological effects of LPA include, for example:

Wound healing: It is now known that, in addition to stimulating cell growth and proliferation, LPA promote cellular tension and cell-surface fibronectin binding, which are important events in wound repair and regeneration.

Apoptosis: Recently, anti-apoptotic activity has also been ascribed to LPA, and it has recently been reported that peroxisome proliferation receptor gamma is a receptor/target for LPA.

Blood vessel maturation: Autotaxin, a secreted lysophospholipase D responsible for producing LPAs, is essential for blood vessel formation during development. In addition, unsaturated LPAs were identified as major contributors to the induction of vascular smooth muscle cell dedifferentiation.

Edema and vascular permeability: LPA induces plasma exudation and histamine release in mice.

Inflammation: LPA acts as inflammatory mediator in human corneal epithelial cells. LPA participates in corneal wound healing and stimulates the release of ROS in lens. LPA can also re-activate HSV-1 in rabbit cornea.

The bite of the venomous spider, *Loxosceles reclusa* (brown recluse spider), causes necrotic ulcers that can cause serious and long lasting tissue damage, and occasionally death. The pathology of wounds generated from the bite of this spider consists of an intense inflammatory response mediated by AA and prostaglandins. The major component of the *L. reclusa* spider venom is the phospholipase D enzyme often referred to as sphingomyelinase D (SMase D), which hydrolyzes sphingomyelin to produce C1P. It has been found, however, that lysophospholipids with a variety of headgroups are hydrolysed by the *L. reclusa* enzyme to release LPA. It is believed that anti-LPA agents such as those of the invention will be useful in reducing or treating inflammation of various types, including but not limited to inflammation resulting from *L. reclusa* envenomation.

Fibrosis and scar formation: LPA inhibits TGF-mediated stimulation of type I collagen mRNA stability via an ERK-dependent pathway in dermal fibroblasts. Moreover, LPA have some direct fibrogenic effects by stimulating collagen gene expression and proliferation of fibroblasts.

Immune response: LPA, like S1P, has been shown to play a role in the immune response through modulation of immune-related cells. These lipids promote T-cell migration to sites of immune response and regulate proliferation of T cells as well as secretion of various cytokines.

Thus agents that reduce the effective concentration of LPA, such as Lpath's anti-LPA mAb, are believed to be useful in methods for treating diseases and conditions such as those associated with wound healing and fibrosis, apoptosis, angiogenesis and neovascularization, vascular permeability and inflammation, that are associated with an undesired, excessive or aberrant level of LPA.

Recently, the applicants have developed several monoclonal antibodies against LPAs. These anti-LPA antibodies can neutralize various LPAs and mitigate their biologic and pharmacologic action. Anti-LPA antibodies are, therefore, believed to be useful in prevention and/or treatment of various diseases and conditions associated with excessive, unwanted or aberrant levels of LPA.

Rapid and specific methods of detecting LPA are also desired. Methods for separating and semi-quantitatively measuring phospholipids such as LPA using techniques such as thin-layer chromatography (TLC) followed by gas chromatography (GC) and/or mass spectrometry (MS) are known. For example, lipids may be extracted from the test sample of bodily fluid. Alternatively, thin-layer chromatography may be used to separate various phospholipids. Phospholipids and lysophospholipids can then be visualized on plates, for example, using ultraviolet light. Alternatively, lysophospholipid concentrations can be identified by NMR or HPLC following isolation from phospholipids or as part of the phospholipid. LPA levels have also been determined in ascites from ovarian cancer patients using an assay that relies on LysoPA-specific effects on eukaryotic cells in culture. However, these prior procedures are time-consuming, expensive and variable and typically only semi-quantitative. Enzymatic methods for detecting lysophospholipids such as LPA in biological fluids, and for correlating and detecting conditions associated with altered levels of lysophospholipids, are also known. U.S. Pat. Nos. 6,255,063 and 6,248,553, originally assigned to Atairgin Technologies, Inc. and now commonly owned with the instant invention. The antibodies disclosed herein provide the basis for sensitive and specific methods for detection of LPA.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

The term "aberrant" means excessive or unwanted, for example in reference to levels or effective concentrations of a cellular target such as a protein or bioactive lipid.

The term "antibody" ("Ab") or "immunoglobulin" (Ig) refers to any form of a peptide, polypeptide derived from, modeled after or encoded by, an immunoglobulin gene, or fragment thereof, that is capable of binding an antigen or epitope. See, e.g., Immunobiology, Fifth Edition, C. A. Janeway, P. Travers, M., Walport, M. J. Shlomchiked., ed. Garland Publishing (2001). The term "antibody" is used herein in the broadest sense, and encompasses monoclonal, polyclonal or multispecific antibodies, minibodies, heteroconjugates, diabodies, triabodies, chimeric, antibodies, synthetic antibodies, antibody fragments, and binding agents that employ the complementarity determining regions (CDRs) (or variants thereof that retain antigen binding activity) of the parent antibody. Antibodies are defined herein as retaining at least one desired activity of the parent antibody. Desired activities can include the ability to bind the antigen specifically, the ability to inhibit proleration in vitro, the ability to inhibit angiogenesis in vivo, and the ability to alter cytokine profile(s) in vitro. Herein, antibodies and antibody fragments, variants, and derivatives may also be referred to as "immune-derived moieties", in that such molecules, or at least the antigen-binding portion(s) thereof, have been derived from an anti-LPA antibody.

Native antibodies (native immunoglobulins) are usually heterotetrameric glycoproteins of about 150,000 Daltons, typically composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH), also referred to as the variable domain, followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues form an interface between the light- and heavy-chain variable domains. The terms "variable domain" and "variable region" are used interchangeably. The terms "constant domain" and "constant region" are also interchangeable with each other.

Three hypervariable regions (also known as complementarity determining regions or CDRs) in each of the VH and VL regions form the unique antigen binding site of the molecule. Most of the amino acid sequence variation in the antibody molecule is within the CDRs, giving the antibody its specificity for its antigen.

The light chains of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An "antibody derivative" is an immune-derived moiety, i.e., a molecule that is derived from an antibody. This comprehends, for example, antibody variants, antibody fragments, chimeric antibodies, humanized antibodies, multivalent antibodies, antibody conjugates and the like, which retain a desired level of binding activity for antigen.

As used herein, "antibody fragment" refers to a portion of an intact antibody that includes the antigen binding site or variable domains of an intact antibody, wherein the portion can be free of the constant heavy chain domains (e.g., CH2, CH3, and CH4) of the Fc region of the intact antibody. Alternatively, portions of the constant heavy chain domains (e.g., CH2, CH3, and CH4) can be included in the "antibody fragment". Antibody fragments retain antigen-binding and include Fab, Fab', F(ab')2, Fd, and Fv fragments; diabodies; triabodies; single-chain antibody molecules (sc-Fv); minibodies, nanobodies, and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. By way of example, a Fab fragment also contains the constant domain of a light chain and the first constant domain (CH1) of a heavy chain. "Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. "Single-chain Fv" or "sFv" antibody fragments comprise the VH and VL domains of antibody, wherein these domains are present in a single polypeptide chain. Generally, the Fv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

An "antibody variant," in this case an anti-LPA antibody variant, refers herein to a molecule which differs in amino acid sequence from a native anti-LPA antibody amino acid sequence by virtue of addition, deletion and/or substitution of one or more amino acid residue(s) in the antibody sequence and which retains at least one desired activity of the parent anti-binding antibody. Desired activities can include the ability to bind the antigen specifically, the ability to inhibit proliferation in vitro, the ability to inhibit angiogenesis in vivo, and the ability to alter cytokine profile in vitro. The amino acid change(s) in an antibody variant may be within a variable domain or a constant region of a light chain and/or a heavy chain, including in the Fc region, the Fab region, the CH1 domain, the CH2 domain, the CH3 domain, and the hinge region. In one embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 65% amino acid sequence identity with the parent antibody heavy or light chain variable domain sequences, more preferably at least 75%, more preferably at 80%, more preferably at least 85%, more preferably at least 90%, and most preferably at least 95%. In some situations a sequence identity of at least 50% is preferred, where other characteristics of the molecule convey desired attributes such as binding and specificity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind LPA and preferably has desired activities which are superior to those of the parent antibody. For example, the variant may have a stronger binding affinity, enhanced ability to reduce angiogenesis and/or halt tumor progression. To analyze such desired properties (for example les immunogenic, longer half-life, enhanced stability, enhanced potency), one should compare a Fab form of the variant to a Fab form of the parent antibody or a full length form of the variant to a full length form of the parent antibody, for example, since it has been found that the format of the anti-sphingolipid antibody impacts its activity in the biological activity assays disclosed herein. The variant antibody of particular interest herein can be one which displays at least about 10 fold, preferably at least about % 5, 25, 59, or more of at least one desired activity. The preferred variant is one that has superior biophysical properties as measured in vitro or superior activities biological as measured in vitro or in vivo when compared to the parent antibody.

An "anti-LPA agent" refers to any therapeutic agent that binds LPA, and includes antibodies, antibody variants, antibody-derived molecules or non-antibody-derived moieties that bind LPA and its variants.

A "bioactive lipid" refers to a lipid signaling molecule. Bioactive lipids are distinguished from structural lipids (e.g., membrane-bound phospholipids) in that they mediate extracellular and/or intracellular signaling and thus are involved in controlling the function of many types of cells by modulating differentiation, migration, proliferation, secretion, survival, and other processes. In vivo, bioactive lipids can be found in extracellular fluids, where they can be complexed with other molecules, for example serum proteins such as albumin and lipoproteins, or in "free" form, i.e., not complexed with another molecule species. As extracellular mediators, some bioactive lipids alter cell signaling by activating membrane-bound ion channels or GPCRs or enzymes or factors that, in turn, activate complex signaling systems that result in changes in cell function or survival. As intracellular mediators, bioactive lipids can exert their actions by directly interacting with intracellular components such as enzymes, ion channels, or structural elements such as actin.

Examples of bioactive lipids include sphingolipids such as ceramide, ceramide-1-phosphate (C1P), sphingosine, sphinganine, sphingosylphosphorylcholine (SPC) and sphingosine-1-phosphate (S1P). Sphingolipids and their derivatives and metabolites are characterized by a sphingoid backbone (derived from sphingomyelin). Sphingolipids and their derivatives and metabolites represent a group of extracellular and intracellular signaling molecules with pleiotropic effects on important cellular processes. They include sulfatides, gangliosides and cerebrosides. Other bioactive lipids are characterized by a glycerol-based backbone; for example, lysophospholipids such as lysophosphatidyl choline (LPC) and various lysophosphatidic acids (LPA), as well as phosphatidylinositol (PI), phosphatidylethanolamine (PEA), phosphatidic acid, platelet activating factor (PAF), cardiolipin, phosphatidylglycerol (PG) and diacylglyceride (DG). Yet other bioactive lipids are derived from arachidonic acid; these include the eicosanoids (including the eicosanoid metabolites such as the HETEs, cannabinoids, leukotrienes, prostaglandins, lipoxins, epoxyeicosatrienoic acids, and isoeicosanoids), non-eicosanoid cannabinoid mediators. Other bioactive lipids, including other phospholipids and their derivatives, may also be used according to the instant invention.

In some embodiments of the invention it may be preferable to target glycerol-based bioactive lipids (those having a glycerol-derived backbone, such as the LPAs) for antibody production, as opposed to sphingosine-based bioactive lipids (those having a sphingoid backbone, such as sphingosine and S1P). In other embodiments it may be desired to target arachidonic acid-derived bioactive lipids for antibody generation, and in other embodiments arachidonic acid-derived and glycerol-derived bioactive lipids but not sphingoid-derived bioactive lipids are preferred. Together the arachidonic acid-derived and glycerol-derived bioactive lipids may be referred to herein as "non-sphingoid bioactive lipids."

Specifically excluded from the class of bioactive lipids according to the invention are phosphatidylcholine and phosphatidylserine, as well as their metabolites and derivatives that function primarily as structural members of the inner and/or outer leaflet of cellular membranes.

The term "biologically active," in the context of an antibody or antibody fragment or variant, refers to an antibody or antibody fragment or antibody variant that is capable of binding the desired epitope and in some ways exerting a biologic effect. Biological effects include, but are not limited to, the modulation of a growth signal, the modulation of an anti-apoptotic signal, the modulation of an apoptotic signal, the modulation of the effector function cascade, and modulation of other ligand interactions.

A "biomarker" is a specific biochemical in the body which has a particular molecular feature that makes it useful for measuring the progress of disease or the effects of treatment. For example, S1P is a biomarker for certain hyperproliferative and/or cardiovascular conditions.

"Cardiovascular therapy" encompasses cardiac therapy (treatment of myocardial ischemia and heart failure) as well as the prevention and/or treatment of other diseases associated with the cardiovascular system, such as heart disease. The term "heart disease" encompasses any type of disease, disorder, trauma or surgical treatment that involves the heart or myocardial tissue. Of particular interest are conditions associated with tissue remodeling. The term "cardiotherapeutic agent" refers to an agent that is therapeutic to diseases and diseases caused by or associated with cardiac and myocardial diseases and disorders.

A "carrier" refers to a moiety adapted for conjugation to a hapten, thereby rendering the hapten immunogenic. A representative, non-limiting class of carriers is proteins, examples of which include albumin, keyhole limpet hemocyanin, hemaglutanin, tetanus, and diptheria toxoid. Other classes and examples of carriers suitable for use in accordance with the invention are known in the art. These, as well as later discovered or invented naturally occurring or synthetic carriers, can be adapted for application in accordance with the invention.

As used herein, the expressions "cell," "cell line," and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "chemotherapeutic agent" means anti-cancer and other anti-hyperproliferative agents. Thus chemotherapeutic agents are a subset of therapeutic agents in general. Chemotherapeutic agents include, but are not limited to: DNA damaging agents and agents that inhibit DNA synthesis: anthracyclines (doxorubicin, donorubicin, epirubicin), alkylating agents (bendamustine, busulfan, carboplatin, carmustine, chlorambucil, cyclophosphamide, dacarbazine, hexamethylmelamine, ifosfamide, lomustine, mechlorethamine, melphalan, mitotane, mytomycin, pipobroman, procarbazine, streptozocin, thiotepa, and triethylenemelamine), platinum derivatives (cisplatin, carboplatin, cis diammine-dichloroplatinum), and topoisomerase inhibitors (Camptosar); antimetabolites such as capecitabine, chlorodeoxyadenosine, cytarabine (and its activated form, ara-CMP), cytosine arabinoside, dacabazine, floxuridine, fludarabine, 5-fluorouracil, 5-DFUR, gemcitabine, hydroxyurea, 6-mercaptopurine, methotrexate, pentostatin, trimetrexate, 6-thioguanine); anti-angiogenics (bevacizumab, thalidomide, sunitinib, lenalidomide, TNP-470, 2-methoxyestradiol, ranibizumab, sorafenib, erlotinib, bortezomib, pegaptanib, endostatin); vascular disrupting agents (flavonoids/flavones, DMXAA, combretastatin derivatives such as CA4DP, ZD6126, AVE8062A, etc.); biologics such as antibodies (Herceptin, Avastin, Panorex, Rituxin, Zevalin, Mylotarg, Campath, Bexxar, Erbitux); endocrine therapy: aromatase inhibitors (4-hydroandrostendione, exemestane, aminoglutehimide, anastrazole, letozole), anti-estrogens (Tamoxifen, Toremifine, Raoxifene, Faslodex), steroids such as dexamethasone; immuno-modulators: cytokines such as IFN-beta and IL2), inhibitors to integrins, other adhesion proteins and matrix metalloproteinases); histone deacetylase inhibitors like suberoylanilide hydroxamic acid; inhibitors of signal transduction such as inhibitors of tyrosine kinases like imatinib (Gleevec); inhibitors of heat shock proteins like 17-N-allylamino-17-demethoxygeldanamycin; retinoids such as all trans retinoic acid; inhibitors of growth factor receptors or the growth factors themselves; anti-mitotic compounds and/or tubulin-depolymerizing agents such as the taxoids (paclitaxel, docetaxel, taxotere, BAY 59-8862), navelbine, vinblastine, vincristine, vindesine and vinorelbine; anti-inflammatories such as COX inhibitors and cell cycle regulators, e.g., check point regulators and telomerase inhibitors.

The term "chimeric" antibody (or immunoglobulin) refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., infra; Morrison et al., Proc. Natl. Acad. Sci. U.S.A., vol. 81:6851 (1984)). One example of a chimeric antibody is an antibody containing murine variable domains (VL and VH) and human constant domains. However, antibody sequences may be vertebrate or invertebrate in origin, e.g., from mammal, bird or fish, including cartilaginous fish, rodents, canines, felines, ungulate animals and primates, including humans.

The term "combination therapy" refers to a therapeutic regimen that involves the provision of at least two distinct therapies to achieve an indicated therapeutic effect. For example, a combination therapy may involve the administration of two or more chemically distinct active ingredients, for example, a fast-acting chemotherapeutic agent and an anti-lipid antibody. Alternatively, a combination therapy may involve the administration of an anti-lipid antibody and/or one or more chemotherapeutic agents, alone or together with the delivery of another treatment, such as radiation therapy and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-lipid antibody species, for example, an anti-LPA antibody, alone or in conjunction with one or more chemotherapeutic agents are combined with, for example, radiation and/or surgery, the drug(s) may be delivered before or after surgery or radiation treatment.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A "derivatized bioactive lipid" is a bioactive lipid, e.g., LPA, which has a polar head group and at least one hydrocarbon chain, wherein a carbon atom within the hydrocarbon chain is derivatized with a pendant reactive group [e.g., a sulfhydryl (thiol) group, a carboxylic acid group, a cyano group, an ester, a hydroxy group, an alkene, an alkyne, an acid chloride group or a halogen atom] that may or may not be protected. This derivatization serves to activate the bioactive lipid for reaction with a molecule, e.g., for conjugation to a carrier.

A "derivatized bioactive lipid conjugate" refers to a derivatized bioactive lipid that is covalently conjugated to a carrier. The carrier may be a protein molecule or may be a moiety such as polyethylene glycol, colloidal gold, adjuvants or silicone beads. A derivatized bioactive lipid conjugate may be used as an immunogen for generating an antibody response according to the instant invention, and the same or a different bioactive lipid conjugate may be used as a detection reagent for detecting the antibody thus produced. In some embodiments the derivatized bioactive lipid conjugate is attached to a solid support when used for detection.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993).

"Effective concentration" refers to the absolute, relative, and/or available concentration and/or activity, for example of certain undesired bioactive lipids. In other words, the effective concentration of a bioactive lipid is the amount of lipid available, and able, to perform its biological function. In the present invention, an immune-derived moiety such as, for example, a monoclonal antibody directed to a bioactive lipid (such as, for example, C1P) is able to reduce the effective concentration of the lipid by binding to the lipid and rendering it unable to perform its biological function. In this example, the lipid itself is still present (it is not degraded by the antibody, in other words) but can no longer bind its receptor or other targets to cause a downstream effect, so "effective concentration" rather than absolute concentration is the appropriate measurement. Methods and assays exist for directly and/or indirectly measuring effective concentrations of bioactive lipids.

An "epitope" or "antigenic determinant" refers to that portion of an antigen that reacts with an antibody antigen-binding portion derived from an antibody.

The term "expression cassette" refers to a nucleotide molecule capable of affecting expression of a structural gene (i.e., a protein coding sequence, such as an antibody of the invention) in a host compatible with such sequences. Expression cassettes include at least a promoter operably linked with the polypeptide-coding sequence, and, optionally, with other sequences, e.g., transcription termination signals. Additional regulatory elements necessary or helpful in effecting expression may also be used, e.g., enhancers. Thus, expression cassettes include plasmids, expression vectors, recombinant viruses, any form of recombinant "naked DNA" vector, and the like.

A "fully human antibody" can refer to an antibody produced in a genetically engineered (i.e., transgenic) animal, typically a mammal, usually a mouse (e.g., as can be obtained from Medarex) that, when presented with a suitable immunogen, can produce a human antibody that does not necessarily require CDR grafting. These antibodies are fully "human" in that they generated from an animal (e.g., a transgenic mouse) in which the non-human antibody genes are replaced or suppressed and replaced with some or all of the human immunoglobulin genes. In other words, antibodies of the invention include those generated against bioactive lipids, specifically LPA, when presented in an immunogenic form to mice or other animals genetically engineered to produce human frameworks for relevant CDRs.

A "hapten" is a substance that is non-immunogenic but can react with an antibody or antigen-binding portion derived from an antibody. In other words, haptens have the property of antigenicity but not immunogenicity. A hapten is generally a small molecule that can, under most circumstances, elicit an immune response (i.e., act as an antigen) only when attached to a carrier, for example, a protein, polyethylene glycol (PEG), colloidal gold, silicone beads, or the like. The carrier may be one that also does not elicit an immune response by itself.

The term "heteroconjugate antibody" can refer to two covalently joined antibodies. Such antibodies can be prepared using known methods in synthetic protein chemistry, including using crosslinking agents. As used herein, the term "conjugate" refers to molecules formed by the covalent attachment of one or more antibody fragment(s) or binding moieties to one or more polymer molecule(s).

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g., murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. In some instances, framework region (FR) residues of the human immunoglobulin are replaced by corresponding non-human residues.

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin. See, e.g., Cabilly, et al., U.S. Pat. No. 4,816,567; Cabilly, et al., European Patent No. 0,125,023 B1; Boss, et al., U.S. Pat. No. 4,816,397; Boss, et al., European Patent No. 0,120,694 B1; Neuberger, et al., WO 86/01533; Neuberger, et al., European Patent No. 0,194, 276 B1; Winter, U.S. Pat. No. 5,225,539; Winter, European Patent No. 0,239,400 B1; Padlan, et al., European Patent Application No. 0,519,596 A1; Queen, et al. (1989), Proc. Nat'l Acad. Sci. USA, vol. 86:10029-10033). For further details, see Jones et al., Nature 321:522-525 (1986); Reichmann et al., Nature 332:323-329 (1988); and Presta, Curr. Op. Struct. Biol. 2:593-596 (1992) and Hansen, WO2006105062.

The term "hyperproliferative disorder" refers to diseases and disorders associated with, the uncontrolled proliferation of cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, age-related macular degeneration and various retinopathies, as well as the proliferation of endothelial cells and smooth muscle cells that cause restenosis as a consequence of stenting in the treatment of atherosclerosis. Hyperproliferative disorders involving fibroblasts (i.e., fibrogenesis) include, without limitation, disorders of excessive scarring (i.e., fibrosis) such as age-related macular degeneration, cardiac remodeling and failure associated with myocardial infarction, as well as excessive wound healing such as commonly occurs as a consequence of surgery or injury, keloids, and fibroid tumors and stenting.

An "immunogen" is a molecule capable of inducing a specific immune response, particularly an antibody response in an animal to whom the immunogen has been administered. In the instant invention, the immunogen is a derivatized bioactive lipid conjugated to a carrier, i.e., a "derivatized bioactive lipid conjugate". The derivatized bioactive lipid conjugate used as the immunogen may be used as capture material for detection of the antibody generated in response to the immunogen. Thus the immunogen may also be used as a detection reagent. Alternatively, the derivatized bioactive lipid conjugate used as capture material may have a different linker and/or carrier moiety from that in the immunogen.

To "inhibit," particularly in the context of a biological phenomenon, means to decrease, suppress or delay. For example, a treatment yielding "inhibition of tumorigenesis" may mean that tumors do not form at all, or that they form more slowly, or are fewer in number than in the untreated control.

An "isolated" composition is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the composition is an antibody and will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition, such as one that is conjugated directly or indirectly to the antibody. The label may itself be detectable by itself (e.g., radioisotope labels or fluorescent labels) or, in the case of an enzymatic label, may catalyze chemical alteration of a substrate compound or composition that is detectable.

A "liposome" is a small vesicle composed of various types of lipids, phospholipids and/or surfactant that is useful for delivery of a drug (such as the anti-sphingolipid antibodies disclosed herein and, optionally, a chemotherapeutic agent) to a mammal. The components of the liposome are commonly arranged in a bilayer formation, similar to the lipid arrangement of biological membranes. An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of non-engineered cells.

In the context of this invention, a "liquid composition" refers to one that, in its filled and finished form as provided from a manufacturer to an end user (e.g., a doctor or nurse), is a liquid or solution, as opposed to a solid. Here, "solid" refers to compositions that are not liquids or solutions. For example, solids include dried compositions prepared by lyophilization, freeze-drying, precipitation, and similar procedures.

The expression "linear antibodies" when used throughout this application refers to the antibodies described in Zapata et al. Protein Eng. 8(10):1057-1062 (1995). Briefly, these antibodies comprise a pair of tandem Fd segments (VH-CH1-VH-CH1) that form a pair of antigen binding regions. Linear antibodies can be bispecific or monospecific.

The term "metabolites" refers to compounds from which LPAs are made, as well as those that result from the degradation of LPAs; that is, compounds that are involved in the lysophospholipid metabolic pathways. The term "metabolic precursors" may be used to refer to compounds from which sphingolipids are made.

The term "monoclonal antibody" (mAb) as used herein refers to an antibody obtained from a population of substantially homogeneous antibodies, or to said population of antibodies. The individual antibodies comprising the population are essentially identical, except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example, or by other methods known in the art. The monoclonal antibodies herein specifically include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Monotherapy" refers to a treatment regimen based on the delivery of one therapeutically effective compound, whether administered as a single dose or several doses over time.

The term "multispecific antibody" can refer to an antibody, or a monoclonal antibody, having binding properties for at least two different epitopes. In one embodiment, the epitopes are from the same antigen. In another embodiment, the epitopes are from two or more different antigens. Methods for making multispecific antibodies are known in the art. Multispecific antibodies include bispecific antibodies (having binding properties for two epitopes), trispecific antibodies (three epitopes) and so on. For example, multispecific antibodies can be produced recombinantly using the co-expression of two or more immunoglobulin heavy chain/light chain pairs. Alternatively, multispecific antibodies can be prepared using chemical linkage. One of skill can produce multispecific antibodies using these or other methods as may be known in the art. Multispecific antibodies include multispecific antibody fragments. One example of a multispecific (in this case, bispecific) antibody comprehended by this invention is an antibody having binding properties for an S1P epitope and a C1P epitope, which thus is able to recognize and bind to both S1P and C1P. Another example of a bispecific antibody comprehended by this invention is an antibody having binding properties for an epitope from a bioactive lipid and an epitope from a cell surface antigen. Thus the antibody is able to recognize and bind the bioactive lipid and is able to recognize and bind to cells, e.g., for targeting purposes.

"Neoplasia" or "cancer" refers to abnormal and uncontrolled cell growth. A "neoplasm", or tumor or cancer, is an abnormal, unregulated, and disorganized proliferation of cell growth, and is generally referred to as cancer. A neoplasm may be benign or malignant. A neoplasm is malignant, or cancerous, if it has properties of destructive growth, invasiveness, and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The "parent" antibody herein is one that is encoded by an amino acid sequence used for the preparation of the variant. The parent antibody may be a native antibody or may already be a variant, e.g., a chimeric antibody. For example, the parent antibody may be a humanized or human antibody.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the non-patentable embodiment(s). Also, the claims appended hereto are to be interpreted both to provide the broadest reasonable scope, as well as to preserve their validity. Furthermore, the claims are to be interpreted in a way that (1) preserves their validity and (2) provides the broadest reasonable interpretation under the circumstances, if one or more of the statutory requirements for patentability are amended or if the standards change for assessing whether a particular statutory requirement for patentability is satisfied from the time this application is filed or issues as a patent to a time the validity of one or more of the appended claims is questioned.

The term "pharmaceutically acceptable salt" refers to a salt, such as used in formulation, which retains the biological effectiveness and properties of the agents and compounds of this invention and which are is biologically or otherwise undesirable. In many cases, the agents and compounds of this invention are capable of forming acid and/or base salts by virtue of the presence of charged groups, for example, charged amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts (see Berge, et al. (1977) J. Pharm. Sci., vol. 66, 1-19).

A "plurality" means more than one.

The term "promoter" includes all sequences capable of driving transcription of a coding sequence in a cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. Transcriptional regulatory regions suitable for use in the present invention include but are not limited to the human cytomegalovirus (CMV) immediate-early enhancer/promoter, the SV40 early enhancer/promoter, the *E. coli* lac or trp promoters, and other promoters known to control expression of genes in prokaryotic or eukaryotic cells or their viruses.

The term "recombinant DNA" refers to nucleic acids and gene products expressed therefrom that have been engineered, created, or modified by man. "Recombinant" polypeptides or proteins are polypeptides or proteins produced by recombinant DNA techniques, for example, from cells transformed by an exogenous DNA construct encoding the desired polypeptide or protein. "Synthetic" polypeptides or proteins are those prepared by chemical synthesis.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, chemical reaction products, non-reacted chemicals, proteins, carbohydrates, lipids, and unbound molecules.

By "solid phase" is meant a non-aqueous matrix such as one to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

The term "species" is used herein in various contexts, e.g., a particular species of chemotherapeutic agent. In each context, the term refers to a population of chemically indistinct molecules of the sort referred in the particular context.

The term "specific" or "specificity" in the context of antibody-antigen interactions refers to the selective, non-random interaction between an antibody and its target epitope. Here, the term "antigen" refers to a molecule that is recognized and bound by an antibody molecule or other immune-derived moiety. The specific portion of an antigen that is bound by an antibody is termed the "epitope". This interaction depends on the presence of structural, hydrophobic/hydrophilic, and/or electrostatic features that allow appropriate chemical or molecular interactions between the molecules. Thus an antibody is commonly said to "bind" (or "specifically bind") or be "reactive with" (or "specifically reactive with), or, equivalently, "reactive against" (or "specifically reactive against") the epitope of its target antigen. Antibodies are commonly described in the art as being "against" or "to" their antigens as shorthand for antibody binding to the antigen. Thus an "antibody that binds C1P," an "antibody reactive against C1P," an "antibody reactive with C1P," an "antibody to C1P" and an "anti-C1P antibody" all have the same meaning in the art. Antibody molecules can be tested for specificity of binding by comparing binding to the desired antigen to binding to unrelated antigen or analogue antigen or antigen mixture under a given set of conditions. Preferably, an antibody according to the invention will lack significant binding to unrelated antigens, or even analogs of the target antigen.

Herein, "stable" refers to an interaction between two molecules (e.g., a peptide and a TLR molecule) that is sufficiently stable such that the molecules can be maintained for the desired purpose or manipulation. For example, a "stable" interaction between a peptide and a TLR molecule refers to one wherein the peptide becomes and remains associated with a TLR molecule for a period sufficient to achieve the desired effect.

A "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-human primates) animals being particularly preferred examples.

A "surrogate marker" refers to laboratory measurement of biological activity within the body that indirectly indicates the effect of treatment on disease state. Examples of surrogate markers for hyperproliferative and/or cardiovascular conditions include SPHK and/or S1PRs.

A "therapeutic agent" refers to a drug or compound that is intended to provide a therapeutic effect including, but not limited to: anti-inflammatory drugs including COX inhibitors and other NSAIDS, anti-angiogenic drugs, chemotherapeutic drugs as defined above, cardiovascular agents, immunomodulatory agents, agents that are used to treat neurodegenerative disorders, opthalmic drugs, etc.

A "therapeutically effective amount" (or "effective amount") refers to an amount of an active ingredient, e.g., an agent according to the invention, sufficient to effect treatment when administered to a subject in need of such treatment. Accordingly, what constitutes a therapeutically effective amount of a composition according to the invention may be readily determined by one of ordinary skill in the art. In the context of cancer therapy, a "therapeutically effective amount" is one that produces an objectively measured change in one or more parameters associated with cancer cell survival or metabolism, including an increase or decrease in the expression of one or more genes correlated with the particular cancer, reduction in tumor burden, cancer cell lysis, the detection of one or more cancer cell death markers in a biological sample (e.g., a biopsy and an aliquot of a bodily fluid such as whole blood, plasma, serum, urine, etc.), induction of induction apoptosis or other cell death pathways, etc. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (i.e., a therapeutic regimen that employs only one chemical entity as the active ingredient).

The compositions of the invention are used in methods of bioactive lipid-based therapy. As used herein, the terms "therapy" and "therapeutic" encompasses the full spectrum of prevention and/or treatments for a disease, disorder or physical trauma. A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of at least one symptom of a disease or disorder being treated; or may act to minimize the time required, the occurrence or extent of any discomfort or pain, or physical limitations associated with recuperation from a disease, disorder or physical trauma; or may be used as an adjuvant to other therapies and treatments.

The term "treatment" or "treating" means any treatment of a disease or disorder, including preventing or protecting against the disease or disorder (that is, causing the clinical symptoms not to develop); inhibiting the disease or disorder (i.e., arresting, delaying or suppressing the development of clinical symptoms; and/or relieving the disease or disorder (i.e., causing the regression of clinical symptoms). As will be appreciated, it is not always possible to distinguish between "preventing" and "suppressing" a disease or disorder because the ultimate inductive event or events may be unknown or latent. Those "in need of treatment" include those already with the disorder as well as those in which the disorder is to be prevented. Accordingly, the term "prophylaxis" will be understood to constitute a type of "treatment" that encompasses both "preventing" and "suppressing". The term "protection" thus includes "prophylaxis".

The term "therapeutic regimen" means any treatment of a disease or disorder using chemotherapeutic and cytotoxic agents, radiation therapy, surgery, gene therapy, DNA vaccines and therapy, siRNA therapy, anti-angiogenic therapy, immunotherapy, bone marrow transplants, aptamers and other biologics such as antibodies and antibody variants, receptor decoys and other protein-based therapeutics.

The "variable" region of an antibody comprises framework and complementarity determining regions (CDRs, otherwise known as hypervariable regions). The variability is not evenly distributed throughout the variable domains of antibodies. It is concentrated in six CDR segments, three in each of the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the beta-sheet structure. The term "hypervariable region" when used herein refers to the amino acid residues of an antibody which are responsible for antigen binding. The hypervariable region comprises amino acid residues from a "complementarity determining region" or "CDR" (for example residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (for example residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

A "vector" or "plasmid" or "expression vector" refers to a nucleic acid that can be maintained transiently or stably in a cell to effect expression of one or more recombinant genes. A vector can comprise nucleic acid, alone or complexed with other compounds. A vector optionally comprises viral or bacterial nucleic acids and/or proteins, and/or membranes. Vectors include, but are not limited, to replicons (e.g., RNA replicons, bacteriophages) to which fragments of DNA may be attached and become replicated. Thus, vectors include, but are not limited to, RNA, autonomous self-replicating circular or linear DNA or RNA and include both the expression and non-expression plasmids. Plasmids can be commercially available, publicly available on an unrestricted basis, or can be constructed from available plasmids as reported with published protocols. In addition, the expression vectors may also contain a gene to provide a phenotypic trait for selection of transformed host cells such as dihydrofolate reductase or neomycin resistance for eukaryotic cell culture, or such as tetracycline or ampicillin resistance in *E. coli*.

SUMMARY OF THE INVENTION

The instant application provides anti-LPA agents that bind LPA and comprise at least one CDR peptide of defined identity with sequences as described. The anti-LPA agents may be antibodies, including chimeric antibodies, humanized antibodies, full-length antibodies, affinity matured antibodies, antibody derivatives, antibody variants or antibody fragments, or may be non-antibody-derived moieties. The anti-LPA agents may be conjugated to a moiety selected from the group consisting of a polymer, a radionuclide, a chemotherapeutic agent, and a detection agent and may be provided in a carrier, optionally a pharmaceutically acceptable carrier. Further, the anti-LPA agent may be provided in combination with a second agent which may be an antibody, an antibody fragment, an antibody derivative or an antibody variant, and which may bind a molecule other than LPA. The anti-LPA agent and the second agent may be linked, optionally by a covalent linkage.

Also provided are isolated nucleic acid molecules comprising a sequence of defined identity with nucleotide sequences described, which encode at least one CDR peptide. The nucleic acid molecules may encode a fragment of an immunoglobulin heavy or light chain or a full length immunoglobulin heavy or light chain, and may be derived from a fish, bird or mammal, optionally a primate, optionally a human. Vectors and host cells comprising these nucleic acid molecules are provided.

Further provided are isolated polypeptides comprising at least one framework region from an animal immunoglobulin heavy chain or light chain and at least one CDR peptide of defined identity with sequences provided. The polypeptides may be full length variable domains of an immunoglobulin heavy or light chains, full length immunoglobulin heavy or light chains or fragments of an immunoglobulin heavy or light chains. Also provided are isolated antibody molecules, comprising two immunoglobulin heavy chains that binds LPA in a physiological context and comprise at least one framework region from a variable domain of an immunoglobulin heavy chain and at least one CDR peptide of defined identity with sequences provided, and, functionally associated with the two immunoglobulin heavy chains, two immunoglobulin light chains that binds LPA in a physiological context and comprise at least one framework region from a variable domain of an immunoglobulin light chain and at least one CDR peptide of defined identity with sequences provided. These isolated antibody molecules may be humanized antibody molecules.

In addition, the instant invention provides multivalent binding molecules that comprise at least first and second ligand binding elements, wherein the first ligand binding element binds LPA and comprises at least one CDR peptide of defined identity with sequences provided. The multivalent binding molecule may be a full length immunoglobulin heavy or light chain or a fragment thereof. The second binding element may also bind LPA and there may be more than two ligand binding elements. The multivalent binding molecule may comprise a scaffold to which the ligand binding elements are linked.

Provided in the instant application are isolated anti-LPA antibody heavy chains with a variable domain of defined sequence, as well as isolated anti-LPA antibody light chains with a variable domain of defined sequence. The combination of two such heavy chains and two such light chains into an isolated anti-LPA antibody is also disclosed, as well as compositions containing such an antibody in a carrier which may be a pharmaceutically acceptable carrier. A consensus anti-LPA heavy chain variable domain sequence and a consensus anti-LPA light chain variable domain sequence are also provided, based on experimental data showing that a large number of amino acid residues are conserved either in type (e.g., acidic, basic, noncharged polar, hydrophobic) or in amino acid identity among four of the five antibodies evaluated.

Also provided are methods of treating or preventing a disease or disorder associated with aberrant levels of LPA, which methods comprise administering to a subject one of the compositions of the invention, including an anti-LPA antibody, in an amount effective to reduce the effective concentration of LPA. The disease or disorder may be a hyperproliferative disease, including cancer; an immune-related disease, including an autoimmune disease, allograft rejection and graft-vs-host disease; a neurodegenerative disease; obesity; type 2 diabetes; an ocular disease, including macular degeneration; pain; or a disease associated with aberrant angiogenesis or neovascularization; apoptosis; fibrogenesis or fibrosis, including scleroderma, pulmonary fibrosis, renal fibrosis, skin fibrosis, cardiac fibrosis and hepatic fibrosis; wound repair and healing; or spider bite. Methods of decreasing aberrant hyperproliferation, immune response, neurodegeneration, angiogenesis, neovascularization, apoptosis, fibrogenesis or fibrosis in an animal with the compositions of the invention are also claimed. The fibrosis to be treated may be hepatic, renal, pulmonary, cardiac, uterine or skin fibrosis. It may be desirable to detect at least one fibrosis marker as well as LPA in a sample from the animal, including a human.

Further provided are diagnostic reagents comprising a derivatized lysophosphatidic acid which comprises a polar head group and at least one hydrocarbon chain, wherein a carbon atom within at least one of said at least one hydrocarbon chain is derivatized with an optionally protected pendant reactive group. The pendant reactive group may be a sulfhydryl (thiol) group, a carboxylic acid group, a cyano group, an ester, a hydroxy group, an alkene, an alkyne, an acid chloride group or a halogen atom, and the derivatized lysophosphatidic acid may be associated with a solid support. The derivatized lysophosphatidic acid may further be conjugated to a carrier moiety which is optionally, polyethylene glycol, colloidal gold, adjuvant, a silicone bead or a protein, and wherein the protein is optionally keyhole limpet hemocyanin, albumin, bovine thyroglobulin, or soybean trypsin inhibitor. This conjugate may be attached to a solid support. Methods of detecting an anti-LPA agent in a sample are provided, comprising detecting binding of an anti-LPA agent in a sample to a diagnostic reagent that comprises a derivatized LPA. The anti-LPA agent may be an antibody, optionally a human anti-LPA antibody. a polyclonal antibody; a monoclonal antibody; a chimeric antibody; an antibody fragment; an antibody derivative; or a non-antibody-derived moiety, and the sample may be a biological sample including a tissue sample, such as a biopsy sample, and a liquid sample, which is optionally whole blood, plasma, serum, urine, semen, bile, aqueous humor, vitreous humor, bronchioalveolar lavage fluid, mucous, or sputum. The method of detection may further include detection of at least one fibrosis marker. Detection of LPA may also include comparison of a level of LPA in the sample to a reference level of LPA to indicate the presence of disease or to monitor a therapeutic regimen for modulation of the effective concentration of LPA. The method of detection may also involve use of a diagnostic device bearing a diagnostic reagent comprising derivatized LPA. Further disclosed are ELISA kits for detecting LPA.

The foregoing and other aspects of the invention will become more apparent from the following detailed description, accompanying drawings, and the claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

A brief summary of each of the figures and tables described in this specification are provided below, as is a list of various nucleotide and amino acid sequences described herein.

FIG. 4. Color-coded amino acid sequence alignment of the variable domain sequences of five anti-LPA monoclonal antibodies, B58, 3A6, B3, B7 and A63. The letters indicate the amino acid sequence of each variable domain, using the single-letter amino acid code. Green indicates a noncharged, polar amino acid residue; blue indicates a hydrophobic amino acid residue, magenta indicates an acidic amino acid residue, orange indicates glycine, yellow indicates proline, red indicates a basic amino acid residue, pink indicates cysteine and teal indicates tyrosine or histidine. Residues in white are not conserved. FIG. 4A: heavy chain variable domain sequences of antibodies B58, 3A6, B3, B7, and A63 (SEQ ID NOs: 122, 124, 118, 120, and 126, respectively); FIG. 4B: light chain variable domain sequences of antibodies B58, 3A6, B3, B7, and A63 (SEQ ID NOs: 123, 125, 119, 121 and 127, respectively).

DETAILED DESCRIPTION OF THE INVENTION

A. Derivatized and/or Conjugated LPA

1. Compositions

Figure 1A:
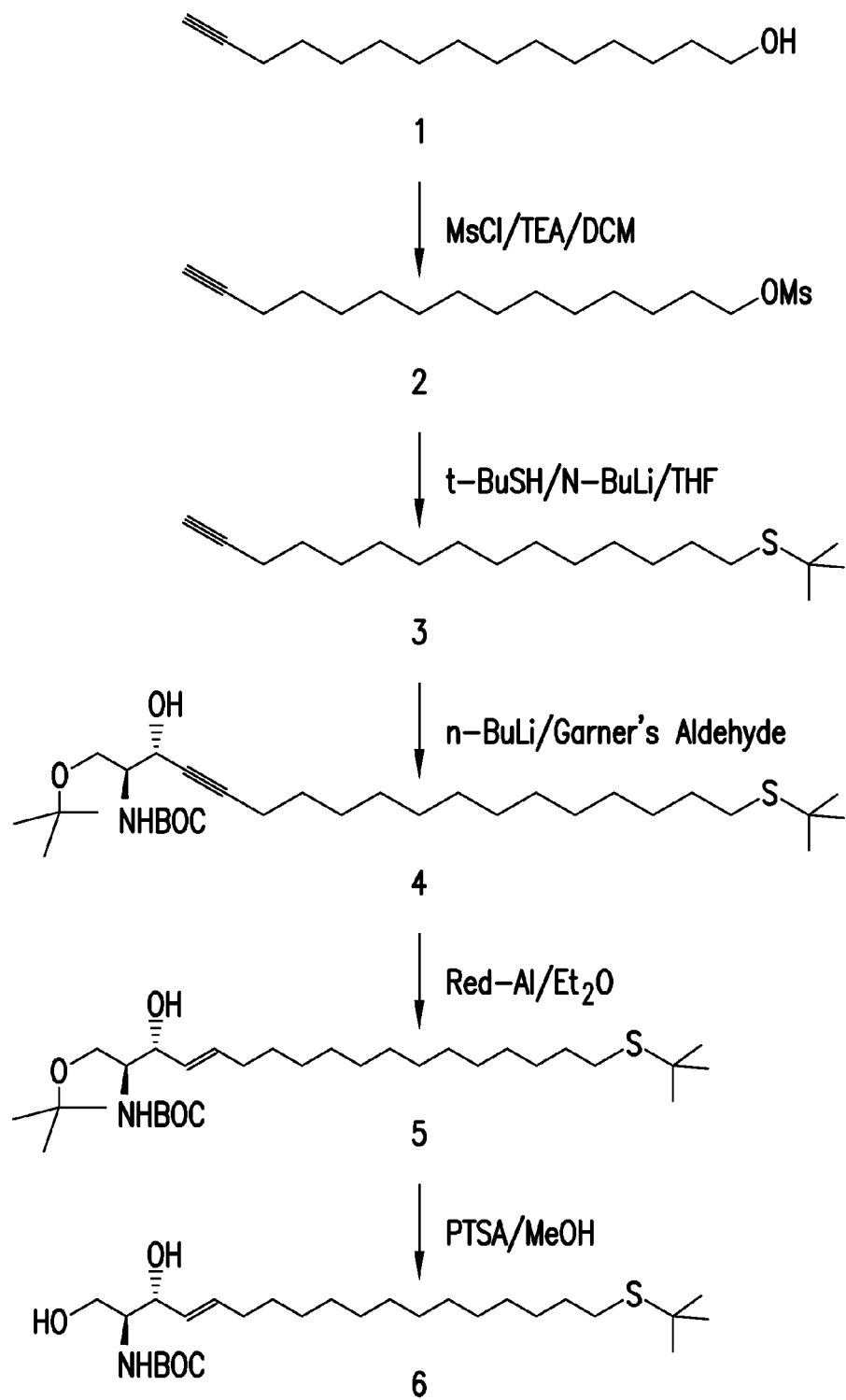
FIG. 1. Organic synthesis scheme for making of a typical thiolated-S1P analog that was used as a key component of an immunogen according to the invention, as well as a key component of the laydown material for the ELISA and BiaCore assays.

The present invention provides LPA which has been derivatized in such a way as to facilitate the immunogenic response (i.e., antibody production). In one embodiment, the LPA may be derivatized in order to allow conjugation of the LPA molecule to a carrier molecule. In one embodiment, a carbon atom within the hydrocarbon chain of the LPA is derivatized with a pendant reactive group [e.g., a sulfhydryl (thiol) group, a carboxylic acid group, a cyano group, an ester, a hydroxy group, an alkene, an alkyne, an acid chloride group or a halogen atom] that may or may not be protected. This derivatization serves to activate the bioactive lipid for reaction with a molecule, e.g., for conjugation to a carrier. In one embodiment, the derivatized LPA is thiolated LPA. In one embodiment, the derivatized LPA is derivatized C12 or C18 LPA. In one embodiment, the thiolated LPA is conjugated via a crosslinker, e.g., a bifunctional crosslinker such as IOA or SMCC, to a carrier, which may be a protein. It may be useful to conjugate the LPA in this way to a protein or other carrier that is immunogenic in the species to be immunized, e.g., keyhole limpet hemocyanin (KLH), serum albumin (including bovine serum albumin or BSA), bovine thyroglobulin, or soybean trypsin inhibitor, using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups. Non-protein carriers (e.g., colloidal gold) are also known in the art for use in antibody production.

The derivatized or derivatized and conjugated LPA may be used to generate anti-LPA antibodies (polyclonal and/or monoclonal). The derivatized or derivatized and conjugated LPA may also be used in the methods of the invention, particularly in diagnostic methods.

2. Research and Diagnostic Uses for Derivatized LPA

The derivatized LPAs of the invention may be used to detect and/or purify anti-LPA antibodies and may be conjugated to a carrier as described above. The derivatives and conjugates are preferably conjugated to a solid support for use in diagnostic methods, including clinical diagnostic methods. For example, detection and/or quantitation of LPA antibodies may be used in diagnosing various medical conditions in LPA plays a role. Quantitation of LPA antibodies is also useful in a clinical setting to evaluate dosing, halflife and drug levels after treatment with, e.g., an anti-LPA antibody such as LT3000 described herein.

In one embodiment, the derivatized LPA conjugate (e.g., thiolated LPA conjugated to BSA or KLH) is used as laydown material in ELISAs which are used to detect anti-LPA antibodies. In one embodiment the LPA is thiolated C12 LPA or thiolated C18 LPA conjugated to BSA. This embodiment is useful, for example, as laydown material (to coat the plate) in ELISA assays for detection of LPA. For example, in an LPA competitive ELISA, the plate is coated with derivatized and/or derivatized and conjugated LPA. A set of one or more LPA standards and one or more samples (e.g., serum or cell culture supernatant) is mixed with the mouse anti-LPA antibody of the invention and added to the derivitized-LPA-coated plate. The antibody competes for binding to either plate-bound LPA or LPA in the sample or standard. Following incubation and several ELISA steps, the absorbance at 450 nm is measured and the LPA concentration in the samples is determined by comparison to the standard curve.

The derivatized or derivatized and conjugated LPA may also be coupled to a solid support (e.g., resin or other column matrix, beads, membrane, plate) and used to isolate and/or purify anti-LPA antibodies, e.g., from blood or serum. Such anti-LPA antibodies may be newly generated antibodies such as those of the invention (e.g., mammalian monoclonal or polyclonal antibodies to LPA) or may be native human anti-LPA antibodies.

Thus the derivatized LPA and derivatized and conjugated LPA of the invention are useful both for research and in clinical diagnostics.

3. Diagnostic Kits Incorporating the Derivatized LPA of the Invention

As a matter of convenience, the derivatized LPAs of the present invention can be provided in a kit, for example, a packaged combination of reagents in predetermined amounts with instructions for performing the diagnostic assay.

As described above, In one embodiment, the derivatized LPA conjugate (e.g., thiolated LPA conjugated to BSA or KLH) is used as laydown material (to coat the plate) in ELISA kits which are used to detect anti-LPA antibodies. Such kits are useful for detection of LPA. For example, in an LPA competitive ELISA kit, the plate (provided) is coated with derivatized and/or derivatized and conjugated LPA. A set of one or more LPA standards (generally provided in the kit) and one or more samples (e.g., serum or cell culture supernatant) is mixed with the mouse anti-LPA antibody of the invention and added to the derivitized-LPA-coated plate. The antibody competes for binding to either plate-bound LPA or LPA in the sample or standard. Following incubation and several ELISA steps (instructions and reagents for which are provided in the kit), the absorbance at 450 nm is measured and the LPA concentration in the samples is determined by comparison to the standard curve. In one embodiment the LPA used for laydown material in the ELISA kit is thiolated C12 LPA or thiolated C18 LPA conjugated to BSA. The antibody used in the kit may be polyclonal or monoclonal antibody, preferably a monoclonal antibody.

A kit incorporating an Lpath derivatized and conjugated LPA of the invention and an Lpath anti-LPA antibody of the invention, is commercially available from Echelon Biosciences, Inc., Salt Lake City, Utah (Lysophosphatidic Assay Kit, Cat. No. K-2800).

B. Anti-LPA Agents, Including Anti-LPA Antibodies

1. Introduction

The use of monoclonal antibodies (mAbs) as a therapeutic treatment for a variety of diseases and disorders is rapidly increasing because they have been shown to be safe and efficacious therapeutic agents. Approved therapeutic monoclonal antibodies include Avastin™, Erbitux™, and Rituxan™. Additional monoclonal antibodies are in various phases of clinical development for a variety of diseases with the majority targeting various forms of cancer. In general, monoclonal antibodies are generated in non-human mammals. The therapeutic utility of murine monoclonal antibodies may be improved with chimerization or humanization of non-human mammalian antibodies. Humanization greatly lessens the development of an immune response against the administered therapeutic monoclonal antibodies and thereby avoids the reduction of half-life and therapeutic efficacy consequent on such a response. For the most part, the humanization process consists of grafting the murine complementary determining regions (CDRs) into the framework region (FR) of a human immunoglobulin. Backmutation to murine amino acid residues of selected residues in the FR is often required to improve or regain affinity that is lost in the initial grafted construct.

The manufacture of monoclonal antibodies is a complex process that stems from the variability of the immunoglobulin protein itself. The heterogeneity can be attributed to the formation of alternative disulfide pairings, deamidation and the formation of isoaspartyl residues, methionine and cysteine oxidation, cyclization of N-terminal glutamine residues to pyroglutamate and partial enzymatic cleavage of C-terminal lysines by mammalian carboxypeptidases. Engineering is commonly applied to antibody molecules to improve their properties, such as enhanced stability, resistance to proteases, aggregation behavior and enhance the expression level in heterologous systems.

2. Disease Associations of LPA and Therapeutic Uses for Anti-LPA Agents

LPA has been associated with a number of diseases and disorders. For review, see Gardell et al., (2006) Trends Mol Med. 12(2):65-75 and Chun J. and Rosen, H., (2006) Curr. Pharma. Design 12:161-171. These include autoimmune disorders such as diabetes, multiple sclerosis and scleroderma; hyperproliferative disorders including cancer; disorders associated with angiogenesis and neovascularization; obesity; neurodegenerative diseases including Alzheimer's disease; schizophrenia, immune-related disorders such as transplant rejection and graft-vs.-host disease, and others.

a. Hyperproliferative Disorders

One aspect of the invention concerns methods for treating hyperproliferative disorders. These methods comprise administering to a mammal (e.g., a bovine, canine, equine, ovine, or porcine animal, particularly a human) known or suspected to suffer from an LPA-associated hyperproliferative disorder a therapeutically effective amount of a composition comprising an agent that interferes with LPA concentration and/or activity, preferably in a pharmaceutically or veterinarily acceptable carrier, as the intended application may require. LPA-associated hyperproliferative disorders include neoplasias, disorders associated with endothelial cell proliferation, and disorders associated with fibrogenesis. Most often, the neoplasia will be a cancer. Typical disorders associated with endothelial cell proliferation are angiogenesis-dependent disorders, for example, cancers caused by a solid tumors, hematological tumors, and age-related macular degeneration. Disorders associated with fibrogenesis include those than involve aberrant cardiac remodeling, such as cardiac failure.

There are many known hyperproliferative disorders, in which cells of various tissues and organs exhibit aberrant patterns of growth, proliferation, migration, signaling, senescence, and death. While a number of treatments have been developed to address some of these diseases, many still remain largely untreatable with existing technologies, while in other cases, while treatments are available, they are frequently less than optimal and are seldom curative.

Cancer represents perhaps the most widely recognized class of hyperproliferative disorders. Cancers are a devastating class of diseases, and together, they have a mortality rate second only to cardiovascular disease. Many cancers are not fully understood on a molecular level. As a result, cancer is a major focus of research and development programs for both the United States government and pharmaceutical companies. The result has been an unprecedented R&D effort and the production of many valuable therapeutic agents to help in the fight against cancer.

Unfortunately the enormous amount of cancer research has not been enough to overcome the significant damage caused by cancer. There are still over one million new cases of cancer diagnosed annually and over five hundred thousand deaths in the United States alone. This is a dramatic demonstration that even though an enormous effort has been put forth to discover new therapeutics for cancer, effective therapeutic agents to combat the disease remain elusive.

Cancer is now primarily treated with one or a combination of three types of therapies, surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism.

Further insult is that current therapeutic agents usually involve significant drawbacks for the patient in the form of toxicity and severe side effects. Therefore, many groups have recently begun to look for new approaches to fighting the war against cancer. These new so-called "innovative therapies" include gene therapy and therapeutic proteins such as monoclonal antibodies.

The first monoclonal antibody used in the clinic for the treatment of cancer was Rituxan (rituximab) which was launched in 1997, and has demonstrated the utility of monoclonal antibodies as therapeutic agents. Thus, not surprisingly, twenty monoclonal antibodies have since been approved for use in the clinic, including nine that are prescribed for cancer. The success of these products, as well as the reduced cost and time to develop monoclonal antibodies as compared with small molecules has made monoclonal antibody therapeutics the second largest category of drug candidates behind small molecules. Further, the exquisite specificity of antibodies as compared to small molecule therapeutics has proven to be a major advantage both in terms of efficacy and toxicity. For cancer alone there are currently more than 270 industry antibody R&D projects with more than 50 companies involved in developing new cancer antibody therapeutics. Consequently, monoclonal antibodies are poised to become a major player in the treatment of cancer and they are estimated to capture an increasing share of the cancer therapeutic market. Generally therapeutic mAbs are targeted to proteins; only recently has it been feasible to raise mAbs to bioactive lipids (for example, antibodies to S1P, see Applicants' US Application Serial No. 20070148168).

The identification of extracellular mediators that promote tumor growth and survival is a critical step in discovering therapeutic interventions that will reduce the morbidity and mortality of cancer. As described below, LPA is considered to be a pleiotropic, tumorigenic growth factor. LPA promotes tumor growth by stimulating cell proliferation, cell survival, and metastasis. LPA also promotes tumor angiogenesis by supporting the migration and survival of endothelial cells as they form new vessels within tumors. Taken together, LPA initiates a proliferative, pro-angiogenic, and anti-apoptotic sequence of events contributing to cancer progression. Thus, therapies that modulate, and, in particular, reduce LPA levels in vivo will be effective in the treatment of cancer.

Typically, the methods of the invention for treating or preventing a hyperproliferative disorder such as cancer involve administering to a subject suffering from a hyperproliferative disorder an effective amount of each of an agent (or a plurality of different agent species) according to the invention and a cytotoxic agent. Cytotoxic agents include chemotherapeutic drugs.

A related aspect concerns methods of reducing toxicity of a therapeutic regimen for treatment or prevention of a hyperproliferative disorder. Such methods comprise administering to a subject suffering from a hyperproliferative disorder an effective amount of an agent (or a plurality of different agent species) according to the invention before, during, or after administration of a therapeutic regimen intended to treat or prevent the hyperproliferative disorder. It is believed that by sensitizing cells, e.g., cancer cells, to chemotherapeutic drugs, efficacy can be achieved at lower doses and hence lower toxicity due to chemotherapeutic drugs.

Yet another aspect of the invention concerns methods of enhancing a survival probability of a subject treated for a hyperproliferative disorder by administering to a subject suffering from a hyperproliferative disorder an agent (or a plurality of different agent species) according to the invention before, during, or after administration of a therapeutic regimen intended to treat or prevent the hyperproliferative disorder to enhance the subject's survival probability.

1. Fibrosis, Wound Healing and Scar Formation

Fibroblasts, particularly myofibroblasts, are key cellular elements in scar formation in response to cellular injury and inflammation (Tomasek et al. (2002), Nat Rev Mol Cell Biol, vol 3: 349-63, and Virag and Murry (2003), Am J Pathol, vol 163: 2433-40). Collagen gene expression by myofibroblasts is a hallmark of remodeling and necessary for scar formation (Sun and Weber (2000), Cardiovasc Res, vol 46: 250-6, and Sun and Weber (1996), J Mol Cell Cardiol, vol 28: 851-8).

Fibrosis can be described as the formation or development of excess or aberrant fibrous connective tissue in an organ or tissue as part of a pathological reparative or reactive process, in contrast to normal wound healing or development. The most common forms of fibrosis are: liver, lung, kidney, skin, uterine and ovarian fibroses. Some conditions, such as scleroderma, sarcoidosis and others, are characterized by fibrosis in multiple organs and tissues.

Recently, the bioactive lysophospholipid lysophosphatidic acid (LPA) has been recognized for its role in tissue repair and wound healing. Watterson et al., Wound Repair Regen. (2007) 15:607-16. As a biological mediator, LPA has been recognized for its role in tissue repair and wound healing (Watterson, 2007). In particular, LPA is linked to pulmonary and renal inflammation and fibrosis. LPA is detectable in human bronchioalveolar lavage (BAL) fluids at baseline and its expression increases during allergic inflammation Georas, S. N. et al. (2007) Clin Exp Allergy. (2007) 37: 311-22. Furthermore, LPA promotes inflammation in airway epithelial cells. Barekzi, E. et al (2006) Prostaglandins Leukot Essent Fatty Acids. 74:357-63. Recently, pulmonary and renal fibrosis have been linked to increased LPA release and signaling though the LPA type 1 receptor ($LPA_1$). LPA levels were elevated in bronchialveolar lavage (BAL) samples from IPF patients and bleomycin-induced lung fibrosis in mice was dependent on activation of $LPA_1$. Tager et al., (2008) Proc Am Thorac Soc. 5: 363. (2008) Following unilateral ureteral obstruction in mice, tubulointerstitial fibrosis was reduced in $LPA_1$ knock-out mice and pro-fibrotic cytokine expression was attenuated in wild-type mice treated with an $LPA_1$ antagonist. J. P. Pradere et al., (2007) J. Am. Soc. Nephrol. 18:3110-3118. LPA has been shown to have direct fibrogenic effects in cardiac fibroblasts by stimulating collagen gene expression and proliferation. Chen, et al. (2006) FEBS Lett. 580:4737-45. Combined, these studies demonstrate a role for LPA in tissue repair and fibrosis, and identify bioactive lipids as a previously unrecognized class of targets in the treatment of fibrotic disorders.

a. Scleroderma

The compositions and methods of the invention will be useful in treating disorders and diseases characterized, at least in part, by aberrant neovascularization, angiogenesis, fibrogenesis, fibrosis, scarring, inflammation, and immune response. One such disease is scleroderma, which is also referred to as systemic sclerosis.

Scleroderma is an autoimmune disease that causes scarring or thickening of the skin, and sometimes involves other areas of the body, including the lungs, heart, and/or kidneys. Scleroderma is characterized by the formation of scar tissue (fibrosis) in the skin and organs of the body, which can lead to thickening and firmness of involved areas, with consequent reduction in function. Today, about 300,000 Americans have scleroderma, according to the Scleroderma Foundation. One-third or less of those affected have widespread disease, while the remaining two-thirds primarily have skin symptoms. When the disease affects the lungs and causing scarring, breathing can become restricted because the lungs can no longer expand as they should. To measure breathing capability, doctors use a device that assesses forced vital capacity (FVC). In people with an FVC of less than 50 percent of the expected reading, the 10-year mortality rate from scleroderma-related lung disease is about 42 percent. One reason the mortality rate is so high is that no effective treatment is currently available.

Without wishing to be bound by any particular theory, it is believed that inappropriate concentrations of lipids such as S1P and/or LPA, and/or their metabolites, cause or contribute to the development of scleroderma. As such, the compositions and methods of the invention can be used to treat scleroderma, particularly by decreasing the effective in vivo concentration of a particular target lipid, for example, LPA.

Evidence indicates that LPA is a pro-fibrotic growth factor that can contribute to fibroblast activation, proliferation, and the resulting increased fibroblast activity associated with maladaptive scarring and remodeling. Moreover, potential roles for LPA in skin fibroblast activity have been demonstrated. For example, it has been shown that LPA stimulates the migration of murine skin fibroblasts (Hama et al., J Biol. Chem. 2004 Apr. 23; 279(17): 17634-9).

b. Pulmonary Fibrosis

Pulmonary fibrosis, sometimes referred to as interstitial lung disease or ILD, affects more than 5 million people worldwide. Within the USA the prevalence of the disease seems to be under-estimated and vary from 3 to 6 cases for 100,000 inhabitants to 28 per 100,000. Within Europe; the numbers vary depending on the countries, and is reported around 1 to 24 cases per 100,000 without a clear gender effect. The disease is usually diagnosed between 40 and 70 years of age. The median survival is 3 to 5 years. Despite its prevalence, there are no therapies available to halt or reverse the progression of IPF and there are no FDA-approved courses of treatment. Thus, there is an unmet need for new therapeutic strategies to treat IPF as well as other diseases that involve pathological tissue fibrosis.

Interstitial lung disease, or ILD, includes more than 180 chronic lung disorders, which are chronic, nonmalignant and noninfectious. Interstitial lung diseases are named for the tissue between the air sacs of the lungs called the interstitium—the tissue affected by fibrosis (scarring). Interstitial lung diseases may also be called interstitial pulmonary fibrosis or pulmonary fibrosis. The symptoms and course of these diseases may vary from person to person, but the common link between the many forms of ILD is that they all begin with an inflammation, e.g.: bronchiolitis—inflammation that involves the bronchioles (small airways); alveolitis—inflammation that involves the alveoli (air sacs); vasculitis—inflammation that involves the small blood vessels (capillaries)

More than 80% of interstitial lung diseases are diagnosed as pneumoconiosis, drug-induced disease, or hypersensitivity pneumonitis. The other types are:

Occupational and environmental exposures: Many jobs, particularly those that involve working with asbestos, ground stone, or metal dust, can cause pulmonary fibrosis. The small particles are inhaled, damage the alveoli, and cause fibrosis. Some organic substances, such as moldy hay can also initiate pulmonary fibrosis; this is known as farmer's lung.

Asbestosis is usually caused when small needle-like particles of asbestos are inhaled into the lungs. This can cause lung scarring (pulmonary fibrosis) and in addition can lead to lung cancer. The key to asbestosis is prevention. In manufacturing asbestos products, both employer and employee must be aware of government standards and should take all precautions against inhaling the particles. The paramount danger in working with asbestos comes when old, friable (crumbly) asbestos-containing products are replaced or destroyed. In those circumstances, particles can be released into the air and breathed into the lungs. Today however, the asbestos fibres usually are "locked in" by binders such as cement, rubber or plastics, thus preventing the particles from floating free in the air. Cigarette smoking has an interactive relationship with asbestos—the asbestos worker who smokes has a much higher chance of developing lung cancer than does the non-smoker.

Silicosis is another disease producing pulmonary fibrosis in which the cause is known. It is a disease that results from breathing in free crystalline silica dust. All types of mining in which the ore is extracted from quartz rock can produce silicosis if precautions are not taken. This includes the mining of gold, lead, zinc, copper, iron, anthracite (hard) coal, and some bituminous (soft) coal. Workers in foundries, sandstone grinding, tunneling, sandblasting, concrete breaking, granite carving, and china manufacturing also encounter silica.

Large silica particles are stopped in the upper airways. But the tiniest specks of silica can be carried down to the alveoli where they lead to pulmonary fibrosis. Silicosis can be either mild or severe, in direct proportion to the percentage and concentration of silica in the air and the duration of exposure. Silicosis can be prevented by measures specifically designed for each industry and each job. Dust control is essential. Sometimes this is accomplished by the wetting down of mines, improved ventilation, or the wearing of masks.

Idiopathic pulmonary fibrosis: Although a number of separate diseases can initiate pulmonary fibrosis, many times the cause is unknown. When this is so, the condition is called "idiopathic (of unknown origin) pulmonary fibrosis". In idiopathic pulmonary fibrosis, careful examination of the patient's environmental and occupational history gives no clues to the cause. Some physicians and scientists believe that the disease is an infectious or allergic condition, however bacteria and other microorganisms are not routinely found in the lungs of such patients. On the other hand, the condition does sometimes appear to follow a viral-like illness. Thus, although the cause of pulmonary fibrosis is known in many cases, the idiopathic variety still remains a mystery.

Sarcoidosis is disease characterized by the formation of granulomas (areas of inflammatory cells), which can attack any area of the body but most frequently affects the lungs.

Certain medicines may have the undesirable side effect of causing pulmonary fibrosis; for example, Nitrofurantoin (sometimes used for urinary tract infections); Amiodarone (sometimes prescribed for an irregular heart rate); Bleomycin, cyclophosphamide, and methotrexate (sometimes prescribed to fight cancer).

Radiation, such as given as treatment for breast cancer, may also cause pulmonary fibrosis. Other diseases characterized, at least in part, by pulmonary fibrosis include tuberculosis, rheumatoid arthritis, systemic lupus erythematosis, systemic sclerosis, grain handler's lung, mushroom worker's lung, bagassosis, detergent worker's lung, maple bark stripper's lung, malt worker's lung, paprika splitter's lung, bird breeder's lung and Hermansky Pudlak syndrome. Pulmonary fibrosis can also be genetically inherited.

Clinical Features:

Breathlessness is the hallmark of pulmonary fibrosis. Many lung diseases show breathlessness as the main symptom—a fact that can complicate and confuse diagnosis. Usually the breathlessness idiopathic pulmonary fibrosis first appears during exercise. The condition may progress to the point where any exertion is impossible. A dry cough is a common symptom. The fingertips may enlarge at the ends and take on a bulbous appearance. This is often referred to as "clubbing".

Additional symptoms may include: shortness of breath, especially with exertion, fatigue and weakness, loss of appetite, loss of weight, dry cough that does not produce phlegm, discomfort in chest, labored breathing and hemorrhage in lungs.

Diagnosis

In addition to a complete medical history and physical examination, the following tests maybe required to refine and/or confirm the diagnosis of pulmonary fibrosis: pulmonary function tests—to determine characteristics and capabilities of the lungs; spirometry—to measure the amount of air that can be forced out; peak flow meter—to evaluate changes in breathing and response to medications; blood tests—to analyze the amount of carbon dioxide and oxygen in the blood; X-ray; computerized axial tomography (CAT) scan; bronchoscopy—to examine the lung using a long, narrow tube called a bronchoscope; bronchoalveolar lavage—to remove cells from lower respiratory tract to help identify inflammation and exclude certain causes; and lung biopsy—to remove tissue from the lung for examination in the pathology laboratory.

Treatment

If one of the known causes of pulmonary fibrosis exists, then treatment of that underlying disease or removal of the patient from the environment causing the disease can be effective. This may include treatment with: oral medications, including corticosteroids; influenza vaccine; pneumococcal pneumonia vaccine, oxygen therapy from portable tanks and/or lung transplantation.

Many times treatment is limited only to treating the inflammatory response that occurs in the lungs. This is done in the hope that stopping the inflammation will prevent the laying down of scar tissue or fibrosis in the lungs and thus stop the progression of the disease.

Corticosteroids are the drugs which are usually administered in an attempt to stop the inflammation. The advantage of this treatment has not been proven in every case, although it does appear that if the drugs are given early on in the course of the disease, there is a better chance of improvement. Corticosteroid medications can have various side effects and so patients taking these medications must be frequently reassessed by their physicians in order to judge the safety and benefit of this therapy.

Other drugs have been tried but convincing evidence of their efficacy is lacking. Although drug therapy of pulmonary fibrosis may not always be successful, there is much that can be done in the way of supportive therapy that will ease the breathlessness that accompanies this condition. Rehabilitation and education programs can help considerably in teaching patients how to breathe more efficiently and to perform their activities of daily living with less breathlessness. Sometimes supplemental oxygen therapy is required in order to treat breathlessness. Early treatment of chest infections is required. Smoking must be discontinued, as the effects of tobacco will aggravate the shortness of breath.

Outcome

Many times the disease is mild with few symptoms and does not progress significantly with the years. In other cases, when pulmonary fibrosis is due to some other underlying disease such as rheumatoid arthritis, progression of the lung condition may reflect progression of the underlying diseases. Very rarely pulmonary fibrosis has a sudden onset and rapidly progresses to death from respiratory failure over a period of weeks. However, the usual course of pulmonary fibrosis, particularly idiopathic pulmonary fibrosis, is one of slowly progressive scarring of the lungs. The duration and speed of this process is variable. Some patients respond to therapy. In other cases, patients do not respond to therapy and have a slow deterioration over months to years, eventually ending in death when lungs can no longer function adequately.

LPA and Pulmonary Fibrosis

Although the exact etiology is not known, IPF is believed to result from an aberrant wound healing response following pulmonary injury. Scotton, C. J. and Chambers, R. C. (2007) Chest, 132:1311-21. In particular, increased proliferation and migration of lung fibroblasts as well as the formation of scar tissue-producing myofibroblasts are key events in the pathogenesis of IPF. Myofibroblasts are smooth muscle-like fibroblasts that express alpha-smooth muscle actin (α-SMA) and contain a contractile apparatus composed of actin filaments and associated proteins that are organized into prominent stress fibers. In addition to their normal role in tissue homeostasis and repair, myofibroblasts are pathological mediators in numerous fibrotic disorders. Hinz, B. (2007) J Invest Dermatol. 127:526-37. Increased number and density of myofibroblasts has been demonstrated in the fibrotic foci of animal models of lung fibrosis. Myofibroblasts are formed following tissue injury whereby increased levels of growth factors, cytokines and mechanical stimuli promote transformation of resident tissue fibroblasts into contractile, scar tissue-producing myofibroblasts. In the lung and other tissues, persistent, elevated levels of biochemical mediators including TGFβ, CTGF, PDGF and various inflammatory cytokines, promotes myofibroblast formation and exaggerated scar tissue production which leads to tissue fibrosis (Scotton, 2007). Thus, current clinical strategies for treating IPF and other fibrotic disorders have targeted biochemical factors that promote myofibroblast formation and subsequent fibrous tissue production.

Recently, the bioactive lysophospholipid lysophosphatidic acid (LPA) has been recognized for its role in tissue repair and wound healing (Watterson, 2007). LPA is a bioactive lysophospholipid (<500 Dalton) with a single hydrocarbon backbone and a polar head group containing a phosphate group. LPA elicits numerous cellular effects through the interaction with specific G protein-coupled receptors (GPCR), designated $EGD2/LPA_1$, $EDG4/LPA_2$, $EDG7/LPA_3$, and $LPA_4$. Anliker B. and J. Chun, (2004) Seminars in Cell & Developmental Biology, 15: 457-465. As a biological mediator, LPA has been recognized for its role in tissue repair and wound healing (Watterson, 2007). In particular, LPA is linked to pulmonary and renal inflammation and fibrosis. LPA is detectable in human bronchioalveolar lavage (BAL) fluids at baseline and its expression increases during allergic inflammation (Georas, 2007). Furthermore, LPA promotes inflammation in airway epithelial cells (Barekzi, 2006). Recently, pulmonary and renal fibrosis have been linked to increased LPA release and signaling though the LPA type 1 receptor ($LPA_1$). LPA levels were elevated in bronchialveolar lavage (BAL) samples from IPF patients and bleomycin-induced lung fibrosis in mice was dependent on activation of $LPA_1$ (Tager, 2008). Following unilateral ureteral obstruction in mice, tubulointerstitial fibrosis was reduced in $LPA_1$ knockout mice and pro-fibrotic cytokine expression was attenuated in wild-type mice treated with an $LPA_1$ antagonist (Pradere, 2007). Combined, these studies demonstrate a role for LPA in tissue repair and fibrosis, and identify bioactive lipids as a previously unrecognized class of targets in the treatment of IPF and other fibrotic disorders.

c. Hepatic (Liver) Fibrosis

The liver possesses a remarkable regenerative capacity, therefore the process of repair by regeneration proceeds to complete restitutio ad integrum (full restoration). If however the damage has affected the reticular framework, the repair will occur by scar formation (fibrosis) which may lead to rearrangement of the blood circulation and to cirrhosis.

The reaction to injury proceeds as is follows: Damage (necrosis), accompanied by cellular changes and tissue changes; inflammatory reaction; and repair (either by regeneration (restitutio ad integrum) or by scarring (fibrosis).

Chronic liver diseases lead to fibrosis which leads to disturbance of the architecture, portal hypertension and may produce such an irreversible rearrangement of the circulation as to cause cirrhosis. There is a fine line between fibrosis and cirrhosis. Fibrosis is not only the result of necrosis, collapse and scar formation but also the result of disturbances in the synthesis and degradation of matrix by injured mesenchymal cells that synthesize the various components of the matrix which in the liver are the following categories: collagens, glycoproteins and proteoglycans.

Evaluation of Liver Fibrosis

Evaluation of Liver Fibrosis can be histological, e.g., with Masson trichrome stain, silver reticulin stain, specific antibodies for collagen types, desmin and vimentin for lipocytes, or vimentin for myofibroblasts, or may be biochemical, e.g, by: determination of various enzymes in matrix or of serum laminin in benign fibrosis.

Classifications of Liver Fibrosis

There are 2 main types, congenital and acquired liver fibrosis. The former is a genetic disorder, which causes polycystic liver diseases. The latter has many different categories and is mainly caused by liver cell injuries. Pathologically, fibrosis can be classified as:

Portal area fibrosis: There is fibroblasts proliferation and fibers expansion from the portal areas to the lobule. Finally, these fibers connected to form bridging septa. This kind of fibrosis is mainly seen in viral hepatitis and malnutritional liver fibrosis.

Intra-lobular fibrosis: There is almost no fibroblast found in normal lobule. When large numbers of liver cells degenerate and undergo necrosis, the reticular fiber frame collapses and becomes thick collagen fibers. At the same time, intra lobule fibrotic tissue proliferates and surrounds the liver cells.

Central fibrosis: Proliferated fibrotic tissue mainly surrounds the center vein and causes the thickening of the wall of the center vein.

Peri-micro-bile-duct fibrosis: Type fibrosis mainly caused by long-term bile retention and mainly happens around the bile ducts. Microscopically, there are connective tissues surrounding the newly formed bile canaliulus and bile-plugs. The base-membrane of the bile canaliulus becomes fibrotic.

Immunologically, liver fibrosis can be classified as:

Passive fibrosis: There is extensive necrosis of the liver cells and secondary liver structure collapse and scar formation, which causes connective tissue proliferation.

Active fibrosis: Lymph cells and other inflammatory cells infiltration and recurrent and consistent inflammation promote the connective tissue to invade the lobule.

Causally, liver fibrosis can be classified as:

Viral hepatitis fibrosis: Usually caused by chronic hepatitis B, C, and D. Worldwide, there are three hundred fifty million of hepatitis B virus carriers, and one hundred seventy million of hepatitis C infected people. About 15% of HBV and 85% of HCV infected persons will develop chronic hepatitis and lead to fibrosis. In which, the liver shows peri-portal area inflammation and piecemeal necrosis and fibrosis. With such large population being affected, this is the most important category of the liver fibrosis.

Parasitic infection fibrosis: This kind of liver fibrosis is mainly happening in developing countries and is caused by schistosomiasis. There are two hundred and twenty million people in Asia, Africa, South and Center America suffering from this infection. The recurrent infection and the eggs of schistosome accumulated in the liver can cause liver fibrosis and cirrhosis.

Alcoholic fibrosis: It is mainly caused by the oxidized metabolite of alcohol, acetaldehyde. In western countries, the incidence of this disorder is positively related to the amount of alcohol consumption. The total cases of alcoholic fibrosis in the USA is about three times higher than the number of hepatitis C. Alcoholic fibrosis causes two morphological changes in the liver: fatty liver and cellular organelles deterioration. The fibrosis first appears around the center veins and at the same time, the liver parenchymal inflammation. Gradually the fibrosis expends to the whole liver.

Biliary fibrosis: There is primary and secondary biliary fibrosis. Primary biliary hepatic fibrosis (PBHF) is an autoimmune disorder in which chronic intra-liver bile retention caused the liver fibrosis. It is more often affect female around the age 40 to 60. In serum tests, elevated gamma globulin and positive for the anti-mitochondria antibody. Pathological studies found that the fibrosis mainly around the micro-bile ducts and peri-portal area fibrosis and inflammation. Secondary biliary fibrosis happens following the obstruction of the bile ducts, which causes peri-portal inflammation and progressive fibrosis.

Metabolic fibrosis: This category is not common and has fewer cases. Wilson's disease or liver lenticular degeneration and hemochromatosis are the main disorders that cause metabolic fibrosis. The former is a genetic disorder and causes cooper metabolism disorder and deposits in the liver. The latter is an iron metabolic disorder and causes hemoglobin deposits in the liver. Both of these metabolic disorders can cause liver fibrosis and cirrhosis.

Intoxication fibrosis: When long-term contact with liver-toxic substances, such as carbon-tetrachloride, organophosphorus, dimethyl nitrosamine, thioacetamide, or taking liver toxic medications, such as isoniazid, thio-oxidizing pyrimidine, wintermin, tetracycline, acetaminophen etc. can all cause various degrees of liver cell injuries, necrosis, bile retention, or allergic inflammation and cause liver fibrosis.

Malnutritional fibrosis: This type is mainly caused by insufficient or imbalanced nutritional intake. A long-term low protein or high fat diet can cause fatty liver and lead to fibrosis.

Cardiogenic fibrosis: Chronic congestive heart failure can cause long lasting liver vein stagnancy causing ischemic degeneration of the liver cells. In this type of liver fibrosis, the connective tissue hypertrophy starts at the center of the liver lobule and gradually expands to rest of the lobule.

Diagnosis and Staging of Liver Fibrosis

The gold standard for assessing the health of the liver is the liver biopsy. However since the procedure requires that a needle be inserted through the skin there is a potential for complications even though the incidence of complications is extremely low. The complications of a liver biopsy can include internal bleeding, and puncturing another organ such as the lungs, stomach, intestines, or any other organs that are close to the liver. In regards to accuracy of the biopsy the sample liver tissue size is important for correctly staging and grading a liver biopsy. Another problem is that the tissue taken from one part of the liver may not be 100% representative of the entire liver. Once the liver tissue sample is collected it is graded and staged by a specialist (pathologist), which could lead to possible human error in interpreting the results. In addition there is no standardized interpretation protocol so it is difficult to compare the results of different biopsies read by different pathologists. Price is also an issue since a typical liver biopsy can cost between \$1,500 and \$2,000.

Given these potential problems it is not surprising that there is a lot of research that is being conducted on the development of non-invasive tests. The tests that have been developed so far have had mixed results in accuracy when compared to the results of a liver biopsy. There have been few prospective clinical trials that have compared the results from various non-invasive markers to the results from a liver biopsy.

In order to objectively evaluate the stage of fibrosis, liver biopsy, especially a series of biopsies, is the main method used today. From the biopsy, it is possible to diagnose the liver inflammation grade and also the stage of the fibrosis. The most commonly used scoring system is Kanel scoring system, which stages the fibrosis from 0 to 5. (At the same time the biopsy diagnosis also give a ranking of inflammation grade, which is from 0 to 4) Stage 0: normal; Stage 1: portal expansion with fibrosis (<$\frac{1}{3}$ tracts with wisps of bridging.); Stage 2: bridging fibrosis; Stage 3: marked bridging fibrosis or early cirrhosis (with thin septa fibrosis); Stage 4: definite cirrhosis with <50% of biopsy fibrosis; Stage 5: definite cirrhosis with >50% of biopsy fibrosis.

Blood tests to diagnose liver fibrosis: Because biopsy is an invasive procedure, many patients are wary of the procedure. Blood tests are being studied as a method to evaluate the fibrosis progression. The most commonly used serum chemical analysis method is by measuring the amount of HA (hyaluronic acid), LN (Laminin), CIV (collagen IV), PCIII (procollagen type III) in the serum. They can be used as a reference index of fibrosis activities. From the blood tests, the ratio of AST/ALT is found and when it is greater than 1, it often shows that the degree of fibrosis is relatively advanced. Combined with whether is there an enlarged spleen and depletion of platelets count and albumin level, we can also estimate the stage of the fibrosis. In advanced fibrosis, the spleen is usually enlarged with platelets counts lower than 100 and albumin lower than 3.5. With blood test results, the evaluation of the severity of fibrosis is only useful to access the stage 0, 1 and 3, 4, and 5. It is not able to distinguish the stages between 2 and 3.

Medical imagery diagnosis B-ultrasonic, CT, and MRI can also be used to evaluate the liver fibrosis. The B-ultrasonic image is often used to check the size of the spleen, measure the diameter of the main stem of the portal vein, the diameters of right and left portal vein branches, the diameter of vein at the portal of the spleen, and the blood flow speed of the portal vein. GI endoscopies can be used to see whether varices exists in the stomach and esophagus. These can be used as a reference for the hepatologist to evaluate the stage of fibrosis.

In general, the term fibrosis refers to the abnormal formation of fibrous (scar) tissue. For hepatitis patients, fibrosis means that the liver has been under assault by the hepatitis for some time. Early stages of fibrosis are identified by discrete, localized areas of scarring in one portal (zone) of the liver. Later stages of fibrosis are identified by "bridging" fibrosis, which is scar tissue that crosses across zones of the liver. The rate at which people progress from inflammation to fibrosis, and eventually to cirrhosis seems to vary tremendously, but in most people the progression is very slow. There is a growing body of evidence that people who respond to interferon therapy for HCV infection may experience a decrease in the amount of tissue scarring. This speaks to the liver's ability to regenerate itself. If fibrosis advances far enough, it is described as cirrhosis. Liver biopsy is conducted to assess the degree of inflammation (grade) and degree of scarring (stage). Diagnosis: One of the major clinical problems facing the hepatology and gastroenterology community is how best to evaluate and manage the increasing numbers of patients identified with hepatitis C virus (HCV). In the last decade, advances in serologic and virologic testing for HCV and improvements in therapy have led more patients to be identified and to seek treatment. However, little progress has been made in improving either our ability to determine the degree of hepatic injury, particularly fibrosis, or to predict the risk of disease progression for the individual patient.

The clinician relies on the biopsy results for both prognostic and therapeutic decision making, which can have a major impact on the patient's life. A single-pass liver biopsy is able to correctly diagnose the stage of fibrosis or presence of cirrhosis in 80% of patients. Factors that improve the diagnostic accuracy of liver biopsy include the presence of a uniform disease throughout the liver such as HCV, multiple passes, type of needle used, and an unfragmented biopsy core of 2 cm or greater in length. Even with experienced physicians performing the liver biopsy and expert pathologists interpreting the biopsy, this gold standard has up to a 20% error rate in staging disease.

d. Renal (Kidney) Fibrosis

LPA is linked to renal inflammation and fibrosis. Recently, renal fibrosis has been linked to increased LPA release and signaling though the LPA type 1 receptor ($LPA_1$). Following unilateral ureteral obstruction in mice, tubulointerstitial fibrosis was reduced in $LPA_1$ knock-out mice and pro-fibrotic cytokine expression was attenuated in wild-type mice treated with an $LPA_1$ antagonist (Pradere, 2007).

e. Other Fibroses

Uterine fibroses are non-malignant tumors known as uterine leiomyomata (commonly called fibroids). They can be isolated or grow in clusters, with sizes varying from the size of an apple seed to the size of a grapefruit or larger. Diagnosis of uterine fibroids is generally achieved by ultrasound, X-rays, CAT scan, laparoscopy and/or hysteroscopy. Treatment of uterine fibroids can be either medical (drug treatment, e.g., non-steroid anti-inflammatory drugs or gonadotropin release hormone agonists) or surgical (e.g., myomectomy, hysterectomy, endometrial ablation or myolysis, with recent development of less invasive methods such as uterine fibroid embolization and thermal ultrasound ablation.

Fibrosis of the skin can be described as a thickening or hardening of the skin, and occurs in scleroderma and other fibrotic skin diseases. When severe, fibrosis can limit movement and normal function. A keloid is an excessive scar that forms in response to trauma, sometimes minor trauma such as ear piercing or acne. Unlike normal scar formation, keloids have disproportionate proliferation of fibroblasts resulting in masses of collagenous tissue. The scar therefore protrudes above the surface of the surrounding skin and infiltrates skin which was not originally traumatized. Roles for LPA in skin fibroblast activity have been demonstrated. For example, it has been shown that LPA stimulates the migration of murine skin fibroblasts (Hama et al., J Biol. Chem. 2004 Apr. 23; 279(17):17634-9). Thus it is believed that anti-LPA agents such as antibodies are useful for treatment of aberrant skin fibrosis such as keloids or skin fibrosis.

Cardiac fibrosis: LPA has also been shown to have direct fibrogenic effects in cardiac fibroblasts by stimulating collagen gene expression and fibroblast proliferation. Chen, et al. (2006) FEBS Lett. 580:4737-45. Thus anti-LPA agents such as antibodies are expected to have anti-fibrotic effects in cardiac cells as well, and thus to be effective in treatment of cardiac fibrosis.

Agents that reduce the effective concentration of LPA, such as Lpath's anti-LPA mAb, are believed to be useful in methods for treating diseases and conditions characterized by aberrant fibrosis.

b. Cardiovascular and Cerebrovascular Disorders

Because LPA is involved in fibrogenesis and wound healing of liver tissue (Davaille et al., J. Biol. Chem. 275:34268-34633, 2000; Ikeda et al., Am J. Physiol. Gastrointest. Liver Physiol 279:G304-G310, 2000), healing of wounded vasculatures (Lee et al., Am. J. Physiol. Cell Physiol. 278:C612-C618, 2000), and other disease states, or events associated with such diseases, such as cancer, angiogenesis and inflammation (Pyne et al., Biochem. J. 349:385-402, 2000), the compositions and methods of the disclosure may be applied to treat not only these diseases but cardiac diseases as well, particularly those associated with tissue remodeling. LPA have some direct fibrogenic effects by stimulating collagen gene expression and proliferation of cardiac fibroblasts. Chen, et al. (2006) FEBS Lett. 580:4737-45.

c. Obesity and Diabetes

Autotaxin, a phospholipase D responsible for LPA synthesis, has been found to be secreted by adipocytes and its expression is up-regulated in adipocytes from obese-diabetic db/db mice as well as in massively obese women subjects and human patients with type 2 diabetes, independently of obesity (Ferry et al. (2003) JBC 278:18162-18169; Boucher et al. (2005) Diabetologia 48:569-577, cited in Pradere et al. (2007) BBA 1771:93-102. LPA itself has been shown to influence proliferation and differentiation of preadipocytes. Pradere et al., 2007. Together this suggests a role for anti-LPA agents in treatment of obesity and diabetes.

d. Pain

A significant role of LPA in the development of neuropathic pain was established using various pharmacological and genetic approaches. LPA is responsible for long-lasting mechanical allodynia and thermal hyperalgesia as well as demyelination and upregulation of pain-related proteins through the LPA1 receptor. In addition, intrathecal injections of LPA induce behavioral, morphological and biochemical changes such as prolonged sensitivity to pain stimuli accompanied by demyelination of dorsal roots, similar to those observed after nerve ligation. Fujita, R., Kiguchi, N. & Ueda, H. (2007) Neurochem Int 50, 351-5. Wild-type animals with nerve injury develop behavioral allodynia and hyperalgesia paralleled by demyelination in the dorsal root and increased expression of both the protein kinase C isoform within the spinal cord dorsal horn and the 21 calcium channel subunit in dorsal root ganglia. It has been demonstrated that mice lacking the LPA1 receptor gene (lpa1−/− mice) lose nerve injury-induced neuropathic pain behaviors and phenomena. Inoue, M. et al. (2004) Nat Med 10, 712-8. Heterozygous mutant mice for the autotaxin gene (atx+/−) showed approximately 50% recovery of nerve injury-induced neuropathic pain. The hyperalgesia was completely abolished in both lpa1−/− and atx+/− mice. Furthermore, inhibitors of Rho and Rho kinase signaling pathways also prevented neuropathic pain. Mueller, B. K., Mack, H. & Teusch, N. (2005) Nat Rev Drug Discov 4, 387-98. Therefore, targeting LPA biosynthesis and/or LPA1 receptor may represent a novel approach to mitigating nerve-injury-induced neuropathic pain At the cellular level, LPA is a potent inducer of morphological changes in neuronal and glial cells66, 151-155. Kingsbury, M. A., et al. (2003) Nat Neurosci 6, 1292-9; Jalink, K. et al., (1993) Cell Growth Differ 4, 247-55; Tigyi, G. & Miledi, R. (1992) J Biol Chem 267, 21360-7 (1992); Fukushima, N. et al. (2000) Dev Biol 228, 6-18; Yuan, X. B. et al. (2003) Nat Cell Biol 5, 38-45; Fukushima, N., et al. (2007) Neurochem Int 50, 302-7.

In primary astrocytes, as well as in glioma-derived cell lines, LPA causes reversal of process outgrowth ('stellation'), a process directed by active RhoA and accompanied by reassembly and activation of focal adhesion proteins. Ramakers, G. J. & Moolenaar, W. H. (1998). Exp Cell Res 245, 252-62. A role for LPA in myelination is also suggested by the finding that LPA promotes cell-cell adhesion and survival in Schwann cells. Weiner, J. A., et al. (2001) J Neurosci 21, 7069-78; Ramer, L. M. et al (2004) J Neurosci 24, 10796-805.

3. Antibody Generation and Characterization

The examples hereinbelow describe the production of anti-LPA agents, particularly anti-LPA antibodies, with desirable properties from a therapeutic perspective including: (a) binding affinity for LPA and/or its variants, including 18:2, 18:1, 18:0, 16:0, 14:0, 12:0 and 20:4 LPA. Antibody affinities may be determined as described in the examples herein below. Preferably antibodies bind LPA with a high affinity, e.g., a $K_d$ value of no more than about $1 \times \times 10^{-7}$ M; possibly no more than about $1 \times 10^{-8}$ M; and possibly no more than about $5 \times 10^{-9}$ M. In a physiological context, it is preferable for an antibody to bind LPA with an affinity that is higher than the LPA's affinity for an LPA receptor. It will be understood that this need not necessarily be the case in a nonphysiological context such as a diagnostic assay.

Aside from antibodies with strong binding affinity for LPA, it is also desirable to select chimeric, humanized or variant antibodies which have other beneficial properties from a therapeutic perspective. For example, the antibody may be one that reduces scar formation or alters tumor progression. One assay for determining the activity of the anti-LPA antibodies of the invention is ELISA. Preferably the humanized or variant antibody fails to elicit an immunogenic response upon administration of a therapeutically effective amount of the antibody to a human patient. If an immunogenic response is elicited, preferably the response will be such that the antibody still provides a therapeutic benefit to the patient treated therewith.

According to one embodiment of the invention, humanized anti-LPA antibodies bind the epitope as herein defined. To screen for antibodies that bind to the epitope on an LPA bound by an antibody of interest (e.g., those that block binding of the antibody to LPA), a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al., J. Biol. Chem. 270:1388-1394 (1995), can be performed to determine whether the antibody binds an epitope of interest.

The antibodies of the invention have a heavy chain variable domain comprising an amino acid sequence represented by the formula: FR1-CDRH1-FR2-CDRH2-FR3-CDRH3-FR4, wherein "FR1-4" represents the four framework regions and "CDRH1-3" represents the three hypervariable regions of an anti-LPA antibody variable heavy domain. FR1-4 may be derived from a consensus sequence (for example the most common amino acids of a class, subclass or subgroup of heavy or light chains of human immunoglobulins) or may be derived from an individual human antibody framework region or from a combination of different framework region sequences. Many human antibody framework region sequences are compiled in Kabat et al., supra, for example. In one embodiment, the variable heavy FR is provided by a consensus sequence of a human immunoglobulin subgroup as compiled by Kabat et al., supra.

The human variable heavy FR sequence may have substitutions therein, e.g. wherein the human FR residue is replaced by a corresponding nonhuman residue (by "corresponding nonhuman residue" is meant the nonhuman residue with the same Kabat positional numbering as the human residue of interest when the human and nonhuman sequences are aligned), but replacement with the nonhuman residue is not necessary. For example, a replacement FR residue other than the corresponding nonhuman residue may be selected by phage display.

The antibodies of the preferred embodiment herein have a light chain variable domain comprising an amino acid sequence represented by the formula: FR1-CDRL1-FR2-CDRL2-FR3-CDRL3-FR4, wherein "FR1-4" represents the four framework regions and "CDRL1-3" represents the three hypervariable regions of an anti-LPA antibody variable light domain. FR1-4 may be derived from a consensus sequence (for example the most common amino acids of a class, subclass or subgroup of heavy or light chains of human immunoglobulins) or may be derived from an individual human antibody framework region or from a combination of different framework region sequences. In one preferred embodiment, the variable light FR is provided by a consensus sequence of a human immunoglobulin subgroup as compiled by Kabat et al., supra.

The human variable light FR sequence may have substitutions therein, e.g. wherein the human FR residue is replaced by a corresponding mouse residue, but replacement with the nonhuman residue is not necessary. For example, a replacement residue other than the corresponding nonhuman residue may be selected by phage display. Methods for generating humanized anti-LPA antibodies of interest herein are elaborated in more detail below.

a. Antibody Preparation

Methods for generating anti-LPA antibodies and variants of anti-LPA antibodies are described in the Examples below. Humanized anti-LPA antibodies may be prepared, based on a nonhuman anti-LPA antibody. Fully human antibodies may also be prepared, e.g., in a genetically engineered (i.e., transgenic) mouse (e.g. from Medarex) that, when presented with an immunogen, can produce a human antibody that does not necessarily require CDR grafting. These antibodies are fully human (100% human protein sequences) from animals such as mice in which the non-human antibody genes are suppressed and replaced with human antibody gene expression. The applicants believe that antibodies could be generated against bioactive lipids when presented to these genetically engineered mice or other animals that might be able to produce human frameworks for the relevant CDRs.

Where a variant is to be generated, the parent antibody is prepared. Exemplary techniques for generating such nonhuman antibody and parent antibodies will be described in the following sections.

(i) Antigen Preparation.

The antigen to be used for production of antibodies may be, e.g., intact LPA or a portion of an LPA (e.g. an LPA fragment comprising the epitope). Other forms of antigens useful for generating antibodies will be apparent to those skilled in the art.

(ii) Polyclonal Antibodies.

Polyclonal antibodies are preferably raised in animals (vertebrate or invertebrates, including mammals, birds and fish, including cartilaginous fish) by multiple subcutaneous (sc) or intraperitoneal (ip) injections of the relevant antigen and an adjuvant. It may be useful to conjugate the relevant antigen to a protein or other carrier that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. Non-protein carriers (e.g., colloidal gold) are also known in the art for antibody production.

Animals are immunized against the antigen, immunogenic conjugates, or derivatives by combining, e.g., 100 ug or 5 ug of the protein or conjugate (for rabbits or mice, respectively) with three volumes of Freund's complete adjuvant and injecting the solution intradermally at multiple sites. One month later the animals are boosted with one-fifth to one-tenth of the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies.

Monoclonal antibodies may be made using the hybridoma method first described by Kohler et al., Nature, 256:495 (1975), or may be made by other methods such as recombinant DNA methods (U.S. Pat. No. 4,816,567). In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbant assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are well known in the art, and which are then transfected into host cells such as *E coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

(iv) Humanization and Amino Acid Sequence Variants.

General methods for humanization of antibodies are described in update U.S. Pat. No. 5,861,155, US19960652558 19960606, U.S. Pat. No. 6,479,284, US20000660169 20000912, U.S. Pat. No. 6,407,213, US19930146206 19931117, U.S. Pat. No. 6,639,055, US20000705686 20001102, U.S. Pat. No. 6,500,931, US19950435516 19950504, U.S. Pat. No. 5,530,101, U.S. Pat. No. 5,585,089, US19950477728 19950607, U.S. Pat. No. 5,693,761, US19950474040 19950607, U.S. Pat. No. 5,693,762, US19950487200 19950607, U.S. Pat. No. 6,180,370, US19950484537 19950607, US2003229208, US20030389155 20030313, U.S. Pat. No. 5,714,350, US19950372262 19950113, U.S. Pat. No. 6,350,861, US19970862871 19970523, U.S. Pat. No. 5,777,085, US19950458516 19950517, U.S. Pat. No. 5,834,597, US19960656586 19960531, U.S. Pat. No. 5,882,644, US19960621751 19960322, U.S. Pat. No. 5,932,448, US19910801798 19911129, U.S. Pat. No. 6,013,256, US19970934841 19970922, U.S. Pat. No. 6,129,914, US19950397411 19950301, U.S. Pat. No. 6,210,671, v, U.S. Pat. No. 6,329,511, US19990450520 19991129, US2003166871, US20020078757 20020219, U.S. Pat. No. 5,225,539, US19910782717 19911025, U.S. Pat. No. 6,548,640, US19950452462 19950526, U.S. Pat. No. 5,624,821, and US19950479752 19950607. In certain embodiments, it may be desirable to generate amino acid sequence variants of these humanized antibodies, particularly where these improve the binding affinity or other biological properties of the antibody.

Amino acid sequence variants of the anti-LPA antibody are prepared by introducing appropriate nucleotide changes into the anti-LPA antibody DNA, or by peptide synthesis. Such variants include, for example, deletions from, and/or insertions into and/or substitutions of, residues within the amino acid sequences of the anti-LPA antibodies of the examples herein. Any combination of deletion, insertion, and substitution is made to arrive at the final construct, provided that the final construct possesses the desired characteristics. The amino acid changes also may alter post-translational processes of the humanized or variant anti-LPA antibody, such as changing the number or position of glycosylation sites.

A useful method for identification of certain residues or regions of the anti-LPA antibody that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with LPA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-LPA antibody variants are screened for the desired activity. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an N-terminal methionyl residue or the antibody fused to an epitope tag. Other insertional variants include the fusion of an enzyme or a polypeptide which increases the serum half-life of the antibody to the N- or C-terminus of the antibody.

Another type of variant is an amino acid substitution variant. These variants have at least one amino acid residue removed from the antibody molecule and a different residue inserted in its place. The sites of greatest interest for substitutional mutagenesis include the hypervariable regions, but FR alterations are also contemplated. Conservative substitutions are preferred, but more substantial changes may be introduced and the products may be screened. Examples of substitutions are listed below:

Exemplary Amino Acid Residue Substitutions
Ala (A) val; leu; ile val
Arg (R) lys; gln; asn lys
Asn (N) gln; his; asp, lys; gln arg
Asp (D) glu; asn glu
Cys (C) ser; ala ser
Gln (Q) asn; glu asn
Glu (E) asp; gln asp
Gly (G) ala ala
His (H) asn; gln; lys; arg arg
Ile (I) leu; val; met; ala; leu phe; norleucine
Leu (L) norleucine; ile; val; ile met; ala; phe
Lys (K) arg; gln; asn arg
Met (M) leu; phe; ile leu
Phe (F) leu; val; ile; ala; tyr tyr
Pro (P) ala ala
Ser (S) thr thr
Thr (T) ser ser
Trp (W) tyr; phe tyr
Tyr (Y) trp; phe; thr; ser phe
Val (V) ile; leu; met; phe; leu ala; norleucine Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked and/or or O-linked. N-linked refers to the attachment of the carbohydrate moiety to the side chain of an asparagine residue. The tripeptide sequences asparagine-X-serine and asparagine-X-threonine, where X is any amino acid except proline, are the most common recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-sphingolipid antibody are prepared by a variety of methods known in the art. These methods include, but are not limited to, isolation from a natural source (in the case of naturally occurring amino acid sequence variants) or preparation by oligonucleotide-mediated (or site-directed)

mutagenesis, PCR mutagenesis, and cassette mutagenesis of an earlier prepared variant or a non-variant version of the anti-sphingolipid antibody.

(v) Human Antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807. Human antibodies can also be derived from phage-display libraries (Hoogenboom et al., J. Mol. Biol., 227:381 (1991); Marks et al., J. Mol. Biol., 222:581-597 (1991); and U.S. Pat. Nos. 5,565,332 and 5,573,905). Human antibodies may also be generated by in vitro activated B cells (see U.S. Pat. Nos. 5,567,610 and 5,229,275).

(vi) Antibody Fragments.

In certain embodiments, the anti-LPA agent is an antibody fragment which retains at least one desired activity, including antigen binding. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science 229:81 (1985)). However, these fragments can now be produced directly by recombinant host cells. For example, Fab'-SH fragments can be directly recovered from $E.\ coli$ and chemically coupled to form $F(ab')_2$ fragments (Carter et al., Bio/Technology 10:163-167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture. Other techniques for the production of antibody fragments will be apparent to the skilled practitioner.

(vii) Multispecific Antibodies and Other Agents.

In some embodiments, the anti-LPA agent will comprise a first binding moiety and a second binding moiety, wherein the first binding moiety is specifically reactive with a first molecule that is an LPA or LPA metabolite and the second binding moiety is specifically reactive with a second molecule that is a molecular species different from the first molecule. Such agents may comprise a plurality of first binding moieties, a plurality of second binding moieties, or a plurality of first binding moieties and a plurality of second binding moieties. Preferably, the ratio of first binding moieties to second binding moieties is about 1:1, although it may range from about 1000:1 to about 1:1000, wherein the ratio is preferably measured in terms of valency.

In those embodiments wherein the first moiety is an antibody, the binding moiety may also be an antibody. In preferred embodiments, the first and second moieties are linked via a linker moiety, which may have two to many 100's or even thousand of valencies for attachment of first and second binding moieties by one or different chemistries. Examples of bispecific antibodies include those which are reactive against two different epitopes; in some embodiment one epitope is an LPA epitope and the second epitope is another bioactive lipid, e.g., S1P. In other embodiments the bispecific antibody is reactive against an epitope on LPA and against an epitope found on the cell surface. This serves to target the LPA-specific antibody moiety to the cell.

The compositions of the invention may also comprise a first agent and a second agent, wherein the first agent comprises a first binding moiety specifically reactive with a first molecule selected from the group consisting of an LPA and an LPA metabolite and the second agent comprises a second binding moiety specifically reactive with a second molecule that is a molecular species different than the first molecule. The first and/or second agent may be an antibody. The ratio of first agent to second agent may range from about 1,000:1 to 1:1,000, although the preferred ratio is about 1:1. In preferred embodiments, the agent that interferes with LPA activity is an antibody specifically reactive with LPA. In some embodiments, it may be desirable to generate multispecific (e.g. bispecific) anti-LPA antibodies having binding specificities for at least two different epitopes. Exemplary bispecific antibodies may bind to two different epitopes of the LPA. Alternatively, an anti-LPA arm (of the antibody) may be combined with an arm which binds to a different molecule; for example, S1P or a cell-surface specific antigen for localization of the antibody to the cell surface. Bispecific antibodies can be prepared as full length antibodies or antibody fragments (e.g., $F(ab')_2$ bispecific antibodies).

According to another approach for making bispecific antibodies, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from $E.\ coli$ can be chemically coupled in vitro to form bispecific antibodies. Shalaby et al., J. Exp. Med. 175:217-225 (1992).

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol. 152:5368 (1994). Alternatively, the bispecific antibody may be a "linear antibody" produced as described in Zapata et al. Protein Eng. 8(10):1057-1062 (1995).

Antibodies with more than two valencies are contemplated. For example, trispecific antibodies can be prepared. Tutt et al., J. Immunol. 147:60 (1991).

The antibody (or polymer or polypeptide) of the invention comprising one or more binding sites per arm or fragment thereof will be referred to herein as "multivalent" antibody. For example a "bivalent" antibody of the invention comprises two binding sites per Fab or fragment thereof whereas a "trivalent" polypeptide of the invention comprises three binding sites per Fab or fragment thereof. In a multivalent polymer of the invention, the two or more binding sites per Fab may be binding to the same or different antigens. For example, the two or more binding sites in a multivalent polypeptide of the invention may be directed against the same antigen, for example against the same parts or epitopes of said antigen or against two or more same or different parts or epitopes of said antigen; and/or may be directed against different antigens; or a combination thereof. Thus, a bivalent polypeptide of the invention for example may comprise two identical binding sites, may comprise a first binding sites directed against a first part or epitope of an antigen and a second binding site directed against the same part or epitope of said antigen or against another part or epitope of said antigen; or may comprise a first binding sites directed against a first part or epitope of an antigen and a second binding site directed against the a different antigen. However, as will be clear from the description hereinabove, the invention is not limited thereto, in the sense that a multivalent polypeptide of the invention may comprise any number of binding sites directed against the same or different antigens. In one embodiment the multivalent polypeptide comprises at least two ligand binding elements, one of which contains one or more CDR peptide sequences shown herein. In another embodiment there multivalent polypeptide comprises three ligand binding sites, each independently selected from the CDR sequences disclosed herein.

At least one of the ligand binding elements binds LPA. In one embodiment at least one of the ligand binding elements binds another target. In one embodiment there are up to to 10,000 binding elements in a multivalent binding molecule, and the ligand binding elements may be linked to a scaffold.

The antibody (or polymer or polypeptide) of the invention that contains at least two binding sites per Fab or fragment thereof, in which at least one binding site is directed against a first antigen and a second binding site directed against a second antigen different from the first antigen, will also be referred to as "multispecific". Thus, a "bispecific" polymer comprises at least one site directed against a first antigen and at least one a second site directed against a second antigen, whereas a "trispecific" is a polymer that comprises at least one binding site directed against a first antigen, at least one further binding site directed against a second antigen, and at least one further binding site directed against a third antigen; etc. Accordingly, in their simplest form, a bispecific polypeptide of the invention is a bivalent polypeptide (per Fab) of the invention. However, as will be clear from the description hereinabove, the invention is not limited thereto, in the sense that a multispecific polypeptide of the invention may comprise any number of binding sites directed against two or more different antigens.

(viii) Other Modifications.

Other modifications of the anti-LPA antibody are contemplated. For example, the invention also pertains to immunoconjugates comprising the antibody described herein conjugated to a cytotoxic agent such as a toxin (e.g., an enzymatically active toxin of bacterial, fungal, plant or animal origin, or fragments thereof), or a radioactive isotope (for example, a radioconjugate). Conjugates are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

The anti-LPA antibodies disclosed herein may also be formulated as immunoliposomes. Liposomes containing the antibody are prepared by methods known in the art, such as described in Epstein et al., Proc. Natl. Acad. Sci. USA 82:3688 (1985); Hwang et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. For example, liposomes can be generated by the reverse phase evaporation method with a lipid composition comprising phosphatidyl choline, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide interchange reaction. Another active ingredient is optionally contained within the liposome.

Enzymes or other polypeptides can be covalently bound to the anti-LPA antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature 312:604-608 (1984)).

In certain embodiments of the invention, it may be desirable to use an antibody fragment, rather than an intact antibody, to increase penetration of target tissues and cells, for example. In this case, it may be desirable to modify the antibody fragment in order to increase its serum half life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO96/32478 published Oct. 17, 1996.

Covalent modifications of the anti-LPA antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

b. Vectors, Host Cells and Recombinant Methods

The invention also provides isolated nucleic acid encoding the anti-LPA antibody, vectors and host cells comprising the nucleic acid, and recombinant techniques for the production of the antibody.

For recombinant production of the antibody, the nucleic acid encoding it may be isolated and inserted into a replicable vector for further cloning (amplification of the DNA) or for expression. In another embodiment, the antibody may be produced by homologous recombination, e.g. as described in U.S. Pat. No. 5,204,244, specifically incorporated herein by reference. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615 issued Jul. 9, 1996 and specifically incorporated herein by reference.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-sphingolipid antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-sphingolipid antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10: 163-167 (1992) describe a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human heavy chains (Lindmark et al., J. Immunol. Meth. 62:1-13 (1983)). Protein G is recommended for all mouse isotypes and for human y3 (Guss et al., EMBO J. 5:15671575 (1986)). The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification, such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

c. Pharmaceutical Formulations, Dosing and Routes of Administration

The present invention provides anti-LPA antibodies and related compositions and methods to reduce blood and tissue levels of the bioactive lipid, LPA.

The therapeutic methods and compositions of the invention are said to be "LPA-based" in order to indicate that these therapies can change the relative, absolute or effective concentration(s) of undesirable or toxic lipids "Undesirable lipids" include toxic bioactive lipids, as well as metabolites, particularly metabolic precursors, of toxic lipids. One example of an undesirable bioactive lipid of particular interest is LPA.

One way to control the amount of undesirable LPA in a patient is by providing a composition that comprises one or more anti-LPA antibodies to bind one or more LPAs, thereby acting as therapeutic "sponges" that reduce the level of free undesirable LPA. When a compound is stated to be "free," the compound is not in any way restricted from reaching the site or sites where it exerts its undesirable effects. Typically, a free compound is present in blood and tissue, which either is or contains the site(s) of action of the free compound, or from which a compound can freely migrate to its site(s) of action. A free compound may also be available to be acted upon by any enzyme that converts the compound into an undesirable compound.

Anti-LPA antibodies may be formulated in a pharmaceutical composition that is useful for a variety of purposes, including the treatment of diseases, disorders or physical trauma. Pharmaceutical compositions comprising one or more anti-LPA antibodies of the invention may be incorporated into kits and medical devices for such treatment. Medical devices may be used to administer the pharmaceutical compositions of the invention to a patient in need thereof, and according to one embodiment of the invention, kits are provided that include such devices. Such devices and kits may be designed for routine administration, including self-administration, of the pharmaceutical compositions of the invention. Such devices and kits may also be designed for emergency use, for example, in ambulances or emergency rooms, or during surgery, or in activities where injury is possible but where full medical attention may not be immediately forthcoming (for example, hiking and camping, or combat situations).

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished for instance by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and .gamma.ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For therapeutic applications, the anti-LPA agents, e.g., antibodies, of the invention are administered to a mammal, preferably a human, in a pharmaceutically acceptable dosage form such as those discussed above, including those that may be administered to a human intravenously as a bolus or by continuous infusion over a period of time, or by intramuscular, intraperitoneal, intra-cerebrospinal, subcutaneous, intra-articular, intrasynovial, intrathecal, oral, topical, or inhalation routes.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 .mu.g/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 µg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic imaging. Detection methods using the antibody to determine LPA levels in bodily fluids or tissues may be used in order to optimize patient exposure to the therapeutic antibody.

According to another embodiment of the invention, the composition comprising an agent, e.g, a mAb, that interferes with LPA activity is administered as a monotherapy, while in other preferred embodiments, the composition comprising the agent that interferes with LPA activity is administered as part of a combination therapy. In some cases the effectiveness of the antibody in preventing or treating disease may be improved by administering the antibody serially or in combination with another agent that is effective for those purposes, such as a chemotherapeutic drug for treatment of cancer. In other cases, the anti-LPA agent may serve to enhance or sensitize cells to chemotherapeutic treatment, thus permitting efficacy at lower doses and with lower toxicity. Preferred combination therapies include, in addition to administration of the composition comprising an agent that interferes with LPA activity, delivering a second therapeutic regimen selected from the group consisting of administration of a chemotherapeutic agent, radiation therapy, surgery, and a combination of any of the foregoing.

Such other agents may be present in the composition being administered or may be administered separately. Also, the antibody is suitably administered serially or in combination with the other agent or modality, e.g., chemotherapeutic drug or radiation for treatment of cancer.

d. Research and Diagnostic Including Clinical Diagnostic Uses for the Anti-LPA Agents of the Invention The anti-LPA agents, e.g., antibodies, of the invention may be used to detect and/or purify LPA, e.g., from bodily fluid(s).

For use of anti-LPA antibodies as affinity purification agents, the antibodies are immobilized on a solid support such as beads, a Sephadex resin or filter paper, using methods well known in the art. The immobilized antibody is contacted with a sample containing the LPA to be purified, and thereafter the support is washed with a suitable solvent that will remove substantially all the material in the sample except the LPA, which is bound to the immobilized antibody. Finally, the support is washed with another suitable solvent, such as glycine buffer, for instance between pH 3 to pH 5.0, that will release the LPA from the antibody.

Anti-LPA antibodies may also be useful in diagnostic assays for LPA, e.g., detecting its presence in specific cells, tissues, or bodily fluids. Such diagnostic methods may be useful in diagnosis, e.g., of a hyperproliferative disease or disorder. Thus clinical diagnostic uses as well as research uses are comprehended by the invention. In these methods, the anti-LPA antibody is preferably attached to a solid support, e.g., bead, column, plate, gel, filter, membrane, etc.

For diagnostic applications, the antibody may be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclicoxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) .beta.-D-galactosidase (.beta.-D-Gal) with a chromogenic substrate (e.g., p-nitrophenyl-β-D-galactosidase) or fluorogenic substrate 4-methylumbelliferyl-.beta.-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-LPA antibody need not be labeled, and the presence thereof can be detected, e.g., using a labeled antibody which binds to the anti-LPA antibody.

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987). ELISA assays (competitive or direct) using the anti-LPA antibodies are useful for detecting LPA and assessing its binding and antigen specificity. An LPA ELISA kit incorporating applicant's anti-LPA antibody is commercially available from Echelon Biosciences, Salt Lake City Utah (cat no. K-2800).

Competitive binding assays rely on the ability of a labeled standard to compete with the test sample analyte for binding with a limited amount of antibody. The amount of LPA in the test sample is inversely proportional to the amount of standard that becomes bound to the antibodies. To facilitate determining the amount of standard that becomes bound, the antibodies generally are insoluble before or after the competition, so that the standard and analyte that are bound to the antibodies may conveniently be separated from the standard and analyte that remain unbound.

Sandwich assays involve the use of two antibodies, each capable of binding to a different immunogenic portion, or epitope, of the protein to be detected. In a sandwich assay, the test sample analyte is bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the blood or tissue sample may be fresh or frozen or may be embedded in paraffin and fixed with a preservative such as formalin, for example.

The antibodies may also be used for in vivo diagnostic assays. Generally, the antibody is labeled with a radionuclide (such as $^{111}$In, $^{99}$Tc, $^{14}$C, $^{131}$I, $^{125}$I, $^{3}$H, $^{32}$P, or $^{35}$S) so that the bound target molecule can be localized using immunoscintillography.

e. Diagnostic Kits Incorporating the Anti-LPA Agents of the Invention

As a matter of convenience, the antibody of the present invention can be provided in a kit, for example, a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

f. Articles of Manufacture

In another aspect of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-sphingolipid antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention will be better understood by reference to the following Examples, which are intended to merely illustrate the best mode now known for practicing the invention. The scope of the invention is not to be considered limited thereto.

EXAMPLES

The invention will be further described by reference to the following detailed examples. These Examples are in no way to be considered to limit the scope of the invention in any manner.

Example 1

Synthetic Scheme for Making a Representative Thiolated Analog of S1P

Figure 1B:
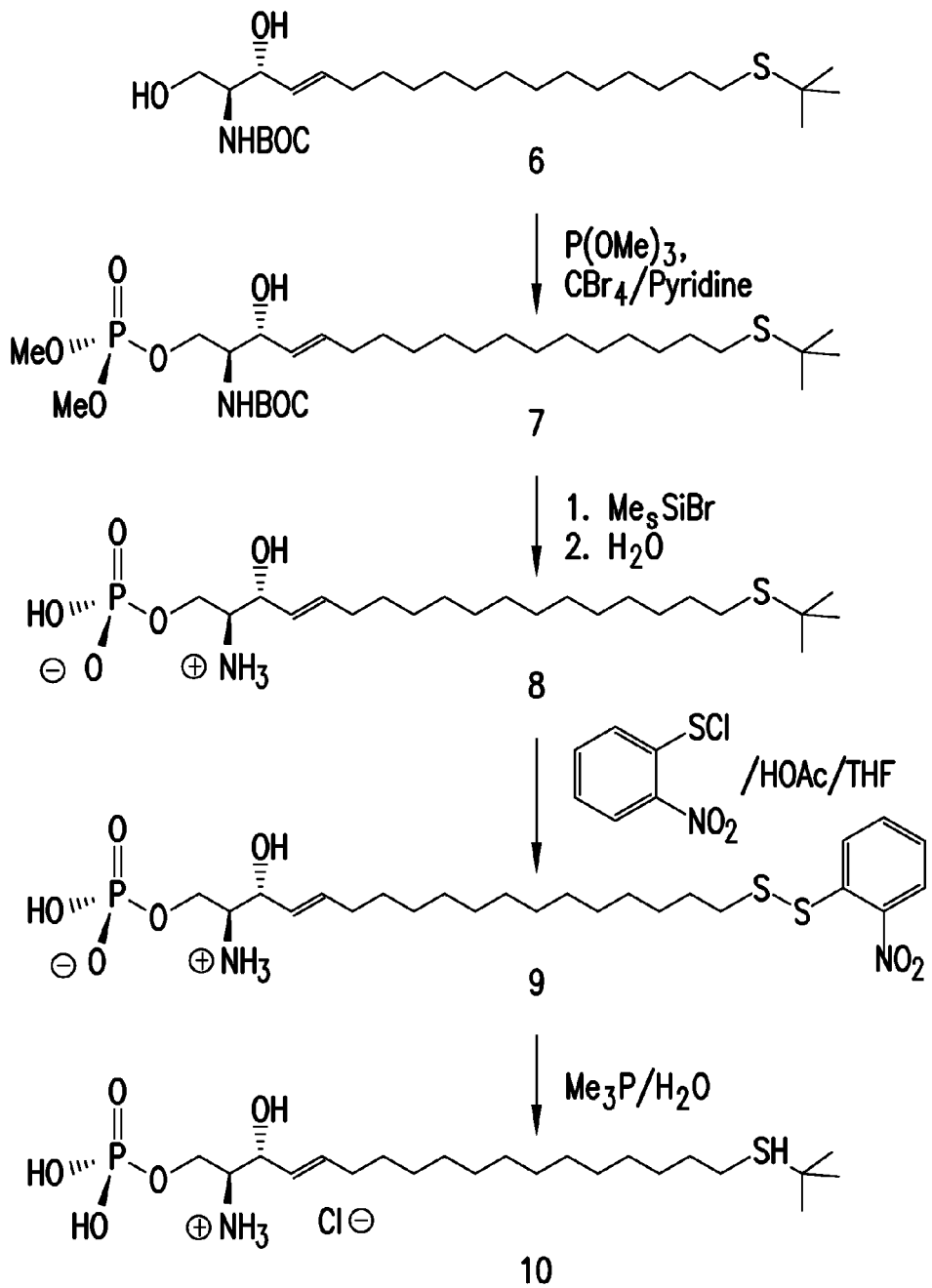
Figure 1C:
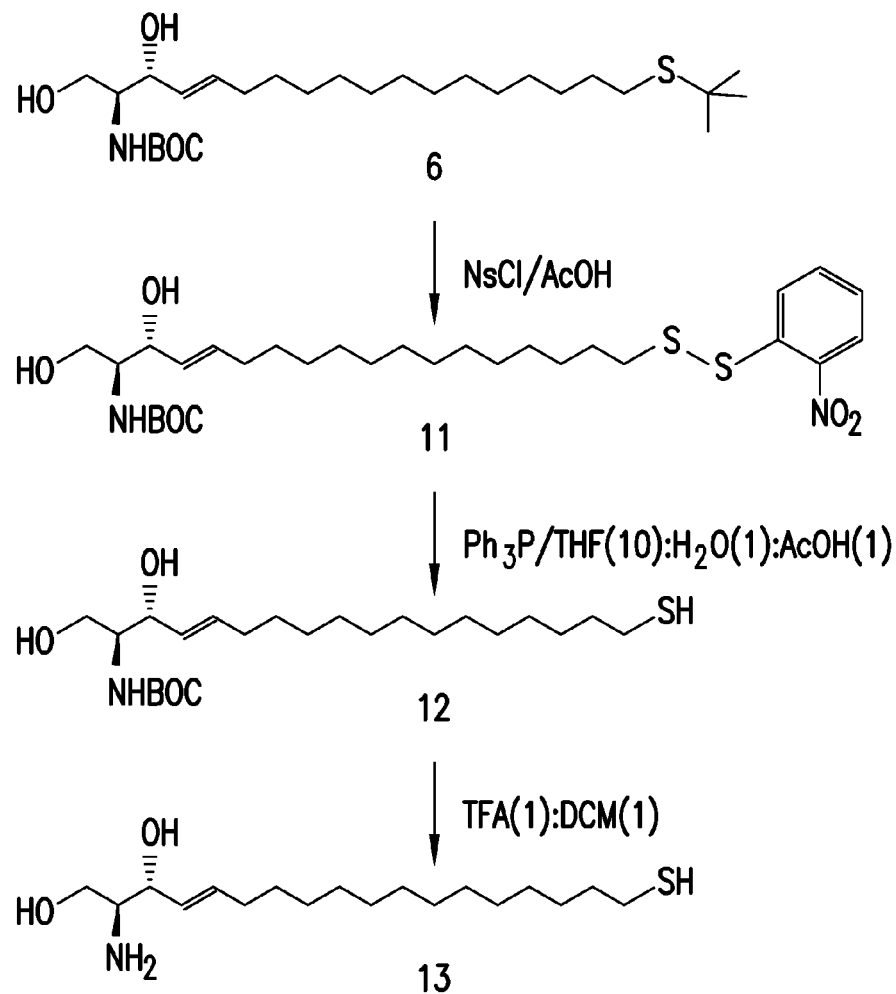

The synthetic approach described in this example results in the preparation of an antigen by serial addition of structural elements using primarily conventional organic chemistry. A scheme for the approach described in this example is provided in FIG. 1, and the compound numbers in the synthetic description below refer to the numbered structures in FIG. 1.

This synthetic approach began with the commercially available 15-hydroxyl pentadecyne, 1, and activation by methyl sulphonyl chloride of the 15-hydroxy group to facilitate hydroxyl substitution to produce the sulphonate, 2. Substitution of the sulphonate with t-butyl thiol yielded the protected thioether, 3, which was condensed with Garner's aldehyde to produce 4. Gentle reduction of the alkyne moiety to an alkene (5), followed by acid catalyzed opening of the oxazolidene ring yielded S-protected and N-protected thiol substituted sphingosine, 6. During this last step, re-derivatization with di-t-butyl dicarbonate was employed to mitigate loss of the N—BOC group during the acid-catalyzed ring opening.

As will be appreciated, compound 6 can itself be used as an antigen for preparing haptens to raise antibodies to sphingosine, or, alternatively, as starting material for two different synthetic approaches to prepare a thiolated S1P analog. In one approach, compound 6 phosphorylation with trimethyl phosphate produced compound 7. Treatment of compound 7 with trimethylsilyl bromide removed both methyl groups from the phosphate and the t-butyloxycarbonyl group from the primary amine, leaving compound 8 with the t-butyl group on the sulfur as the only protecting group. To remove this group, the t-butyl group was displaced by NBS to form the disulfide, 9, which was then reduced to form the thiolated S1P analog, 10.

Another approach involved treating compound 6 directly with NBSCl to form the disulfide, 11, which was then reduced to form the N-protected thiolated S1P analog, 12. Treatment of this compound with mild acid yielded the thiolated sphingosine analog, 13, which can be phosphorylated enzymatically with, e.g., sphingosine kinase, to yield the thiolated S1P analog, 10.

Modifications of the presented synthetic approach are possible, particularly with regard to the selection of protecting and de-protecting reagents, e.g., the use of trimethyl disulfide triflate described in Example 3 to de-protect the thiol.

Compound 2.

DCM (400 mL) was added to a 500 mL RB flask charged with 1 (10.3 g, 45.89 mmol), and the resulting solution cooled to 0° C. Next, TEA (8.34 g, 82.60 mmol, 9.5 mL) was added all at once followed by MsCl (7.88 g, 68.84 mmol, 5.3 mL) added drop wise over 10 min. The reaction was allowed to stir at RT for 0.5 h or until the disappearance of starting material ($R_f$=0.65, 5:1 hexanes:EtOAc). The reaction was quenched with $NH_4Cl$ (300 mL) and extracted (2×200 mL) DCM. The organic layers were dried over $MgSO_4$, filtered and the filtrate evaporated to a solid (13.86 g, 99.8% yield). $^1H$ NMR ($CDCl_3$) δ 4.20 (t, J=6.5 Hz, 2H), 2.98 (s, 3H), 2.59 (td, J=7 Hz, 3 Hz, 2H), 1.917 (t, J=3 Hz, 1H), 1.72 (quintet, J=7.5 Hz, 2H), 1.505 (quintet, J=7.5 Hz, 2H), 1.37 (br s, 4H), 1.27 (br s, 14H). $^{13}C\{^1H\}$ NMR ($CDCl_3$) δ 85.45, 70.90, 68.72, 46.69, 38.04, 30.22, 30.15, 30.14, 30.07, 29.81, 29.76, 29.69, 29.42, 29.17, 26.09, 19.06, 9.31. The principal ion observed in a HRMS analysis (ES-TOF) of compound 2 was m/z=325.1804 (calculated for $C_{16}H_{30}O_3S$: M+Na$^+$ 325.1808).

Compound 3.

A three-neck 1 L RB flask was charged with t-butylthiol (4.54 g, 50.40 mmol) and THF (200 mL) and then placed into an ice bath. n-BuLi (31.5 mL of 1.6 M in hexanes) was added over 30 min. Next, compound 2 (13.86 g, 45.82 mmol), dissolved in THF (100 mL), was added over 2 min. The reaction is allowed to stir for 1 hour or until starting material disappeared ($R_f$=0.7, 1:1 hexanes/EtOAc). The reaction was quenched with saturated $NH_4Cl$ (500 mL) and extracted with $EtO_2$ (2×250 mL), dried over $MgSO_4$, filtered, and the filtrate evaporated to yield a yellow oil (11.67 g, 86% yield). $^1H$ NMR ($CDCl_3$) δ 2.52 (t, J=7.5 Hz, 2H), 2.18 (td, J=7 Hz, 2.5 Hz, 2H), 1.93 (t, J=2.5 Hz, 1H), 1.55 (quintet, J=7.5 Hz, 2H), 1.51 (quintet, J=7 Hz, 2H), 1.38 (br s, 4H), 1.33 (s, 9H), 1.26 (s, 14H). $^{13}C\{^1H\}$ NMR ($CDCl_3$) δ 85.42, 68.71, 68.67, 54.07, 42.37, 31.68, 30.58, 30.28, 30.26, 30.19, 30.17, 29.98, 29.78, 29.44, 29.19, 29.02, 19.08.

Compound 4.

A 250 mL Schlenk flask charged with compound 3 (5.0 g, 16.85 mmol) was evacuated and filled with nitrogen three times before dry THF (150 mL) was added. The resulting solution cooled to −78° C. Next, n-BuLi (10.5 mL of 1.6M in hexanes) was added over 2 min. and the reaction mixture was stirred for 18 min. at −78° C. before the cooling bath was removed for 20 min. The dry ice bath was returned. After 15 min., Garner's aldeyde (3.36 g, 14.65 mmol) in dry THF (10 mL) was then added over 5 min. After 20 min., the cooling bath was removed. Thin layer chromatography (TLC) after 2.7 hr. showed that the Garner's aldehyde was gone. The reaction was quenched with saturated aqueous $NH_4Cl$ (300 mL) and extracted with $Et_2O$ (2×250 mL). The combined $Et_2O$ phases were dried over $Na_2SO_4$, filtered, and the filtrate evaporated to give crude compound 4 and its syn diastereomer (not shown in FIG. 1) as a yellow oil (9.06 g). This material was then used in the next step without further purification.

Compound 5.

To reduce the triple bond in compound 4, the oil was dissolved in dry $Et_2O$ (100 mL) under nitrogen. RED-Al (20 mL, 65% in toluene) was slowly added to the resulting solution at RT to control the evolution of hydrogen gas ($H_2$). The reaction was allowed to stir at RT overnight or when TLC showed the disappearance of the starting material ($R_f$=0.6 in 1:1 EtOAc:hexanes) and quenched slowly with cold MeOH or aqueous $NH_4Cl$ to control the evolution of $H_2$. The resulting white suspension was filtered through a Celite pad and the filtrate was extracted with EtOAc (2×400 mL). Combined EtOAc extracts were dried over $MgSO_4$, filtered, and the filtrate evaporated to leave crude compound 5 and its syn diastereomer (not shown in FIG. 1) as a yellow oil (7.59 g).

Compound 6.

The oil containing compound 5 was dissolved in MeOH (200 mL), PTSA hydrate (0.63 g) was added, and the solution stirred at RT for 1 day and then at 50° C. for 2 days, at which point TLC suggested that all starting material (5) was gone. However, some polar material was present, suggesting that the acid had partially cleaved the BOC group. The reaction was worked up by adding saturated aqueous $NH_4Cl$ (400 mL), and extracted with ether (3×300 mL). The combined ether phases were dried over $Na_2SO_4$, filtered, and the filtrate evaporated to dryness, leaving 5.14 g of oil. In order to re-protect whatever amine had formed, the crude product was dissolved in $CH_2Cl_2$ (150 mL), to which was added $BOC_2O$ (2.44 g) and TEA (1.7 g). When TLC (1:1 hexanes/EtOAc) showed no more material remaining on the baseline, saturated aqueous $NH_4Cl$ (200 mL) was added, and, after separating the organic phase, the mixture was extracted with $CH_2Cl_2$ (3×200 mL). Combined extracts were dried over $Na_2SO_4$, filtered, and the filtrated concentrated to dryness to yield a yellow oil (7.7 g) which was chromatographed on a silica column using a gradient of hexanes/EtOAc (up to 1:1) to separate the diastereomers. By TLC using 1:1 PE/EtOAc, the $R_f$ for the anti isomer, compound 6, was 0.45. For the syn isomer (not shown in FIG. 1) the $R_f$ was 0.40. The yield of compound 6 was 2.45 g (39% overall based on Garner's aldehyde). $^1$H NMR of anti isomer ($CDCl_3$) δ 1.26 (br s, 20H), 1.32 (s, 9H), 1.45 (s, 9H), 1.56 (quintet, 2H, J=8 Hz), 2.06 (q, 2H, J=7 Hz), 2.52 (t, 2H, J=7 Hz), 2.55 (br s, 2H), 3.60 (br s, 1H), 3.72 (ddd, 1H, J=11.5 Hz, 7.0 Hz, 3.5 Hz), 3.94 (dt, 1H, J=11.5 Hz, 3.5 Hz), 4.32 (d, 1H, J=4.5 Hz), 5.28 (br s, 1H), 5.54 (dd, 1H, J=15.5 Hz, 6.5 Hz), 5.78 (dt, 1H, J=15.5 Hz, 6.5 Hz). $^{13}$C {$^1$H} NMR ($CDCl_3$) δ 156.95, 134.80, 129.66, 80.47, 75.46, 63.33, 56.17, 42.44, 32.98, 31.70, 30.58, 30.32, 30.31, 30.28, 30.20, 30.16, 30.00, 29.89, 29.80, 29.08, 29.03.

Anal. Calculated for $C_{27}H_{53}NO_4S$: C, 66.48; H, 10.95; N, 2.87. Found: C, 65.98; H, 10.46; N, 2.48.

Compound 7.

To a solution of the alcohol compound 6 (609.5 mg, 1.25 mmol) dissolved in dry pyridine (2 mL) was added $CBr_4$ (647.2 mg, 1.95 mmol, 1.56 equiv). The flask was cooled in an ice bath and $P(OMe)_3$ (284.7 mg, 2.29 mmol, 1.84 equiv) was added drop wise over 2 min. After 4 min. the ice bath was removed and after 12 hr. the mixture was diluted with ether (20 mL). The resulting mixture washed with aqueous HCl (10 mL, 2 N) to form an emulsion which separated on dilution with water (20 mL). The aqueous phase was extracted with ether (2×10 mL), then EtOAc (2×10 mL). The ether extracts and first EtOAc extract were combined and washed with aqueous HCl (10 mL, 2 N), water (10 mL), and saturated aqueous $NaHCO_3$ (10 mL). The last EtOAc extract was used to back-extract the aqueous washes. Combined organic phases were dried over $MgSO_4$, filtered, and the filtrate concentrated to leave crude product (1.16 g), which was purified by flash chromatography over silica (3×22 cm column) using $CH_2Cl_2$, then $CH_2Cl_2$-EtOAc (1:20, 1:6, 1:3, and 1:1—product started to elute, 6:4, 7:3). Early fractions contained 56.9 mg of oil. Later fractions provided product (compound 7, 476.6 mg, 64%) as clear, colorless oil.

Anal. Calculated for $C_{29}H_{58}NO_7PS$ (595.82): C, 58.46; H, 9.81; N, 2.35. Found: C, 58.09; H, 9.69; N, 2.41.

Compound 8.

A flask containing compound 7 (333.0 mg, 0.559 mmol) and a stir bar was evacuated and filled with nitrogen. Acetonitrile (4 mL, distilled from $CaH_2$) was injected by syringe and the flask now containing a solution was cooled in an ice bath. Using a syringe, $(CH_3)_3SiBr$ (438.7 mg, 2.87 mmol, 5.13 equiv.) was added over the course of 1 min. After 35 min., the upper part of the flask was rinsed with an additional portion of acetonitrile (1 mL) and the ice bath was removed. After another 80 min., an aliquot was removed, the solution dried by blowing nitrogen gas over it, and the residue analyzed by $^1$H NMR in $CDCl_3$, which showed only traces of peaks ascribed to P—$OCH_3$ moieties. After 20 min., water (0.2 mL) was added to the reaction mixture, followed by the $CDCl_3$ solution used to analyze the aliquot, and the mixture was concentrated to ca. 0.5 mL volume on a rotary evaporator. Using acetone (3 mL) in portions the residue was transferred to a tared test tube, forming a pale brown solution. Water (3 mL) was added in portions. After addition of 0.3 mL, cloudiness was seen. After a total of 1 mL, a gummy precipitate had formed. As an additional 0.6 mL of water was added, more cloudiness and gum separated, but the final portion of water seemed not to change the appearance of the mixture. Overall, this process was accomplished over a period of several hours. The tube was centrifuged and the supernatant removed by pipet. The solid, no longer gummy, was dried over $P_4O_{10}$ in vacuo, leaving compound 8 (258.2 mg, 95%) as a monohydrate.

Anal. Calculated. for $C_{22}H_{46}NO_5PS+H_2O$ (485.66): C, 54.40; H, 9.96; N, 2.88. Found: C, 54.59; H, 9.84; N, 2.95.

Compound 9.

Compound 8 (202.6 mg, 0.417 mmol) was added in a glove box to a test tube containing a stir bar, dry THF (3 mL) and glacial HOAc (3 mL). NBSCl (90 mg, 0.475 mmol, 1.14 equiv) were added, and after 0.5 hr., a clear solution was obtained. After a total of 9 hr., an aliquot was evaporated to dryness and the residue analyzed by $^1$H NMR in $CDCl_3$. The peaks corresponding to $CH_2$StBu and $CH_2$SSAr suggested that reaction was about 75% complete, and comparison of the spectrum with that of pure NBSCl in $CDCl_3$ suggested that none of the reagent remained in the reaction. Therefore, an additional portion (24.7 mg, 0.130 mmol, 0.31 equiv) was added, followed 3 hr. later by an additional portion (19.5 mg, 0.103 mmol, 0.25 equiv). After another 1 hr., the mixture was transferred to a new test tube using THF (2 mL) to rinse and water (1 mL) was added.

Compound 10.

$PMe_3$ (82.4 mg, 1.08 mmol, 1.52 times the total amount of 2-nitrobenzenesulfenyl chloride added) was added to the clear solution compound 9 described above. The mixture grew warm and cloudy, with precipitate forming over time. After 4.5 hr., methanol was added, and the tube centrifuged. The precipitate settled with difficulty, occupying the bottom 1 cm of the tube. The clear yellow supernatant was removed using a pipet. Methanol (5 mL, deoxygenated with nitrogen) was added, the tube was centrifuged, and the supernatant removed by pipet. This cycle was repeated three times. When concentrated, the final methanol wash left only 4.4 mg of residue. The bulk solid residue was dried over $P_4O_{10}$ in vacuo, leaving compound 10 (118.2 mg, 68%) as a monohydrochloride.

Anal. Calculated for $C_{18}H_{38}NO_5S+HCl$ (417.03): C, 51.84; H, 9.43; N, 3.36. Found: C, 52.11; H, 9.12; N, 3.30.

Compound 11.

Compound 6 (1.45 g, 2.97 mmol) was dissolved in AcOH (20 mL), and NBSCl (0.56 g, 2.97 mmol) was added all at once. The reaction was allowed to stir for 3 hr. or until the disappearance of the starting material and appearance of the product was observed by TLC [product $R_f$=0.65, starting material $R_f$=0.45, 1:1 EtOAc/hexanes]. The reaction was concentrated to dryness on a high vacuum line and the residue dissolved in THF/$H_2O$ (100 mL of 10:1).

Compound 12.

$Ph_3P$ (0.2.33 g, 8.91 mmol) was added all at once to the solution above that contained compound 11 and the reaction was allowed to stir for 3 hr. or until the starting material disappeared. The crude reaction mixture was concentrated to dryness on a high vacuum line, leaving a residue that contained compound 12.

Compound 13.

The residue above containing compound 12 was dissolved in DCM (50 mL) and TFA (10 mL). The mixture was stirred at RT for 5 hr. and concentrated to dryness. The residue was the loaded onto a column with silica gel and chromatographed with pure DCM, followed by DCM containing 5% MeOH, then 10% MeOH, to yield the final product, compound 13, as a sticky white solid (0.45 g, 46% yield from 5). $^1$H NMR ($CDCl_3$) δ 1.27 (s), 1.33 (br m), 1.61 (p, 2H, J=7.5 Hz), 2.03 (br d, 2H, J=7 Hz), 2.53 (q, 2H, J=7.5 Hz), 3.34 (br s, 1H), 3.87 (br d, 2H, J=12 Hz), 4.48 (br s, 2H), 4.58 (br s, 2H), 5.42 (dd, 1H, J=15 Hz, 5.5 Hz), 5.82 (dt, 1H, J=15 Hz, 5.5 Hz), 7.91 (br s, 4H). $^{13}C\{^1H\}$ NMR ($CDCl_3$) δ 136.85, 126.26, 57.08, 34.76, 32.95, 30.40, 30.36, 30.34, 30.25, 30.19, 30.05, 29.80, 29.62, 29.09, 25.34.

Example 2

Synthetic Schemes for Making Thiolated Fatty Acids

Figure 2A:
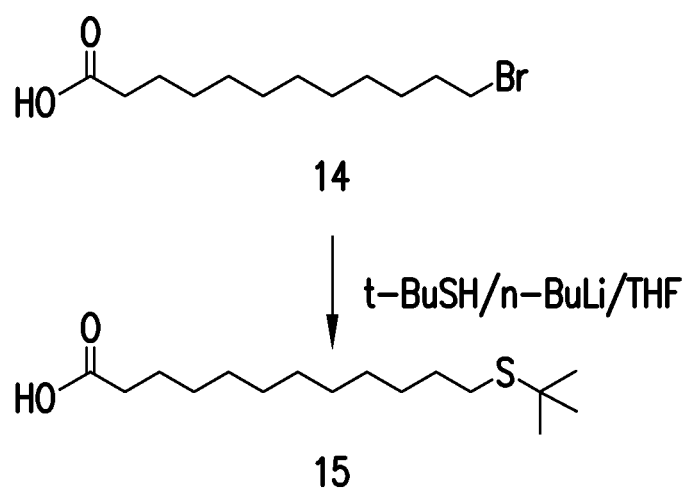
FIG. 2. Organic synthesis scheme for making the thiolated-related fatty acid used in the synthesis of the thiolated-LPA analog of FIG. 3.
Figure 2B:
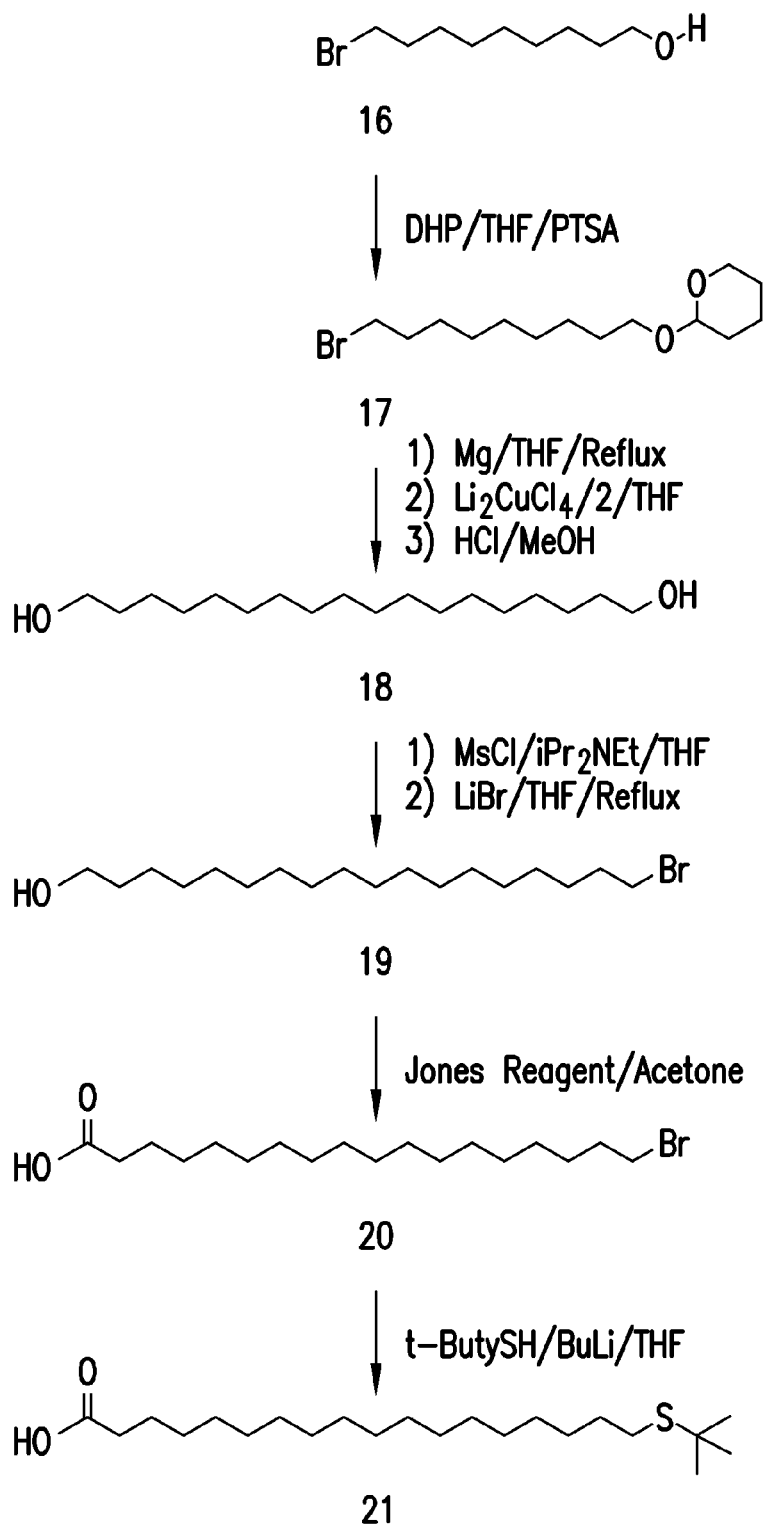

The synthetic approach described in this example details the preparation of a thiolated fatty acid to be incorporated into a more complex lipid structure that could be further complexed to a protein or other carrier and administered to an animal to elicit an immune response. The approach uses using conventional organic chemistry. A scheme showing the approach taken in this example is provided in FIG. 2, and the compound numbers in the synthetic description below refer to the numbered structures in FIG. 2.

Two syntheses are described. The first synthesis, for a C-12 thiolated fatty acid, starts with the commercially available 12-dodecanoic acid, compound 14. The bromine is then displaced with t-butyl thiol to yield the protected C-12 thiolated fatty acid, compound 15. The second synthesis, for a C-18 thiolated fatty acid, starts with the commercially available 9-bromo-nonanol (compound 16). The hydroxyl group in compound 16 is protected by addition of a dihydroyran group and the resulting compound, 17, is dimerized through activation of half of the brominated material via a Grignard reaction, followed by addition of the other half. The 18-hydroxy octadecanol (compound 18) produced following acid-catalyzed removal of the dihydropyran protecting group is selectively mono-brominated to form compound 19. During this reaction approximately half of the alcohol groups are activated for nucleophilic substitution by formation of a methane sulfonic acid ester. The alcohol is then oxidized to form the 18-bromocarboxylic acid, compound 20, which is then treated with t-butyl thiol to displace the bromine and form the protected, thiolated C-18 fatty acid, compound 21.

The protected thiolated fatty acids, each a t-butyl thioether, can be incorporated into a complex lipid and the protecting group removed using, e.g., one of the de-protecting approaches described in Examples 1 and 3. The resulting free thiol then can be used to complex with a protein or other carrier prior to inoculating animal with the hapten.

A. Synthesis of a C-12 Thiolated Fatty Acid

Compound 15.

t-Butyl thiol (12.93 g, 143 mmol) was added to a dry Schlenk flask, and Schlenk methods were used to put the system under nitrogen. Dry, degassed THF (250 mL) was added and the flask cooled in an ice bath. n-BuLi (55 mL of 2.5 M in hexanes, 137.5 mmol) was slowly added over 10 min by syringe. The mixture was allowed to stir at 0° C. for an hour. The bromoacid, compound 14 (10 g, 36 mmol), was added as a solid and the reaction heated and stirred at 60° C. for 24 hr. The reaction was quenched with 2 M HCl (250 mL), and extracted with ether (2×300 mL). The combined ethereal layers were dried with magnesium sulfate, filtered, and the filtrate concentrated by rotary evaporation to yield the thioether acid, compound 15 (10 g, 99% yield) as a beige powder. $^1$H NMR ($CDCl_3$, 500 MHz) δ 1.25-1.35 (br s, 12H), 1.32 (s, 9H), 1.35-1.40 (m, 2H), 1.50-1.60 (m, 2H), 1.60-1.65 (m, 2H), 2.35 (t, 2H, J=7.5 Hz), 2.52 (t, 2H, J=7.5 Hz). Principal ion in HRMS (ES-TOF) was observed at m/z 311.2020, calculated for M+Na$^+$ 311.2015.

B. Synthesis of a C-12 Thiolated Fatty Acid

Compound 17.

A dry Schlenk flask was charged with compound 16 (50 g, 224.2 mmol) and dissolved in dry degassed THF (250 mL) distilled from sodium/benzophenone. The flask was cooled in an ice bath and then PTSA (0.5 g, 2.6 mmol) was added. Dry, degassed DHP (36 g, 42.8 mmol) was then added slowly over 5 min. The mixture was allowed to warm up to RT and left to stir overnight and monitored by TLC (10:1 PE:EtOAc) until the reaction was deemed done by the complete disappearance of the spot for the bromoalcohol. TEA (1 g, 10 mmol) was then added to quench the PTSA. The mixture was then washed with cold sodium bicarbonate solution and extracted with EtOAc (3×250 mL). The organic layers were then dried with magnesium sulfate and concentrated to yield 68.2 g of crude product which was purified by column chromatography (10:1 PE:EtOAc) to yield 60 g (99% yield) of a colorless oil. $^1$H NMR ($CDCl_3$, 500 MHz) δ 1.31 (br s, 6H), 1.41-1.44 (m, 2H), 1.51-1.62 (obscured multiplets, 6H), 1.69-1.74 (m, 1H), 1.855 (quintet, J=7.6 Hz, 2H), 3.41 (t, J=7 Hz, 2H), 3.48-3.52 (m, 2H), 3.73 (dt, 2H, J=6.5 Hz), 3.85-3.90 (m, 2H), 4.57 (t, 2H, J=3 Hz).

Compound 18.

Magnesium shavings (2.98 g, 125 mmol) were added to a flame-dried Schlenk flask along with a crystal of iodine. Dry THF (200 mL) distilled from sodium was then added and the system was degassed using Schlenk techniques. Compound 17 (30 g, 97 mmol) was then slowly added to the magnesium over 10 min. and the solution was placed in an oil bath at 65° C. and allowed to stir overnight. The reaction was deemed complete by TLC by quenching an aliquot with acetone and observing the change in RF in a 10:1 PE:EtOAc mixture. The Grignard solution was then transferred by cannula to a three-necked flask under nitrogen containing additional compound 17 (30 g, 97 mmol). The flask containing the resulting mixture was then cooled to 0° C. in an ice bath and a solution of $Li_2CuCl_4$ (3 mL of 1 M) was then added via syringe. The reaction mixture turned a very dark blue within a few minutes. This mixture was left to stir overnight. The next morning the reaction was deemed complete by TLC (10:1 PE:EtOAc), quenched with a saturated $NH_4Cl$ solution, and then extracted into ether (3×250 mL). The ether layers were dried with magnesium sulfate and concentrated to yield crude product (40 g), which was dissolved in MeOH. Concentrated HCl (0.5 mL) was then added, which resulted in the formation of a white emulsion, which was left to stir for 3 hr. The white emulsion was then filtered to yield 16 g (58% yield) of the pure diol, compound 18. $^1$H NMR (CDCl$_3$, 200 MHz) δ 1.26 (br s, 24H), 1.41-1.42 (m, 4H), 1.51-1.68 (m, 4H), 3.65 (t, 4H, J=6.5 Hz).

Compound 19.

The symmetrical diol, compound 18 (11 g, 38.5 mmol), was added to a dry Schlenk flask under nitrogen, then dry THF (700 mL) distilled from sodium was added. The system was degassed and the flask put in an ice bath. Diisopropylethylamine (6.82 mL, 42.3 mmol) was added via syringe, followed by MsCl (3.96 g, 34.4 mmol) added slowly, and the mixture was left to stir for 1 hr. The reaction was quenched with saturated NaH$_2$PO$_4$ solution (300 mL), and then extracted with EtOAc (3×300 mL). The organic layers were then combined, dried with MgSO$_4$, and concentrated to yield 14 g of a mixture of the diol, monomesylate, and dimesylate. NMR showed a 1:0.8 mixture of CH$_2$OH: CH$_2$O Ms protons. The mixture was then dissolved in dry THF (500 mL), deoxygenated, and to it was added LiBr (3.5 g, 40.23 mmol). This mixture was allowed reflux overnight, upon which the reaction was quenched with water (150 mL), and extracted with EtOAc (3×250 mL). The organic layer was then dried with MgSO$_4$, and concentrated to yield a mixture of brominated products that were then purified by flash chromatography (DCM) to yield compound 19 (3.1 g, 25% yield) as a white powder. $^1$H NMR (CDCl$_3$, 500 MHz) δ 1.26 (br s, 26H), 1.38-1.46 (m, 2H), 1.55 (quintet, 2H, J=7.5 Hz), 1.85 (quintet, 2H, J=7.5 Hz), 3.403 (t, 2H, J=6.8 Hz), 3.66 (t. 2H, J=6.8 Hz).

Compound 20.

A round bottom flask was charged with compound 19 (2.01 g, 5.73 mmol) and the solid dissolved in reagent grade acetone (150 mL). Simultaneously, Jones reagent was prepared by dissolving CrO$_3$ (2.25 g, 22 mmol) in H$_2$SO$_4$ (4 mL) and then slowly adding 10 mL of cold water and letting the solution stir for 10 min. The cold Jones reagent was then added to the round bottom flask slowly over 5 min., after which the solution stirred for 1 hr. The resulting orange solution turned green within several minutes. The mixture was then quenched with water (150 mL) extracted twice in ether (3×150 mL). The ether layers were then dried with magnesium sulfate, and concentrated to yield compound 20 (2.08 g, 98% yield) as a white powder. $^1$H NMR (CDCl$_3$, 200 MHz) δ 1.27 (br s, 26H), 1.58-1.71 (m, 2H), 1.77-1.97 (m, 2H), 2.36 (t, 2H, J=7.4 Hz), 3.42 (t, 2H, J=7 Hz).

Compound 21.

t-Butylthiol (11.32 g, 125 mmol) was added to a dry Schlenk flask and dissolved in dry THF (450 mL) distilled from sodium. The solution was deoxygenated by bubbling nitrogen through it before the flask was placed in an ice bath. n-BuLi solution in hexanes (70 mL of 1.6 M) was then added slowly via syringe over 10 min. This mixture was allowed to stir for 1 hr., then compound 20 (5.5 g, 16.2 mmol) was added and the solution was left to reflux at 60° C. overnight. The next morning an aliquot was worked up, analyzed by NMR, and the reaction deemed complete. The reaction was quenched with HCl (200 mL of 2 M) and extracted with ether (3×250 mL). The ethereal layers were then dried with magnesium sulfate, filtered, and the filtrate concentrated to yield the product, compound 21, as a white solid (5 g, 90% yield). $^1$H NMR (CDCl$_3$, 200 MHz) δ 1.26 (br s, 26H), 1.32 (br s, 9H), 1.48-1.70 (m, 4H), 2.35 (t, 2H, J=7.3 Hz), 2.52 (t, 2H, J=7.3 Hz). $^{13}$C NMR (CDCl$_3$, 200 MHz) δ 24.69, 28.35, 29.05, 29.21, 29.28, 29.39, 29.55, 29.89, 31.02 (3C), 33.98, 41.75, 179.60.

Example 3

Synthetic Scheme for Making a Thiolated Analog of LPA

Figure 3A:
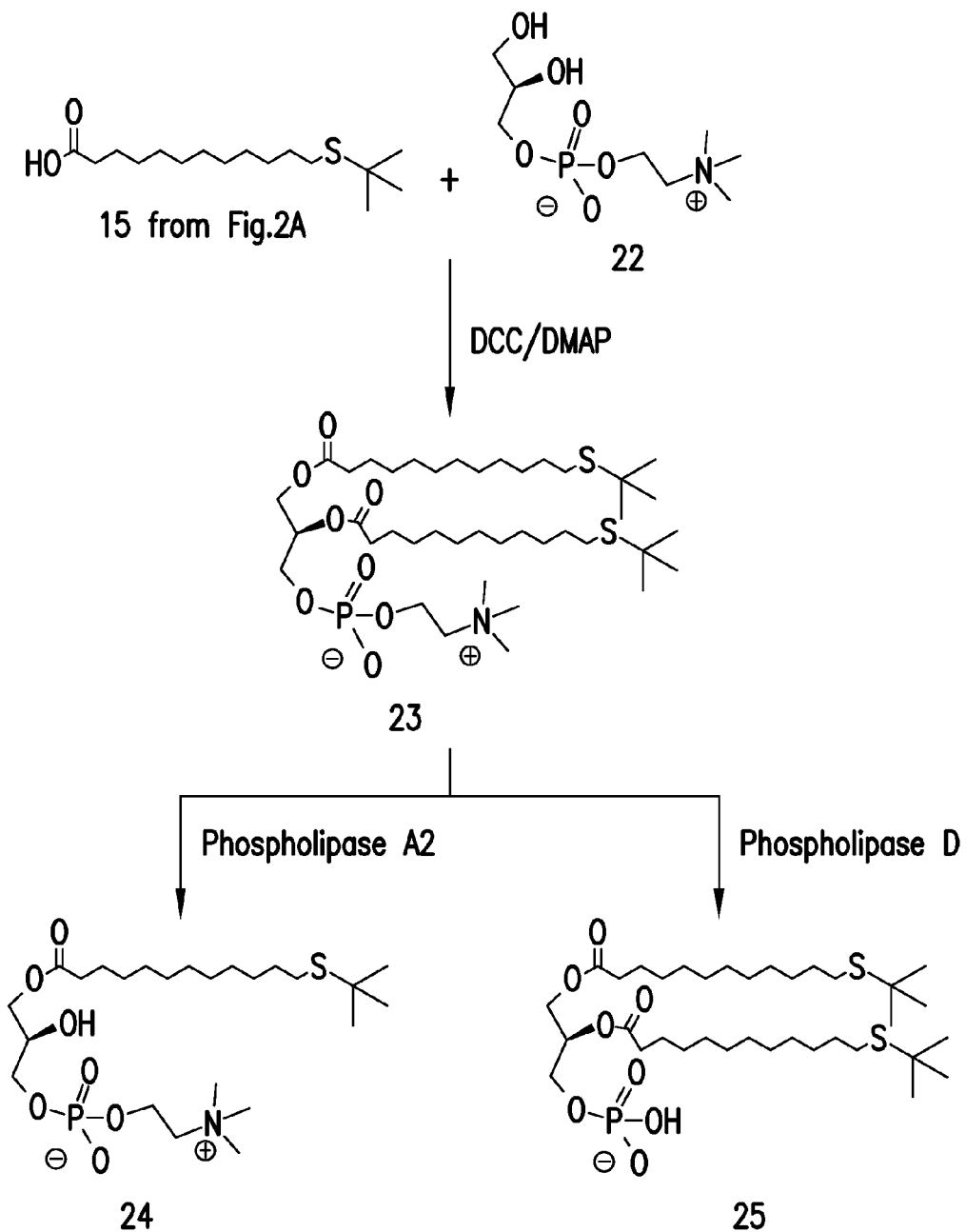
FIG. 3. Organic synthesis scheme for making the thiolated-LPA analog that is a key component of an immunogen according to the invention, as well as a key component of the laydown material for the ELISA and other assays.
Figure 3B:
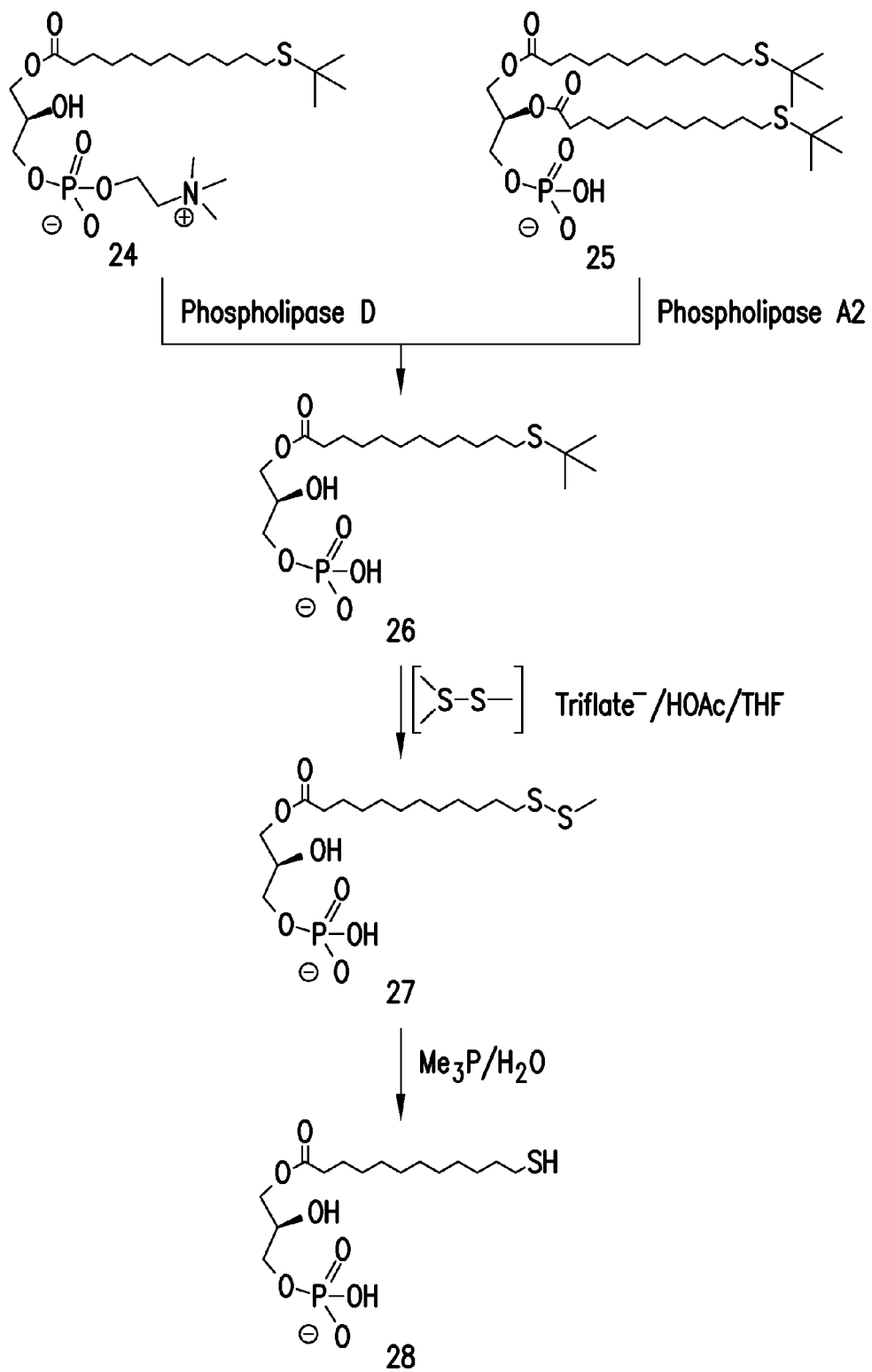

The synthetic approach described in this example results in the preparation of thiolated LPA. The LPA analog can then be further complexed to a carrier, for example, a protein carrier, which can then be administered to an animal to elicit an immugenic response to LPA. This approach uses both organic chemistry and enzymatic reactions, the synthetic scheme for which is provided in FIG. 3. The compound numbers in the synthetic description below refer to the numbered structures in FIG. 3.

The starting materials were compound 15 in Example 2 and enantiomerically pure glycerophoshocholine (compound 22). These two chemicals combined to yield the di-acetylated product, compound 23, using DCC to facilitate the esterification. In one synthetic process variant, the resulting di-acylated glycerophosphocholine was treated first with phospholipase-A2 to remove the fatty acid at the sn-2 position of the glycerol backbone to produce compound 24. This substance was further treated with another enzyme, phospholipase-D, to remove the choline and form compound 26. In another synthetic process variant, the phospholipase-D treatment preceded the phospholipase-A2 treatment to yield compound 25, and treatment of compound 25 with phospholipase-D then yields compound 26. Both variants lead to the same product, the phosphatidic acid derivative, compound 26. The t-butyl protecting group in compound 26 is then removed, first using trimethyl disulfide triflate to produce compound 27, followed by a disulfide reduction to produce the desired LPA derivative, compound 28. As those in the art will appreciate, the nitrobenzyl sulfenyl reaction sequence described in Example 1 can also be used to produce compound 28.

Compound 23.

To a flame-dried Schlenk flask were added the thioether acid, compound 15 (10 g, 35.8 mmol), compound 22 (glycerophosphocholine-CdCl$_2$ complex, 4.25 g, 8.9 mmol), DCC (7.32 g, 35.8 mmol), and DMAP (2.18 g, 17.8 mmol), after which the flask was evacuated and filled with nitrogen. A minimal amount of dry, degassed DCM was added (100 mL), resulting in a cloudy mixture. The flask was covered with foil and then left to stir until completed, as by TLC (silica, 10:5:1 DCM:MeOH:concentrated NH$_4$OH). The insolubility of compound 16 precluded monitoring its disappearance by TLC, but the reaction was stopped when the product spot of R$_f$ 0.1 was judged not to be increasing in intensity. This typically required 3 to 4 days, and in some cases, addition of more DCC and DMAP. Upon completion, the reaction mixture was filtered, and the filtrate concentrated to yield a yellow oil, which was purified using flash chromatography using the solvent system described above to yield 3.6 g (50% yield) of a clear wax containing a mixture of compound 23 and monoacylated products in a ratio of 5 to 1, as estimated from comparing the integrals for the peaks for the (CH$_3$)$_3$N—, —CH$_2$StBu and —CH$_2$COO— moieties. Analysis of the oil by HRMS (ESI-TOF) produced a prominent ion at m/z 820.4972, calculated for M+Na$^+$=C$_{40}$H$_{80}$NNaO$_8$PS$_2$$^+$ 820.4960.

A. Synthesis Variant 1—Phospholipase-A2 Treatment

Compound 24.

A mixture of compound 23 and monoacetylated products as described above (3.1 g, 3.9 mmol) was dissolved in Et$_2$O (400 mL) and methanol (30 mL). Borate buffer (100 mL, pH 7.4 0.1M, 0.072 mM in CaCl$_2$) was added, followed by phospholipase-A2 (from bee venom, 130 units, Sigma). The resulting mixture was left to stir for 10 hr., at which point TLC (silica, MeOH:water 4:1—the previous solvent system 10:5:1 DCM:MeOH:concentrated NH$_4$OH proved ineffective) showed the absence of the starting material (R$_f$=0.7) and the appearance of a new spot (R$_f$=0.2). The organic and aqueous layers were separated and the aqueous layer was washed with ether (2×250 mL). The product was extracted from the aqueous layer with a mixture of DCM:MeOH (2:1, 2×50 mL). The organic layers were then concentrated by rotary evaporation to yield product as a white wax (1.9 g, 86% yield) that NMR showed to be a pure product (compound 24). $^1$H NMR (CDCl$_3$, 500 MHz) δ 1.25-1.27 (br s, 12H), 1.31 (s, 9H), 1.35-1.45 (m, 2H), 1.52-1.60 (m, 4H), 2.31 (t, 2H, J=7.5 Hz), 2.51 (t, 2H, J=7.5 Hz), 3.28 (br s, 9H) 3.25-3.33 (br s, 2H), 3.78-3.86 (m, 1H), 3.88-3.96 (m, 2H), 4.04-4.10 (m, 2H), 4.26-4.34 (m, 2H). Analysis of the wax by HRMS (ESI-TOF) produced a prominent ion at m/z 550.2936, calculated for M+Na$^+$ 550.2943 ($C_{24}H_{50}NNaO_7PS_2^+$), and an m/z at 528.3115, calculated for MH$^+$ 528.3124 ($C_{24}H_{51}NO_7PS_2^+$)

Anal. Calculated. for $C_{24}H_{50}NO_7PS+2H_2O$ (563.73): C, 51.13; H, 9.66; N, 2.48. Found: C, 50.90; H, 9.37; N, 2.76.

Compound 26.

The lyso compound 24 (1.5 g, 2.7 mmol) was dissolved in a mixture of sec-butanol (5 mL) and Et$_2$O (200 mL), and the resulting cloudy mixture was sonicated until the cloudiness dissipated. Buffer (200 mL, pH 5.8, 0.2 M NaOAc, 0.08 M CaCl$_2$) was added, followed by cabbage extract (80 mL of extract from savoy cabbage (which contains phospholipase-D), containing 9 mg of protein/mL). The reaction was stirred for 1 day and monitored by TLC ($C_{18}$ RP SiO$_2$, 5:1 ACN: water), R$_f$ of starting material and product=0.3 and 0.05, respectively. In order to push the reaction to completion, as needed an additional portion of cabbage extract (50 mL) was added and the reaction stirred a further day. This process was repeated twice more, as needed to complete the conversion. When the reaction was complete, the mixture was concentrated on the rotary evaporator to remove the ether, and then EDTA solution (0.5 M, 25 mL) was added and the product extracted into a 5:4 mixture of MeOH: DCM (300 mL). Concentration of the organic layer followed by recrystallization of the residue from DCM and acetone afforded pure product (0.9 g, 75% yield). $^1$H NMR (CDCl$_3$, 200 MHz) δ 1.25-1.27 (br s, 12H), 1.33 (s, 9H), 1.52-1.60 (m, 4H), 2.34 (t, 2H, J=7.5 Hz), 2.52 (t, 2H, J=7.5 Hz), 3.6-3.8 (br s, 1H), 3.85-3.97 (br s, 2H), 4.02-4.18 (m, 2H)

Compound 27.

The protected sample LPA, compound 26 (0.150 g, 0.34 mmol), was methanol washed and added to a vial in the glove box. This was then suspended in a mixture of AcOH:THF (1:1, 10 mL), which never fully dissolved even after 1 hr. of sonication. Solid [Me$_2$SSMe]OTf (0.114 g, 0.44 mmol) was then added. This was left to stir for 18 hr. The reaction was monitored by removing an aliquot, concentrating it to dryness under vacuum, and re-dissolving or suspending the residue in CD$_3$OD for observing the $^1$H NMR shift of the CH$_2$ peak closest to the sulfur. The starting material had a peak at 2.52 ppm, whereas the unsymmetrical disulfide formed at this juncture had a peak at around 2.7 ppm. This material (compound 27) was not further isolated or characterized.

Compound 28.

The mixture containing compound 27 was treated with water (100 μL) immediately followed by PMe$_3$ (0.11 g, 1.4 mmol). After stirring for 3 hr. the solvent was removed by vacuum to yield an insoluble white solid. Methanol (5 mL) was added, the mixture centrifuged, and the mother liquor decanted. Vacuum concentration yielded 120 mg (91% yield) of compound 28, a beige solid. Compound 28 is a thiolated LPA hapten that can be conjugated to a carrier, for example, albumin or KLH, via disulfide bond formation. Characterization of compound 28: $^1$H NMR (1:1 CD$_3$OD:CD$_3$CO$_2$D, 500 MHz) δ 1.25-1.35 (br s, 12H), 1.32-1.4 (m, 2H), 1.55-1.6 (m, 4H), 2.34 (t, 2H, J=7), 2.47 (t, 2H, J=8.5), 3.89-3.97 (br s, 2H), 3.98-4.15 (m, 2H), 4.21 (m, 1H). Negative ion ES of the sample dissolved in methanol produced a predominant ion at m/z=385.1.

Example 4

Antibodies to S1P

One type of therapeutic antibody specifically binds undesirable sphingolipids to achieve beneficial effects such as, e.g., (1) lowering the effective concentration of undesirable, toxic sphingolipids (and/or the concentration of their metabolic precursors) that would promote an undesirable effect such as a cardiotoxic, tumorigenic, or angiogenic effect; (2) to inhibit the binding of an undesirable, toxic, tumorigenic, or angiogenic sphingolipids to a cellular receptor therefore, and/or to lower the concentration of a sphingolipid that is available for binding to such a receptor. Examples of such therapeutic effects include, but are not limited to, the use of anti-S1P antibodies to lower the in vivo serum concentration of available S1P, thereby blocking or at least limiting S1P's tumorigenic and angiogenic effects and its role in post-MI heart failure, cancer, or fibrogenic diseases.

Thiolated S1P (compound 10 of FIG. 1) was synthesized to contain a reactive group capable of cross-linking the essential structural features of S1P to a carrier moiety such as KLH. Prior to immunization, the thio-S1P analog was conjugated via IOA or SMCC cross-linking to protein carriers (e.g., KLH) using standard protocols. SMCC is a heterobifunctional crosslinker that reacts with primary amines and sulfhydryl groups, and represents a preferred crosslinker.

Swiss Webster or BALB-C mice were immunized four times over a two month period with 50 μg of immunogen (SMCC facilitated conjugate of thiolated-S1P and KLH) per injection. Serum samples were collected two weeks after the second, third, and fourth immunizations and screened by direct ELISA for the presence of anti-S1P antibodies. Spleens from animals that displayed high titers of the antibody were subsequently used to generate hybridomas per standard fusion procedures. The resulting hybridomas were grown to confluency, after which the cell supernatant was collected for ELISA analysis. Of the 55 mice that were immunized, 8 were good responders, showing significant serum titers of antibodies reactive to S1P. Fusions were subsequently carried out using the spleens of these mice and myeloma cells according to established procedures. The resulting 1,500 hybridomas were then screened by direct ELISA, yielding 287 positive hybridomas. Of these 287 hybridomas screened by direct ELISA, 159 showed significant titers. Each of the 159 hybridomas was then expanded into 24-well plates. The cell-conditioned media of the expanded hybridomas were then re-screened to identify stable hybridomas capable of secreting antibodies of interest. Competitive ELISAs were performed on the 60 highest titer stable hybridomas.

Of the 55 mice and almost 1,500 hybridomas screened, one hybridoma was discovered that displayed performance characteristics that justified limited dilution cloning, as is required to ultimately generate a true monoclonal antibody. This process yielded 47 clones, the majority of which were deemed positive for producing SiP antibodies. Of these 47 clones, 6 were expanded into 24-well plates and subsequently screened by competitive ELISA. From the 4 clones that remained positive, one was chosen to initiate large-scale production of the S1P monoclonal antibody. SCID mice were injected with these cells and the resulting ascites was protein A-purified (50% yield) and analyzed for endotoxin levels (<3 EU/mg). For one round of ascites production, 50 mice were injected, producing a total of 125 mL of ascites. The antibodies were isotyped as IgG1 kappa, and were deemed >95% pure by HPLC. The antibody was prepared in 20 mM sodium phosphate with 150 mM sodium chloride (pH 7.2) and stored at −70° C.

The positive hybridoma clone (designated as clone 306D326.26) was deposited with the ATCC (safety deposit storage number SD-5362), and represents the first murine mAb (Sphingomab™) directed against S1P. The clone also contains the variable domains of the antibody heavy and light chains that could be used for the generation of a "humanized" antibody variant, as well as the sequence information needed to construct a chimeric antibody.

Screening of serum and cell supernatant for S1P-specific antibodies was by direct ELISA using the thiolated S1P analog described in Example 1 (i.e., compound 10) as the antigen. A standard ELISA was performed, as described below, except that 50 ul of sample (serum or cell supernatant) was diluted with an equal volume of PBS/0.1% Tween-20 (PBST) during the primary incubation. ELISAs were performed in 96-well high binding ELISA plates (Costar) coated with 0.1 µg of chemically-synthesized compound 10 conjugated to BSA in binding buffer (33.6 mM Na2CO3, 100 mM NaHCO3; pH 9.5). The thiolated-S1P-BSA was incubated at 37° C. for 1 hr. at 4° C. overnight in the ELISA plate wells. The plates were then washed four times with PBS (137 mM NaCl, 2.68 mM KCl, 10.14 mM Na2HPO4, 1.76 mM KH2PO4; pH 7.4) and blocked with PBST for 1 hr. at room temperature. For the primary incubation step, 75 uL of the sample (containing the S1P to be measured), was incubated with 25 uL of 0.1 ug/mL anti-S1P mAb diluted in PBST and added to a well of the ELISA plate. Each sample was performed in triplicate wells. Following a 1 hr. incubation at room temperature, the ELISA plates were washed four times with PBS and incubated with 100 ul per well of 0.1 ug/mL HRP goat anti-mouse secondary (Jackson Immunoresearch) for 1 hr. at room temperature. Plates were then washed four times with PBS and exposed to tetramethylbenzidine (Sigma) for 1-10 minutes. The detection reaction was stopped by the addition of an equal volume of 1M H2SO4. Optical density of the samples was determined by measurement at 450 nm using an EL-X-800 ELISA plate reader (Bio-Tech).

For cross reactivity, a competitive ELISA was performed as described above, except for the following alterations. The primary incubation consisted of the competitor (S1P, SPH, LPA, etc.) and a biotin-conjugated anti-SiP mAb. Biotinylation of the purified monoclonal antibody was performed using the EZ-Link Sulfo-NHS-Biotinylation kit (Pierce). Biotin incorporation was determined as per kit protocol and ranged from 7 to II biotin molecules per antibody. The competitor was prepared as follows: lipid stocks were sonicated and dried under argon before reconstitution in DPBS/BSA [1 mg/ml fatty acid-free BSA (Calbiochem) in DPBS (Invitrogen 14040-133)]. Purified anti-S1P mAb was diluted as necessary in PBS/0.5% Triton X-100. Competitor and antibody solutions were mixed together so to generate 3 parts competitor to 1 part antibody. A HRP-conjugated streptavidin secondary antibody (Jackson Immunoresearch) was used to generate signal.

Another aspect of the competitive ELISA data is that it shows that the anti-S1P mAb was unable to distinguish the thiolated-S1P analog (compound 10) from the natural S1P that was added in the competition experiment. It also demonstrates that the antibody does not recognize any oxidation products because the analog was constructed without any double bonds (as is also also true for the LPA analog described in Example 3). The anti-SiP mAb was also tested against natural product containing the double bond that was allowed to sit at room temperature for 48 hours. Reverse phase HPLC of the natural S1P was performed according to methods reported previously (Deutschman, et al. (July 2003), Am Heart J., vol. 146(1):62-8), and the results showed no difference in retention time. Further, a comparison of the binding characteristics of the monoclonal antibody to the various lipids tested indicates that the epitope recognized by the antibody do not involve the hydrocarbon chain in the region of the double bond of natural S1P. On the other hand, the epitope recognized by the monoclonal antibody is the region containing the amino alcohol on the sphingosine base backbone plus the free phosphate. If the free phosphate is linked with a choline (as is the case with SPC), then the binding was somewhat reduced. If the amino group is esterified to a fatty acid (as is the case with C1P), no antibody binding was observed. If the sphingosine amino alcohol backbone was replaced by a glycerol backbone (as is the case with LPA), there the S1P-specific monoclonal exhibited no binding. These epitope mapping data indicate that there is only one epitope on S1P recognized by the monoclonal antibody, and that this epitope is defined by the unique polar headgroup of S1P.

In a similar experiment using ELISA measurements, suitable control materials were evaluated to ensure that this anti-S1P monoclonal antibody did not recognize either the protein carrier or the crosslinking agent. For example, the normal crosslinker SMCC was exchanged for IOA in conjugating the thiolated-S1P to BSA as the laydown material in the ELISA. When IOA was used, the antibody's binding characteristics were nearly identical to when BSA-SMCC-thiolated-S1P was used. Similarly, KLH was exchanged for BSA as the protein that was complexed with thiolated-S1P as the laydown material. In this experiment, there was also no significant difference in the binding characteristics of the antibody.

Binding kinetics: The binding kinetics of S1P to its receptor or other moieties has, traditionally, been problematic because of the nature of lipids. Many problems have been associated with the insolubility of lipids. For BIAcore measurements, these problems were overcome by directly immobilizing S1P to a BIAcore chip. Antibody was then flowed over the surface of the chip and alterations in optical density were measured to determine the binding characteristics of the antibody to S1P. To circumvent the bivalent binding nature of antibodies, S1P was coated on the chip at low densities. Additionally, the chip was coated with various densities of S1P (7, 20, and 1000 RU) and antibody binding data was globally fit to a 1:1 interaction model. Changes in optical density resulted due to the binding of the monoclonal antibody to S1P at three different densities of S1P. Overall, the affinity of the monoclonal antibody to S1P was determined to be very high, in the range of approximately 88 picomolar (pM) to 99 nM, depending on whether a monovalent or bivalent binding model was used to analyze the binding data.

Example 5

Chimeric mAb to S1P

A chimeric antibody to S1P was generated using the variable domains (Fv) containing the active S1P binding regions of the murine antibody from a particular hybridoma (ATCC safety deposit storage number SD-5362) with the Fc region of a human IgG1 immunoglobulin. The Fc regions contained the CL, ChL, and Ch3 domains of the human antibody. Without being limited to a particular method, chimeric antibodies could also have been generated from Fc regions of human IgG1, IgG2, IgG3, IgG4, IgA, or IgM. As those in the art will appreciate, "humanized" antibodies can be generated by grafting the complementarity determining regions (CDRs, e.g. CDR1-4) of the murine anti-S1P mAb with a human antibody framework regions (e.g., Fr1, Fr4, etc.) such as the framework regions of an IgG1.

For the direct ELISA experiments, the chimeric antibody to S1P had similar binding characteristics to the fully murine monoclonal antibody. ELISAs were performed in 96-well high-binding ELISA plates (Costar) coated with 0.1 ug of chemically-synthesized, thiolated S1P conjugated to BSA in binding buffer (33.6 mM Na2CO3, 100 mM NaHCO3; pH 9.5). The thiolated S1P-BSA was incubated at 37° C. for 1 hr. or at 4° C. overnight in the ELISA plate. Plates were then washed four times with PBS (137 mM NaCl, 2.68 mM KCl, 10.14 mM Na2HPO4, 1.76 mM KH2PO4; pH 7.4) and blocked with PBST for 1 hr. at room temperature. For the primary incubation step, 75 uL of the sample (containing the S1P to be measured), was incubated with 25 μL of 0.1 μg/mL anti-S1P monoclonal antibody diluted in PBST and added to a well of the ELISA plate. Each sample was performed in triplicate wells. Following a 1 hr incubation at room temperature, the ELISA plates were washed four times with PBS and incubated with 100 ul per well of 0.1 ug/mL HRP goat anti-mouse secondary (Jackson Immunoresearch) for 1 hr. at room temperature. Plates were then washed four times with PBS and exposed to tetramethylbenzidine (Sigma) for 1-10 minutes. The detection reaction was stopped by the addition of an equal volume of 1M H2SO4. Optical density of the samples was determined by measurement at 450 nm using an EL-X-800 ELISA plate reader (Bio-Tech).

The preferred method of measuring either antibody titer in the serum of an immunized animal or in cell-conditioned media (i.e., supernatant) of an antibody-producing cell such as a hybridoma, involves coating the ELISA plate with a target ligand (e.g., a thiolated analog of S1P, LPA, etc.) that has been covalently linked to a protein carrier such as BSA.

Example 6

Monoclonal Antibodies to LPA

Antibody Production

Although polyclonal antibodies against naturally-occurring LPA have been reported in the literature (Chen J H, et al., Bioorg Med Chem Lett. 2000 Aug. 7; 10(15):1691-3), monoclonal antibodies have not been described. Using an approach similar to that described in Example 4, a C-12 thio-LPA analog (compound 28 in Example 3) as the key component of a hapten formed by the cross-linking of the analog via the reactive SH group to a protein carrier (KLH) via standard chemical cross-linking using either IOA or SMCC as the cross-linking agent, monoclonal antibodies against LPA were generated. To do this, mice were immunized with the thio-LPA-KLH hapten (in this case, thiolated-LPA:SMCC:KLH) using methods described in Example 4 for the generation of anti-S1P monoclonal antibodies. Of the 80 mice immunized against the LPA analog, the five animals that showed the highest titers against LPA (determined using an ELISA in which the same LPA analog (compound 28) as used in the hapten was conjugated to BSA using SMCC and laid down on the ELISA plates) were chosen for moving to the hybridoma phase of development.

The spleens from these five mice were harvested and hybridomas were generated by standard techniques. Briefly, one mouse yielded hybridoma cell lines (designated 504A). Of all the plated hybridomas of the 504A series, 66 showed positive antibody production as measured by the previously-described screening ELISA.

Table 1, below, shows the antibody titers in cell supernatants of hybridomas created from the spleens of two of mice that responded to an LPA analog hapten in which the thiolated LPA analog was cross-linked to KLH using heterobifunctional cross-linking agents. These data demonstrate that the anti-LPA antibodies do not react either to the crosslinker or to the protein carrier. Importantly, the data show that the hybridomas produce antibodies against LPA, and not against S1P.

TABLE 1

| LPA hybridomas | | | | |
|---|---|---|---|---|
| mouse # | 3rd bleed titer OD at 1:312,500 | Supernatants from 24 well | LPA binding OD at 1:20 | S1P binding OD at 1:20 | Cross reactivity w/ S1P* |
| 1 | 1.242 | 1.A.63 | 1.197 | 0.231 | low |
|  |  | 1.A.65 | 1.545 | 0.176 | none |
| 2 | 0.709 | 2.B.7 | 2.357 | 0.302 | low |
|  |  | 2.B.63 | 2.302 | 0.229 | low |
|  |  | 2.B.83 | 2.712 | 0.175 | none |
|  |  | 2.B.104 | 2.57 | 0.164 | none |
|  |  | 2.B.IB7 | 2.387 | 0.163 | none |
|  |  | 2.B.3A6 | 2.227 | 0.134 | none |

*Cross reactivity with S1P from 24 well supernatants: high = OD > 1.0-2.0 at [1:20]; mid = OD 0.4-1.0 at [1:20]; low = OD 0.4-0.2 at [1:20]; none = OD < 0.2 OD at [1:20].

The development of anti-LPA mAbs in mice was monitored by ELISA (direct binding to 12:0 and 18:1 LPA and competition ELISA). A significant immunological response was observed in at least half of the immunized mice and five mice with the highest antibody titer were selected to initiate hybridoma cell line development following spleen fusion.

After the initial screening of over 2000 hybridoma cell lines generated from these 5 fusions, a total of 29 anti-LPA secreting hybridoma cell lines exhibited high binding to 18:1 LPA. Of these hybridoma cell lines, 24 were further subcloned and characterized in a panel of ELISA assays. From the 24 clones that remained positive, six hybridoma clones were selected for further characterization. Their selection was based on their superior biochemical and biological properties. Mouse hybridoma cell lines 504B3-6C2, 504B7.1, 504B58/3F8, 504A63.1 and 504B3A6 (corresponding to clones referred to herein as B3, B7, B58, A63, and B3A6, respectively) were received on May 8, 2007 by the American Type Culture Collection (ATCC Patent Depository, 10801 University Blvd., Manassas, Va. 20110) for patent deposit purposes on behalf of LPath Inc. and were granted deposit numbers PTA-8417, PTA-8420, PTA-8418, PTA-8419 and PTA-8416, respectively.

All anti-LPA antibodies and portions thereof referred to herein were derived from these cell lines.

Direct Binding Kinetics

The binding of 6 anti-LPA mAbs (B3, B7, B58, A63, B3A6, D22) to 12:0 and 18:1 LPA (0.1 uM) was measured by ELISA. $EC_{50}$ values were calculated from titration curves using 6 increasing concentrations of purified mAbs (0 to 0.4 ug/ml). $EC_{50}$ represents the effective antibody concentration with 50% of the maximum binding. Max denotes the maximal binding (expressed as OD450). Results are shown in Table 2.

TABLE 2

Direct Binding Kinetics of Anti-LPA mAbs

|  |  | B3 | B7 | B58 | D22 | A63 | B3A6 |
|---|---|---|---|---|---|---|---|
| 12:0 LPA | $EC_{50}$ (nM) | 1.420 | 0.413 | 0.554 | 1.307 | 0.280 | 0.344 |
|  | Max (OD450) | 1.809 | 1.395 | 1.352 | 0.449 | 1.269 | 1.316 |
| 18:1 LPA | $EC_{50}$ (nM) | 1.067 | 0.274 | 0.245 | 0.176 | 0.298 | 0.469 |
|  | Max (OD450) | 1.264 | 0.973 | 0.847 | 0.353 | 1.302 | 20.027 |

The kinetics parameters $k_a$ (association rate constant), $k_d$ (disassociation rate constant) and $K_D$ (association equilibrium constant) were determined for the 6 lead candidates using the BIAcore 3000 Biosensor machine. In this study, LPA was immobilized on the sensor surface and the anti-LPA mAbs were flowed in solution across the surface. As shown, all six mAbs bound LPA with similar $K_D$ values ranging from 0.34 to 3.8 pM and similar kinetic parameters.

The Anti-LPA Murine mAbs Exhibit High Affinity to LPA

LPA was immobilized to the sensor chip at densities ranging 150 resonance units. Dilutions of each mAb were passed over the immobilized LPA and kinetic constants were obtained by nonlinear regression of association/dissociation phases. Errors are given as the standard deviation using at least three determinations in duplicate runs. Results are shown in Table 3. Apparent affinities were determined by $K_D=k_d/k_a$.

$k_a$=Association rate constant in $M^{-1}s^{-1}$ $k_d$=Dissociation rate constant in $s^{-1}$

TABLE 3

Affinity of anti-LPA mAb for LPA

| mAbs | $k_a$ ($M^{-1}s^{-1}$) | $k_d$ ($s^{-1}$) | $K_D$ (pM) |
|---|---|---|---|
| A63 | $4.4 \pm 1.0 \times 10^5$ | $1 \times 10^{-6}$ | $2.3 \pm 0.5$ |
| B3 | $7.0 \pm 1.5 \times 10^5$ | $1 \times 10^{-6}$ | $1.4 \pm 0.3$ |
| B7 | $6.2 \pm 0.1 \times 10^5$ | $1 \times 10^{-6}$ | $1.6 \pm 0.1$ |
| D22 | $3.0 \pm 0.9 \times 10^4$ | $1 \times 10^{-6}$ | $33 \pm 10$ |
| B3A6 | $1.2 \pm 0.9 \times 10^6$ | $1.9 \pm 0.4 \times 10^{-5}$ | $16 \pm 1.2$ |

Specificity Profile of Six Anti-LPA mAbs.

Many isoforms of LPA have been identified to be biologically active and it is preferable that the mAb recognize all of them to some extent to be of therapeutic relevance. The specificity of the anti-LPA mAbs was evaluated utilizing a competition assay in which the competitor lipid was added to the antibody-immobilized lipid mixture.

Competition ELISA assays were performed with the anti-LPA mAbs to assess their specificity. 18:1 LPA was captured on ELISA plates. Each competitor lipid (up to 10 uM) was serially diluted in BSA (1 mg/ml)-PBS and then incubated with the mAbs (3 nM). Mixtures were then transferred to LPA coated wells and the amount of bound antibody was measured with a secondary antibody. Data are normalized to maximum signal ($A_{450}$) and are expressed as percent inhibition. Assays were performed in triplicate. $IC_{50}$: Half maximum inhibition concentration; MI: Maximum inhibition (% of binding in the absence of inhibitor); ---: not estimated because of weak inhibition. A high inhibition result indicates recognition of the competitor lipid by the antibody. As shown in Table 4, all the anti-LPA mAbs recognized the different LPA isoforms.

TABLE 4

Specificity profile of anti-LPA mAbs.

|  | 14:0 LPA | | 16:0 LPA | | 18:1 LPA | | 18:2 LPA | | 20:4 LPA | |
|---|---|---|---|---|---|---|---|---|---|---|
|  | $IC_{50}$ uM | MI % | $IC_{50}$ uM | MI % | $IC_{50}$ uM | MI % | $IC_{50}$ uM | MI % | $IC_{50}$ uM | MI % |
| B3 | 0.02 | 72.3 | 0.05 | 70.3 | 0.287 | 83 | 0.064 | 72.5 | 0.02 | 67.1 |
| B7 | 0.105 | 61.3 | 0.483 | 62.9 | >2.0 | 100 | 1.487 | 100 | 0.161 | 67 |
| B58 | 0.26 | 63.9 | 5.698 | >100 | 1.5 | 79.3 | 1.240 | 92.6 | 0.304 | 79.8 |
| B104 | 0.32 | 23.1 | 1.557 | 26.5 | 28.648 | >100 | 1.591 | 36 | 0.32 | 20.1 |
| D22 | 0.164 | 34.9 | 0.543 | 31 | 1.489 | 47.7 | 0.331 | 31.4 | 0.164 | 29.5 |
| A63 | 1.147 | 31.9 | 5.994 | 45.7 | — | — | — | — | 0.119 | 14.5 |
| B3A6 | 0.108 | 59.9 | 1.151 | 81.1 | 1.897 | 87.6 | — | — | 0.131 | 44.9 |

Interestingly, the anti-LPA mAbs were able to discriminate between 12:0 (lauroyl), 14:0 (myristoyl), 16:0 (palmitoyl), 18:1 (oleoyl), 18:2 (linoleoyl) and 20:4 (arachidonoyl) LPAs. A desirable $EC_{50}$ rank order for ultimate drug development is 18:2>18:1>20:4 for unsaturated lipids and 14:0>16:0>18:0 for the saturated lipids, along with high specificity. The specificity of the anti-LPA mAbs was assessed for their binding to LPA related biolipids such as distearoyl-phosphatidic acid, lysophosphatidylcholine, S1P, ceramide and ceramide-1-phosphate. None of the antibodies demonstrated cross-reactivity to distearoyl PA and LPC, the immediate metabolic precursor of LPA.

Example 7

Anti-Cancer Activities of Anti-LPA Monoclonal Antibodies

Cancer Cell Proliferation

LPA is a potent growth factor supporting cell survival and proliferation by stimulation of $G_i$, $G_q$ and $G_{12/13}$ via GPCR-receptors and activation of downstream signaling events. Cell lines were tested for their proliferative response to LPA (0.01 mM to 10 mM). Cell proliferation was assayed by using the cell proliferation assay kit from Chemicon (Temecula Calif.) (Panc-1) and the Cell-Blue titer from Pierce (Caki-1). Each data point is the mean of three independent experiments. LPA increased proliferation of 7 human-derived tumor cell lines in a dose dependent manner including SKOV3 and OVCAR3 (ovarian cancer), Panc-1 (pancreatic cancer), Caki-1 (renal carcinoma cell), DU-145 (prostate cancer), A549 (lung carcinoma), and HCT-116 (colorectal adenocarcinoma) cells and one rat-derived tumor cell line, RBL-2H3 (rat leukemia cells). Even though tumor-derived cells normally have high basal levels of proliferation, LPA appears to further augment proliferation in most tumor cell lines. Anti-LPA mAbs (B7 and B58) were assessed for the ability to inhibit LPA-induced proliferation in selected human cancer cell lines. The increase in proliferation induced by LPA was shown to be mitigated by the addition of anti-LPA mAb.

Anti-LPA mAb Sensitizes Tumor Cells to Chemotherapeutic Agents

The ability of LPA to protect ovarian tumor cells against apoptosis when exposed to clinically-relevant levels of the chemotherapeutic agent, paclitaxel (Taxol) was investigated. SKVO3 cells were treated with 1% FBS (S), Taxol (0.5 mM), +/−anti-LPA mAbs for 24 h. LPA protected SKOV3 cells from Taxol-induced apoptosis. Apoptosis was assayed by measurement of the caspase activity as recommended by the manufacturer (Promega). As anticipated, LPA protected most of the cancer cell lines tested from taxol-induced cell death. When the anti-LPA antibody B7 was added to a selection of the LPA responsive cells, it blocked the ability of LPA to protect cells from death induced by the cytotoxic chemotherapeutic agent. Moreover, the anti-LPA antibody was able to remove the protection provided by serum. Serum is estimated to contain about 5-20 uM LPA. Taxol induced caspase-3,7 activation in SKOV3 cells and the addition of serum to cells protected cells from apoptosis. Taxol-induced caspase activation was enhanced by the addition of LT3000 to the culture medium. This suggests that the protective and antiapoptotic effects of LPA were removed by the selective antibody mediated neutralization of the LPA present in serum.

Anti-LPA mAb Inhibits LPA-Mediated Migration of Tumor Cells

An important characteristic of metastatic cancers is that the tumor cells escape contact inhibition and migrate away from their tissue of origin. LPA has been shown to promote metastatic potential in several cancer cell types. Accordingly, we tested the ability of anti-LPA mAb to block LPA-dependent cell migration in several human cancer cell lines by using the cell monolayer scratch assay. Cells were seeded in 96 well plates and grown to confluence. After 24 h of starvation, the center of the wells was scratched with a pipette tip. In this art-accepted "scratch assay," the cells respond to the scratch wound in the cell monolayer in a stereotypical fashion by migrating toward the scratch and close the wound. Progression of migration and wound closure are monitored by digital photography at 10× magnification at desired timepoints. Cells were not treated (NT), treated with LPA (2.5 mM) with or w/o mAb B7 (10 µg/ml) or an isotype matching non-specific antibody (NS) (10 µg/ml). In untreated cells, a large gap remains between the monolayer margins following the scratch. LPA-treated cells in contrast, have only a small gap remaining at the same timepoint, and a few cells are making contact across the gap. In cells treated with both LPA and the anti-LPA antibody B7, the gap at this timepoint was several fold larger than the LPA-only treatment although not as large as the untreated control cells. This shows that the anti-LPA antibody had an inhibitory effect on the LPA-stimulated migration of renal cell carcinoma (Caki-1) cells. Similar data were obtained with mAbs B3 and B58. This indicates that the anti-LPA mAb can reduce LPA-mediated migration of cell lines originally derived from metastatic carcinoma.

Anti-LPA mAbs Inhibit Release of Pro-Tumorgenic Cytokines from Tumor Cells

LPA is involved in the establishment and progression of cancer by providing a pro-growth tumor microenvironment and promoting angiogenesis. In particular, increases of the pro-growth factors such as IL-8 and VEGF have been observed in cancer cells. IL-8 is strongly implicated in cancer progression and prognosis. IL-8 may exert its effect in cancer through promoting neovascularization and inducing chemotaxis of neutrophils and endothelial cells. In addition, overexpression of IL-8 has been correlated to the development of a drug resistant phenotype in many human cancer types.

Three anti-LPA mAbs (B3, B7 and B58) were tested for their abilities to reduce in vitro IL-8 production compared to a non-specific antibody (NS). Caki-1 cells were seeded in 96 well plates and grown to confluency. After overnight serum starvation, cells were treated with 18:1 LPA (0.2 mM) with or without anti-LPA mAb B3, B7, B58 or NS (Non-Specific). After 24 h, cultured supernatants of renal cancer cells (Caki-1), treated with or without LPA and in presence of increasing concentrations of the anti-LPA mAbs B3, B7 and B58, were collected and analyzed for IL-8 levels using a commercially available ELISA kit (Human Quantikine Kit, R&D Systems, Minneapolis, Minn.). In cells pre-treated with the anti-LPA mAbs, IL-8 expression was significantly reduced in a dose-dependent manner (from 0.1-30 µg/mL mAb) whereas LPA increased the expression of IL-8 by an average of 100% in non-treated cells. The inhibition of IL-8 release by the anti-LPA mAbs was also observed in other cancerous cell lines such as the pancreatic cell line Panc-1. These data suggest that the blockade of the pro-angiogenic factor release is an additional and potentially important effect of these anti-LPA mAbs.

Anti-LPA mAbs Inhibit Angiogenesis In Vivo

One of the anti-LPA mAbs (B7) was tested for its ability to mitigate angiogenesis in vivo using the Matrigel Plug assay. This assay utilizes Matrigel, a proprietary mixture of tumor remnants including basement membranes derived from murine tumors. When Matrigel, or its derivate growth factor-reduced (GFR) Matrigel, is injected sc into an animal, it solidifies and forms a 'plug.' If pro-angiogenic factors are mixed with the matrix prior to placement, the plug will be invaded by vascular endothelial cells which eventually form blood vessels. Matrigel can be prepared either alone or mixed with recombinant growth factors (bFGF, VEGF), or tumor cells and then injected sc in the flanks of 6-week old nude (NCr Nu/Nu) female mice. In this example, Caki-1 (renal carcinoma) cells were introduced inside the Matrigel and are producing sufficient levels of VEGF and/or IL8 and LPA. Matrigel plugs were prepared containing $5 \times 10^5$ Caki-1 cells from mice treated with saline or with 10 mg/kg of anti-LPA mAb-B7, every 3 days starting 1 day prior to Matrigel implantation. Plugs were stained for endothelial CD31, followed by quantitation of the micro-vasculature formed in the plugs. Quantitation data were means+/−SEM of at least 16 fields/section from 3 plugs. The plugs from mice treated with the anti-LPA mAb B7 demonstrated a prominent reduction in blood vessel formation, as assayed by endothelial staining for CD31, compared to the plugs from saline-treated mice. Quantification of stained vessels demonstrates a greater than 50% reduction in angiogenesis in Caki-1-containing plugs from animals treated with mAb B7 compared to saline-treated animals. This was a statistically significant reduction (p<0.05 for mAb B7 vs. Saline as determined by Student's T-test) in tumor cell angiogenesis as a result of anti-LPA mAb treatment.

Anti-LPA mAbs Reduces Tumor Progression in a Murine Model of Metastasis

One important characteristic of tumor progression is the ability of a tumor to metastasize and form secondary tumor nodules at remote sites. In vitro studies described hereinabove have demonstrated the ability of LPA to induce tumor cells to escape contact inhibition and promote migration in a scratch assay for cell motility. In these studies, the anti-LPA mAbs also inhibited LPA's tumor growth promoting effectors. The efficacy of the anti-LPA mAb to inhibit tumor metastasis in vivo was also evaluated. The phenomenon of tumor metastasis has been difficult to mimic in animal models. Many investigators utilize an "experimental" metastasis model in which tumor cells are directly injected into the blood stream.

Blood vessel formation is an integral process of metastasis because an increase in the number of blood vessels means cells have to travel a shorter distance to reach circulation. It is believed that anti-LPA mAb will inhibit in vivo tumor cell metastasis, based on the finding that the anti-LPA mAb can block several integral steps in the metastatic process.

Study: The highly metastatic murine melanoma (B16-F10) was used to examine the therapeutic effect of anti-LPA mAbs on metastasis in vivo. This model has demonstrated to be highly sensitive to cPA inhibitors of autotaxin. 4 week old female (C57BL/6) mice received an injection of B 16-F10 murine melanoma tumor cells (100 uL of $5 \times 10^4$ cells/animal) via the tail vein. Mice (10 per group) were administered 25 mg/kg of the anti-LPA mAb (either B3 or B7) or saline every three days by i.p. injection. After 18 days, lungs were harvested and analyzed. The pulmonary organs are the preferred metastatic site of the melanoma cells, and were therefore closely evaluated for metastatic nodules. The lungs were inflated with 10% buffered formalin via the trachea, in order to inflate and fix simultaneously, so that even small foci could be detectable on histological examination. Lungs were separated into five lobes and tumors were categorized by dimension (large ≥5 mm; medium 1-4 mm; small <1 mm) and counted under a dissecting microscope. Upon examination of the lungs, the number of tumors was clearly reduced in antibody-treated animals. For animals treated with mAb B3, large tumors were reduced by 21%, medium tumors by 17% and small tumors by 22%. Statistical analysis by student's T-test gave a $p<0.05$ for number of small tumors in animals treated with mAb B3 vs saline.

As shown in the above examples, it has now been shown that the tumorigenic effects of LPA are extended to renal carcinoma (e.g., Caki-1) and pancreatic carcinoma (Panc-1) cell lines. LPA induces tumor cell proliferation, migration and release of pro-angiogenic and/or pro-metastatic agents, such as VEGF and IL-8, in both cell lines. It has now been shown that three high-affinity and specific monoclonal anti-LPA antibodies demonstrate efficacy in a panel of in vitro cell assays and in vivo tumor models of angiogenesis and metastasis.

Example 8

Cloning of the Murine Anti-LPA
Antibodies—Overview

Chimeric antibodies to LPA were generated using the variable domains (Fv) containing the active LPA binding regions of one of three murine antibodies from hybridomas with the Fc region of a human IgG1 immunoglobulin. The Fc regions contained the CH1, CH2, and CH3 domains of the human antibody. Without being limited to a particular method, chimeric antibodies could also have been generated from Fc regions of human IgG1, IgG2, IgG3, IgG4, IgA, or IgM. As those in the art will appreciate, "humanized" antibodies can be generated by grafting the complementarity determining regions (CDRS, e.g. CDR1-4) of the murine anti-LPA mAbs with a human antibody framework regions (e.g., Fr1, Fr4, etc.) such as the framework regions of an IgG1.

The overall strategy for cloning of the murine mAb against LPA consisted of cloning the murine variable domains of both the light chain (VL) and the heavy chain (VH) from each antibody. The consensus sequences of the genes show that the constant region fragment is consistent with a gamma isotype and that the light chain is consistent with a kappa isotype. The murine variable domains were cloned together with the constant domain of the human antibody light chain (CL) and with the constant domain of the human heavy chain (CH1, CH2, and CH3), resulting in a chimeric antibody construct.

The variable domains of the light chain and the heavy chain were amplified by PCR. The amplified fragments were cloned into an intermediate vector (pTOPO). After verification of the sequences, the variable domains were then assembled together with their respective constant domains. The variable domain of the light chain was cloned into pCONkappa2 and the variable domain of the heavy chain was cloned into pCONgamma1f. The cloning procedure included the design of an upstream primer to include a signal peptide sequence, a consensus Kozak sequence preceding the ATG start codon to enhance translation initiation, and the 5' cut site, HindIII. The downstream primer was designed to include the 3' cut site ApaI for the heavy chain and BsiWI for the light chain.

The vectors containing the variable domains together with their respective constant domains were transfected into mammalian cells. Three days after transfections, supernatants were collected and analyzed by ELISA for binding to LPA. Detailed methods for cloning, expression and characterization of the anti-LPA antibody variable domains are shown on the following pages.

Binding characteristics for the chimeric antibodies are shown in Table 5. "HC" and "LC" indicate the identities of the heavy chain and light chain, respectively.

TABLE 5

Binding characteristics of the chimeric anti-LPA antibodies B3, B7, and B58.

| | HC | x | LC | Titer (ug/ml) | EC50 (ng/ml) | Max OD |
|---|---|---|---|---|---|---|
| 1 | B7 | | B7 | 3.54 | 43.24 | 2.237 |
| 2 | B7 | | B58 | 1.84 | 25.79 | 1.998 |
| 3 | B7 | | B3 | 2.58 | 24.44 | 2.234 |
| 4 | B58 | | B7 | 3.80 | 38.99 | 2.099 |
| 5 | B58 | | B58 | 3.42 | 41.3 | 2.531 |
| 6 | B58 | | B3 | 2.87 | 29.7 | 2.399 |
| 7 | B3 | | B7 | 4.18 | 49.84 | 2.339 |
| 8 | B3 | | B58 | 0.80 | 20.27 | 2.282 |
| 9 | B3 | | B3 | 4.65 | 42.53 | 2.402 |

It can be seen from Table 5 that it is possible to optimize antibody binding to LPA by recombining light chains and heavy chains from different hybridomas (i.e., different clones) into chimeric molecules.

Materials and Methods for the Cloning, Expression and Characterization of the Anti-LPA Antibody variable domains
Cloning of the variable domains from hybridoma cell lines
Clones from the anti-LPA hybridoma cell lines were grown in DMEM (Dulbecco's Dulbecco's Modified Eagle Medium with GlutaMAX™ 1,4500 mg/L D-Glucose, Sodium Puruvate; Gibco/Invitrogen, Carlsbad, Calif., 111-035-003), 10% FBS (Sterile Fetal Clone I, Perbio Science), and 1× glutamine/Penicillin/Streptomycin (Gibco/Invitrogen). Total RNA was isolated from $10^7$ hybridoma cells using a procedure based on the RNeasy Mini kit (Qiagen, Hilden Germany). The RNA was used to generate first strand cDNA following the manufacturer's protocol for SMART RACE cDNA Amplification Kit (Clonetech).

The immunoglobulin heavy chain variable domain (VH) cDNA was amplified by PCR using primers listed in Table 6. Heavy Chain variable domain PCR set-up was as follows:

MHCG1 (known IgG1 constant region primer) combined with Group 1 and Group 2 V region primers for all five antibodies. The product of each reaction was ligated into the pCR2.1®-TOPO® vector (Invitrogen, Carlsbad Calif.) using the TOPO-TA Cloning® kit and sequence.

Similarly, the immunoglobulin light chain variable domains (VK) were amplified using the primers listed in Table 7. The light chain variable domain PCR set-up was as follows: Two constant region primers were each combined with Group 1, Group 2 and Group 3 V region primers for all five antibodies. The product of each reaction was ligated into the pCR2.1®-TOPO® vector using the TOPO-TA Cloning® kit and sequence.

The list of oligonucleotides was designed according to the literature (Dattamajumdar, A. K., Jacobson, D. P., Hood, L. E. and Osman, G. E. (1991) Rapid cloning of any rearranged mouse immunoglobulin variable genes. Immunogenetics. 43(3): 141-51; Coloma, M. J., Hastings, A., Wims, L. A. and Morrison, S. L. (1992) Novel vectors for the expression of antibody molecules using variable domains generated by polymerase chain reaction. J Immunol Methods, 152(1):89-104; Coronella, J. A., Telleman, P., Truong, T. D., Ylera, F. and Junghans, R. P. (2000) Amplification of IgG VH and VL (Fab) from single human plasma cells and B cells. Nucleic Acids Res., 28(20):E85).

TABLE 6

List of oligonucleotides for the cloning of the heavy chain variable domains from the anti-LPA monoclonal antibodies.

| | Heavy Chain | | SEQ ID NO: |
|---|---|---|---|
| Variable | | | |
| Group 1 | MHV1 | ATGAAATGCAGCTGGGGCATSTTCTTC | 1 |
| | MHV2 | ATGGGATGGAGCTRTATCATSYTCTT | 2 |
| | MHV3 | ATGAAGWTGTGGTTAAACTGGGTTTTT | 3 |
| | MHV4 | ATGRACTTTGGGYTCAGCTTGRTTT | 4 |
| | MHV5 | ATGGACTCCAGGCTCAATTTAGTTTTCCTT | 5 |
| | MHV6 | ATGGCTGTCYTRGSGCTRCTCTTCTGC | 6 |
| Group 2 | MHV7 | ATGGRATGGAGCKGGRTCTTTMTCTT | 7 |
| | MHV8 | ATGAGAGTGCTGATTCTTTTGTG | 8 |
| | MHV9 | ATGGMTTGGGTGTGGAMCTTGCTATTCCTG | 9 |
| | MHV10 | ATGGGCAGACTTACATTCTCATTCCTG | 10 |
| | MHV11 | ATGGATTTTGGGCTGATTTTTTTTATTG | 11 |
| | MHV12 | ATGATGGTGTTAAGTCTTCTGTACCTG | 12 |
| | MH1: | ATATCCACCA TGGRATGSAG CTGKGTMATS CTCTT | 13 |
| Constant | | | |
| | MHCG1 | CAGTGGATAGACAGATGGGGG | 14 |
| | MHCG2a | CAGTGGATAGACCGATGGGGC | 15 |
| | MHCG2b | CAGTGGATAGACTGATGGGGG | 16 |
| | MHCG3 | CAAGGGATAGACAGATGGGGC | 17 |
| | MVG1R | 5'-GGCAGCACTAGTAGGGGCCAGTGGATA-3' | 18 |

TABLE 7

List of oligonucleotides used for the cloning of the light chain variable domains from the anti-LPA monoclonal antibodies.

| | Light chain | | SEQ ID NO: |
|---|---|---|---|
| Variable | | | |
| Group 1 | MLALT1 | GGGCACCATGGAGACAGACACACTCCTGCTAT | 19 |
| | MLALT2 | GGGCACCATGGATTTTCAAGTGCAGATTTTCAG | 20 |
| | MLALT3 | GGGCACCATGGAGWCACAKWCTCAGGTCTTTRTA | 21 |
| | MLALT4 | GGGCACCATGKCCCCWRCTCAGYTYCTKGT | 22 |
| | MLALT5 | 5'-CACCATGAAGTTGCCTGTTAGGCTGTTG-3' | 23 |
| Group 2 | MKV1a | ATGAAGTTGVVTGTTAGGCTGTTGGTGCTG | 24 |
| | MKV2 | ATGGAGWCAGACACACTCCTGYTATGGGTG | 25 |
| | MKV3 | ATGAGTGTGCTCACTCAGGTCCTGGSGTTG | 26 |
| | MKV4 | ATGAGGRCCCCTGCTCAGWTTYTTGGMWTCTTG | 27 |
| | MKV5 | ATGGATTTWAGGTGCAGATTWTCAGCTTC | 28 |
| | MKV6 | ATGAGGTKCKKTGKTSAGSTSCTGRGG | 29 |
| | MKV7 | ATGGGCWTCAAGATGGAGTCACAKWYYCWGG | 30 |
| | MKV8 | ATGTGGGGAYCTKTTTYCMMTTTTTCAATTG | 31 |
| | MKV9 | ATGGTRTCCWCASCTCAGTTCCTTG | 32 |
| | MKV10 | ATGTATATATGTTTGTTGTCTATTTCT | 33 |
| | MKV11 | ATGGAAGCCCCAGCTCAGCTTCTCTTCC | 34 |
| | VK8 | TGGGTATCTGGTRCSTGTG | 35 |
| | MKV20 | ATGGAGWCAGACACACTSCTG | 36 |
| Group 3 | CL12A | ATGRAGTYWCAGACCCAGGTCTTYRT | 37 |
| | CL12B | ATGGAGACACATTCTCAGGTCTTTGT | 38 |
| | CL13 | ATGGATTCACAGGCCCAGGTTCTTAT | 39 |
| | CL14 | ATGATGAGTCCTGCCCAGTTCCTCTT | 40 |
| | CL15 | ATGAATTTGCCTGTTCATCTCTTGGTGCT | 41 |
| | CL16 | ATGGATTTTCAATTGGTCCTCATCTCCTT | 42 |
| | CL17A | ATGAGGTGCCTARCTSAGTTCCTGRG | 43 |
| | CL17B | ATGAAGTACTCTGCTCAGTTTCTAGG | 44 |
| | CL17C | ATGAGGCATTCTCTTCAATTCTTGGG | 45 |
| Constant | | | |
| | MKC | ACTGGATGGTGGGAAGATGG | 46 |
| | 33615: | 5'GAAGATCTAGACTTACTATGCAGCATCAGC-3' | 47 |

TOPO2.1 clones containing the heavy and light chain variable domains were sequenced and CDR regions were determined. The variable domain of the light chain was then amplified by PCR adding a leader sequence and cut sites suggested by the manufacturer for cloning into the Lonza light chain expression vector, pCONkappa2 (5' HindIII, 3' BsiWI, LC leader sequence: ATG TCT GTG CCT ACC CAG GTG CTG GGA CTG CTG CTG CTG TGG CTG ACA GAC GCC CGC TGT, SEQ ID NO: 48). The variable domain of the heavy chain was then amplified by PCR adding a leader sequence and cut sites suggested by Lonza for cloning into the Lonza heavy chain expression vector, pCONgamma1f (5' HindIII, 3' ApaI, HC leader sequence: ATG GAA TGG AGC TGG GTG TTC CTG TTC TTT CTG TCC GTG ACC ACA GGC GTG CAT TCT, SEQ ID NO: 49). Final products were then inserted into light or heavy chain expression vectors, containing the constant regions, with digestion and ligation the Rapid Ligation Kit (Roche).

The heavy and light chain plasmids were transformed into One Shot® TOP10 chemically competent bacterial cells (Invitrogen) and stocked in glycerol. Large-scale plasmid DNA was prepared as described by the manufacturer (Qiagen, endotoxin-free MAXIPREP™ kit). DNA samples, purified using Qiagen's QIAprep Spin Miniprep Kit or EndoFree Plasmid Mega/Maxi Kit, were sequenced using an ABI 3730xl automated sequencer, which also translates the fluorescent signals into their corresponding nucleobase sequence. Primers were designed at the 5' and 3' ends so that the sequence obtained would overlap.

PCR Amplification of the Variable Domains

The Polymerase Chain Reactions (PCR) were performed using Invitrogen's Pfx DNA polymerase kit with 10× buffer and 50 mM MgSO4 (cat #11708-013) and 10 mM dNTPs (Invitrogen, cat #18427-013). The reaction mixture consisted of 5 ul 10× pfx amplification buffer, 1.5 ul 10 mM dNTPs, 1 ul 50 mM MgSO4, 1.5 ul oligonucleotide 1, 1.5 ul oligonucleotide 2, 0.5 ul template (~50 ng), 0.5 ul Pfx DNA polymerase, 38.5 ul sterile water. All reagents were added minus Pfx and then Pfx was added immediately before starting the thermocycler. After denaturation of the templates at 95° C. for 3 minutes, 35 cycles of 95° C. for 30 seconds, annealing at 58° C. with a 5° C.+/−gradient and extension at 68° C. for 30 seconds were performed. After a final extension at 68° C. for 5 minutes, the samples were kept at 4° C.

Restriction Digest and Ligation Reactions to Clone the Variable Domains

The restriction digests were performed on DNA to prepare fragment for ligation or for cloning verification prior to checking the molecular sequence. All restriction enzymes were purchased from Invitrogen or New England Biolabs which come with the corresponding buffers required for each enzyme. The DNA (usually 5-10 ul to check for positive clones and 20-26 ul for DNA to be ligated) were mixed with the enzyme buffer, 0.5 to 1.0 ul of the restriction enzyme, and sterile water (to a total of 30 ul reaction). The reactions were incubated at appropriate temperature for the enzyme for 1 hr. Most enzymes were active at 37° C. however the incubation temperature could vary from room temperature to 55° C. depending on the enzymes. After adequate restriction enzyme digest, the GeneClean kit was used to clean the insert fragment and vector from agarose gel and any enzymes and buffers. Ligations were performed using Roche Rapid Ligation Kit (catalog #11635379001) that included T4 DNA 2× Ligation buffer, 5×DNA dilution buffer, and T4 DNA ligase. Inserts and vectors were ligated in a final 3:1 molar ratio for best results. Insert fragments were diluted appropriately for efficient ligations. 5 to 7 ul of the reaction was used to transformed E. coli TOP10 chemically competent cells.

Quantitative ELISA

Microtiter ELISA plates (Costar, Cat No. 3361) were coated with rabbit anti-mouse IgG, F(ab')$_2$ fragment specific antibody (Jackson, 315-005-047) diluted in 1M Carbonate Buffer (pH 9.5) at 37° C. for 1 h. Plates were washed with PBS and blocked with PBS/BSA/Tween-20 for 1 hr at 37° C. For the primary incubation, dilutions of non-specific mouse IgG or human IgG, whole molecule (used for calibration curve) and samples to be measured were added to the wells. Plates were washed and incubated with 100 ul per well of HRP conjugated anti-human diluted 1:50,000 (Jackson 109-035-003) for 1 hr at 37° C. After washing, the enzymatic reaction was detected with tetramethylbenzidine (Sigma, cat No T0440) and stopped by adding 1 M H$_2$SO$_4$. The optical density (OD) was measured at 450 nm using a Thermo Multiskan EX. Raw data were transferred to GraphPad software for analysis.

Direct ELISA

Microtiter ELISA plates (Costar, Cat No. 3361) were coated with LPA-BSA diluted in 1M Carbonate Buffer (pH 9.5) at 37° C. for 1 h. Plates were washed with PBS (137 mM NaCl, 2.68 mM KCl, 10.1 mM Na$_2$HPO$_4$, 1.76 mM KH$_2$PO$_4$; pH 7.4) and blocked with PBS/BSA/Tween-20 for 1 h at room temperature or overnight at 4° C. The samples to be tested were diluted at 0.4 ug/mL, 0.2 ug/mL, 0.1 ug/mL, 0.05 ug/mL, 0.0125 ug/mL, and 0 ug/mL and 100 ul added to each well. Plates were washed and incubated with 100 ul per well of HRP anti-human diluted 1:50,000 (Jackson 109-035-003) for 1 hr at 37° C. After washing, the enzymatic reaction was detected with tetramethylbenzidine (Sigma, Cat No T0440) and stopped by adding 1 M H$_2$SO$_4$. The optical density (OD) was measured at 450 nm using a Thermo Multiskan EX. Raw data were transferred to GraphPad software for analysis.

Transient Expression

The vectors were transfected into the human embryonic kidney cell line 293F using 293fectin and using 293F-FreeStyle Media for culture. Transfections were performed at a cell density of $10^6$ cells/mL with 0.5 μg/mL. Supernatants were collected by centrifugation at 1100 rpm for 5 minutes at 25° C. 3 days after transfection. The expression level was quantified by quantitative ELISA and the binding was measured in a binding ELISA as described above.

The mouse $V_H$ and $V_L$ domains were sequenced using standard methods. Tables 8-17 show nucleic acid and amino acid sequences for the complementarity-determining regions (CDRs) of the variable ($V_H$ and $V_L$) domains for five mouse anti-LPA monoclonal antibody clones. For each CDRH1 amino acid sequence, the CDR defined according to Kabat is the 10-amino acid sequence shown. The five-amino acid portion of the Kabat sequence that is shown in bold is the canonical CDRH1 sequence.

TABLE 8

Mouse LPA CDR nucleic acid sequences of the mouse $V_H$ and $V_L$ domains for clone B3 of mouse anti-LPA monoclonal antibody

| CLONE | | CDR | SEQ ID NO: |
|---|---|---|---|
| | $V_H$ CDR | | |
| B3 | GGAGACGCCTTCACAAATTACTTAATAGAG | CDRH1 | 50 |
| B3 | CTGATTTATCCTGATAGTGGTTACATTAACTACAATGAGAACTTCAAGGGC | CDRH2 | 51 |
| B3 | AGATTTGCTTACTACGGTAGTGGCTACTACTTTGACTAC | CDRH3 | 52 |
| | $V_L$ CDR | | |
| B3 | AGATCTAGTCAGAGCCTTCTAAAAACTAATGGAAACACCTATTTACAT | CDRL1 | 53 |
| B3 | AAAGTTTCCAACCGATTTTCT | CDRL2 | 54 |
| B3 | TCTCAAAGTACACATTTTCCATTCACG | CDRL3 | 55 |

TABLE 9

Mouse LPA CDR amino acid sequences of the mouse $V_H$ and $V_L$ domains for clone B3 of mouse anti-LPA monoclonal antibody

| CLONE | CDR | | SEQ ID NO: |
|---|---|---|---|
| | $V_H$ CDR | | |
| B3 | GDAFTNYLIE\* | CDRH1 | 56 |
| B3 | LIYPDSGYINYNENFKG | CDRH2 | 57 |
| B3 | RFAYYGSGYYFDY | CDRH3 | 58 |
| | $V_L$ CDR | | |
| B3 | RSSQSLLKTNGNTYLH | CDRL1 | 59 |
| B3 | KVSNRFS | CDRL2 | 60 |
| B3 | SQSTHFPFT | CDRL3 | 61 |

\*The CDRH1 sequence defined according to Chothia/AbM is the 10-amino acid sequence shown. The five-amino acid portion of this sequence shown in bold (NYLIE; SEQ ID NO: 62) is the CDRH1 sequence defined according to Kabat.

TABLE 10

Mouse LPA CDR nucleic acid sequences of the mouse $V_H$ and $V_L$ domains for clone B7 of mouse anti-LPA monoclonal antibody

| CLONE | CDR | | SEQ ID NO: |
|---|---|---|---|
| | $V_H$ CDR | | |
| B7 | GGATACGGCTTCATTAATTACT TAATAGAG | CDRH1 | 63 |
| B7 | CTGATTAATCCTGGAAGTGATT ATACTAACTACAATGAGAACT TCAAGGGC | CDRH2 | 64 |
| B7 | AGATTTGGTTACTACGGTAGC GGCAACTACTTTGACTAC | CDRH3 | 65 |
| | $V_L$ CDR | | |
| B7 | ACATCTGGTCAGAGCCTTGTCC ACATTAATGGAAACACCTATT TACAT | CDRL1 | 66 |
| B7 | AAAGTTTCCAACCTATTTTCT | CDRL2 | 67 |
| B7 | TCTCAAAGTACACATTTTCCAT TCACG | CDRL3 | 68 |

TABLE 11

Mouse LPA CDR amino acid sequences of the mouse $V_H$ and $V_L$ domains for clone B7 of mouse anti-LPA monoclonal antibody

| CLONE | CDR | | SEQ ID NO: |
|---|---|---|---|
| | $V_H$ CDR | | |
| B7 | GYGFINYLIE\* | CDRH1 | 69 |
| B7 | LINPGSDYTNYNENFKG | CDRH2 | 70 |
| B7 | RFGYYGSGNYFDY | CDRH3 | 71 |

TABLE 11-continued

Mouse LPA CDR amino acid sequences of the mouse $V_H$ and $V_L$ domains for clone B7 of mouse anti-LPA monoclonal antibody

| CLONE | CDR | | SEQ ID NO: |
|---|---|---|---|
| | $V_L$ CDR | | |
| B7 | TSGQSLVHINGNTYLH | CDRL1 | 72 |
| B7 | KVSNLFS | CDRL2 | 73 |
| B7 | SQSTHFPFT | CDRL3 | 74 |

\*The CDRH1 sequence defined according to Chothia/AbM is the 10-amino acid sequence shown. The five-amino acid portion of this sequence shown in bold (NYLIE; SEQ ID NO: 62) is the CDRH1 sequence defined according to Kabat.

TABLE 12

Mouse LPA CDR nucleic acid sequences of the mouse $V_H$ and $V_L$ domains for clone B58 of mouse anti-LPA monoclonal antibody

| CLONE | CDR | | SEQ ID NO: |
|---|---|---|---|
| | $V_H$ CDR | | |
| B58 | GGAGACGCCTTCACTAATTACTTGATC GAG | CDRH1 | 75 |
| B58 | CTGATTATTCCTGGAACTGGTTATACT AACTACAATGAGAACTTCAAGGGC | CDRH2 | 76 |
| B58 | AGATTTGGTTACTACGGTAGTAGCAAC TACTTTGACTAC | CDRH3 | 77 |
| | $V_L$ CDR | | |
| B58 | AGATCTAGTCAGAGCCTTGTACACAGT AATGGAAACACCTATTTACAT | CDRL1 | 78 |
| B58 | AAAGTTTCCAACCGATTTTCT | CDRL2 | 79 |
| B58 | TCTCAAAGTACACATTTTCCATTCACT | CDRL3 | 80 |

TABLE 13

Mouse LPA CDR amino acid sequences of the mouse $V_H$ and $V_L$ domains for clone B58 of mouse anti-LPA monoclonal antibody

| CLONE | CDR | | SEQ ID NO: |
|---|---|---|---|
| | $V_H$ CDR | | |
| B58 | GDAFTNYLIE\* | CDRH1 | 81 |
| B58 | LIIPGTGYTNYNENFKG | CDRH2 | 82 |
| B58 | RFGYYGSSNYFDY | CDRH3 | 83 |
| | $V_L$ CDR | | |
| B58 | RSSQSLVHSNGNTYLH | CDRL1 | 84 |
| B58 | KVSNRFS | CDRL2 | 85 |
| B58 | SQSTHFPFT | CDRL3 | 86 |

\*The CDRH1 sequence defined according to Chothia/AbM is the 10-amino acid sequence shown. The five-amino acid portion of this sequence shown in bold (NYLIE; SEQ ID NO: 62) is the CDRH1 sequence defined according to Kabat.

TABLE 14

Mouse LPA CDR nucleic acid sequences of the mouse V$_H$ and V$_L$ domains for clone 3A6 of mouse anti-LPA monoclonal antibody

| CLONE | CDR | | SEQ ID NO: |
|---|---|---|---|
| | V$_H$ CDR | | |
| 3A6 | GGAGACGCCTTCACTAATTACTTGATCGAG | CDRH1 | 87 |
| 3A6 | CTGATTATTCCTGGAACTGGTTATACTAACTACAATGAGAACTTCAAGGGC | CDRH2 | 88 |
| 3A6 | AGATTTGGTTACTACGGTAGTGGCTACTACTTTGACTAC | CDRH3 | 89 |
| | V$_L$ CDR | | |
| 3A6 | AGATCTAGTCAGAGCCTTGTACACAGTAATGGAAACACCTATTTACAT | CDRL1 | 90 |
| 3A6 | AAAGTTTCCAACCGATTTTCT | CDRL2 | 91 |
| 3A6 | TCTCAAAGTACACATTTTCCATTCACG | CDRL3 | 92 |

TABLE 15

Mouse LPA CDR amino acid sequences of the mouse V$_H$ and V$_L$ domains for clone 3A6 of mouse anti-LPA monoclonal antibody

| CLONE | CDR | | SEQ ID NO: |
|---|---|---|---|
| | V$_H$ CDR | | |
| 3A6 | GDAFTNYLIE\* | CDRH1 | 93 |
| 3A6 | LIIPGTGYTNYNENFKG | CDRH2 | 94 |
| 3A6 | RFGYYGSGYYFDY | CDRH3 | 95 |
| | V$_L$ CDR | | |
| 3A6 | RSSQSLVHSNGNTYLH | CDRL1 | 96 |
| 3A6 | KVSNRFS | CDRL2 | 97 |
| 3A6 | SQSTHFPFT | CDRL3 | 98 |

\*The CDRH1 sequence defined according to Chothia/AbM is the 10-amino acid sequence shown. The five-amino acid portion of this sequence shown in bold (NYLIE; SEQ ID NO: 62) is the CDRH1 sequence defined according to Kabat.

TABLE 16

Mouse LPA CDR nucleic acid sequences of the mouse V$_H$ and V$_L$ domains for clone A63 of mouse anti-LPA monoclonal antibody

| CLONE | CDR | | SEQ ID NO: |
|---|---|---|---|
| | V$_H$ CDR | | |
| A63 | GGCTTCTCCATCACCAGTGGTTATTACTGGACC | CDRH1 | 99 |
| A63 | TACATAGGCTACGATGGTAGCAATGACTCCAACCCATCTCTCAAAAAT | CDRH2 | 100 |
| A63 | GCGATGTTGCGGCGAGGATTTGACTAC | CDRH3 | 101 |

TABLE 16-continued

Mouse LPA CDR nucleic acid sequences of the mouse V$_H$ and V$_L$ domains for clone A63 of mouse anti-LPA monoclonal antibody

| CLONE | CDR | | SEQ ID NO: |
|---|---|---|---|
| | V$_L$ CDR | | |
| A63 | AGTGCCAGCTCAAGTTTAAGTTACATGCAC | CDRL1 | 102 |
| A63 | GACACATCCAAACTGGCTTCT | CDRL2 | 103 |
| A63 | CATCGGCGGAGTAGTTACACG | CDRL3 | 104 |

TABLE 17

Mouse LPA CDR amino acid sequences of the mouse V$_H$ and V$_L$ domains for clone A63 of mouse anti-LPA monoclonal antibody

| CLONE | CDR | | SEQ ID NO: |
|---|---|---|---|
| | V$_H$ CDR | | |
| A63 | GFSITSGYYWT\* | CDRH1 | 105 |
| A63 | YIGYDGSNDSNPSLKN | CDRH2 | 106 |
| A63 | AMLRRGFDY | CDRH3 | 107 |
| | V$_L$ CDR | | |
| A63 | SASSSLSYMH | CDRL1 | 108 |
| A63 | DTSKLAS | CDRL2 | 109 |
| A63 | HRRSSYT | CDRL3 | 110 |

\*The CDRH1 sequence defined according to Chothia/AbM is the 11-amino acid sequence shown. The six-amino acid portion of this sequence shown in bold (SGYYWT; SEQ ID NO: 111) is the CDRH1 sequence defined according to Kabat.

Tables 18-27 show nucleotide and amino acid sequences (nucleotides in Tables 18, 20, 22, 24 and 26, amino acids in Tables 19, 21, 23, 25 and 27) of the variable domains (V$_H$ and V$_L$) of the anti-LPA antibodies. In each heavy chain amino acid sequence in Tables 18-27, amino acids 1-2 (KL) represent enzymatic cut sites recommended for use with the pCON expression vectors and amino acids 2-5 (AAT) are Kozak sequences in the corresponding nucleotide sequence. Amino acids 6-24 (SEQ ID NO: 49) are leader sequences recommended for use with the pCON heavy chain expression vector. The last five amino acids of the heavy chain sequences shown (ASTKG) are the beginning of the constant region sequence contained within the pCON heavy chain vector.

In each light chain amino acid sequence in Tables 18-27, amino acids 1-2 (KL) are enzymatic cut sites recommended for use with the pCON expression vectors and amino acids 2-5 (AAT) are Kozak sequences in the corresponding nucleotide sequence. Amino acids 6-25 (SEQ ID NO: 48) are leader sequences recommended for use with the pCON light chain expression vector. The last two amino acids (RT) of the light chain sequences shown are the cut site recommended for use with the pCON light chain vector.

Thus the actual heavy chain sequence (minus Kozak sequences, leaders and cut sites can be seen to be amino acids 25-146 of each amino acid sequence in Tables 18-27 and the actual light chain sequence (minus Kozak sequences, leaders and cut sites) can be seen to be amino acids 26-137 of each amino acid sequence in Tables 18-27. One of ordinary skill can readily determine which of the nucleic acid sequences in Tables 18-27 (even numbered tables) correspond to these amino acid sequences.

TABLE 18

Clone B3 nucleic acid sequences with leader sequence and cut sites added

| Sequence | SEQ ID NO: |
|---|---|
| B3 Heavy Chain | |
| AAGCTTGCCGCCACCATGGAATGGAGCTGGGTGTTCCTGTTCT TTTCTGTCCGTGACCACAGGCGTGCATTCTCAGGTCAAGCTGCA GCAGTCTGGACCTGAGCTGGTAAGGCCTGGGACTTCAGTGAA GGTGTCCTGCACGGCTTCTGGAGACGCCTTCACAAATTACTTA ATAGAGTGGGTAAAACAGAGGCCTGGACAGGGCCTTGAGTGG ATTGGACTGATTTATCCTGATAGTGGTTACATTAACTACAATG AGAACTTCAAGGGCAAGGCAACACTGACTGCAGACAGATCCT CCAGCACTGCCTACATGCAGCTCAGCAGCCTGACATCTGAGGA CTCTGCGGTCTATTTCTGTGCAAGAAGATTTGCTTACTACGGTA GTGGCTACTACTTTGACTACTGGGGCCAAGGCACCACTCTCAC AGTCTCCTCAGCCTCCACCAAGGGCCC | 112 |
| B3 Light Chain | |
| AAGCTTGCCGCCACCATGTCTGTGCCTACCCAGGTGCTGGGAC TGCTGCTGCTGTGGCTGACAGACGCCCGCTGTGATGTTGTGAT GACCCAAACTCCACTCTCCCTGCCTGTCAGTCTTGGAGATCAA GCCTCCATCTCTTGCAGATCTAGTCAGAGCCTTCTAAAAACTA ATGGAAACACCTATTTACATTGGTACCTGCAGAAGCCAGGCCA GTCTCCAAAACTCCTAATCTTCAAAGTTTCCAACCGATTTTCTG GGGTCCCGGACAGGTTCAGTGGCAGTGGATCAGGGACAGACT TCACACTCAAGATCAGCAGAGTGGAGGCTGAGGATCTGGGAG TTTATTTCTGCTCTCAAAGTACACATTTTCCATTCACGTTCGGC ACGGGGACAAAATTGGAAATAAAACGTACG | 113 |

TABLE 19

Clone B3 amino acid sequences with leader sequence and cut sites added

| Sequence | SEQ ID NO: |
|---|---|
| B3 Heavy Chain | |
| KLAATMEWSWVFLFFLSVTTGVHSQVKLQQSGPELVRPGTSVKV SCTASGDAFTNYLIEWVKQRPGQGLEWIGLIYPDSGYINYNENFK GKATLTADRSSSTAYMQLSSLTSEDSAVYFCARRFAYYGSGYYF DYWGQGTTLTVSSASTKG | 114 |
| B3 Light Chain | |
| KLAATMSVPTQVLGLLLLWLTDARCDVVMTQTPLSLPVSLGDQ ASISCRSSQSLLKTNGNTYLHWYLQKPGQSPKLLIFKVSNRFSGVP DRFSGSGSGTDFTLKISRVEAEDLGVYFCSQSTHFPFTFGTGTKLEI KRT | 115 |

TABLE 20

Clone B7 nucleic acid sequences with leader sequence and cut sites added

| Sequence | SEQ ID NO: |
|---|---|
| B7 Heavy Chain | |
| AAGCTTGCCGCCACCATGGAATGGAGCTGGGTGTTCCTGTTCT TTTCTGTCCGTGACCACAGGCGTGCATTCTCAGGTCCAACTGCA GCAGTCTGGAGCTGAGCTGGTAAGGCCTGGGACTTCAGTGAA GGTGTCCTGCAAGGCTTCTGGATACGGCTTCATTAATTACTTA | 116 |

TABLE 20-continued

Clone B7 nucleic acid sequences with leader sequence and cut sites added

| Sequence | SEQ ID NO: |
|---|---|
| ATAGAGTGGATAAAACAGAGGCCTGGACAGGGCCTTGAGTGG ATTGGACTGATTAATCCTGGAAGTGATTATACTAACTACAATG AGAACTTCAAGGGCAAGGCAACACTGACTGCAGACAAGTCCT CCAGCACTGCCTACATGCACCTCAGCAGCCTGACATCTGAGGA CTCTGCGGTCTATTTCTGTGCAAGAAGATTTGGTTACTACGGT AGCGGCAACTACTTTGACTACTGGGGCCAAGGCACCACTCTCA CAGTCTCCTCAGCCTCCACCAAGGGCCC | |
| B7 Light Chain | |
| AAGCTTGCCGCCACCATGTCTGTGCCTACCCAGGTGCTGGGAC TGCTGCTGCTGTGGCTGACAGACGCCCGCTGTGATGTTGTGAT GACCCAAACTCCACTCTCCCTGCCTGTCAGTCTTGGAGATCAA GCCTCCATCTCTTGCACATCTGGTCAGAGCCTTGTCCACATTAA TGGAAACACCTATTTACATTGGTACCTGCAGAAGCCAGGCCAG TCTCCAAAGCTCCTCATCTACAAAGTTTCCAACCTATTTTCTGG GGTCCCAGACAGGTTCAGTGGCAGTGGATCAGGGACAGATTT CACACTCAAGATCAGCAGAGTGGAGGCTGAGGATCTGGGAGT TTATTTCTGCTCTCAAAGTACACATTTTCCATTCACGTTCGGCA CGGGGACAAAATTGGAAATAAAACGTACG | 117 |

TABLE 21

Clone B7 amino acid sequences wit leader sequence and cut sites added

| Sequence | SEQ ID NO: |
|---|---|
| B7 Heavy Chain | |
| KLAATMEWSWVFLFFLSVTTGVHSQVQLQQSGAELVRPGTSVK VSCKASGYGFINYLIEWIKQRPGQGLEWIGLINPGSDYTNYNENF KGKATLTADKSSSTAYMHLSSLTSEDSAVYFCARRFGYYGSGNY FDYWGQGTTLTVSSASTKG | 118 |
| B7 Light Chain | |
| KLAATMSVPTQVLGLLLLWLTDARCDVVMTQTPLSLPVSLGDQ ASISCTSGQSLVHINGNTYLHWYLQKPGQSPKLLIYKVSNLFSGVP DRFSGSGSGTDFTLKISRVEAEDLGVYFCSQSTHFPFTFGTGTKLEI KRT | 119 |

TABLE 22

Clone B58 nucleic acid sequences with leader sequence and cut sites added

| Sequence | SEQ ID NO: |
|---|---|
| B58 Heavy Chain | |
| AAGCTTGCCGCCACCATGGAATGGAGCTGGGTGTTCCTGTTCT TTTCTGTCCGTGACCACAGGCGTGCATTCTCAGGTCCAGCTGCA GCAGTCTGGAGCTGAGCTGGTGGTCAGCCTGGGACTTCAGTGAA GGTGTCCTGCAAGGCTTCTGGAGACGCCTTCACTAATTACTTG ATCGAGTGGGTAAAGCAGAGGCCTGGACAGGGCCTTGAGTGG ATTGGACTGATTATTCCTGGAACTGGTTATACTAACTACAATG AGAACTTCAAGGGCAAGGCAACACTGACTGCAGACAAATCCT CCAGCACTGCCTACATGCAGCTCAGCAGCCTGACATCTGAGGA CTCTGCGGTCTATTTCTGTGCAAGAAGATTTGGTTACTACGGT AGTAGCAACTACTTTGACTACTGGGGCCAAGGCACCACTCTCA CAGTCTCCTCAGCCTCCACCAAGGGCCC | 120 |

TABLE 22-continued

Clone B58 nucleic acid sequences with leader sequence and cut sites added

| Sequence | SEQ ID NO: |
|---|---|
| B58 Light Chain | |
| AAGCTTGCCGCCACCATGTCTGTGCCTACCCAGGTGCTGGGAC TGCTGCTGCTGTGGCTGACAGACGCCCGCTGTGATGTTGTGAT GACCCAAACTCCACTCTCCCTGCCTGTCAGTCTTGGAGATCAA GCCTCCATCTCTTGCAGATCTAGTCAGAGCCTTGTACACAGTA ATGGAAACACCTATTTACATTGGTACCTGCAGAAGCCAGGCCA GTCTCCAAAGCTCCTGATCTACAAAGTTTCCAACCGATTTTCTG GGGTCCCAGACAGGTTCAGTGGCAGTGGACCAGGGACAGATT TCACACTCAAGATCAGCAGAGTGGAGGCTGAGGATCTGGGAA TTTATTTCTGCTCTCAAAGTACACATTTTCCATTCACTTTCGGC ACGGGGACAAAATTGGAAATAAAACGTACG | 121 |

TABLE 23

Clone B58 amino acid sequences with leader sequence and cut sites added

| Sequence | SEQ ID NO: |
|---|---|
| B58 Heavy Chain | |
| KLAATMEWSWVFLFFLSVTTGVHSQVQLQQSGAELVRPGTSVK VSCKASGDAFTNYLIEWVKQRPGQGLEWIGLIIPGTGYTNYNENF KGKATLTADKSSSTAYMQLSSLTSEDSAVYFCARRFGYYGSSNY FDYWGQGTTLTVSSASTKG | 122 |
| B58 Light Chain | |
| KLAATMSVPTQVLGLLLLWLTDARCDVVMTQTPLSLPVSLGDQ ASISCRSSQSLVHSNGNTYLHWYLQKPGQSPKLLIYKVSNRFSGV PDRFSGSGPGTDFTLKISRVEAEDLGIYFCSQSTHFPFTFGTGTKLE IKRT | 123 |

TABLE 24

Clone 3A6 nucleic acid sequences with leader sequence and cut sites added

| Sequence | SEQ ID NO: |
|---|---|
| 3A6 Heavy Chain | |
| AAGCTTGCCGCCACCATGGAATGGAGCTGGGTGTTCCTGTTCT TTCTGTCCGTGACCACAGGCGTGCATTCTCAGGTCCAGCTGCA GCAGTCTGGAGCTGAGCTGGTCAGGCCTGGGACTTCAGTGAA GTTGTCCTGCAAGGCTTCTGGAGACGCCTTCACTAATTACTTG ATCGAGTGGGTAAAGCAGAGGCCTGGACAGGGCCTTGAGTGG ATTGGACTGATTATTCCTGGAACTGGTTATACTAACTACAATG AGAACTTCAAGGGCAAGGCAACACTGACTGCAGACAAGTCCT CCAGCACTGCCTACATGCAGCTCAGCAGCCTGACATCTGAGGA CTCTGCGGTCTATTTCTGTGCAAGAAGATTTGGTTACTACGGT AGTGGCTACTACTTTGACTACTGGGGCCAAGGCACCACTCTCA CAGTCTCCTCAGCCTCCACCAAGGGCCC | 124 |
| 3A6 Light Chain | |
| AAGCTTGCCGCCACCATGTCTGTGCCTACCCAGGTGCTGGGAC TGCTGCTGCTGTGGCTGACAGACGCCCGCTGTGATGTTGTGAT GACCCAAACTCCACTCTCCCTGCCTGTCAGTCTTGGAGATCAA GCCTCCATCTCTTGCAGATCTAGTCAGAGCCTTGTACACAGTA ATGGAAACACCTATTTACATTGGTACCTGCAGAAGCCAGGCCA GTCTCCAAAGCTCCTGATCTACAAAGTTTCCAACCGATTTTCTG GGGTCCCAGACAGGTTCAGTGGCAGTGGACCAGGGACAGATT TCACACTCAAGATCAGCAGAGTGGAGGCTGAGGATCTGGGAG TTTATTTCTGCTCTCAAAGTACACATTTTCCATTCACGTTCGGC ACGGGCACAAAATTGGAAATAAAACGTACG | 125 |

TABLE 25

Clone 3A6 amino acid sequences with leader sequence and cut sites added

| Sequence | SEQ ID NO: |
|---|---|
| 3A6 Heavy Chain | |
| KLAATMEWSWVFLFFLSVTTGVHSQVQLQQSGAELVRPGTSVKL SCKASGDAFTNYLIEWVKQRPGQGLEWIGLIIPGTGYTNYNENFK GKATLTADKSSSTAYMQLSSLTSEDSAVYFCARRFGYYGSYYF DYWGQGTTLTVSSASTKG | 126 |
| 3A6 Light Chain | |
| KLAATMSVPTQVLGLLLLWLTDARCDVVMTQTPLSLPVSLGDQ ASISCRSSQSLVHSNGNTYLHWYLQKPGQSPKLLIYKVSNRFSGV PDRFSGSGPGTDFTLKISRVEAEDLGVYFCSQSTHFPFTFGTGTKL EIKRT | 127 |

TABLE 26

Clone A63 nucleic acid sequences with leader sequence and cut sites added

| Sequence | SEQ ID NO: |
|---|---|
| A63 Heavy Chain | |
| AAGCTTGCCGCCACCATGGAATGGAGCTGGGTGTTCCTGTTCT TTCTGTCCGTGACCACAGGCGTGCATTCTGATATACAGCTTCA GGAGTCAGGACCTGGCCTCGTGAAACCTTCTCAGTCTCTGTCT CTCACCTGCTCTGTCACTGGCTTCTCCATCACCAGTGGTTATTA CTGGACCTGGATCCGGCAGTTTCCAGGAAACAAACTGGAGTG GGTGGCCTACATAGGCTACGATGGTAGCAATGACTCCAACCCA TCTCTCAAAAATCGAATCTCCATCACCCGTGACACATCAAGA ACCAGTTTTTTCCTGAAGTTGAATTCTGTGACTACTGAGGACAC AGCCACATATTACTGTGCAAGAGCGATGTTGCGGCGAGGATTT GACTACTGGGGCCAAGGCACCACTCTCACAGTCTCCTCAGCCT CCACCAAGGGCCC | 128 |
| A63 Light Chain | |
| AAGCTTGCCGCCACCATGTCTGTGCCTACCCAGGTGCTGGGAC TGCTGCTGCTGTGGCTGACAGACGCCCGCTGTCAAATTGTTCT CACCCAGTCTCCAGCAATCATGTCTCCATCTCCAGGGGAGAAG GTCACCATGACCTGCAGTGCCAGCTCAAGTTTAAGTTACATGC ACTGGTACCAGCAGAAGCCAGGCACCTCCCCCAAAAGATGGA TTTATGACACATCCAAACTGGCTTCTGGAGTCCCTGCTCGCTTC AGTGGCAGTGGGTCTGGGACCTCTTATTCTCTCACAATCAGCA GCATGGAGGCTGAAGATGCTGCCACTTATTACTGCCATCAGCG GAGTAGTTACACGTTCGGAGGGGGGACCAAGCTGGAAATAAA ACGTACG | 129 |

TABLE 27

Clone A63 amino acid sequences with leader sequence and cut sites added

| Sequence | SEQ ID NO: |
|---|---|
| A63 Heavy Chain | |
| KLAATMEWSWVFLFFLSVTTGVHSDIQLQESGPGLVKPSQSLSLT CSVTGFSITSGYYWTWIRQFPGNKLEWVAYIGYDGSNDSNPSLK NRISITRDTSKNQFFLKLNSVTTEDTATYYCARAMLRRGFDYWG QGTTLTVSSASTKG | 130 |

TABLE 27-continued

Clone A63 amino acid sequences with leader sequence and cut sites added

| Sequence | SEQ ID NO: |
|---|---|
| A63 Light Chain | |
| KLAATMSVPTQVLGLLLLWLTDARCQIVLTQSPAIMSASPGEKVT MTCSASSSLSYMHWYQQKPGTSPKRWIYDTSKLASGVPARFSGS GSGTSYSLTISSMEAEDAATYYCHRRSSYTFGGGTKLEIKRT | 131 |

For purposes of convenience, Tables 28-32 below are provided to show the amino acid sequences of the anti-LPA antibody variable domains shown in Tables 19-27 (odd numbered tables), without the leader and cut sites.

TABLE 28

Clone B3 variable domain amino acid sequences without leader sequence and cut sites

| Sequence | SEQ ID NO: |
|---|---|
| B3 Heavy Chain | |
| QVKLQQSGPELVRPGTSVKVSCTASGDAFTNYLIEWVKQRPGQG LEWIGLIYPDSGYINYNENFKGKATLTADRSSSTAYMQLSSLTSE DSAVYFCARRFAYYGSGYYFDYWGQGTTLTVSS | 132 |
| B3 Light Chain | |
| DVVMTQTPLSLPVSLGDQASISCRSSQSLLKTNGNTYLHWYLQKP GQSPKLLIFKVSNRFSGVPDRFSGSGSGTDFTLKISRVEAEDLGVY FCSQSTHFPFTFGTGTKLEIK | 133 |

TABLE 29

Clone B7 variable domain amino acid sequences without leader sequence and cut sites

| Sequence | SEQ ID NO: |
|---|---|
| B7 Heavy Chain | |
| QVQLQQSGAELVRPGTSVKVSCKASGYGFINYLIEWIKQRPGQGL EWIGLINPGSDYTNYNENFKGKATLTADKSSSTAYMHLSSLTSED SAVYFCARRFGYYGSGNYFDYWGQGTTLTVSS | 134 |
| B7 Light Chain | |
| DVVMTQTPLSLPVSLGDQASISCTSGQSLVHINGNTYLHWYLQKP GQSPKLLIYKVSNLFSGVPDRFSGSGSGTDFTLKISRVEAEDLGVY FCSQSTHFPFTFGTGTKLEIK | 135 |

TABLE 30

Clone B58 variable domain amino acid sequences without leader sequence and cut sites

| Sequence | SEQ ID NO: |
|---|---|
| B58 Heavy Chain | |
| QVQLQQSGAELVRPGTSVKVSCKASGDAFTNYLIEWVKQRPGQG LEWIGLIIPGTGYTNYNENFKGKATLTADKSSSTAYMQLSSLTSE DSAVYFCARRFGYYGSSNYFDYWGQGTTLTVSS | 136 |

TABLE 30-continued

Clone B58 variable domain amino acid sequences without leader sequence and cut sites

| Sequence | SEQ ID NO: |
|---|---|
| B58 Light Chain | |
| DVVMTQTPLSLPVSLGDQASISCRSSQSLVHSNGNTYLHWYLQK PGQSPKLLIYKVSNRFSGVPDRFSGSGPGTDFTLKISRVEAEDLGI YFCSQSTHFPFTFGTGTKLEIK | 137 |

TABLE 31

Clone 3A6 variable domain amino acid sequences without leader sequence and cut sites

| Sequence | SEQ ID NO: |
|---|---|
| 3A6 Heavy Chain | |
| QVQLQQSGAELVRPGTSVKLSCKASGDAFTNYLIEWVKQRPGQG LEWIGLIIPGTGYTNYNENFKGKATLTADKSSSTAYMQLSSLTSE DSAVYFCARRFGYYGSGYYFDYWGQGTTLTVSS | 138 |
| 3A6 Light Chain | |
| DVVMTQTPLSLPVSLGDQASISCRSSQSLVHSNGNTYLHWYLQK PGQSPKLLIYKVSNRFSGVPDRFSGSGPGTDFTLKISRVEAEDLGV YFCSQSTHFPFTFGTGTKLEIK | 139 |

TABLE 32

Clone A63 variable domain amino acid sequences without leader sequence and cut sites

| Sequence | SEQ ID NO: |
|---|---|
| A63 Heavy Chain | |
| DIQLQESGPGLVKPSQSLSLTCSVTGFSITSGYYWTWIRQFPGNKL EWVAYIGYDGSNDSNPSLKNRISITRDTSKNQFFLKLNSVTTEDT ATYYCARAMLRRGFDYWGQGTTLTVSS | 140 |
| A63 Light Chain | |
| QIVLTQSPAIMSASPGEKVTMTCSASSSLSYMHWYQQKPGTSPKR WIYDTSKLASGVPARFSGSGSGTSYSLTISSMEAEDAATYYCHRR SSYTFGGGTKLEIK | 141 |

Example 9

Lpath's Lead Murine Antibody, Lpathomab™ (LT3000)—Overview

Murine antibody clone B7 was chosen as the lead compound and renamed Lpathomab™, also known as LT3000. As described above, this murine anti-LPA mAb, was derived from a hybridoma cell line following immunization of mice with a protein-derivatized LPA immunogen. A hybridoma cell line with favorable properties was identified and used to produce a monoclonal antibody using standard hybridoma culture techniques.

Applicant has performed a comprehensive series of preclinical efficacy studies to confirm the potential therapeutic utility of an anti-LPA-antibody-based approach. It is believed that antibody neutralization (e.g., reduction in effective concentration) of extracellular LPA could result in a marked decrease in disease progression in humans. For cancer, LPA neutralization could result in inhibition of tumor proliferation and the growing vasculature needed to support tumor growth. Furthermore, recent research suggests that many angiogenesis inhibitors may also act as anti-invasive and anti-metastatic compounds that could also mitigate the spread of cancer to sites distant from the initial tumor. For fibrosis, LPA neutralization could result in a reduction of the inflammation and fibrosis associated with the aberrant wound-healing response following tissue injury. Thus, Lpathomab™ could have several mechanisms of action, including:

- A direct effect on tumor cell growth, migration and susceptibility to chemotherapeutic agents
- An indirect effect on tumors through anti-angiogenic effects
- An additional indirect effect on tumors by preventing the release and neutralization of synergistic pro-angiogenic growth factors
- A direct effect on proliferation, migration, and transformation of fibroblasts to the myofibroblast phenotype and collagen production by myofibroblasts
- An indirect effect on tissue fibrosis by preventing the expression and release of synergistic pro-angiogenic, pro-inflammatory and pro-fibrotic growth factors Example 10

Biophysical Properties of Lpathomab/LT3000

Lpathomab/LT3000 has high affinity for the signaling lipid LPA ($K_D$ of 1-50 pM as demonstrated by surface plasmon resonance in the BiaCore assay, and in a direct binding ELISA assay); in addition, LT3000 demonstrates high specificity for LPA, having shown no binding affinity for over 100 different bioactive lipids and proteins, including over 20 bioactive lipids, some of which are structurally similar to LPA. The murine antibody is a full-length IgG1k isotype antibody composed of two identical light chains and two identical heavy chains with a total molecular weight of 155.5 kDa. The biophysical properties are summarized in Table 33.

TABLE 33

General Properties of Lpathomab (LT3000)

| Identity | LT3000 |
| --- | --- |
| Antibody isotype | Murine IgG1k |
| Specificity | Lysophosphatidic acid (LPA) |
| Molecular weight | 155.5 kDa |
| OD of 1 mg/mL | 1.35 (solution at 280 nm) |
| $K_D$ | 1-50 pM |
| Apparent Tm | 67° C. at pH 7.4 |
| Appearance | Clear if dissolved in 1x PBS buffer (6.6 mM phosphate, 154 mM sodium chloride, pH 7.4) |
| Solubility | >40 mg/mL in 6.6 mM phosphate, 154 mM sodium chloride, pH 7.4 |

Lpathomab has also shown biological activity in preliminary cell based assays such as cytokine release, migration and invasion; these are summarized in Table 34 along with data showing specificity of LT3000 for LPA isoforms and other bioactive lipids, and in vitro biological effects of LT3000.

TABLE 34

LT3000 (Lpathomab, B7 antibody)

| A. Competitor Lipid | 14:0 LPA | 16:0 LPA | 18:1 LPA | 18:2 LPA | 20:4 LPA |
| --- | --- | --- | --- | --- | --- |
| $IC_{50}$ (μM) | 0.105 | 0.483 | >2.0 | 1.487 | 0.161 |
| MI (%) | 61.3 | 62.9 | 100 | 100 | 67 |

| B. Competitor Lipid | LPC | S1P | C1P | Cer | DSPA |
| --- | --- | --- | --- | --- | --- |
| MI (%) | 0 | 2.7 | 1.0 | 1 | 0 |

| C. Cell based assay | LPA isoform | % Inhibition (over LPA taken as 100) |
| --- | --- | --- |
| Migration | 18:1 | 35* |
| Invasion | 14:0 | 95* |
| IL-8 Release | 18:1 | 20 |
| IL-6 Release | 18:1 | 23* |
| | | % Induction (over LPA + TAXOL taken as 100) |
| Apoptosis | 18:1 | 79 |

A. Competition ELISA assay was performed with Lpathomab and 5 LPA isoforms. 18:1 LPA was captured on ELISA plates. Each competitor lipid (up to 10 μM) was serially diluted in BSA/PBS and incubated with 3 nM Lpathomab. Mixtures were then transferred to LPA coated wells and the amount of bound antibody was measured.
B. Competition ELISA was performed to assess specificity of Lpathomab. Data were normalized to maximum signal ($A_{450}$) and were expressed as percent inhibition (n = 3). $IC_{50}$: half maximum inhibition concentration; MI %: maximum inhibition (% of binding in the absence of inhibitor).
C. Migration assay: Lpathomab (150 μg/mL) reduced SKOV3 cell migration triggered by 1 μM LPA (n = 3); Invasion assay: Lpathomab (15 mg/mL) blocked SKOV3 cell invasion triggered by 2 μM LPA (n = 2); Cytokine release of human IL-8 and IL-6: Lpathomab (300-600 μg/mL, respectively) reduced 1 μM LPA-induced release of pro-angiogenic and metastatic IL-8 and IL-6 in SKOV3 conditioned media (n = 3). Apoptosis: SKOV3 cells were treated with 1 μM Taxol; 1 μM LPA blocked Taxol induced caspase-3 activation. The addition to Lpathomab (150 μg/mL) blocked LPA-induced protection from apoptosis (n = 1). Data Analysis: Student-t test, *denotes p < 0.05.

The potent and specific binding of Lpathomab/LT3000 to LPA results in reduced availability of extracellular LPA with potentially therapeutic effects against cancer-, angiogenic- and fibrotic-related disorders.

A second murine anti-LPA antibody, B3, was also subjected to binding analysis as shown in Table 35.

TABLE 35

Biochemical characteristics of B3 antibody

| A. BIACORE | | High density surface | Low density surface |
| --- | --- | --- | --- |
| Lipid Chip | | 12:0 LPA | 18:0 LPA |
| $K_D$ (pM), site 1 (site2) | | 61(32) | 1.6 (0.3) |
| B. Competition Lipid Cocktail ($C_{16}$:$C_{18:1}$:$C_{18:2}$:$C_{20:4}$, ratio 3:2:5:11:2) | | (μM) | |
| $IC_{50}$ | | 0.263 | |
| C. Neutralization Assay | | | |
| B3 antibody (nmol) | | LPA (nmol) | |
| 0 | | 0.16 | |
| 0.5 | | 0.0428 | |
| 1 | | 0.0148 | |
| 2 | | under limit of detection | |

A. Biacore analysis for B3 antibody. 12:0 and 18:0 isoforms of LPA were immobilized onto GLC sensor chips; solutions of B3 were passed over the chips and sensograms were obtained for both 12:0 and 18:0 LPA chips. Resulted sensograms showed complex binding kinetics of the antibody due to monovalent and bivalent antibody binding capacities. $K_D$ values were calculated approximately for both LPA 12 and LPA 18.
B. Competition ELISA assay was performed with B3 and a cocktail of LPA isoforms ($C_{16}$:$C_{18:1}$:$C_{18:2}$:$C_{20:4}$ in ratio 3:2:5:11:2). Competitor/Cocktail lipid (up to 10 μM) was serially diluted in BSA/PBS and incubated with 0.5 μg/mL B3. Mixtures were then transferred to a LPA coated well plate and the amount of bound antibody was measured. Data were normalized to maximum signal ($A_{450}$) and were expressed as $IC_{50}$ (half maximum inhibition concentration).
C. Neutralization assay: Increasing concentrations of B3 were conjugated to a gel. Mouse plasma was then activated to increase endogenous levels of LPA. Activated plasma samples were then incubated with the increasing concentrations of the antibody-gel complex. LPA leftover which did not complex to the antibody was then determined by ELISA. LPA was sponged up by B3 in an antibody concentration dependent way.

Selected studies conducted with Lpathomab/LT3000/B7 and B3 are described in the following examples.

Example 11

Lpathomab™ in Cancer and Angiogenesis Models

The pleiotropic effects of LPA suggest that reduced availability (effective concentration) of extracellular LPA will (i) reduce growth, metastasis and angiogenesis of primary tumors and (ii) counter-act LPA's protective anti-apoptotic effect on tumor. Because of Lpathomab™/LT3000's potent and specific binding to LPA, we hypothesized that in vivo treatment of LT3000 in preclinical models of cancer would result in various therapeutic benefits.

Preclinical studies were conducted using a variety of in vitro and in vivo systems, demonstrating that Lpathomab™/LT3000 (administered every 3 days at doses of 10-50 mg/kg) exhibits a profile of activity that is consistent with various mechanisms of action, including:

Inhibition of tumor growth in human tumor xenograft models in vivo;

Reduction in LPA-dependent cell proliferation and invasion of human tumor in vitro;

Reduction in angiogenesis, together with reductions in circulating levels of tumorigenic/angiogenic growth factors including IL6, IL8, GM-CSF, MMP2 in vivo;

Reduced metastatic potential; and

Neutralization of LPA-induced protection against tumor-cell death.

In In Vitro Models:

Reduced proliferation of OVCAR3 ovarian cancer cells;

Neutralization of LPA-induced release of IL-8 from Caki-1, IL-8 and IL-6 from SKOV3 (ovarian) tumor cells in vitro;

Mitigation of LPA's effects in protecting SKOV3 tumor cells from apoptosis (which suggests enhanced efficacy when used in combination with standard chemotherapeutic agents);

Inhibition of LPA-induced tumor cell migration and invasion from chemotherapeutic agents.

In In Vivo Models:

Inhibition of metastasis and progression of orthotopic and subcutaneous human tumors implanted in nude mice;

Reduction of tumor-associated angiogenesis in subcutaneous SKOV3 xenograft models and in prostate DU145 cancer cells;

Neutralization of bFGF- and VEGF-induced angiogenesis in the murine Matrigel plug assay (see example below); and Reduced choroidal neovascularization in a model of laser-induced injury of Bruch's membrane in the eye (see example below).

Example 12

Anti-Angiogenic Efficacy of LT3000 in the Matrigel Model

LT3000 administered q2d by intraperitoneal (IP) injection mitigates FGF- and VEGF-induced vascularization of Matrigel plugs implanted in female C57BL/6 mice. This study was conducted at Southern Research Institute (Birmingham, Ala.).

Objective.

To determine the anti-angiogenic efficacy of LT3000 to retard vascularization of FGF— and VEGF-supplemented Matrigel plugs implanted in female C57/BL6 mice.

Study Design.

Matrigel alone or supplemented with bFGF or VEGF (N=5 mice/treatment group) was injected subcutaneously (SC) into the flank of each mouse. One day prior to Matrigel-plug implantation, treatment with 10 mg/kg of LT3000 or saline was initiated by IP administration. Treatments were administered every other day (q2d). Upon sacrifice, the Matrigel plugs were harvested and processed for microvascular density (MVD) analysis by CD-31 staining.

Results.

Microvascular density was reduced by approximately 41% in bFGF— and VEGF-supplemented plugs in mice treated with LT3000 when compared with mice treated with saline. This reduction was statistically significant ($p<0.0001$) and was confirmed histologically by CD31 staining.

Conclusion.

This study shows that the anti-angiogenic efficacy of systemically administered LT3000 resulted in a significant decrease in neovascularization of Matrigel plugs supplemented with bFGF and VEGF.

Example 13

Anti-Angiogenic Efficacy of LT3000 in the CNV Model

LT3000 administered by intravitreal injection reduced choroidal neovascularization in a model of laser-induced injury of Bruch's membrane in female C57BL/6 mice. This study was performed at the University of Florida, Gainesville (laboratory of Maria Grant, M.D.).

Objective.

To investigate the efficacy of LT3000 to limit new blood-vessel formation in choroidal vasculature.

Study Design.

Mice were subjected to laser-induced ruptures of Bruch's membrane. Mice were treated with 0.5 µg of the anti-LPA antibody LT3000, 0.5 µg of an isotype-matched non-specific monoclonal antibody (NSA) or an equal volume of saline.

Treatments were administered by intravitreal injection after laser rupture and once per week (q7d) for the duration of the study. Two to four weeks after rupture of Bruch's membrane, the mice were sacrificed and their eyes removed. The RPE-choroid-sclera complex was isolated from the neural retina and stained with rhodamine-conjugated R. communis agglutinin I to evaluate CNV. All determinations were performed for 2 to 3 burns per animal.

Results.

Vascularization of CNV lesions was reduced from 2185014±377010 (mean CNV volume±SEM) to 697924±92182 in mice treated with LT3000 (n=5) when compared with NSA-treated mice (n=4). This is a 68% reduction in the LT3000-treated mice compared to NSA-treated mice ($p \leq 0.05$).

Conclusion.

This study shows that intravitreal administration of anti-LPA antibody significantly reduced new blood-vessel formation in choroidal tissue in response to injury.

Example 14

Anti-Tumorigenic Efficacy of LT3000

A. Human COLO205 Colorectal Cancer

LT3000 administered by IP injection (30 mg/kg q3d) inhibited tumor progression in a subcutaneous COLO205 (colorectal) tumor xenograft in nude Ncr mice. This study was conducted at Southern Research Institute (Birmingham, Ala.).

Objective.

To determine the efficacy of LT3000 alone to retard the progression of human colorectal (COLO205) carcinoma tumors grafted subcutaneously (sc) and established in female Ncr (nu/nu) mice.

Study Design.

Nude mice were engrafted sc with COLO205 tumor fragments and tumors were allowed to establish. The mice were then treated with either 30 mg/kg of LT3000, 40 mg/kg Avastin™, 15 mg/kg Paclitaxel™ or vehicle (saline). LT3000 was administered every three days (q3d) by IP injection, Avastin™ was administered every 7 days (q7d) and Paclitaxel was administered every day for 5 days (qldx5) by ip injection. During the course of the study tumor growth was monitored by measuring the sc tumors on three axes and calculating the weight.

Results.

LT3000 significantly inhibited tumor progression by 27% when compared with tumors from saline-treated animals. One animal from the LT3000 group was sacrificed at day 42 due to ulcerations and was taken out from the final data set analysis. Data were analyzed at day 52 when all animals were alive. LT3000 showed efficacy (*p<0.05) in reducing final tumor weights as well as Avastin (**p<0.01, 31% reduction). The positive control, Paclitaxel, eliminated the pre-established tumors starting from day 28.

Conclusion.

The study suggests that systemic administration of anti-LPA antibody can inhibit tumor progression of COLO205 tumor cells.

TABLE 36

Numerical summary of findings for the murine COLO205 xenograft model to assess the anti-tumorigenic activity of LT3000

| Analysis | Mean tumor weight (mg) ±SD | Significance (p-value) | % Reduction compared to Vehicle-Treated Mice |
|---|---|---|---|
| Vehicle | 2444 ± 623.1 (n = 10) | N/A | N/A |
| LT3000* | 1777 ± 419.3 (n = 9) | p = 0.015 | 27 |

*Mean ± SD.
[*p < 0.05]

D. Allograft Melanoma Metastasis Model

1. This model measured the response of murine melanoma C56Bl/6 mice to treatment with 50 mg/kg LT3000 alone administered q3d by intraperitoneal injection. This study was conducted at Lpath.

Objective.

To determine the efficacy of LT3000 to reduce the progression of pulmonary metastases induced by the murine melanoma cell line B16-F10.

Study Design.

C57BL/6 mice were injected with a suspension of B16-F10 tumors cells intravenously (IV) by tail vein. After randomization, animals were divided into two groups and treated with vehicle (saline) or 10 mg/kg of LT3000 administered via IP q3d, starting the day of cell inoculation. After 20 days, animals were sacrificed, plasma samples were collected by heart puncture and lungs were isolated. Final lung weights were determined and correlated to body weights. In addition, the peritoneal cavity and organs (liver, stomach, ovaries, intestine etc.) of each animal were analyzed for the presence of metastatic foci as well.

Results.

The metastatic volume in the lungs was reduced by 27% in the LT3000-treated mice versus the saline-treated mice, as shown in Table 37.

Conclusion.

The study shows that systemic administration of anti-LPA antibody can result in the reduction of B16-F10 pulmonary metastases.

TABLE 37

Numerical summary of findings for the murine melanoma model to assess the anti-metastatic activity of LT3000

| Analysis | Saline-Treated Mice* | LT3000-Treated Mice* | Percentage Reduction |
|---|---|---|---|
| Pulmonary Index lung weight (mg)/body weight (g) | 67.00 ± 4.35 (n = 11) | 48.57 ± 6.44 (n = 9)# | 27.5% |

*Mean ± SD.
[p < 0.002]

2. Anti-LPA murine monoclonal antibody B3 was also tested in this classical experimental model of tumor metastasis to determine its efficacy to retard the metastatic progression of the murine melanoma cell line B16-F10 in the lungs of C57Bl/6 mice.

Objective.

To determine the efficacy of B3 to reduce the progression of pulmonary metastasis induced by the murine melanoma cell line B16-F10. This model measured the response of murine melanoma C56Bl/6 mice in treatment with 50 mg/kg B3 antibody administered q3d by intraperitoneal injection. This study was conducted at Lpath.

Study Design.

C57Bl/6 mice were inoculated IV with $5 \times 10^4$ B16-F10 melanoma tumor cells in order to seed the lungs and initiate formation of metastatic foci. Treatments with vehicle (PBS) and 10 mg/kg of B3 were started on the same day and administered every three days. At the end of the study animals were sacrificed, body weights and lung weights (as a measure of metastatic volume) were recorded.

Results.

Metastatic progression of the B16-F10 melanoma cells into lungs, measured as a ratio of lung weight over body weight (metastatic index; Welch, D. R. (1997) Clin. Exp. Metastasis 15:272-306) was decreased in the antibody-treated animals when compared to vehicle controls, showing the administration of B3 resulted in a 54% reduction in lung metastasis. In a similar experiment using the other murine mAb, Lpathomab (B7) (50 mg/kg, q3d) the reduction in lung metastatic volume was 39.5%. The benefits observed following anti-LPA antibody treatment indicate that molecular absorption of LPA may represent an innovative approach to block tumor metastasis.

Conclusions.

The study suggests that neutralization of LPA by systemic administration of Lpathomab can result in the reduction of B16-F10 pulmonary metastasis.

Example 15

Anti-Fibrosis Activity of Lpathomab (LT3000) in Lung Fibroblasts

Cell Culture and Reagents.

WI-38 human lung fibroblasts were purchased from ATCC (Manassas, Va.). Lung fibroblasts were maintained at 37° C. in 5% $CO_2$ in minimum essential medium supplemented with 10% fetal bovine serum (FBS) and Penicillin/Streptomycin (100 units/ml). Alpha-smooth muscle actin (α-SMA) and FAK Y397 antibodies were purchased from Sigma (St. Louis, Mo.). LPA was purchased from Avanti Polar Lipids (Alabaster, Ala.) and prepared according to manufacturer's recommendations.

PCR.

Cells from a single, confluent T150 flask were removed using trypsin, pelleted by centrifugation and frozen at −80° C. for RNA isolation. Total RNA isolation was performed using the Qiagen RNeasy Mini Kit (Qiagen, Valencia, Calif.) following the manufacturer's protocol for total RNA isolation in animal cells. Briefly, two micrograms of total RNA was used to make first-strand cDNA using Superscript III First-Strand Synthesis System for RT-PCR (Invitrogen; Carlsbad, Calif.) according to the manufacturer's protocol using random hexamers as the first strand primer. Two microliters of first-strand cDNA were amplified using oligos for $LPA_{1-3}$ receptors and GAPDH was a control in each reaction. PCR was set up using Platinum Pfx DNA Polymerase (Invitrogen; Carlsbad, Calif.). PCR products were then run on a 1% agarose gel and imaged using UVP BioImaging Systems EpiChemi$^3$ Darkroom with ethidium bromide filter (UVP Inc. Upland, Calif.).

Cell Proliferation, Collagen Production and α-SMA Expression by Cell-Based ELISA.

Lung fibroblasts were plated overnight on 96 well plates at a density of $5 \times 10^3$ cells/well. Plated cells were serum-starved for 48 hr in basal media (Minimum Essential Media/0.1% Fatty acid free BSA/100 units/mL penicillin streptomycin) and then stimulated for 72 hr with basal media alone (control) or containing the indicated concentrations of LPA. Cell proliferation was assessed using the Cell Titer 96 Aqueous cell proliferation assay (Promega, Madison, Wis.) according to manufacturer's protocol. Absorbance was measured at OD450 and data are expressed as the fold change relative to control. Absorbance measurements were performed in quadruplicate. For collagen production, the concentration of C-Terminal Propeptide of Type I Collagen (PICP) in the conditioned media was measured with a PICP enzyme-linked immunosorbent assay (ELISA) kit, according to the manufacturer's protocol (TaKaRa Biochemicals Co., Osaka, Japan). For α-SMA expression, cell based ELISA was performed as previously described {Micera, 2005 #8093} with the following modifications. Cells were fixed in 10% neutral buffered formalin, permeabilized with PBS/0.1% Triton X-100 and endogenous peroxidases were quenched with 0.3% $H_2O_2$. The cell monolayer was blocked using PBS/10% FBS and then primary antibody to α-SMA was diluted in PBS/1% BSA/0.1% Tween 20 (1:1000 dilution) and incubated with cells overnight at 4° C. Following primary antibody incubation, plates were washed 3 times with of PBS/0.1% Tween and incubated with the HRP-conjugated goat anti-mouse antibody, diluted in PBS/1% BSA/0.1% Tween 20 (1:1000 dilution), for 1 hr at room temperature. Plates were washed 4 times with PBS and incubated with TMB calorimetric solution for 1-3 min. The reaction was stopped using an equal volume of 1M $H_2SO_4$ and absorbances were read on a plate reader at 450 nm. All cell proliferation, collagen Production and α-SMA expression assays were performed in triplicate.

Cell Migration.

Lung fibroblasts were plated overnight on 96 well plates at a density of $1.5 \times 10^4$ cells/well. Plated cells were synchronized for 24 hr in basal media (Minimum Essential Media/0.1% fatty acid free BSA/100 units/mL Penicillin Streptomycin). At time 0, cells were scratched with a p200 pipet tip down the center of each well, washed with minimal media and pictures were taken prior to treatment. Cells were then treated with LPA (C18:1) at 0.1-10 μM concentrations or positive control (10% FBS). Cells were stimulated for 17 hrs at 37° C. in a 5% $CO_2$ incubator. Pictures were again taken at 17 hr post-treatment and % wound closure was measured by adjusting pictures to the same size and measuring the width of the scratch at time 0 and time 17 hr with a ruler.

$LPA_{1-3}$ Receptor Expression and in Lung Fibroblasts.

RT-PCR analysis of lung fibroblasts revealed prominent expression of $LPA_{1-3}$ receptors, with $LPA_1$ and $LPA_3$ receptors being the most highly expressed.

LPA Stimulates Proliferation and Migration by Lungfibroblasts.

LPA is implicated in the regulation of wound healing. Therefore the dose-dependent effects of LPA on fibroblast proliferation and migration, two cellular mechanisms that contribute to wound repair, were examined. LPA stimulated fibroblast proliferation in a dose-dependent manner with a maximal increase at 10 μM LPA. The effects of LPA on cell migration were also investigated using an in vitro wound healing assay. In contrast to the dose-dependent increase in cell proliferation, LPA appeared to stimulate cell migration at the low (0.1 μM) LPA concentration. At increasing concentrations of LPA, a dose-dependent reduction in cell migration back to basal levels was observed. These data suggest that there is an inverse relationship between concentration-dependent effects of LPA proliferation and migration of lung fibroblasts.

LPA Promotes Myofibroblast Transformation and Collagen Type I Production by Lung Fibroblasts.

To assess the pro-fibrotic potential of LPA the lung, LPA-mediated stimulation of myofibroblast transformation and collagen type I production by lung fibroblasts was examined using ELISA and immunohistochemistry. LPA promoted α-SMA (myofibroblast marker) expression and pro-collagen type I C-terminal peptide (PICP) release in a dose-dependent manner resulting in maximal stimulation at the 10 μM LPA concentration. In addition, LPA increased the incorporation of α-SMA into cytoskeletal stress fibers and stimulated focal adhesion kinase ($FAK^{Y397}$) phosphorylation, events which are required for myofibroblast transformation. Consistently, these transformed cells also exhibited increased cellular expression of collagen type I following LPA stimulation, which is indicative of their transformation to the pro-fibrotic cellular phenotype.

Example 16

LT3000 Reduces Inflammation and Fibrosis Following Bleomycin Injury in Animals Animals.

Female, 20-25 g, C57BL/6J mice were obtained form Harlan. Animals were treated in accordance with the Bioquant (San Diego, Calif.) Institutional Animal Care and Use Committee (IACUC). Mice were housed in an air-conditioned room with a 12 hr light-dark cycle and given standard chow with free access to tap water. Animals were supplied with ad libitum access to normal chow (autoclaved) and water.

Induction of Lung Injury by Bleomycin.

Mice were anesthetized with a mixture of ketamine (20 mg/kg) and xylazine (2 mg/kg) and received a single intratracheal instillation (50 µl volume) of saline (0.9%) alone or containing bleomycin (2.5 mg/kg) via a 20 gauge feeding needle. Mice were killed 14 days later.

Experimental Groups.

Mice were randomly assigned to the following treatment groups. (i) Saline. Mice were subjected to intratracheal (IT) instillation of saline and received i.p injection of sterile PBS (vehicle). (ii) BLEO group. Mice were subjected to IT instillation of bleomycin and received i.p injection of sterile PBS (vehicle). (iii) BLEO+25 mg/kg group. Mice were subjected to IT instillation of bleomycin and received i.p injection of LT3000 (25 mg/kg). (iv) 25 mg/kg group. Mice were subjected to IT instillation of saline and received i.p injection of LT3000 (25 mg/kg). All antibody treatments were administered via intraperitoneal (i.p.) injection every 2 days. The effects of each treatment on body weight and mouse mortality were recorded over the study period.

Bronchioalveolar Lavage Fluid (BALF) Isolation.

Mice were killed and then mice intubated with a 20 gauge angiocatheter attached to a 1 ml syringe. The catheter was secured in place using nylon thread tied around the trachea. Lungs were lavaged once with 1.0 ml of saline and then again with 0.8 ml of saline. Lavages were pooled and the BALF was centrifuged for 5 min at 1200 rpm. The supernatant was removed and frozen at −80° C. for subsequent analysis. The pellet was re-suspended in 0.3 ml of PBS/2% fetal bovine serum and cells were sorted and counted by flow cytometry. Protein levels in the BALF were assessed using the BCA protein assay reagent (Pierce, Rockford, Ill.).

Analysis of BALF Cells by Flow Cytometry.

Individual populations of inflammatory cells were identified and quantitated using Trucount tubes (BD Biosciences, cat#340334) according to the manufacturer's protocol. Briefly, a single-cell suspension was prepared with staining buffer (PBS/2% FCS). Approximately 300 µl of the cell suspension was placed into 12×75 polypropylene Trucount tubes. Tubes were centrifuged at 250-300×g for 5 minutes at 4° C. Liquid was aspirated using a pipet, being careful not to disturb the pellet. The following monoclonal antibodies were then added to each tube. PE-conjugated anti-CD16 (BD Biosciences cat#555407), FITC-conjugated anti-CD14 (BD Biosciences cat #555397), and PE-Cy5-conjugated anti-CD5 (BD Biosciences cat #555354) to yield a three color cocktail. The antibody amount was provided by the manufacturer. The tubes were vortex and kept on ice in a covered bucket (in the dark) for approximately 30 minutes. The suspension was washed by adding 2 ml of staining buffer. The suspension was vortexed and then centrifuged at 250-300×g for 5 minutes at 4° C. to remove the supernatant. Step 6 was repeated 2 times. The pellet was then re-suspended in 1 ml of staining buffer and the individual cell populations were analyzed by Fluorescence Assisted Cell Sorting (FACS) analysis. For FACS analyses, stained cells were analyzed by flow cytometry using BD FACScan (San Jose, Calif.) with 1 laser (488 nm argon laser) and 3 detectors. 10,000 cells were collected, and data were analyzed with CellQuest version 3.3 software.

Histological Examination.

Lungs were excised, separated into individual lobes and fixed overnight in 10% buffered formalin at room temperature. Individual lobes were cut into 3 horizontal sections and embedded in paraffin. Lobes were sectioned at a thickness of 5 µm and stained with hematoxylin and eosin (H&E). All sections were studied by light microscopy (10× magnification) and the severity of fibrosis was semiquantitatively assessed suing the Ashcroft methods, as previously described (Ashcroft et al., (1988) J Clin Pathol. 41:467-70). Briefly, the severity of fibrosis in the horizontal sections from each lobe was scored on a scale from 0 to 8. The grading criterion are as follows: grade 0, normal lung; grade 1, minimal fibrous thickening of alveolar or bronchiolar walls; grade 3, moderate thickening of walls without obvious damage to lung architecture; grade 5, increased fibrosis with definite damage to lung structure and formation of fibrous bands or small fibrous masses; grade 7, severe distortion of structure and large fibrous areas; and grade 8, total fibrous obliteration of the fields. Values were averaged for the different sections from each lobe and then the values for all of the lobes were averaged to provide a representative fibrosis score for each animal.

Immunohistochemistry.

Lung sections were deparaffinized in 3 washes of Xylene (Richard Allen Scientific, Cat #9900) for 5 min each. Rehydration of slides was performed by a series of washes in alcohols for 5 min each: 100% alcohol (Richard Allen Scientific, Cat #8101), 95% alcohol (Richard Allen Scientific, Cat #8201), and 80% alcohol (Richard Allen Scientific, Cat #8301R). Rehydration was completed by washing slides in running tap water for 5 min. Exogenous peroxidases were then quenched for 13 min in 3% $H_2O_2$ (30% diluted in water, Sigma, Cat # H1009). $H_2O_2$ was removed by washing slides in running tap water for 15 min. Meanwhile, Citrate Buffer (10 mM Citric Acid, pH 6.0 (Fisher, Cat # A940)) was pre-warmed to 95° C. in a steamer (Black and Decker, Sku # HS900) for 40 min. For antigen retrieval slides were transferred to pre-warmed Citrate Buffer and heated for 35 min at 95° C. in the steamer. Subsequently, slides were washed twice for 5 min in PBS (Cellgro, Cat #21-040-CM). Slides were stained for α-smooth muscle actin (α-SMA) or connective tissue growth factor (CTGF) using Mouse IgG Vectastain ABC Kit (Vector, Cat #6102) or Goat IgG Vectastain ABC Kit (Vector, Cat # PK-6105) according to manufacturer's protocol. For all steps requiring a buffer, PBS was used. Avidin/Biotin Blocking Kit (Vector, Cat # SP-2001) was used in conjunction with ABC Kit to block endogenous biotin signals according to manufacturer's suggested protocol. Primary antibodies directed against α-Smooth Muscle Actin (Sigma, Cat # A2547) diluted 1:5000 or primary antibody directed again CTGC (Santa Cruz Biotechnology, Cat # sc-14939) diluted 1:50 were applied as directed. The signal was detected using Peroxidase Substrate Kit DAB (Vector, Cat # SK-4100) prepared as directed by the manufacturer and applied to slides for 2 min. Slides were washed in $diH_2O$. Counterstaining was performed by staining with Hematoxylin (Sigma, Cat # HHS32) for 30 sec. Slides were rinsed in tap water to remove Hematoxylin and then dehydrated by reversing the alcohol to xylenes used to hydrate them originally. Finally, slides were mounted with glass cover slips using 20 µl of Permount (Fisher, Cat # SP 15-100) per slide.

Data Analysis.

The study was completely blinded to all those collecting and analyzing the data until all data were finalized. Data was analyzed using GraphPad software. Statistical significance of the differences between experimental groups was calculated by an unpaired Student's t-test.

Results

LT3000 Reduces Inflammation and Fibrosis Following Bleomycin Injury.

Using the murine bleomycin model, we examined the role of LPA in pulmonary inflammation and fibrosis following lung injury and the efficacy of a novel, monoclonal mouse LPA antibody (LT3000) to mitigate these effects. Histological examination of mouse lungs following bleomycin-instillation revealed significant damage to the lung tissue, including thickening of the alveolar septae, pneumonitis and fibrous obliteration of the lung parenchyma. In mice treated with LT3000 there was a dramatic reduction in inflammation and fibrosis and maintenance of normal lung morphology. Semi-quantitative analysis of lung inflammation and fibrosis in these mice revealed a 56% and 48% reduction, respectively, in these parameters as a result of LT3000 treatment. No inflammation, fibrosis or changes in normal lung morphology were seen healthy mice treated with LT3000 alone.

LT3000 Reduces Cellularity and Protein Levels in BAL Fluid and Maintains Body Weight in Mice Following Bleomycin Lung Injury.

Consistent with the degree of tissue injury, the number of inflammatory cells was nearly double that of controls and the amount of protein in the BAL fluid of bleomycin-instilled mice was significantly increased about tenfold. Administration of LT3000 reduced the cellularity of BAL fluid by about 95%, both in control and bleomycin-treated mice. In addition, protein levels in the BAL fluid were decreased by 40% in bleomycin-instilled mice that received LT3000. Consistent with the degree of lung injury, a 16% reduction in body weight was observed in bleomycin-instilled mice, compared to control mice at the 14 day timepoint. In contrast, the body weights of bleomycin-instilled mice that were treated with LT3000 treated mice were not significantly different than controls.

LT3000 Decreases Macrophage and Myofibroblast Density in Lung Tissue Following Bleomycin Injury.

To further investigate the ability of LT3000 to reduce lung inflammation and fibrosis, we examined macrophage infiltration and myofibroblast density in mouse lung tissue. Similarly, myofibroblast density, as indicated by α-SMA staining, was increased in the fibrotic area of bleomycin-instilled mice. LT3000 treatment also decreased myofibroblast density, in the lungs of bleomycin-instilled mice. The effects on lung fibrosis and inflammation were confirmed following semi-quantitative grading of lung fibrosis (Ashcroft score) and inflammation (inflammatory score) using previously described methods. LT3000 treatment reduced lung fibrosis and inflammation by 48% and 56%, respectively.

Example 17

LT3000 Reduces Inflammation and Fibrosis Following Bleomycin Injury in an Interventional Study Findings outlined in the previous examples demonstrated both anti-inflammatory and anti-fibrotic effects of LT3000 in the bleomycin-induced lung fibrosis model. Therefore, additional studies were conducted to assess the ability of LT3000 to prevent or intervene in the progression of lung fibrosis following bleomycin injury. For this experiment, mice were randomly assigned to the following treatment groups (Table 38). (i) Saline. Mice were subjected to intratracheal (IT) instillation of saline and received i.p injection of sterile PBS (vehicle). (ii) BLEO group. Mice were subjected to IT instillation of bleomycin and received i.p injection of sterile PBS (vehicle). (iii) Prevention group. Mice were subjected to IT instillation of bleomycin and received i.p injection of LT3000 (50 mg/kg) q2d for 6 days starting on the same day as bleomycin instillation. (iv) Intervention group. Mice were subjected to IT instillation of bleomycin and received i.p injection of LT3000 (50 mg/kg) q2d starting on day 6 after bleomycin instillations. All antibody treatments were administered via intraperitoneal (i.p.) injection. At the termination of the study (day 14), mice were sacrificed and the effects of LT3000 on bleomycin-induced pulmonary inflammation and fibrosis were assessed as flows: (i) tissue fibrosis was assessed semi-quantitatively in H&E stained lung sections using the methods of Aschroft et al. (J Clin Pathol. 1988 April; 41(4): 467-70); (ii) inflammatory cells in Lung Lavage Fluid were measured using flow cytometry; (iii) protein levels in lung lavage fluid were assessed using the BCA protein assay reagent (Pierce, Rockford, Ill.) and (iv) body weight was measured in each mouse on day 14 after bleomycin instillation. A numerical summary of the effects of LT3000 on bleomycin-induced pulmonary inflammation and fibrosis is shown in Table 39.

TABLE 38

Dosing schedule.

| Intratracheal instillation | Treatment | Group (n) | Dose (mg/kg) | Number of Doses | Route | Treatment |
|---|---|---|---|---|---|---|
| Saline | PBS | 10 | — | 7 | IP | Start Day 0 q2d dosing |
| Bleomycin | PBS | 13 | — | 7 | IP | Start Day 0 q2d dosing |
| Bleomycin | Intervention | 13 | LT3000 (50 mg/kg) | 4 | IP | Start Day 0 End day 6 q2d dosing |
| Bleomycin | Prevention | 13 | LT3000 (50 mg/kg) | 4 | IP | Start Day 6 End day 12 q2d dosing |

TABLE 39

Summary of Pathophysiological Findings

| | Percent Reduction Compared to Bleomycin Alone | |
|---|---|---|
| | Prevention study | Intervention study |
| Tissue Fibrosis | 20% (p > 0.05) | 22% (p > 0.05) |
| Inflammatory cells in Lung Lavage Fluid | 50% (p < 0.01) | 41% (p < 0.05) |
| Protein Levels in Lung Lavage Fluid | 35% (p > 0.05) | 67% (p > 0.05) |
| Body weight | Same as saline control | Same as saline control |

Thus anti-LPA antibody (LT3000, Lpathomab) was shown to be effective both prophylactically and interventionally in a well-accepted animal model of pulmonary fibrosis. These findings demonstrate a profound role for the bioactive lipid LPA in the extracellular matrix production and tissue remodeling following injury. Furthermore these studies identify LPA as a novel clinical target in treating fibrosis associated with a number of diseases and organ systems. Monoclonal antibodies to LPA are believed to have great clinical potential for treatment of fibrosis.

Example 18

Modulation of Cytokines and Growth Factors by LT3000

There is a long-felt need for less invasive ways to monitor fibrosis (especially, but not limited to, lung and liver fibrosis)

than the biopsies that are currently the standard of care. Researchers have tried to correlate circulating levels of cytokines and growth factors with extent of fibrosis in order to allow less invasive monitoring of disease progression and/or of treatment efficacy through monitoring of markers for disease. See Morais et al. (2006) Mem Inst Oswaldo Cruz, Rio de Janeiro, Vol. 101(Suppl. I): 353-354. A method for detecting fibrosis is a patient sample by correlating LPA levels with levels of one or more fibrogenic markers (e.g., cytokines or growth factors) is believed to be useful for monitoring fibrosis in the clinical setting.

In order to further investigate the anti-inflammatory effects of LT3000, the level of cytokine and growth factors was assessed in BAL fluid using the pathways specific cytokine protein arrays (Raybiotech Inc., Norcross Ga.). Table 40 summarizes the preliminary (n=3) findings regarding inflammatory cytokines that exhibited the greatest degree of regulation by LT3000.

TABLE 40

Summary of Cytokine Expression Levels in BAL Fluid.

| Cytokine | Percent Reduction Compared to Bleomycin Alone | |
|---|---|---|
| | Prevention Study | Intervention Study |
| Interleukin 6 | 79% ($p > 0.05$) | ND |
| MIP-3 beta | 23% ($p > 0.05$) | 28% ($p > 0.05$) |
| Eotaxin | 63% ($p > 0.05$) | 53% ($p > 0.05$) |
| Interleukin 13 | 28% ($p > 0.05$) | 11% ($p > 0.05$) |
| Granulocyte-colony Stimulating Factor | 45% ($p > 0.05$) | 24% ($p > 0.05$) |
| Thymus and Activation-Regulated Chemokine (TARC) | 18% ($p > 0.05$) | ND |
| Tissue inhibitor of metalloproteinases-1 (TIMP-1) | 82% ($p < 0.01$) | 86% ($p < 0.01$) |
| Tumor necrosis factor-alpha (TNFa) | 82% ($p > 0.05$) | 86% ($p > 0.05$) |

(ND = No significant different compared to bleomycin-treated group)

It can be seen from Table 40 that mice with bleomycin lung injury demonstrated a decrease of IL-13 and TIMP-1 levels, as well as reduction in other relevant growth factors, after treatment with the anti-LPA antibody Lpathomab (LT3000) and consequent reduction in lung fibrosis. It is believed that the pattern of cytokine and growth factor levels shown in Table 40 is indicative of a decrease in fibrosis in response to treatment. Thus a panel of cytokine and growth factor changes, including those shown in Table 40, is believed to be a useful clinical assay and marker for effective treatment of fibrosis, including pulmonary fibrosis, e.g., with the anti-LPA agents of the invention. This would be a minimally invasive clinical assay, and less expensive and risky than tissue biopsy.

Example 19

LPA in Renal Fibrosis

Because LPA can mediate a number of processes involved in fibrosis and kidney disease, it and its receptors were studied in an animal model of renal fibrosis. The unilateral ureteral obstruction (UUO) model mimics the development of renal fibrosis in accelerated form, including inflammation, fibroblast activation and accumulation of extracellular matrix. J. P. Pradere et al., (2007) J. Am. Soc. Nephrol. 18:3110-3118, J.-P. Pradère, et al., Lysophosphatidic acid and renal fibrosis, Biochim. Biophys. Acta (2008), doi:10.106/j.bbalip.2008.04.001.

After UUO, $LPA_1$ receptor expression was induced and renal LPA production was increased 3.3-fold. This indicated a role for LPA and the $LPA_1$ receptor in renal fibrosis caused by the UUO. This was confirmed by the finding that the development of renal fibrosis in mice was attenuated in $LPA_1$−/− mutants. In a different, slower model of renal fibrosis, the nephrotoxic serum nephritis model, which more closely mimics the slow progression of human disease, $LPA_1$ expression was also increased. Thus the evidence points to a role for LPA in renal fibrosis and thus an anti-LPA agent such as the anti-LPA monoclonal antibodies of the invention is believed to be a good candidate for treatment of renal fibrosis.

Lpathomab (LT3000) is tested in the mouse UUO model according to Pradere et al., 2007. Reduction in inflammation and extracellular matrix after LT3000 treatment compared to control is examined histologically and quantitated.

Example 20

Humanization of Lpathomab (LT3000)

Materials 3,3',55'-tetramethylbenzidine liquid substrate (TMB) was from Sigma-Aldrich (St. Louis, Mo.). Fatty acid-free bovine serum albumin (BSA) was from Calbiochem (La Jolla, Calif.). Immobilized Protein A, Immobilized Papain and protein desalting spin column were from Pierce (Rockford, Ill.). Anti-human IgG (Fc specific) antibody was purchased from Bethyl (Montgomery, Tex.). Reference IgGs (non-specific human IgG and mouse IgG), anti-human IgG (H+ L)-horseradish peroxidase conjugate and anti-mouse IgG (H+ L)-horseradish peroxidase conjugate were from Jackson ImmunoResearch Laboratories (West Grove, Pa.). Lysophosphatidic acid (LPA) and other lipids used in the competition ELISA were purchased from Avanti Polar Lipids (Alabaster, Ala.). Biotinylated LPA was purchased from Echelon Biosciences (Salt Lake City, Utah).

Humanization of LT3000

The variable domains of the murine anti-LPA monoclonal antibody, LT3000 (Lpathomab) were humanized by grafting the murine CDRs into human framework regions (FR). Lefranc, M. P, (2003). Nucleic Acids Res, 31: 307-10; Martin, A. C. and J. M. Thornton, (1996) J Mol Biol, 1996. 263: 800-15; Morea, V., A. M. Lesk, and A. Tramontano (2000) Methods, 20: 267-79; Foote, J. and G. Winter, (1992) J Mol Biol, 224: 487-99; Chothia, C., et al., (1985). J Mol Biol, 186:651-63.

Suitable acceptor human FR sequences were selected from the IMGT and Kabat databases based on a homology to LT3000 using a sequence alignment and analysis program (SR v7.6). Lefranc, M. P. (2003) Nucl. Acids Res. 31:307-310; Kabat, E. A. et al. (1991) Sequences of Proteins of Immunological Interest, NIH National Techn. Inform. Service, pp. 1-3242. Sequences with high identity at FR, vernier, canonical and VH-VL interface residues (VCI) were initially selected. From this subset, sequences with the most non-conservative VCI substitutions, unusual proline or cysteine residues and somatic mutations were excluded. AJ002773 was thus selected as the human framework on which to base the humanized version of LT3000 heavy chain variable domain and DQ187679 was thus selected as the human framework on which to base the humanized version of LT3000 light chain variable domain.

A three-dimensional (3D) model containing the humanized VL and VH sequences was constructed to identify FR residues juxtaposed to residues that form the CDRs. These FR residues potentially influence the CDR loop structure and the ability of the antibody to retain high affinity and specificity for the antigen. Based on this analysis, 6 residues in AJ002773 and 3 residues in DQ187679 were identified, deemed significantly different from LT3000, and considered for mutation back to the murine sequence.

Antibody Expression and Production in Mammalian Cells

The murine antibody genes were cloned from hybridomas. Synthetic genes containing the human framework sequences and the murine CDRs were assembled from synthetic oligonucleotides and cloned into pCR4Blunt-TOPO using blunt restriction sites. After sequencing and observing 100% sequence congruence, the heavy and light chains were cloned and expressed as a full length IgG1 chimeric antibody using the pConGamma vector for the heavy chain gene and pConKappa vector for the light chain gene (Lonza Biologics, Portsmouth N.H.). The expression cassette for each of these genes contained a promoter, a kozak sequence, and a terminator. These plasmids were transformed into *E. coli* (One Shot Top 10 chemically competent *E. coli* cells, Invitrogen, Cat No. C4040-10), grown in LB media and stocked in glycerol. Large scale plasmid DNA was prepared as described by the manufacturer (Qiagen, endotoxin-free MAXIPREP™ kit, Cat. No 12362). Plasmids were transfected into the human embryonic kidney cell line 293F using 293fectin and using 293F-FreeStyle Media for culture. The transfected cultures expressed approximately 2-12 mg/L of humanized antibody.

Antibody Purification

Monoclonal antibodies were purified from culture supernatants using protein A affinity chromatography. Aliquots containing 0.5 ml of ProSep-vA-Ultra resin (Millipore, Cat. No 115115827) were added to gravity-flow disposable columns (Pierce, Cat. No 29924) and equilibrated with 10-15 ml of binding buffer (Pierce, Cat. No 21001). Culture supernatants containing transiently expressed humanized antibody were diluted 1:1 with binding buffer and passed over the resin. The antibody retained on the column was washed with 15 ml of binding buffer, eluted with low pH elution buffer (Pierce, Cat. No 21004) and collected in 1 ml fractions containing 100 ul of binding buffer to neutralize the pH. Fractions with absorbance (280 nm)>0.1 were dialyzed overnight (Slide-A-Lyzer Cassettes, 3500 MWCO, Pierce, Cat. No 66382) against 1 liter of PBS buffer (Cellgro, Cat. No 021-030). The dialyzed samples were concentrated using centricon-YM50 (Amicon, Cat. No 4225) concentrators and filtered through 0.22 uM cellulose acetate membranes (Costar, Cat. No 8160). The purity of each preparation was accessed using SDS-PAGE.

SDS-PAGE Electrophoresis

Each antibody sample was diluted to 0.5 ug/ul using gel loading buffer with (reduced) or without (non-reduced) 2-mercaptoethanol (Sigma, Cat. No M-3148). The reduced samples were heated at 95° C. for 5 min while the non-reduced samples were incubated at room temperature. A 4-12% gradient gel (Invitrogen, Cat. No NP0322) was loaded with 2 ug of antibody per lane and ran at 170 volts for 1 hour at room temperature in 1× NuPAGE MOPS SDS running buffer (Invitrogen, Cat. No NP0001). After electrophoresis, the antibodies were fixed by soaking the gel in 50% methanol, 10% acetic acid for ~10 min. The gel was then washed with 3×200 ml distilled water. Finally, the bands were visualized by staining the gel overnight in GelCode® Blue Stain (Pierce, Cat. No 2490) and destaining with water.

Quantitative ELISA

The antibody titer was determined using a quantitative ELISA. Goat-anti human IgG-Fc antibody (Bethyl A80-104A, 1 mg/ml) was diluted 1:100 in carbonate buffer (100 mM $NaHCO_3$, 33.6 mM $Na_2CO_3$, pH 9.5). Plates were coated by incubating 100 ul/well of coating solution at 37° C. for 1 hour. The plates were washed 4× with TBS-T (50 mM Tris, 0.14 M NaCl, 0.05% tween-20, pH 8.0) and blocked with 200 ul/well TBS/BSA (50 mM Tris, 0.14 M NaCl, 1% BSA, pH 8.0) for 1 hour at 37° C. Samples and standard were prepared on non-binding plates with enough volume to run in duplicate. The standard was prepared by diluting human reference serum (Bethyl RS10-110; 4 mg/ml) in TBS-T/BSA (50 mM Tris, 0.14 NaCl, 1% BSA, 0.05% Tween-20, pH 8.0) to the following concentrations: 500 ng/ml, 250 ng/ml, 125 ng/ml, 62.5 ng/ml, 31.25 ng/ml, 15.625 ng/ml, 7.8125 ng/ml, and 0.0 ng/ml. Samples were prepared by making appropriate dilutions in TBS-T/BSA, such that the optical density (OD) of the samples fell within the range of the standard; the most linear range being from 125 ng/ml 15.625 ng/ml. After washing the plates 4× with TBS-T, 100 ul of the standard/samples preparation was added to each well and incubated at 37° C. for 1 hour. Next the plates were washed 4× with TBS-T and incubated for 1 hour at 37° C. with 100 ul/well of HRP-goat anti-human IgG antibody (Bethyl A80-104P, 1 mg/ml) diluted 1:150,000 in TBS-T/BSA. The plates were washed 4× with TBS-T and developed using 100 ul/well of TMB substrate chilled to 4° C. After 7 minutes, the reaction was stopped with 1M $H_2SO_4$ (100 ul/well). The OD was measured at 450 nm, and the data was analyzed using Graphpad Prizm software. The standard curve was fit using a four parameter equation and used to calculate the human IgG content in the samples.

Direct Binding ELISA

The LPA-binding affinities of the humanized antibodies were determined using a direct binding ELISA assay. Microtiter ELISA plates (Costar) were coated overnight with 1.0 ug/ml C12:0 LPA conjugated to Imject malieimide activated bovine serum albumin (BSA) (Pierce Co.) diluted in 0.1 M carbonate buffer (pH 9.5) at 37° C. for 1 h. Plates were washed with PBS (137 mM NaCl, 2.68 mM KCl, 10.1 mM $Na_2HPO_4$, 1.76 mM $KH_2PO_4$; pH 7.4) and blocked with PBS/BSA/tween-20 for 1 hr at room temp or overnight at 4° C. For the primary incubation (1 hr at room temperature), a dilution series of the anti-LPA antibodies (0.4 ug/mL, 0.2 ug/mL, 0.1 ug/mL, 0.05 ug/mL, 0.0125 ug/mL, and 0 ug/mL) was added to the microplate (100 ml per well). Plates were washed and incubated with 100 ul per well of HRP conjugated goat anti-human (H+ L) diluted 1:20,000 (Jackson, cat #109-035-003) for 1 hr at room temperature. After washing, the peroxidase was developed with tetramethylbenzidine substrate (Sigma, cat No T0440) and stopped by adding 1 M $H_2SO_4$. The optical density (OD) was measured at 450 nm using a Thermo Multiskan EX. The $EC_{50}$ (half-maximal binding concentration) was determined by a least-squares fit of the dose-response curves with a four parameter equation using the Graphpad Prism software.

LPA Competition ELISA

The specificity of the humanized antibody was determined by competition ELISA. C18:0 LPA coating material was diluted to 0.33 ug/ml with carbonate buffer (100 mM NaHCO3, 33.6 mM Na2CO3, pH 9.5). Plates were coated with 100 ul/well of coating solution and incubated at 37° C. for 1 hour. The plates were washed 4 times with PBS (100 mM Na2HPO4, 20 mM KH2PO4, 27 mM KCl, 1.37 mM NaCl, pH 7.4) and blocked with 150 ul/well of PBS, 1% BSA, 0.1% tween-20 for 1 h at room temperature. The humanized, anti-LPA antibodies were tested against lipid competitors (14:0 LPA (Avanti, Cat. No 857120), 18:1 LPA (Avanti, Cat. No 857130), 18:1 LPC (Avanti, Cat. No 845875), cLPA (Avanti, Cat. No 857328), 18:1 PA (Avanti, Cat. No 840875), PC (Avanti, Cat. No 850454) at 5 uM, 2.5 uM, 1.25 uM, 0.625 uM, and 0.0 uM. The antibody was diluted to 0.5 ug/ml in PBS, 0.1% tween-20 and combined with the lipid samples at a 1:3 ratio of antibody to sample on a non-binding plate. The plates were washed 4 times with PBS and incubated for 1 hour at room temperature with 100 ul/well of the primary antibody/lipid complex. Next the plates were washed 4 times with PBS and incubated for 1 h at room temperature with 100 ul/well of HRP-conjugated goat anti-human antibody diluted 1:20,000 in PBS, 1% BSA, 0.1% tween-20. Again the plates were washed 4 times with PBS and developed using TMB substrate (100 ul/well) at 4° C. After 8 minutes, the reaction was stopped with 100 ul/well of 1M H2SO4. The optical density (OD) was measured at 450 nm using a Thermo Multiskan EX. Raw data were transferred to GraphPad software for analysis.

Thermostability

The thermostability of the humanized antibodies were studied by measuring their LPA-binding affinity (EC50) after heating using the direct binding ELISA. Antibodies dissolved in PBS (Cellgo, Cat. No 021-040) were diluted to 25 ug/ml and incubated at 60° C., 65° C., 70° C., 75° C. and 80° C. for 10 min. Prior to increasing the temperature, 10 ul of each sample was removed and diluted with 90 ul of PBS and stored on ice. The samples were then vortexed briefly and the insoluble material was removed by centrifugation for 1 min at 13,000 rpm. The binding activity of the supernatant was determined using the direct LPA-binding ELISA and compared to a control, which consisted of the same sample without heat treatment.

Surface Plasmon Resonance

All binding data were collected on a ProteOn optical biosensor (BioRad, Hercules Calif.). 12:0 LPA-thiol and 18:0 LPA-thiol were coupled to a maleimide modified GLC sensor chip (Cat. No 176-5011). First, the GLC chip was activated with an equal mixture of sulfo-NHS/EDC for seven minutes followed by a 7 minute blocking step with ethyldiamine. Next sulfo-MBS (Pierce Co., cat #22312) was passed over the surfaces at a concentration of 0.5 mM in HBS running buffer (10 mM HEPES, 150 mM NaCl, 0.005% tween-20, pH 7.4). LPA-thiol was diluted into the HBS running buffer to a concentration of 10, 1 and 0.1 uM and injected for 7 minutes producing 3 different density LPA surfaces (~100, ~300 and ~1400 RU). Next, binding data for the humanized antibodies was collected using a 3-fold dilution series starting with 25 nM as the highest concentration (original stocks were each diluted 1 to 100). Surfaces were regenerated with a 10 second pulse of 100 mM HCl. All data were collected at 25° C. Controls were processed using a reference surface as well as blank injections. The response data from each surface showed complex binding behavior which a likely caused by various degrees of multivalent binding. In order to extract estimates of the binding constants, data from the varying antibody concentrations were globally fit using 1-site and 2-site models. This produced estimates of the affinity for the bivalent (site 1) and monovalent site (site 2).

LPA Molar Binding Capacity

The molar ratio of LPA:mAb was determined using a displacement assay. Borosilicate tubes (Fisherbrand, Cat. No 14-961-26) were coated with 5 nanomoles of biotinylated LPA (50 ug of lipid (Echelon Biosciences, Cat. No L-012B, Lot No F-66-136 were suspended in 705 ul of 1:1 chloroform:methanol yielding a 100 uM solution) using a dry nitrogen stream. The coated tubes were incubated with 75 ul (125 pmoles) of antibody dissolved in PBS (Cellgro, Cat. No 021-030) at room temperature. After 3 hours of incubation, the LPA:mAb complexes were separated from free lipid using protein desalting columns (Pierce, Cat, No 89849), and the molar concentration of bound biotinylated LPA was determined using the HABA/Avidin displacement assay (Pierce, Cat. No 28010) according to the manufacturer's instructions.

Measurement of LPA-Induced IL-8 Release in SKOV3 Cells

Anti-LPA antibodies inhibit the LPA-dependant release of human CXCL8/IL-8 in conditioned media of SKOV3 ovarian cells. SKOV3 cells (Lot No 4255558, passage 14) were harvested with 2 ml of 1× Trypsin EDTA (Mediatech Inc, Cat. No 25-053-CV) and resuspended in 8 ml of complete medium (10% FBS, Mediatech Inc. Cat. no 35-011-CV). The cells were centrifuged for 5 min (11,000 rpm) and re-suspended in 5 ml of complete medium. Cells were counted in duplicate with 0.4% Trypan blue (10 ul cells plus 90 ul Trypan blue, Invitrogen, Cat. No 15250-061) using a hemocytometer. In a 96-well plate, $1 \times 10^5$ cells per well were seeded (final volume 100 ul/well). The cells were allowed to attach and form a confluent monolayer by incubating overnight at 37° C. On the following day, cells were gently washed two times with minimum media (1 mg/ml BSA in McCoy's medium with L-glutamine, Mediatech, Cat. No 10-050-CV). The media was adjusted to 1% penicillin/streptomycin (Mediatech, Cat. No 30-002 CI) and 2.2 g/L sodium-bicarbonate (Mediatech, Cat. No 25-035-CI). Next, the cells were serum-starved at 37° C. for exactly 24 h, followed by cytokine stimulation with 100 uM C18:1 LPA (Avanti, Cat. No 857130) dissolved in 1 mg/ml BSA/PBS (Calbiochem, Cat. No 126575) in presence or absence of LPA antibody. After 22 h of stimulation, the cells were centrifuged for 5 min (13,500 rpm) at 4° C. and the supernatants were collected. The CXCL8/IL-8 levels in each supernatant were measured using the Quantikine human CXCL8/IL-8 kit according to vendor instructions (R&D Systems, Cat. No D8000C).

Measurement of Tumor Cell Migration in the Scratch Assay

SKOV3 cells were plated at 15,000 cells per well in a 96-well plate. The following day the cells were serum starved in minimal media (McCoy's Media 5a, adjusted to contain L-Glutamine, 2.2 g/L Sodium Bicarbonate, 1% penicillin/streptomycin and 1 mg/ml BSA) for 24 hrs. At time 0 cells were scratched with a p200 pipet tip down the center of each well, washed with minimal media and pictures were taken prior to treatment. Cells were then treated with LPA (C18:1) at 0.2 uM, 1.0 uM and 10 uM concentrations which were pre-incubated at 37° C. with 1.0 uM LPA in the presence or absence of antibody at 150 ug/ml. Positive control (10% FBS treated cells) and antibody alone were also tested. Cells were stimulated for 17 hrs at 37° C. in a 5% $CO_2$ incubator. Pictures were taken again 17 hr post-treatment and % wound closure was measured by adjusting pictures to the same size and measuring the width of the scratch at time 0 and time 17 hr with a ruler.

Matrigel Assays

Female C57BL/6 mice around 8 to 10-weeks old and Matrigel Matrix High Concentration purchased from BD BioSciences (Franklin Lakes, N.J. (from BD) mixed with 50 ng/ml VEGF and 50 ng/ml bFGF, heparin 3 ng/ml as angiogenic stimuli were used for this study. There were five groups of mice, 10 Matrigel plugs were inoculated into five mice for each group on Day 0. One mouse group served as a control; four others receive drug treatment in four different doses by ip injection every other day. All treatments start at Day −1 and finish at Day 8.

Thirty C57bl/6 mice were implanted with Matrigel plugs in order to obtain 25 healthy mice with two well-shaped Matrigel plugs per mouse. On Day 0, 500 ul Matrigel at 40° C. was subcutaneously injected to each side of the mouse, injection area was shaved. To increase the contact area of injected Matrigel into subcutaneous tissues and form a round shape plug, a wide subcutaneous pocket was formed by swaying the needlepoint right and left after a routine subcutaneous insertion. The injection was done rapidly with an appropriate size needle (21G-25G) to ensure the entire content was delivered in one plug. The injected Matrigel rapidly formed a single solid gel plug.

Animals were treated with 8 or 2 mg/kg of antibody or saline beginning 1 day prior to the implantation of Matrigel plugs or with the vehicle. Treatments were administered ip, on a q2d schedule.

Plugs from each group were collected at Day 12. The mice were euthanized and mouse skin was pulled back to expose the plug. The plugs was dissected out and fixed for histological analysis. Sections of 5 μm from paraffin-embedded plugs were stained with anti-CD-31 antibodies. Blood vessel density in a cross sectional area of each Matrigel plugs were analyzed. For each treatment group, at least six or more Matrigel plugs were quantitatively analyzed to assess any statistical significant difference of microvessel density between groups.

Results

The sequence of the murine anti-LPA mAb LT3000 was humanized with the goal of producing an antibody that retains high affinity, specificity and binding capacity for LPA.

Engineering of the Humanized Variants

The murine anti-LPA antibody was humanized by grafting of the Kabat CDRs from LT3000 $V_H$ and $V_L$ into acceptor human frameworks. Seven humanized variants were transiently expressed in HEK 293 cells in serum-free conditions, purified and then characterized in a panel of assays. Plasmids containing sequences of each light chain and heavy chain were transfected into mammalian cells for production. After 5 days of culture, the mAb titer was determined using quantitative ELISA. All combinations of the heavy and light chains yielded between 2-12 ug of antibody per ml of cell culture.

Characterization of the Humanized Variants

All the humanized anti-LPA mAb variants exhibited binding affinity in the low picomolar range similar to the chimeric anti-LPA antibody (also known as LT3010) and the murine antibody LT3000. All of the humanized variants exhibited a $T_M$ similar to or higher than that of LT3000. With regard to specificity, the humanized variants demonstrated similar specificity profiles to that of LT3000. For example, LT3000 demonstrated no cross-reactivity to lysophosphatidyl choline (LPC), phosphatidic acid (PA), various isoforms of lysophosphatidic acid (14:0 and 18:1 LPA, cyclic phosphatidic acid (cPA), and phosphatidylcholine (PC).

Activity of the Humanized Variants

Five humanized variants were further assessed in in vitro cell assays. LPA is known to play an important role in eliciting the release of interleukin-8 (IL-8) from cancer cells. LT3000 reduced IL-8 release from ovarian cancer cells in a concentration-dependent manner. The humanized variants exhibited a similar reduction of IL-8 release compared to LT3000.

Some humanized variants were also tested for their effect on microvessel density (MVD) in a Matrigel tube formation assay for neovascularization. Both were shown to decrease MVD formation.

TABLE 41

Quantitation of microblood vessel density using CD31 immunostain with H & E counterstaining in matrigel plugs.

| | Control | LT3000 murine (8 mg/kg) | LT3000 murine (2 mg/kg) | Humanized variant #1 (8 mg/kg) | Humanized variant #1 (2 mg/kg) | Humanized variant #2 (2 mg/kg) |
|---|---|---|---|---|---|---|
| Average | 64.2 | 41.5 | 34 | 34.4 | 49 | 50.8 |
| S.E. | 8.0 | 14.2 | 13.7 | 4.2 | 31.5 | 18.8 |
| N = | 5 | 4 | 5 | 5 | 5 | 6 |
| Percent Inhibition | | 35.4 | 47.0 | 46.4 | 23.7 | 20.8 |

Example 21

Preliminary Animal Pharmacokinetics of Lpathomab

Preliminary PK studies were conducted with Lpathomab. For IV dosed groups, mice were injected with a single 30 mg/kg dose and sacrificed at time points up to 15 days. Antibody was also given via i.p. administration and animals were sacrificed during the first 24 hrs to compare levels of mAb in the blood over this period of time for different routes of delivery. Pharmacokinetic parameters were assessed by WinNonlin. Three mice were sacrificed at each time point and plasma samples were collected and analyzed for mAb levels by ELISA. The half-life of Lpathomab in mice was determined to be 102 hrs (4.25 days) by i.v. administration. Moreover, the antibody is fully distributed to the blood within 6-12 hrs when given i.p., suggesting that the i.p. administration is suitable for xenografts and other studies.

TABLE 42

Pharmacokinetic profile of Lpathomab in mice
Pharmacokinetic Parameters

| Group | Treatment (mg/kg) | Route | | Estimate | SD | CV % |
|---|---|---|---|---|---|---|
| 1 | 30 | IV | AUC | 88.35 | 60.23 | 68.18 |
| | | | K10-HL | 102.7 | 77.48 | 75.91 |
| | | | Cmax | 0.6 | 0.13 | 21.71 |
| | | | Cl | 0.34 | 0.23 | 68.24 |
| | | | AUMC | 13009.8 | 18549.2 | 142.58 |
| | | | MRT | 147.25 | 111.78 | 75.91 |
| | | | Vss | 50 | 10.86 | 21.73 |

Software used to calculate the parameters: WinNonlin v1.1
AUC Area under the curve
K10-HL Elimination half-life
Cmax Dose related peak value
Cl Clearance
AUMC Area under the first moment curve
MRT Mean residence time
Vss Apparent volume of distribution, steady state

Example 22

Safety of Lpathomab Given by Intravenous Injection

Objective. This study assessed the safety of Lpathomab following intravenous injection of the antibody. C57BL/6N mice received Lpathomab for 7 consecutive days followed by a 7 day recovery period for selected animals of each treatment (recovery groups). Blood samples were collected and processed for multiple study parameters including classical hematology, coagulation time and clinical chemistry. Selected organs were weighed and compared with vehicle only controls.

Study design. Once a day, single iv bolus injections of Lpathomab or vehicle control were given at the following doses: 0, 30, 60, 120, and 240 mg/kg. After 7 days of treatment, animals were euthanized with the only exception of the recovery groups which were observed for an additional 7 days (recovery period). For each animal, necropsy consisted of an external examination, including identification of all clinically recorded lesions, as well as a detailed internal examination.

Results. There were no significant differences in the hematology parameters of antibody-treated groups compared to the control group. Almost all of the clinical chemistry parameters tested showed no significant changes when compared to control animals. There was, however a statistically significant reduction in triglycerides in both female and male mice (female, mean±SD: vehicle 89±17, mAb 120 mg/kg, 36±8 p<0.003*; mAb 240 mg/kg 46±18 p*<0.001; male, mean±SD: vehicle 133±24, mAb 240 mg/kg 50±8 p<0.01*; Student t-test). However, there were no statistically significant reductions in glucose, cholesterol, and ALT (alanine aminotransferase) or other CBC parameters. No changes were observed in the weights of mouse brains, hearts, lungs, pituitary glands, ovaries, spleens, testes, thymus glands, thyroid or uterus after Lpathomab treatment. There were, however, significant reductions in liver weights for both genders at certain doses. The highest treatment group of female mice showed significant reduction in liver weights compared to controls (mean±SD: vehicle 1.2±0.27, mAb 240 mg/kg 0.89±0.26 p<0.014*), and the three highest treatment groups in male mice (60, 120, and 240 mg/kg mAb) showed significant reductions when compared to controls (mean±SD: vehicle 1.28±0.06, mAb 1.03±0.07, p<0.0001; 1.08±0.11 p<0.002, 1.11±0.11 p<0.004 respectively; Student t-test).

Example 23

Antibody B3 Reduces the Release of Pro-Angiogenic and Pro-Metastatic Cytokines, Interleukin 8 (IL-8) and Interleukin 6 (IL-6) in Tumor Cell Conditioned Media Rationale:
LPA has shown to be a key player in several aspects of ovarian cancer cell biology. LPA stimulates proliferation, migration and invasion of several ovarian cell types, including OVCAR3 and SKOV3. Fang, X et al. (2000) Ann. NY Acad. Sci. 905:188-208. Therefore, we conducted a set of in vitro studies examining the ability of B3 anti-LPA antibody to block LPA mediated effects on the ovarian cell type SKOV3.

Study:
Tumor cells were plated at the density of $1 \times 10^4$ cell/well in a 96-well plate. After 24 hrs of serum starvation, tumor cells were treated with LPA pre-incubated or not with increasing concentration of B3 (150-600 µg/mL). Tumor conditioned media were then collected after 18 hrs and analyzed for levels of human IL-8 and IL-6 by ELISA. Data analysis: ANOVA (p<0.0001), followed by Bonferroni's post test, n=3 independent experiments, No Treatment vs 1 µM LPA or 5 M LPA; 1 µM LPA vs 1 µM LPA+mAb).

Results:
Animals treated with B3 demonstrated substantial reduction of both cytokines in the conditioned media of SKOV3 cells. The reductions were dose dependent: for IL-8, 69% and 83% at 150 and 300 µg/mL mAb concentration, respectively; for IL-6, 66% and 85% at 150 and 300 µg/mL mAb concentration, respectively.

Example 24

B3 Antibody Reduced the Release of the Pro-Angiogenic Growth Factor VEGF in Tumor Cell Conditioned Media Rationale:
It has been shown that SKOV3 cells produce and release relevant levels of the pro-angiogenic factor VEGF in their conditioned media. It is also well documented that LPA is a key player in the release of VEGF which is secreted from both tumor cells and stromal components of the ovarian tumor microenvironment [Hu, Y. L. et al. (2001) J. Nat. Cancer Inst. 93:734-735; Lee J. et al. (2006) Clin. Cancer Res. 12:6351-6358] and the maintenance of high levels of this growth factor in the peritoneal cavity contribute to the imbalance of pro-angiogenic versus anti-angiogenic factors and to the promotion of new blood vessels metastasis. Ren, J. et al. (2006) Cancer Res. 66:3006-3014. For this reason, we evaluated the ability of B3 to interfere with the LPA/VEGF signaling network in the SKOV3 cells.

Study:
Tumor cells were plated at the density of $1 \times 10^4$ cell/well in a 96-well plate. After 24 hrs of serum starvation, tumor cells were treated with LPA, pre-incubated or not with increasing concentration of B3 (150-1200 µg/mL). Tumor conditioned media were then collected after 16 hrs and analyzed for levels of human VEGF by ELISA. Levels of VEGF were measured by Quantikine Human VEGF ELISA (R&D Systems, Minneapolis Minn.). Levels of VEGF were expressed as pg/well equivalent to pg/$10 \times 10^4$ cells. Data were analyzed using a "Nonlin Fit equation" (Log B3 vs respond; GraphPad software). The $IC_{50}$ value for B3 (n=1) was calculated to be 443 µg/mL.

Results:
Animals treated with B3 demonstrated substantial reduction in levels of both cytokines in the conditioned media of SKOV3 cells. The reductions were dose-dependent (n=1 independent experiments).

Example 25

Efficacy of Lpathomab in the Human SKOV3 Ovarian Cancer Model

Rationale.
LPA has shown to be a key player in several aspects of ovarian cancer biology. LPA is found elevated in ascites fluid and sera of cancer patients. Tokumura, A. et al. (2007) Life Sci 80:1641-1649. Preliminary in vitro cell assays demonstrated that Lpathomab could mitigate several biological effects of LPA in the ovarian cancer cell SKOV3 (see Table 34). Therefore, we conducted an in vivo study to examine the ability of Lpathomab to mitigate the progression of SKOV3 tumors in an in vivo cancer model.

Objective.

To determine the efficacy of Lpathomab to block the progression of human ovarian (SKOV3) tumors grafted into the abdominal cavity of female athymic nude mice.

SKOV3 Study 1.

Lpathomab administered by IP injection inhibited tumor progression in the intraperitoneally implanted SKOV3 ovarian tumors model in athymic nude mice.

Study Design:

Nude (nCr Nu/Nu) mice were implanted with $5 \times 10^6$ SKOV3 ovarian tumor cells by i.p injection. Tumors were allowed to establish for 10 days; mice were then randomized and treated with 10 mg/kg Lpathomab every three days for all the duration of the experiment. At the termination of the study mice were sacrificed, tumors were collected and weighed, and ascites fluid volumes were recorded. Blood samples were collected for serum analysis. Data analysis was by ANOVA and Student t-test.

Results.

Animals treated with Lpathomab demonstrated substantial reductions in tumor burden and in serum and ascites levels of the cytokines IL-6 and IL-8, and GM-CSF. Tumor weights were reduced by 34% ($p<0.05$) in animals treated with Lpathomab compared to PBS (vehicle)-treated animals.

In serum, IL-8 levels were reduced by ~27% in Lpathomab-treated animals compared to PBS-treated mice; IL-6 levels were reduced by ~58% in Lpathomab-treated animals compared to PBS-treated mice ($p<0.05$), and GM-CSF was reduced by 56% in Lpathomab-treated animals compared to PBS-treated mice.

In ascites, IL-8 levels were reduced by ~70% in Lpathomab-treated animals compared to PBS-treated mice ($p<0.001$); IL-6 levels were reduced by ~55% in Lpathomab-treated animals compared to PBS-treated mice ($p<0.05$), and GM-CSF was reduced by ~60% in Lpathomab-treated animals compared to PBS-treated mice ($p<0.01$).

Conclusions.

The study suggests that neutralization of LPA by systemic administration of Lpathomab results in a significant inhibition of SKOV3 tumor progression.

SKOV3 Study 2.

Murine antibody B3 administered by IP injection (10 mg/kg q3d) greatly inhibited tumor progression in the intraperitoneally implanted SKOV3 ovarian tumors model in athymic nude mice.

Study Design.

Nude (nCr Nu/Nu) mice were implanted with $5 \times 10^6$ SKOV3 ovarian tumor cells by i.p injection. Tumors were allowed to establish for 10 days; mice were then randomized in three groups and treated with PBS, 10 mg/kg of B3 q3d, or Taxol at the dose of 2 mg/kg q14d, for all the duration of the experiment (56 days). At the termination of the study mice were sacrificed, tumors were collected and weighed, and ascites fluid volumes were recorded. Blood samples were collected for serum analysis. Data were analyzed using ANOVA ($p<0.001$) followed by Bonferroni's comparison (PBS vs. B3).

Results.

Animals treated with B3 antibody demonstrated substantial and significant ($p<0.05$) reductions in tumor burden (49% decrease in tumor weights compared to PBS-treated animals) and in ascites fluid volumes (~83% decrease compared to PBS-treated animals). Taxol decreased tumor weights by ~69% ($p<0.01$) and ascites volume by ≥90% compared to PBS-treated animals. Furthermore, in the B3 treatment group the incidence of animals with ascites was lower than in the PBS group (4/12 vs. 6/11, respectively, and 1/6 for Taxol-treated animals).

Conclusions.

The study suggests that neutralization of LPA by systemic administration of B3 results in a significant inhibition of SKOV3 tumor progression.

Example 26

Efficacy of Lpathomab in the Xenograft CAM Model

Objective.

To investigate the efficacy of Lpathomab to limit COLO205 tumors in the Shell-free Chicken Embryo Chorioallantoic Membrane (CAM) Assay. The study was performed at Southern Research, Alabama.

Study Design.

To establish tumors, a disc of dissolvable gelfoam was placed on the surface of the CAM on embryonic day 5 (E5). Tumor cells ($1 \times 10^6$) were then co-implanted with 20 μg of Lpathomab or vehicle on the top of the gelfoam in a total volume of 110 L. Tumor xenografts received an additional topical treatment of 5 μL (50 μg) of antibody or vehicle on day E7. Digital images of each CAM xenograft were acquired on day E10 after injection of dyed non-fat milk as enhancing contrast agent. Tumor size in each CAM was calculated using the image analysis software Image Pro Plus and expressed as tumor area (pixels$^2$). The vascular density index (VDI) was determined by quantifying the number of blood vessels at the periphery of tumor xenografts. Data were acquired from viable embryos only and were analyzed with Student's t-test using SPSS statistical software.

Results.

Lpathomab produced a statistically significant ($P=0.019$) decrease of 60% in COLO205 tumor size compared to vehicle controls.

Conclusions.

This study suggests that Lpathomab can significantly reduce COLO205 tumor progression.

Example 27

Purification of Antibody with Low Lipid Carry-Over

Generating highly pure, highly qualified antibodies for pre-clinical or clinical use is of paramount importance for therapeutic drug development. In addition to being free of cellular proteins, DNA and viruses, the antibody preparation should also not contain any of the antigen, so the antibody is fully active and able to bind its target when administered to a patient. Normally, purification and formulation of an antibody removes the antigen, but after purification of the anti-sphingosine-1-phosphate (S1P) monoclonal antibody, LT1009, Lpath sometimes observes significant levels of S1P carried over from the antibody production. Lipid carryover is also seen with the anti-LPA monoclonal antibodies; the following example of methods of reducing lipid carryover is also relevant to anti-LPA antibodies, although anti-S1P antibodies are exemplified herein.

S1P is a bioactive lipid that is synthesized by mammalian cells, including Chinese Hamster Ovary (CHO) cells. During production of LT1009, e.g., from the transfected CHO cell line LH1 275 (ATCC Accession No. PTA-8422), intracellular pools of S1P can be released into the media as a result of normal cellular signaling and/or as a consequence of cell rupture after cell death. The LT1009 antibody expressed in the cell-conditioned medium (supernatant) is able to bind to this S1P. As production continues, more S1P may be released and accumulate in the supernatant as a complex with LT1009. While not wishing to be bound by theory, it is believed that the more time the antibody has in contact with the S1P in the medium, the more of that extracellular S1P would be bound to the LT1009 and carried over into the antibody preparation. When produced in CHO cells, LT1009 antibody preparations may contain in excess of 0.5 moles (50 mole percent, mol %) of S1P per mole of antibody. Thus in order to reduce the amount of S1P carry-over, steps must be taken in both upstream and downstream processing to minimize the amount of S1P in the crude harvest and to promote removal of that S1P during purification.

S1P Quantification Methods:

The S1P concentrations in various preparations of the LT1009 antibody were measured at WindRose Analytica by RP-HPLC-MS-MS method. Mass spectrometry is rapid and sensitive and, if applied properly, can quantify picogram amounts of analyte. The approach taken in this analytical method is to introduce the S1P into an electrospray mass spectrometer source by reversed phase liquid chromatography (RPC). The RPC step separates the S1P from protein, salts and other contaminants. Following the chromatographic step the S1P is ionized in the source and passed onto an ion trap mass analyzer. All ions except those of the appropriate mass-to-charge ratio (m/z=380) are ejected from the trap. The remaining ions are fragmented in the ion trap and a specific daughter ion (m/z=264) is monitored. The results verify sample identity in three dimensions of analysis: RPC retention time, parent ion m/z of 380, and daughter ion m/z of 264. It is unlikely that any other compound would satisfy all three of these criteria. Additionally, the MS-MS step maximizes signal-to-noise and therefore increases sensitivity significantly. Since there is no extraction step required there is no need for an internal standard. Additionally, the direct injection of sample into the HPLC-MS increases recovery and sensitivity and decreases complexity and analysis time.

For comparison, the concentration of S1P in extracts of selected antibody preparations was determined using a S1P-quantification ELISA. A 4-fold excess of 1:2 chloroform: methanol was added to 1 mg/ml antibody samples to extract the S1P. The aqueous/organic solution was extensively vortexed and sonicated to disrupt antibody-lipid complexes and incubated on ice. After centrifugation, the soluble fraction was evaporated using a speed-vac, and the dried S1P was resuspened in delipidated human serum. The S1P concentration in the resuspended sample was determined by a competitive ELISA using an anti-S1P antibody and a S1P-coating conjugate. The coating conjugate, a covalently linked S1P-BSA, was prepared by coupling a chemically synthesized thiolated S1P with maleimide-activated BSA. For the S1P standard, mono-layer S1P was solubilized in 1% BSA in PBS (137 mM NaCl, 2.68 mM KCl, 10.1 mM Na2HPO4, 1.76 mM KH2PO4; pH 7.4) by sonication to obtain 10 uM S1P (S1P-BSA complex). The S1P-BSA complex solution was further diluted with delipidated human serum to appropriate concentrations (up to 2 uM). Microtiter ELISA plates (Costar, high-binding plate) were coated with S1P-coating material diluted in 0.1M sodium carbonate buffer (pH 9.5) at 37° C. for 1 hour. Plates were washed with PBS and blocked with PBS/1% BSA/0.1% Tween-20 for 1 hr at room temperature. For the primary incubation, 0.4 ug/mL biotin-labeled anti-S1P antibody, designated amounts of S1P-BSA complex and samples to be tested were added to wells of the ELISA plates. After 1 hour-incubation at room temperature, plates were washed followed by incubation with 100 ul per well of HRP conjugated streptavidin (1:20,000 dilution) for 1 hour at room temperature. After washing, the peroxidase reaction was developed with TMB substrate and stopped by adding 1 M H2SO4. The optical density was measured at 450 nm using a Thermo Multiskan EX.

Upstream Processing to Minimize S1P:

For upstream processing, culturing the CHO cells in serum-free medium (Invitrogen, Cat #10743-029) is essential because serum contains contaminating S1P that could add to that produced by the CHO cells themselves. In addition to use of serum-free medium, harvesting the antibody from the bioreactor prior to extensive cell death will prevent intracellular pools of S1P to be released into the medium. Finally, initiating the downstream processing immediately after harvest minimizes the time the LT1009 spends in the presence of S1P and the amount of lipid carried over to the final preparation. Despite attempts to minimize the S1P levels during upstream processing, significant S1P often remains in the crude harvest which typically ranges between 0.1-0.2 molar ratio (10-20 mol %) of bound S1P per mol of antibody.

Therefore, Lpath developed downstream methods to remove lipids from antibody preparations in order to generate LT1009 material with very low S1P carry-over levels. These methods (described immediately below) were developed by Lpath and transferred to Laureate Pharma, Inc. to incorporate into their processing methods. As a result, the final drug product produced by Laureate has very low levels of bound S1P (<0.4 mol % measured by HPLC-MS-MS).

Downstream Processing to Reduce S1P:

Traditionally, purification of antibodies from cultured supernatant or ascites fluid involves affinity chromatography. This one-step methods uses recombinant protein-A covalently bond to highly cross-linked agarose (GE healthcare, Cat No 17-5199-04). The protein-A acts as a ligand for Fc domains of monoclonal antibodies. Since the protein-A and S1P binding sites are distinct, S1P does not displace when LT1009 binds the protein-A resin. The high affinity for LT1009 and low solubility in aqueous buffers ensures that S1P remains associated with LT1009 even through extensive washes with high salt buffers (see below). Therefore, conventional antibody purification process that included: Protein A Chromatography, Low pH Viral Inactivation, followed by Neutralization, Q Anion Exchange Chromatography, Viral Nanofiltration and Final Ultrafiltration/Diafiltration did not remove co-purified (bound to LT1009) S1P. In order to dissociate S1P from the bound LT1009, Lpath exploits a special feature in the mechanism of binding.

Lpath in-house research demonstrated that S1P binding activity of LT1009 was reduced at pH<4.0, or at pH>8.5. However, conducting Protein A chromatography at pH<4.0 in order to reduce bound S1P was not feasible because antibody will not bind to Protein A resin at such low pH. Therefore, high salt, pH 8.5 wash step was incorporated in protein A chromatography to reduce S1P bound to LT1009. Further studies demonstrated that the high salt buffer (650 mM NaCl) and 50 mM Sodium Phosphate buffer pH 8.5 did not effectively remove S1P from LT1009. Further increasing of salt concentration from 0.65 M to 1 M (pH 8.5) and extending of the high salt wash step from four column volumes to five column volumes did not yield product with lower bound S1P.

Use of Metal Chelators to Remove S1P:

Lpath developed a method that involved premixing of two volumes of crude LT1009 antibody harvest, produced from CHO cells bioreactor campaign, with one volume of Protein A IgG binding buffer ("Pierce binding buffer," Pierce Protein Research Products, Thermo Fisher Scientific, Rockford Ill.), containing 50 mM Potassium Phosphate, 1M NaCl, 2 mM EDTA and 5% glycerol, pH 8.0. According to this procedure the Protein A column was equilibrated with Pierce binding buffer, loaded with premixed crude harvest and washed with 10 column volumes of the same binding buffer. The resulting purified LT1009 contained 2-fold less mole percent of S1P as judged by the S1P-quantification ELISA.

It is currently believed that a metal chelator (e.g., EDTA) is important or even essential for effective reduction of S1P carryover in LT1009 antibody preparations. Indeed, titration of LT1009 with EDTA, which chelates divalent metal cations, abrogates S1P binding (FIG. 14). The ability of EDTA to dissociate S1P from LT1009 is believed to facilitate removal of S1P during purification of LT1009. Addition of 2 mM EDTA in the binding and washing buffers effectively lowered the S1P carryover twofold in the eluted antibody fractions. It should be noted that the S1P levels in this study are relatively low initially, and including EDTA should produce greater reduction in lipid carryover in samples with higher initial S1P levels. Without being limited by the following examples, other metal chelators such as EGTA, histidine, malate and phytochelatin may be useful in dissociating S1P from the antibody. EGTA and EDTA are presently preferred divalent metal chelators for separating S1P from anti-S1P antibodies.

Based on these results, a new high salt buffer was developed by Lpath that was comparable in pH and conductivity to the Pierce buffer, and the new premixing step was incorporated in the LT1009 manufacturing process.

Current Downstream Purification Process Includes:
  Premixing of crude harvest with 4× potassium high salt EDTA buffer (200 mM KPi, 4M NaCl, 8 mM EDTA, 20% glycerol, pH 8.0) in ratio of 2 L crude harvest to 0.182 L KPi high salt-EDTA buffer. This step is intended to disrupt and dissociate S1P from LT1009
  Capture of Crude Harvest-High Salt mix on Protein A column and washing the column with 10 column volumes of High Salt-EDTA buffer to remove S1P
- Elution of LT1009 from Protein A resin at low pH (3.6-3.8)
- Low pH hold of Protein A Eluate at pH 3.6-3.8 for a viral inactivation followed by neutralization of the eluate to neutral pH
- Sartobind Q anion exchange chromatography to remove residual host cell proteins and nucleotides, as well as any leached protein A.
- Nanofiltration using Virosart CPV nanofilter as an additional step for virus removal
- Final UF/DF filtration for protein concentration and final formulation Use of Low pH and C8 Resins to Remove S1P:

In addition to the use of metal chelators such as EDTA during the purification, one can also exploit the hydrophobic nature of S1P to remove the lipid from purified antibody preparations. This method involves a two-step process: 1) dissociation of the lipid from the antibody, and 2) physical separation of the lipid from the aqueous environment. The applicant employs a pH induced Lipid removal (pHiL) treatment as an easy, robust method to promote dissociation from antibody preparations.

Antibodies generally exhibit markedly reduced antigen-binding affinity at low pH. Antibodies generated against phospholipids (e.g. S1P and LPA) fail to bind lipids at pH 3.0-3.5, depending on the specific antibody and the lipid (FIG. 14). In determining the correct pH to promote dissociation, a pH titration experiment should be performed to determine the pH that abrogates binding yet maintains an intact IgG, such that binding activity is restored once the pH is increased. In other words the antibody should not be irreversibly inactivated. Once this pH has been determined, the antibody is dialyzed against buffer below the critical pH (e.g. 50 mM sodium acetate, pH 3.0-3.5) at 4° C. Under these conditions, both the lipid and antibody exist as isolated components in solution. The dialyzed solution is passed through a material, such as C8 silica resin (e.g., SepPak cartridges, Waters, Cat no WAT036775), that binds the lipid and facilitates separation of the protein free of lipid. As a consequence, the free lipid irreversibly binds the hydrophobic resin (in the case of C8 silica resin) while the antibody flows through without significant loss (~90% recovery). Most of the lipid can be removed with one pass through the cartridge, but modest gains in lipid removal can be achieved with an additional pass (Table 43).

The metal chelation and pHiL methods described above can easily be incorporated into a single purification procedure. EDTA is compatible with most buffers and does not adversely affect antibody stability, solubility or protein-A binding. During purification, washing the bound IgG with copious amount of EDTA-containing buffer will remove a portion of the S1P from the S1P-LT1009 complex as well as potentially dissociate other metal-dependant antigens-antibody complexes. If the EDTA wash does not sufficiently remove the lipid, the eluate from the protein-A column can be treated using the pHiL method. Elution of bound IgG from protein-A is typically achieved using low pH buffers (pH<3.0). If the anti-lipid antibody elutes from the column at a pH or below the critical pH for lipid binding, the sample can simply be applied to the C8 silica resin to remove the lipid. If necessary, the pH can be easily adjusted prior to applying it to the resin.

TABLE 43

Lipid removal using pHiL method

| | Mole percent of lipid in sample (relative to amount of antibody) | | | Antibody Recovery |
|---|---|---|---|---|
| Monoclonal Antibody | Before treatment | After $1^{st}$ treatment | After $2^{nd}$ treatment | % Yield (after $1^{st}$ treatment) |
| Murine Anti-S1P | 60% | 6.3% | 0.97% | 88% |
| Humanized Anti-S1P | 46% | 4.3% | 0.81% | 89% |
| Humanized Anti-LPA | 14 | 4.5 | 6.0 | 91% |

Example 28

Formulations Containing the Humanized Monoclonal Antibody LT1009

1. Introduction

This example describes experiments to assess the stability of several formulations containing the humanized monoclonal antibody LT1009, which is reactive against the bioactive signaling lipid sphingosine 1-phosphate (S1P). LT1009 is an engineered full-length IgG1k isotype antibody that contains two identical light chains and two identical heavy chains, and has a total molecular weight of about 150 kDa. The complementarity determining regions (CDRs) of the light and heavy chains were derived from a murine monoclonal antibody generated against S1P, and further include a Cys to Ala substitution in one of the CDRs. In LT1009, human framework regions contribute approximately 95% of the total amino acid sequences in the antibody, which binds S1P with high affinity and specificity.

The purpose of the testing described in this example was to develop one or more preferred formulations suitable for systemic administration that are capable of maintaining stability and bioactivity of LT1009 over time. As is known, maintenance of molecular conformation, and hence stability, is dependent at least in part on the molecular environment of the protein and on storage conditions. Preferred formulations should not only stabilize the antibody, but also be tolerated by patients when injected. Accordingly, in this study the various formulations tested included either 11 mg/mL or 42 mg/mL of LT1009, as well as different pH, salt, and nonionic surfactant concentrations. Additionally, three different storage temperatures (5° C., 25° C., and 40° C.) were also examined (representing actual, accelerated, and temperature stress conditions, respectively). Stability was assessed using representative samples taken from the various formulations at five different time points: at study initiation and after two weeks, 1 month, 2 months, and 3 months. At each time point, testing involved visual inspection, syringeability (by pulling through a 30-gauge needle), and size exclusion high performance liquid chromatography (SE-HPLC). Circular dichroism (CD) spectroscopy was also used to assess protein stability since above a certain temperature, proteins undergo denaturation, followed by some degree of aggregate formation. The observed transition is referred to as an apparent denaturation or "melting" temperature ($T_m$) and indicate the relative stability of a protein.

2. Materials and Methods a. LT1009

The formulation samples (~0.6 mL each) were generated from an aqueous stock solution containing 42 mg/mL LT1009 in 24 mM sodium phosphate, 148 mM NaCl, pH 6.5. Samples containing 11 mg/mL LT1009 were prepared by diluting a volume of aqueous stock solution to the desired concentration using a 24 mM sodium phosphate, 148 mM NaCl, pH 6.5, solution. To prepare samples having the different pH values, the pH of each concentration of LT1009 (11 mg/mL and 42 mg/mL) was adjusted to 6.0 or 7.0 with 0.1 M HCl or 0.1 M NaOH, respectively, from the original 6.5 value. To prepare samples having different NaCl concentrations, 5 M NaCl was added to the samples to bring the salt concentration to either 300 mM or 450 mM from the original 148 mM. To prepare samples having different concentrations of nonionic surfactant, polysorbate-80 was added to the samples to a final concentration of either 200 ppm or 500 ppm. All samples were aseptically filtered through 0.22 µm PVDF membrane syringe filters into sterile, depyrogenated 10 mL serum vials. The vials were each then sealed with a non-shedding PTFE-lined stopper that was secured in place and protected from contamination with a crimped on cap. Prior to placement into stability chambers, the vials were briefly stored at 2-8° C.; thereafter, they were placed upright in a stability chamber adjusted to one of three specified storage conditions: 40° C. (±2° C.)/75% (±5%) relative humidity (RH); 25° C. (±2° C.)/60% (±5%) RH; or 5° C. (±3° C.)/ambient RH. A summary of the formulation variables tested appears in Table 44, below.

TABLE 44

Formulation Summary

| LT1009, 11 mg/mL | | | LT1009, 42 mg/mL | | |
|---|---|---|---|---|---|
| Polysorbate 80 | NaCl | pH | Polysorbate 80 | NaCl | pH |
| 0.02% Polysorbate | 148 mM NaCl | 7<br>6.5<br>6 | 0.02% Polysorbate | 148 mM NaCl | 7<br>6.5<br>6 |
|  | 300 mM NaCl | 7<br>6.5<br>6 |  | 300 mM NaCl | 7<br>6.5<br>6 |
|  | 450 mM NaCl | 7<br>6.5<br>6 |  | 450 mM NaCl | 7<br>6.5<br>6 |
| 0.05% Polysorbate | 148 mM NaCl | 7<br>6.5<br>6 | 0.05% Polysorbate | 148 mM NaCl | 7<br>6.5<br>6 |
|  | 300 mM NaCl | 7<br>6.5<br>6 |  | 300 mM NaCl | 7<br>6.5<br>6 |
|  | 450 mM NaCl | 7<br>6.5<br>6 |  | 450 mM NaCl | 7<br>6.5<br>6 | b. Taking of Samples

Samples of each formulation were analyzed according to the schedule listed in Table 45, below. One vial was used for each storage condition for all time points. On a date when samples were to be taken, vials were pulled from each stability chamber and 150 µL of each sample were transferred into correspondingly labeled separate vials that were placed on the bench for 1 hour prior to testing. The original vial was immediately placed back into the specified stability chamber after withdrawing the aliquot to be tested.

TABLE 45

Drug Product Formulation Study Stability Matrix

| Storage Conditions | Intervals (months) | | | | |
|---|---|---|---|---|---|
|  | T = 0 | 0.5 | 1 | 2 | 3 |
| | Protein Concentration LT1009, 11 mg/mL | | | | |
| 40° C. | x, y | x, y | x | x | x, y |
| 25° C. |  | x, y | x | x | x, y |
| 5° C. |  | x, y | x | x | x, y |
| | Protein Concentration LT1009, 42 mg/mL | | | | |
| 40° C. | x, y | x, y | x | x | x, y |
| 25° C. |  | x, y | x | x | x, y |
| 5° C. |  | x, y | x | x | x, y | x = Appearance, pH, SDS-PAGE, SE-HPLC, UV OD-280, IEF
y = Syringeability (performed by aseptically drawing 200 µL of a sample with a 30-gauge needle connected to a disposable 1-mL syringe)

c. Analytical Procedures

For a given time point, aliquots from each sample were subjected to a series of standard analyses, including visual inspection, syringeability, pH, SDS-PAGE (under both reducing and non-reducing conditions), SE-HPLC, and IEF. Protein concentrations were determined by UV spectroscopy (OD-280). Circular dichroism (CD) studies were also performed.

Circular dichroism spectroscopy was performed separately from the formulation studies. An Aviv 202 CD spectrophotometer was used to perform these analyses. Near UV CD spectra were collected from 400 nm to 250 nm. In this region, the disulfides and aromatic side chains contribute to the CD signals. In the far UV wavelength region (250-190 nm), the spectra are dominated by the peptide backbone. Thermal denaturation curves were generated by monitoring at 205 nm, a wavelength commonly used for b-sheet proteins. Data was collected using 0.1 mg/ml samples with heating from 25° C. to 85° C. Data were collected in 1° C. increments. The total time for such a denaturation scan was between 70 and 90 minutes. The averaging time was 2 seconds.

3. Results and Discussion

For all samples analyzed, visual appearance did not change over time. Likewise, syringeability testing demonstrated that samples could be pulled into a syringe equipped with a 30-gauge needle without difficulty. The results of the various analytical tests were consistent, and SE-HPLC was determined to be an excellent stability-indicating method for LT1009. These results showed that increasing salt concentration reduced both the generation of aggregates and the generation of smaller non-aggregate impurities. It was also found that decreasing pH also reduced aggregate and impurity formation. In addition, it was determined that increasing the polysorbate-80 concentration above 200 ppm did not further stabilize LT1009. FIG. 15 illustrates the results of the SE-HPLC experiments performed on samples containing 11 mg/mL LT1009. Comparable results were obtained for samples containing 42 mg/mL LT1009, although lower LT1009 concentrations showed less potential for aggregate formation as compared to the higher concentration, indicating that the antibody appeared to be slightly less stable under all conditions tested at the higher concentration.

From the circular dichroism studies, it was found that LT1009 adopts a well-defined tertiary structure in aqueous solution, with well-ordered environments around both Tyr and Trp residues. It also appeared that at least some of the disulfides in antibody molecules experience some degree of bond strain, although this is not uncommon when both intra- and inter-chain disulfides are present. The secondary structure of LT1009 was found to be unremarkable, and exhibited a far UV CD spectrum consistent with β-sheet structure. The observed transition is referred to as an apparent denaturation or "melting" temperature ($T_m$). Upon heating, LT1009 displayed an apparent $T_m$ of approximately 73° C. at pH 7.2. The apparent $T_m$ increased to about 77° C. at pH 6.0. These results indicate that a slightly acidic pH could enhance long-term stability of aqueous formulations of LT1009. Addition of NaCl and/or polysorbate-80 also provided additional stabilization.

Together, the data from these experiments indicate that LT1009 is most stable around pH 6 and 450 mM NaCl independent of antibody concentration. Indeed, SE-HPLC testing indicated that increasing the salt concentration to 450 mM and decreasing the pH to 6.0 while maintaining the polysorbate-80 concentration at 200 ppm had a very beneficial effect on the stability of LT1009. Inclusion of polysorbate-80 above 200 ppm had no further mitigating effect against aggregate formation, probably because it was already above its critical micelle concentration at 200 ppm. While not wishing to be bound by any particular theory, the fact that aggregate formation in LT1009 was reduced with increasing salt concentration under the studied conditions could indicate that aggregate formation is at least in part based more on ionic interactions between molecules rather than hydrophobic interactions. The observation that lowering the pH from 7 to 6 also reduces aggregate formation could be explained by reduced hydrophobicity of the amino acid histidine at the lower pH. Finally, the observed increased tendency of aggregate formation at increased LT11009 concentration can simply be explained by the greater chance of molecules hitting each other at the right time at the right place for aggregate formation.

As these experiments show, a preferred aqueous LT1009 formulation is one having 24 mM phosphate, 450 mM NaCl, 200 ppm polysorbate-80, pH 6.1. The relatively high tonicity of this formulation should not pose a problem for systemic applications since the drug product will likely be diluted by injection into iv-bags containing a larger volume of PBS prior to administration to a patient.

While the foregoing was written with the anti-S1P antibody LT1009 as exemplification, it is believed that this formulation is also relevant and useful for anti-LPA antibodies, including but not limited to LT3000 (B7, Lpathomab), B3, and others including humanized anti-LPA antibodies.

Example 29

Consensus of Anti-LPA Antibody Variable Domain Amino Acid Sequences

The heavy chain variable domain amino acid sequences from the five antibody clones provided in Tables 28-32 were aligned using the ClustalX program. As shown in FIG. 4A, a significant amount of identity, and an even greater amount of similarity, was found among four of the five sequences at each position. Antibody A63, in contrast, was markedly less similar to the other four sequences A significant amount of identity, and an even greater amount of similarity, was also found among four of the five light chain variable domain sequences, also from Tables 28-32. Again clone A63 is dissimilar. This can be seen in FIG. 4B. It should be noted that in examples above, antibody A63 was the only mAb that did not bind 18:2 or 18:1 LPA isoforms; this antibody was not pursued in further testing.

Based on these observations it is possible to identify consensus sequences which show particular amino acid residues, or types of amino acid residues, which are conserved at particular locations in the variable domains of the remaining four antibodies. While not wishing to be bound by theory, such residues are presently believed to be important for anti-LPA mAb structure and/or function. These sequences are shown in Tables 46 (LPA antibody heavy chain variable domain consensus sequence) and 47 (LPA antibody light chain variable domain consensus sequence). At each position, the amino acid type (noncharged polar, hydrophobic, acidic or basic, tyrosine or histidine, cysteine, or proline) is shown wherever all four antibodies have the same type of amino acid or precisely the same amino acid residue at a given position. Where the table contains a dash (-) there may be variation of amino acid type and/or identity at this position. Amino acid positions in Tables 46 and 47 are numbered according to the Kabat numbering scheme.

TABLE 46

Anti-LPA heavy chain variable domain consensus sequence

| Position (Kabat) | Amino acid type | Amino acid identity |
|---|---|---|
| 1 | noncharged polar | Q |
| 2 | hydrophobic | V |
| 3 | — | — |
| 4 | hydrophobic | L |
| 5 | noncharged polar | Q |
| 6 | noncharged polar | Q |
| 7 | noncharged polar | S |
| 8 | glycine | G |
| 9 | — | — |
| 10 | acidic | E |
| 11 | hydrophobic | L |
| 12 | hydrophobic | V |
| 13 | basic | R |
| 14 | proline | P |
| 15 | glycine | G |
| 16 | noncharged polar | T |
| 17 | noncharged polar | S |
| 18 | hydrophobic | V |
| 19 | basic | K |
| 20 | hydrophobic | V or L |
| 21 | noncharged polar | S |
| 22 | cysteine | C |
| 23 | — | — |
| 24 | hydrophobic | A |
| 25 | noncharged polar | S |
| 26 | glycine | G |
| 27 | — | — |
| 28 | — | — |
| 29 | hydrophobic | F |
| 30 | — | — |
| 31 | noncharged polar | N |
| 32 | tyrosine or histidine | Y |
| 33 | hydrophobic | L |
| 34 | hydrophobic | I |
| 35 | acidic | E |
| 36 | hydrophobic | W |
| 37 | hydrophobic | V or I |
| 38 | basic | K |
| 39 | noncharged polar | Q |
| 40 | basic | R |
| 41 | proline | P |
| 42 | glycine | G |
| 43 | noncharged polar | Q |
| 44 | glycine | G |
| 45 | hydrophobic | L |
| 46 | acidic | E |
| 47 | hydrophobic | W |
| 48 | hydrophobic | I |
| 49 | glycine | G |
| 50 | hydrophobic | L |
| 51 | hydrophobic | I |
| 52 | — | — |
| 52A | proline | P |
| 53 | — | — |
| 54 | noncharged polar | T or S |
| 55 | — | — |
| 56 | tyrosine or histidine | Y |
| 57 | — | — |
| 58 | noncharged polar | N |
| 59 | tyrosine or histidine | Y |
| 60 | noncharged polar | N |
| 61 | acidic | E |
| 62 | noncharged polar | N |
| 63 | hydrophobic | F |
| 64 | basic | K |
| 65 | glycine | G |
| 66 | basic | K |
| 67 | hydrophobic | A |

TABLE 46-continued

Anti-LPA heavy chain variable domain consensus sequence

| Position (Kabat) | Amino acid type | Amino acid identity |
|---|---|---|
| 68 | noncharged polar | T |
| 69 | hydrophobic | L |
| 70 | noncharged polar | T |
| 71 | hydrophobic | A |
| 72 | acidic | D |
| 73 | basic | K or R |
| 74 | noncharged polar | S |
| 75 | noncharged polar | S |
| 76 | noncharged polar | S |
| 77 | noncharged polar | T |
| 78 | hydrophobic | A |
| 79 | tyrosine or histidine | Y |
| 80 | hydrophobic | M |
| 81 | — | — |
| 82 | hydrophobic | L |
| 82A | noncharged polar | S |
| 82B | noncharged polar | S |
| 82C | hydrophobic | L |
| 83 | noncharged polar | T |
| 84 | noncharged polar | S |
| 85 | acidic | E |
| 86 | acidic | D |
| 87 | noncharged polar | S |
| 88 | hydrophobic | A |
| 89 | hydrophobic | V |
| 90 | tyrosine or histidine | Y |
| 91 | hydrophobic | F |
| 92 | cysteine | C |
| 93 | hydrophobic | A |
| 94 | basic | R |
| 95 | basic | R |
| 96 | hydrophobic | F |
| 97 | — | — |
| 98 | tyrosine or histidine | Y |
| 99 | tyrosine or histidine | Y |
| 100 | glycine | G |
| 100A | noncharged polar | S |
| 100B | — | — |
| 100C | — | — |
| 100D | tyrosine or histidine | Y |
| 100K | hydrophobic | F |
| 101 | acidic | D |
| 102 | tyrosine or histidine | Y |
| 103 | hydrophobic | W |
| 104 | glycine | G |
| 105 | noncharged polar | Q |
| 106 | glycine | G |
| 107 | noncharged polar | T |
| 108 | noncharged polar | T |
| 109 | hydrophobic | L |
| 110 | noncharged polar | T |
| 111 | hydrophobic | V |
| 112 | noncharged polar | S |
| 113 | noncharged polar | S |

TABLE 47

Anti-LPA light chain variable domain consensus sequence

| Position (Kabat) | Amino acid type | Amino acid identity |
|---|---|---|
| 1 | Acidic | D |
| 2 | Hydrophobic | V |
| 3 | Hydrophobic | V |
| 4 | Hydrophobic | M |
| 5 | Noncharged polar | T |
| 6 | Noncharged polar | Q |
| 7 | Noncharged polar | T |
| 8 | Proline | P |

TABLE 47-continued

Anti-LPA light chain variable domain consensus sequence

| Position (Kabat) | Amino acid type | Amino acid identity |
|---|---|---|
| 9 | hydrophobic | L |
| 10 | Noncharged polar | S |
| 11 | Hydrophobic | L |
| 12 | Proline | P |
| 13 | Hydrophobic | V |
| 14 | Noncharged polar | S |
| 15 | Noncharged polar | L |
| 16 | Glycine | G |
| 17 | Acidic | D |
| 18 | Noncharged polar | Q |
| 19 | Hydrophobic | A |
| 20 | Noncharged polar | S |
| 21 | Hydrophobic | I |
| 22 | Noncharged polar | S |
| 23 | Cysteine | C |
| 24 | — | — |
| 25 | Noncharged polar | S |
| 26 | — | — |
| 27 | Noncharged polar | Q |
| 27A | Noncharged polar | S |
| 27B | Hydrophobic | L |
| 27C | Hydrophobic | V or L |
| 27D | — | — |
| 27E | — | — |
| 28 | Noncharged polar | N |
| 29 | Glycine | G |
| 30 | Noncharged polar | N |
| 31 | Noncharged polar | T |
| 32 | Tyrosine or histidine | Y |
| 33 | Hydrophobic | L |
| 34 | Tyrosine or histidine | H |
| 35 | Hydrophobic | W |
| 36 | Tyrosine or histidine | Y |
| 37 | Hydrophobic | L |
| 38 | Noncharged polar | Q |
| 39 | Basic | K |
| 40 | Proline | P |
| 41 | Glycine | G |
| 42 | Noncharged polar | Q |
| 43 | Noncharged polar | S |
| 44 | Proline | P |
| 45 | Basic | K |
| 46 | Hydrophobic | L |
| 47 | Hydrophobic | L |
| 48 | Hydrophobic | I |
| 49 | — | — |
| 50 | Basic | K |
| 51 | Hydrophobic | V |
| 52 | Noncharged polar | S |
| 53 | Noncharged polar | N |
| 54 | — | — |
| 55 | Hydrophobic | F |
| 56 | Noncharged polar | S |
| 57 | Glycine | G |
| 58 | Hydrophobic | V |
| 59 | Proline | P |
| 60 | Acidic | D |
| 61 | Basic | R |
| 62 | Hydrophobic | F |
| 63 | Noncharged polar | S |
| 64 | Glycine | G |
| 65 | Noncharged polar | S |
| 66 | Glycine | G |
| 67 | — | — |
| 68 | Glycine | G |
| 69 | Noncharged polar | T |
| 70 | Acidic | D |
| 71 | Hydrophobic | F |
| 72 | Noncharged polar | T |
| 73 | Hydrophobic | L |
| 74 | Basic | K |
| 75 | Hydrophobic | I |
| 76 | Noncharged polar | S |
| 77 | Basic | R |
| 78 | Hydrophobic | V |
| 79 | Acidic | E |
| 80 | Hydrophobic | A |
| 81 | Acidic | E |
| 82 | Acidic | D |
| 83 | Hydrophobic | L |
| 84 | Glycine | G |
| 85 | — | — |
| 86 | Tyrosine or histidine | Y |
| 87 | Hydrophobic | F |
| 88 | Cysteine | C |
| 89 | Noncharged polar | S |
| 90 | Noncharged polar | Q |
| 91 | Noncharged polar | S |
| 92 | Noncharged polar | T |
| 93 | Tyrosine or histidine | H |
| 94 | Hydrophobic | F |
| 95 | Proline | P |
| 96 | Hydrophobic | F |
| 97 | Noncharged polar | T |
| 98 | Hydrophobic | F |
| 99 | Glycine | G |
| 100 | Noncharged polar | T |
| 101 | Glycine | G |
| 102 | Noncharged polar | T |
| 103 | Acidic | K |
| 104 | Hydrophobic | L |
| 105 | Acidic | E |
| 106 | Hydrophobic | I |
| 107 | Basic | K |

All of the compositions and methods described and claimed herein can be made and executed without undue experimentation in light of the present disclosure. While the compositions and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modifica-

What is claimed is:

1. A diagnostic reagent comprising a derivatized lysophosphatidic acid (LPA) conjugated to a solid support or carrier, wherein the derivatized LPA is selected from the group consisting of 18:2, 18:1, 18:0, 16:0 and 20:4 LPA, and wherein the hydrocarbon chain of the derivatized LPA includes a reactive group at the most distal carbon position of the hydrocarbon chain.

2. A diagnostic reagent according to claim 1 wherein the LPA is covalently conjugated to the solid support or carrier.

3. A diagnostic reagent according to claim 2 wherein the carrier is selected from the group consisting of polyethylene glycol, colloidal gold, adjuvant, a silicone bead, and a protein.

4. A diagnostic reagent according to claim 3 wherein the carrier is a protein selected from the group consisting of keyhole limpet hemocyanin, albumin, bovine thyroglobulin, and soybean trypsin inhibitor.

5. A diagnostic reagent according to claim 1 wherein the reactive group is selected from the group consisting of a sulfhydryl (thiol) group, a carboxylic acid group, a cyano group, an ester group, a hydroxyl group, an alkene group, an alkyne group, an acid chloride group, and a halogen atom group.

6. A diagnostic reagent according to claim 1 wherein the reactive group comprises a sulfhydryl (thiol) group.

* * * * *

SEQUENCE LISTING

```
<160> NUMBER OF SEQ ID NOS: 143

<210> SEQ ID NO 1
<211> LENGTH: 27
<212> TYPE: DNA
<213> ORGANISM: Artificial Sequence
<220> FEATURE:
<223> OTHER INFORMATION: Oligonucleotide

<400> SEQUENCE: 1
atgaaatgca gctggggcat sttcttc                                             27

<210> SEQ ID NO 2
<211> LENGTH: 26
<212> TYPE: DNA
<213> ORGANISM: Artificial Sequence
<220> FEATURE:
<223> OTHER INFORMATION: oligonucleotide

<400> SEQUENCE: 2
atgggatgga gctrtatcat sytctt                                              26

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide

<400> SEQUENCE: 3
atgaagwtgt ggttaaactg ggttttt                                             27

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide

<400> SEQUENCE: 4
atgractttg ggytcagctt grttt                                               25

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide

<400> SEQUENCE: 5
atggactcca ggctcaattt agttttcctt                                          30

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide

<400> SEQUENCE: 6
atggctgtcy trgsgctrct cttctgc                                             27

<210> SEQ ID NO 7
```

```
<211> LENGTH: 26
<212> TYPE: DNA
<213> ORGANISM: Artificial Sequence
<220> FEATURE:
<223> OTHER INFORMATION: Oligonucleotide

<400> SEQUENCE: 7
atggratgga gckggrtctt tmtctt                                          26

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide

<400> SEQUENCE: 8
atgagagtgc tgattctttt gtg                                             23

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide

<400> SEQUENCE: 9
atggmttggg tgtggamctt gctattcctg                                      30

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide

<400> SEQUENCE: 10
atgggcagac ttacattctc attcctg                                         27

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide

<400> SEQUENCE: 11
atggattttg ggctgatttt ttttattg                                        28

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide

<400> SEQUENCE: 12
atgatggtgt taagtcttct gtacctg                                         27

<210> SEQ ID NO 13
<211> LENGTH: 35
<212> TYPE: DNA
<213> ORGANISM: Artificial Sequence
<220> FEATURE:
<223> OTHER INFORMATION: Oligonucleotide

<400> SEQUENCE: 13
```

```
atatccacca tggratgsag ctgkgtmats ctctt                    35

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide

<400> SEQUENCE: 14
cagtggatag acagatgggg g                                   21

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide

<400> SEQUENCE: 15
cagtggatag accgatgggg c                                   21

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide

<400> SEQUENCE: 16
cagtggatag actgatgggg g                                   21

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide

<400> SEQUENCE: 17
caagggatag acagatgggg c                                   21

<210> SEQ ID NO 18
<211> LENGTH: 27
<212> TYPE: DNA
<213> ORGANISM: Artificial Sequence
<220> FEATURE:
<223> OTHER INFORMATION: Oligonucleotide

<400> SEQUENCE: 18
ggcagcacta gtaggggcca gtggata                             27

<210> SEQ ID NO 19
<211> LENGTH: 32
<212> TYPE: DNA
<213> ORGANISM: Artificial Sequence
<220> FEATURE:
<223> OTHER INFORMATION: Oligonucleotide

<400> SEQUENCE: 19
gggcaccatg gagacagaca cactcctgct at                       32

<210> SEQ ID NO 20
<211> LENGTH: 33
<212> TYPE: DNA
```

```
<213> ORGANISM: Artificial Sequence
<220> FEATURE:
<223> OTHER INFORMATION: Oligonucleotide

<400> SEQUENCE: 20
gggcaccatg gattttcaag tgcagatttt cag                          33

<210> SEQ ID NO 21
<211> LENGTH: 34
<212> TYPE: DNA
<213> ORGANISM: Artificial Sequence
<220> FEATURE:
<223> OTHER INFORMATION: Oligonucleotide

<400> SEQUENCE: 21
gggcaccatg gagwcacakw ctcaggtctt trta                         34

<210> SEQ ID NO 22
<211> LENGTH: 30
<212> TYPE: DNA
<213> ORGANISM: Artificial Sequence
<220> FEATURE:
<223> OTHER INFORMATION: Oligonucleotide

<400> SEQUENCE: 22
gggcaccatg kccccwrctc agytyctkgt                              30

<210> SEQ ID NO 23
<211> LENGTH: 28
<212> TYPE: DNA
<213> ORGANISM: Artificial Sequence
<220> FEATURE:
<223> OTHER INFORMATION: Oligonucleotide

<400> SEQUENCE: 23
caccatgaag ttgcctgtta ggctgttg                                28

<210> SEQ ID NO 24
<211> LENGTH: 30
<212> TYPE: DNA
<213> ORGANISM: Artificial Sequence
<220> FEATURE:
<223> OTHER INFORMATION: Oligonucleotide

<400> SEQUENCE: 24
atgaagttgv vtgttaggct gttggtgctg                              30

<210> SEQ ID NO 25
<211> LENGTH: 30
<212> TYPE: DNA
<213> ORGANISM: Artificial Sequence
<220> FEATURE:
<223> OTHER INFORMATION: Oligonucleotide

<400> SEQUENCE: 25
atggagwcag acacactcct gytatgggtg                              30

<210> SEQ ID NO 26
<211> LENGTH: 30
<212> TYPE: DNA
<213> ORGANISM: Artificial Sequence
<220> FEATURE:
<223> OTHER INFORMATION: Oligonucleotide

<400> SEQUENCE: 26
atgagtgtgc tcactcaggt cctggsgttg                              30
```

<210> SEQ ID NO 27
<211> LENGTH: 33
<212> TYPE: DNA
<213> ORGANISM: Artificial Sequence
<220> FEATURE:
<223> OTHER INFORMATION: Oligonucleotide

<400> SEQUENCE: 27
atgaggrccc ctgctcagwt tyttggmwtc ttg                          33

<210> SEQ ID NO 28
<211> LENGTH: 29
<212> TYPE: DNA
<213> ORGANISM: Artificial Sequence
<220> FEATURE:
<223> OTHER INFORMATION: Oligonucleotide

<400> SEQUENCE: 28
atggatttwa ggtgcagatt wtcagcttc                              29

<210> SEQ ID NO 29
<211> LENGTH: 27
<212> TYPE: DNA
<213> ORGANISM: Artificial Sequence
<220> FEATURE:
<223> OTHER INFORMATION: Oligonucleotide

<400> SEQUENCE: 29
atgaggtkck ktgktsagst sctgrgg                                27

<210> SEQ ID NO 30
<211> LENGTH: 31
<212> TYPE: DNA
<213> ORGANISM: Artificial Sequence
<220> FEATURE:
<223> OTHER INFORMATION: Oligonucleotide

<400> SEQUENCE: 30
atgggcwtca agatggagtc acakwyycwg g                           31

<210> SEQ ID NO 31
<211> LENGTH: 31
<212> TYPE: DNA
<213> ORGANISM: Artificial Sequence
<220> FEATURE:
<223> OTHER INFORMATION: Oligonucleotide

<400> SEQUENCE: 31
atgtggggay ctktttycmm tttttcaatt g                           31

<210> SEQ ID NO 32
<211> LENGTH: 25
<212> TYPE: DNA
<213> ORGANISM: Artificial Sequence
<220> FEATURE:
<223> OTHER INFORMATION: Oligonucleotide

<400> SEQUENCE: 32
atggtrtccw casctcagtt ccttg                                  25

<210> SEQ ID NO 33
<211> LENGTH: 27
<212> TYPE: DNA
<213> ORGANISM: Artificial Sequence
<220> FEATURE:

<223> OTHER INFORMATION: Oligonucleotide

<400> SEQUENCE: 33
atgtatatat gtttgttgtc tatttct                                              27

<210> SEQ ID NO 34
<211> LENGTH: 28
<212> TYPE: DNA
<213> ORGANISM: Artificial Sequence
<220> FEATURE:
<223> OTHER INFORMATION: Oligonucleotide

<400> SEQUENCE: 34
atggaagccc cagctcagct tctcttcc                                             28

<210> SEQ ID NO 35
<211> LENGTH: 19
<212> TYPE: DNA
<213> ORGANISM: Artificial Sequence
<220> FEATURE:
<223> OTHER INFORMATION: Oligonucleotide

<400> SEQUENCE: 35
tgggtatctg gtrcstgtg                                                       19

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide

<400> SEQUENCE: 36
atggagwcag acacactsct g                                                    21

<210> SEQ ID NO 37
<211> LENGTH: 26
<212> TYPE: DNA
<213> ORGANISM: Artificial Sequence
<220> FEATURE:
<223> OTHER INFORMATION: Oligonucleotide

<400> SEQUENCE: 37
atgragtywc agacccaggt cttyrt                                               26

<210> SEQ ID NO 38
<211> LENGTH: 26
<212> TYPE: DNA
<213> ORGANISM: Artificial Sequence
<220> FEATURE:
<223> OTHER INFORMATION: Oligonucleotide

<400> SEQUENCE: 38
atggagacac attctcaggt ctttgt                                               26

<210> SEQ ID NO 39
<211> LENGTH: 26
<212> TYPE: DNA
<213> ORGANISM: Artificial Sequence
<220> FEATURE:
<223> OTHER INFORMATION: Oligonucleotide

<400> SEQUENCE: 39
atggattcac aggcccaggt tcttat                                               26

```
<210> SEQ ID NO 40
<211> LENGTH: 26
<212> TYPE: DNA
<213> ORGANISM: Artificial Sequence
<220> FEATURE:
<223> OTHER INFORMATION: Oligonucleotide

<400> SEQUENCE: 40
atgatgagtc ctgcccagtt cctctt                                          26

<210> SEQ ID NO 41
<211> LENGTH: 29
<212> TYPE: DNA
<213> ORGANISM: Artificial Sequence
<220> FEATURE:
<223> OTHER INFORMATION: Oligonucleotide

<400> SEQUENCE: 41
atgaatttgc ctgttcatct cttggtgct                                       29

<210> SEQ ID NO 42
<211> LENGTH: 29
<212> TYPE: DNA
<213> ORGANISM: Artificial Sequence
<220> FEATURE:
<223> OTHER INFORMATION: Oligonucleotide

<400> SEQUENCE: 42 atggatttc aattggtcct catctcctt                                        29

<210> SEQ ID NO 43
<211> LENGTH: 26
<212> TYPE: DNA
<213> ORGANISM: Artificial Sequence
<220> FEATURE:
<223> OTHER INFORMATION: Oligonucleotide

<400> SEQUENCE: 43
atgaggtgcc tarctsagtt cctgrg                                          26

<210> SEQ ID NO 44
<211> LENGTH: 26
<212> TYPE: DNA
<213> ORGANISM: Artificial Sequence
<220> FEATURE:
<223> OTHER INFORMATION: Oligonucleotide

<400> SEQUENCE: 44
atgaagtact ctgctcagtt tctagg                                          26

<210> SEQ ID NO 45
<211> LENGTH: 26
<212> TYPE: DNA
<213> ORGANISM: Artificial Sequence
<220> FEATURE:
<223> OTHER INFORMATION: Oligonucleotide

<400> SEQUENCE: 45
atgaggcatt ctcttcaatt cttggg                                          26

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide
```

```
<400> SEQUENCE: 46
actggatggt gggaagatgg                                          20

<210> SEQ ID NO 47
<211> LENGTH: 30
<212> TYPE: DNA
<213> ORGANISM: Artificial Sequence
<220> FEATURE:
<223> OTHER INFORMATION: Oligonucleotide

<400> SEQUENCE: 47
gaagatctag acttactatg cagcatcagc                               30

<210> SEQ ID NO 48
<211> LENGTH: 60
<212> TYPE: DNA
<213> ORGANISM: Artificial Sequence
<220> FEATURE:
<223> OTHER INFORMATION: leader sequence

<400> SEQUENCE: 48
atgtctgtgc ctacccaggt gctgggactg ctgctgctgt ggctgacaga cgcccgctgt   60

<210> SEQ ID NO 49
<211> LENGTH: 57
<212> TYPE: DNA
<213> ORGANISM: Artificial Sequence
<220> FEATURE:
<223> OTHER INFORMATION: leader sequence

<400> SEQUENCE: 49
atggaatgga gctgggtgtt cctgttcttt ctgtccgtga ccacaggcgt gcattct       57

<210> SEQ ID NO 50
<211> LENGTH: 30
<212> TYPE: DNA
<213> ORGANISM: Mus musculus

<400> SEQUENCE: 50
ggagacgcct tcacaaatta cttaatagag                               30

<210> SEQ ID NO 51
<211> LENGTH: 51
<212> TYPE: DNA
<213> ORGANISM: Mus musculus

<400> SEQUENCE: 51
ctgatttatc ctgatagtgg ttacattaac tacaatgaga acttcaaggg c         51

<210> SEQ ID NO 52
<211> LENGTH: 39
<212> TYPE: DNA
<213> ORGANISM: Mus musculus

<400> SEQUENCE: 52
agatttgctt actacggtag tggctactac tttgactac                     39

<210> SEQ ID NO 53
<211> LENGTH: 48
<212> TYPE: DNA
<213> ORGANISM: Mus musculus

<400> SEQUENCE: 53
agatctagtc agagccttct aaaaactaat ggaaacacct atttacat            48
```

<210> SEQ ID NO 54
<211> LENGTH: 21
<212> TYPE: DNA
<213> ORGANISM: Mus musculus

<400> SEQUENCE: 54
aaagtttcca accgattttc t                                              21

<210> SEQ ID NO 55
<211> LENGTH: 27
<212> TYPE: DNA
<213> ORGANISM: Mus musculus

<400> SEQUENCE: 55
tctcaaagta cacattttcc attcacg                                        27

<210> SEQ ID NO 56
<211> LENGTH: 10
<212> TYPE: PRT
<213> ORGANISM: Mus musculus

<400> SEQUENCE: 56

Gly Asp Ala Phe Thr Asn Tyr Leu Ile Glu
1               5                   10

<210> SEQ ID NO 57
<211> LENGTH: 17
<212> TYPE: PRT
<213> ORGANISM: Mus musculus

<400> SEQUENCE: 57

Leu Ile Tyr Pro Asp Ser Gly Tyr Ile Asn Tyr Asn Glu Asn Phe Lys
1               5                   10                  15

Gly

<210> SEQ ID NO 58
<211> LENGTH: 13
<212> TYPE: PRT
<213> ORGANISM: Mus musculus

<400> SEQUENCE: 58

Arg Phe Ala Tyr Tyr Gly Ser Gly Tyr Tyr Phe Asp Tyr
1               5                   10

<210> SEQ ID NO 59
<211> LENGTH: 16
<212> TYPE: PRT
<213> ORGANISM: Mus musculus

<400> SEQUENCE: 59

Arg Ser Ser Gln Ser Leu Leu Lys Thr Asn Gly Asn Thr Tyr Leu His
1               5                   10                  15

<210> SEQ ID NO 60
<211> LENGTH: 7
<212> TYPE: PRT
<213> ORGANISM: Mus musculus

<400> SEQUENCE: 60

Lys Val Ser Asn Arg Phe Ser
1               5

```
<210> SEQ ID NO 61
<211> LENGTH: 9
<212> TYPE: PRT
<213> ORGANISM: Mus musculus

<400> SEQUENCE: 61

Ser Gln Ser Thr His Phe Pro Phe Thr
1               5

<210> SEQ ID NO 62
<211> LENGTH: 5
<212> TYPE: PRT
<213> ORGANISM: Mus musculus

<400> SEQUENCE: 62

Asn Tyr Leu Ile Glu
1               5

<210> SEQ ID NO 63
<211> LENGTH: 30
<212> TYPE: DNA
<213> ORGANISM: Mus musculus

<400> SEQUENCE: 63
ggatacggct tcattaatta cttaatagag                                      30

<210> SEQ ID NO 64
<211> LENGTH: 51
<212> TYPE: DNA
<213> ORGANISM: Mus musculus

<400> SEQUENCE: 64
ctgattaatc ctggaagtga ttatactaac tacaatgaga acttcaaggg c              51

<210> SEQ ID NO 65
<211> LENGTH: 39
<212> TYPE: DNA
<213> ORGANISM: Mus musculus

<400> SEQUENCE: 65
agatttggtt actacggtag cggcaactac tttgactac                            39

<210> SEQ ID NO 66
<211> LENGTH: 48
<212> TYPE: DNA
<213> ORGANISM: Mus musculus

<400> SEQUENCE: 66
acatctggtc agagccttgt ccacattaat ggaaacacct atttacat                  48

<210> SEQ ID NO 67
<211> LENGTH: 21
<212> TYPE: DNA
<213> ORGANISM: Mus musculus

<400> SEQUENCE: 67
aaagtttcca acctattttc t                                               21

<210> SEQ ID NO 68
<211> LENGTH: 27
<212> TYPE: DNA
<213> ORGANISM: Mus musculus

<400> SEQUENCE: 68
```

```
tctcaaagta cacattttcc attcacg                                              27
```

<210> SEQ ID NO 69
<211> LENGTH: 10
<212> TYPE: PRT
<213> ORGANISM: Mus musculus

<400> SEQUENCE: 69

Gly Tyr Gly Phe Ile Asn Tyr Leu Ile Glu
1               5                   10

<210> SEQ ID NO 70
<211> LENGTH: 17
<212> TYPE: PRT
<213> ORGANISM: Mus musculus

<400> SEQUENCE: 70

Leu Ile Asn Pro Gly Ser Asp Tyr Thr Asn Tyr Asn Glu Asn Phe Lys
1               5                   10                  15

Gly

<210> SEQ ID NO 71
<211> LENGTH: 13
<212> TYPE: PRT
<213> ORGANISM: Mus musculus

<400> SEQUENCE: 71

Arg Phe Gly Tyr Tyr Gly Ser Gly Asn Tyr Phe Asp Tyr
1               5                   10

<210> SEQ ID NO 72
<211> LENGTH: 16
<212> TYPE: PRT
<213> ORGANISM: Mus musculus

<400> SEQUENCE: 72

Thr Ser Gly Gln Ser Leu Val His Ile Asn Gly Asn Thr Tyr Leu His
1               5                   10                  15

<210> SEQ ID NO 73
<211> LENGTH: 7
<212> TYPE: PRT
<213> ORGANISM: Mus musculus

<400> SEQUENCE: 73

Lys Val Ser Asn Leu Phe Ser
1               5

<210> SEQ ID NO 74
<211> LENGTH: 9
<212> TYPE: PRT
<213> ORGANISM: Mus musculus

<400> SEQUENCE: 74

Ser Gln Ser Thr His Phe Pro Phe Thr
1               5

<210> SEQ ID NO 75
<211> LENGTH: 30
<212> TYPE: DNA
<213> ORGANISM: Mus musculus

<400> SEQUENCE: 75

```
ggagacgcct tcactaatta cttgatcgag                                           30
```

<210> SEQ ID NO 76
<211> LENGTH: 51
<212> TYPE: DNA
<213> ORGANISM: Mus musculus

<400> SEQUENCE: 76
ctgattattc tggaactgg ttatactaac tacaatgaga acttcaaggg c            51

<210> SEQ ID NO 77
<211> LENGTH: 39
<212> TYPE: DNA
<213> ORGANISM: Mus musculus

<400> SEQUENCE: 77
agatttggtt actacggtag tagcaactac tttgactac                         39

<210> SEQ ID NO 78
<211> LENGTH: 48
<212> TYPE: DNA
<213> ORGANISM: Mus musculus

<400> SEQUENCE: 78
agatctagtc agagccttgt acacagtaat ggaaacacct atttacat               48

<210> SEQ ID NO 79
<211> LENGTH: 21
<212> TYPE: DNA
<213> ORGANISM: Mus musculus

<400> SEQUENCE: 79
aaagtttcca accgattttc t                                            21

<210> SEQ ID NO 80
<211> LENGTH: 27
<212> TYPE: DNA
<213> ORGANISM: Mus musculus

<400> SEQUENCE: 80
tctcaaagta cacattttcc attcact                                      27

<210> SEQ ID NO 81
<211> LENGTH: 10
<212> TYPE: PRT
<213> ORGANISM: Mus musculus

<400> SEQUENCE: 81

Gly Asp Ala Phe Thr Asn Tyr Leu Ile Glu
1               5                   10

<210> SEQ ID NO 82
<211> LENGTH: 17
<212> TYPE: PRT
<213> ORGANISM: Mus musculus

<400> SEQUENCE: 82

Leu Ile Ile Pro Gly Thr Gly Tyr Thr Asn Tyr Asn Glu Asn Phe Lys
1               5                   10                  15

Gly

<210> SEQ ID NO 83
<211> LENGTH: 13
<212> TYPE: PRT

<213> ORGANISM: Mus musculus

<400> SEQUENCE: 83

Arg Phe Gly Tyr Tyr Gly Ser Ser Asn Tyr Phe Asp Tyr
1               5                   10

<210> SEQ ID NO 84
<211> LENGTH: 16
<212> TYPE: PRT
<213> ORGANISM: Mus musculus

<400> SEQUENCE: 84

Arg Ser Ser Gln Ser Leu Val His Ser Asn Gly Asn Thr Tyr Leu His
1               5                   10                  15

<210> SEQ ID NO 85
<211> LENGTH: 7
<212> TYPE: PRT
<213> ORGANISM: Mus musculus

<400> SEQUENCE: 85

Lys Val Ser Asn Arg Phe Ser
1               5

<210> SEQ ID NO 86
<211> LENGTH: 9
<212> TYPE: PRT
<213> ORGANISM: Mus musculus

<400> SEQUENCE: 86

Ser Gln Ser Thr His Phe Pro Phe Thr
1               5

<210> SEQ ID NO 87
<211> LENGTH: 30
<212> TYPE: DNA
<213> ORGANISM: Mus musculus

<400> SEQUENCE: 87
ggagacgcct tcactaatta cttgatcgag                                     30

<210> SEQ ID NO 88
<211> LENGTH: 51
<212> TYPE: DNA
<213> ORGANISM: Mus musculus

<400> SEQUENCE: 88
ctgattattc ctggaactgg ttatactaac tacaatgaga acttcaaggg c             51

<210> SEQ ID NO 89
<211> LENGTH: 39
<212> TYPE: DNA
<213> ORGANISM: Mus musculus

<400> SEQUENCE: 89
agatttggtt actacggtag tggctactac tttgactac                           39

<210> SEQ ID NO 90
<211> LENGTH: 48
<212> TYPE: DNA
<213> ORGANISM: Mus musculus

<400> SEQUENCE: 90
agatctagtc agagccttgt acacagtaat ggaaacacct atttacat                 48

```
<210> SEQ ID NO 91
<211> LENGTH: 21
<212> TYPE: DNA
<213> ORGANISM: Mus musculus

<400> SEQUENCE: 91
aaagtttcca accgattttc t                                              21

<210> SEQ ID NO 92
<211> LENGTH: 27
<212> TYPE: DNA
<213> ORGANISM: Mus musculus

<400> SEQUENCE: 92
tctcaaagta cacattttcc attcacg                                        27

<210> SEQ ID NO 93
<211> LENGTH: 10
<212> TYPE: PRT
<213> ORGANISM: Mus musculus

<400> SEQUENCE: 93

Gly Asp Ala Phe Thr Asn Tyr Leu Ile Glu
1               5                   10

<210> SEQ ID NO 94
<211> LENGTH: 17
<212> TYPE: PRT
<213> ORGANISM: Mus musculus

<400> SEQUENCE: 94

Leu Ile Ile Pro Gly Thr Gly Tyr Thr Asn Tyr Asn Glu Asn Phe Lys
1               5                   10                  15

Gly

<210> SEQ ID NO 95
<211> LENGTH: 13
<212> TYPE: PRT
<213> ORGANISM: Mus musculus

<400> SEQUENCE: 95

Arg Phe Gly Tyr Tyr Gly Ser Gly Tyr Tyr Phe Asp Tyr
1               5                   10

<210> SEQ ID NO 96
<211> LENGTH: 16
<212> TYPE: PRT
<213> ORGANISM: Mus musculus

<400> SEQUENCE: 96

Arg Ser Ser Gln Ser Leu Val His Ser Asn Gly Asn Thr Tyr Leu His
1               5                   10                  15

<210> SEQ ID NO 97
<211> LENGTH: 7
<212> TYPE: PRT
<213> ORGANISM: Mus musculus

<400> SEQUENCE: 97

Lys Val Ser Asn Arg Phe Ser
1               5
```

```
<210> SEQ ID NO 98
<211> LENGTH: 9
<212> TYPE: PRT
<213> ORGANISM: Mus musculus

<400> SEQUENCE: 98

Ser Gln Ser Thr His Phe Pro Phe Thr
1               5

<210> SEQ ID NO 99
<211> LENGTH: 33
<212> TYPE: DNA
<213> ORGANISM: Mus musculus

<400> SEQUENCE: 99
ggcttctcca tcaccagtgg ttattactgg acc                               33

<210> SEQ ID NO 100
<211> LENGTH: 48
<212> TYPE: DNA
<213> ORGANISM: Mus musculus

<400> SEQUENCE: 100
tacataggct acgatggtag caatgactcc aacccatctc tcaaaaat              48

<210> SEQ ID NO 101
<211> LENGTH: 27
<212> TYPE: DNA
<213> ORGANISM: Mus musculus

<400> SEQUENCE: 101
gcgatgttgc ggcgaggatt tgactac                                      27

<210> SEQ ID NO 102
<211> LENGTH: 30
<212> TYPE: DNA
<213> ORGANISM: Mus musculus

<400> SEQUENCE: 102
agtgccagct caagtttaag ttacatgcac                                   30

<210> SEQ ID NO 103
<211> LENGTH: 21
<212> TYPE: DNA
<213> ORGANISM: Mus musculus

<400> SEQUENCE: 103
gacacatcca aactggcttc t                                            21

<210> SEQ ID NO 104
<211> LENGTH: 21
<212> TYPE: DNA
<213> ORGANISM: Mus musculus

<400> SEQUENCE: 104
catcggcgga gtagttacac g                                            21

<210> SEQ ID NO 105
<211> LENGTH: 11
<212> TYPE: PRT
<213> ORGANISM: Mus musculus

<400> SEQUENCE: 105

Gly Phe Ser Ile Thr Ser Gly Tyr Tyr Trp Thr
```

<210> SEQ ID NO 106
<211> LENGTH: 16
<212> TYPE: PRT
<213> ORGANISM: Mus musculus

<400> SEQUENCE: 106

Tyr Ile Gly Tyr Asp Gly Ser Asn Asp Ser Asn Pro Ser Leu Lys Asn
1               5                   10                  15

<210> SEQ ID NO 107
<211> LENGTH: 9
<212> TYPE: PRT
<213> ORGANISM: Mus musculus

<400> SEQUENCE: 107

Ala Met Leu Arg Arg Gly Phe Asp Tyr
1               5

<210> SEQ ID NO 108
<211> LENGTH: 10
<212> TYPE: PRT
<213> ORGANISM: Mus musculus

<400> SEQUENCE: 108

Ser Ala Ser Ser Ser Leu Ser Tyr Met His
1               5                   10

<210> SEQ ID NO 109
<211> LENGTH: 7
<212> TYPE: PRT
<213> ORGANISM: Mus musculus

<400> SEQUENCE: 109

Asp Thr Ser Lys Leu Ala Ser
1               5

<210> SEQ ID NO 110
<211> LENGTH: 7
<212> TYPE: PRT
<213> ORGANISM: Mus musculus

<400> SEQUENCE: 110

His Arg Arg Ser Ser Tyr Thr
1               5

<210> SEQ ID NO 111
<211> LENGTH: 6
<212> TYPE: PRT
<213> ORGANISM: Mus musculus

<400> SEQUENCE: 111

Ser Gly Tyr Tyr Trp Thr
1               5

<210> SEQ ID NO 112
<211> LENGTH: 455
<212> TYPE: DNA
<213> ORGANISM: Artificial Sequence
<220> FEATURE:
<223> OTHER INFORMATION: Antibody variable domain with leader and cut
      site sequences added

<400> SEQUENCE: 112

```
aagcttgccg ccaccatgga atggagctgg gtgttcctgt tctttctgtc cgtgaccaca    60
ggcgtgcatt ctcaggtcaa gctgcagcag tctggacctg agctggtaag gcctgggact   120
tcagtgaagg tgtcctgcac ggcttctgga gacgccttca caaattactt aatagagtgg   180
gtaaaacaga ggcctggaca gggccttgag tggattggac tgatttatcc tgatagtggt   240
tacattaact acaatgagaa cttcaagggc aaggcaacac tgactgcaga cagatcctcc   300
agcactgcct acatgcagct cagcagcctg acatctgagg actctgcggt ctatttctgt   360
gcaagaagat ttgcttacta cggtagtggc tactactttg actactgggg ccaaggcacc   420
actctcacag tctcctcagc ctccaccaag ggccc                               455
```

<210> SEQ ID NO 113
<211> LENGTH: 417
<212> TYPE: DNA
<213> ORGANISM: Artificial Sequence
<220> FEATURE:
<223> OTHER INFORMATION: Antibody variable domain with leader and cut
      site sequences added

<400> SEQUENCE: 113

```
aagcttgccg ccaccatgtc tgtgcctacc caggtgctgg gactgctgct gctgtggctg    60
acagacgccc gctgtgatgt tgtgatgacc caaactccac tctccctgcc tgtcagtctt   120
ggagatcaag cctccatctc ttgcagatct agtcagagcc ttctaaaaac taatggaaac   180
acctatttac attggtacct gcagaagcca ggccagtctc caaaactcct aatcttcaaa   240
gtttccaacc gattttctgg ggtcccggac aggttcagtg gcagtggatc agggacagac   300
ttcacactca agatcagcag agtggaggct gaggatctgg gagtttattt ctgctctcaa   360
agtacacatt ttccattcac gttcggcacg gggacaaaat tggaaataaa acgtacg      417
```

<210> SEQ ID NO 114
<211> LENGTH: 151
<212> TYPE: PRT
<213> ORGANISM: Artificial Sequence
<220> FEATURE:
<223> OTHER INFORMATION: Antibody variable domain with leader and cut
      site sequences added

<400> SEQUENCE: 114

```
Lys Leu Ala Ala Thr Met Glu Trp Ser Trp Val Phe Leu Phe Phe Leu
1               5                   10                  15

Ser Val Thr Thr Gly Val His Ser Gln Val Lys Leu Gln Gln Ser Gly
            20                  25                  30

Pro Glu Leu Val Arg Pro Gly Thr Ser Val Lys Val Ser Cys Thr Ala
        35                  40                  45

Ser Gly Asp Ala Phe Thr Asn Tyr Leu Ile Glu Trp Val Lys Gln Arg
    50                  55                  60

Pro Gly Gln Gly Leu Glu Trp Ile Gly Leu Ile Tyr Pro Asp Ser Gly
65                  70                  75                  80

Tyr Ile Asn Tyr Asn Glu Asn Phe Lys Gly Lys Ala Thr Leu Thr Ala
                85                  90                  95

Asp Arg Ser Ser Ser Thr Ala Tyr Met Gln Leu Ser Ser Leu Thr Ser
            100                 105                 110

Glu Asp Ser Ala Val Tyr Phe Cys Ala Arg Arg Phe Ala Tyr Tyr Gly
        115                 120                 125

Ser Gly Tyr Tyr Phe Asp Tyr Trp Gly Gln Gly Thr Thr Leu Thr Val
    130                 135                 140
```

Ser Ser Ala Ser Thr Lys Gly
145                 150

<210> SEQ ID NO 115
<211> LENGTH: 139
<212> TYPE: PRT
<213> ORGANISM: Artificial Sequence
<220> FEATURE:
<223> OTHER INFORMATION: Antibody variable domain with leader and cut
      site sequences added

<400> SEQUENCE: 115

Lys Leu Ala Ala Thr Met Ser Val Pro Thr Gln Val Leu Gly Leu Leu
1               5                   10                  15

Leu Leu Trp Leu Thr Asp Ala Arg Cys Asp Val Val Met Thr Gln Thr
            20                  25                  30

Pro Leu Ser Leu Pro Val Ser Leu Gly Asp Gln Ala Ser Ile Ser Cys
        35                  40                  45

Arg Ser Ser Gln Ser Leu Leu Lys Thr Asn Gly Asn Thr Tyr Leu His
    50                  55                  60

Trp Tyr Leu Gln Lys Pro Gly Gln Ser Pro Lys Leu Leu Ile Phe Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Phe Cys Ser Gln Ser Thr His Phe Pro Phe Thr Phe
        115                 120                 125

Gly Thr Gly Thr Lys Leu Glu Ile Lys Arg Thr
    130                 135

<210> SEQ ID NO 116
<211> LENGTH: 455
<212> TYPE: DNA
<213> ORGANISM: Artificial Sequence
<220> FEATURE:
<223> OTHER INFORMATION: Antibody variable domain with leader and cut
      site sequences added

<400> SEQUENCE: 116
aagcttgccg ccaccatgga atggagctgg gtgttcctgt tctttctgtc cgtgaccaca     60
ggcgtgcatt ctcaggtcca actgcagcag tctggagctg agctggtaag gcctgggact    120
tcagtgaagg tgtcctgcaa ggcttctgga tacggcttca ttaattactt aatagagtgg    180
ataaaacaga ggcctggaca gggccttgag tggattggac tgattaatcc tggaagtgat    240
tatactaact acaatgagaa cttcaagggc aaggcaacac tgactgcaga caagtcctcc    300
agcactgcct acatgcacct cagcagcctg acatctgagg actctgcggt ctatttctgt    360
gcaagaagat ttggttacta cggtagcggc aactactttg actactgggg ccaaggcacc    420
actctcacag tctcctcagc tccaccaag ggccc                                455

<210> SEQ ID NO 117
<211> LENGTH: 417
<212> TYPE: DNA
<213> ORGANISM: Artificial Sequence
<220> FEATURE:
<223> OTHER INFORMATION: Antibody variable domain with leader and cut
      site sequences added

<400> SEQUENCE: 117

```
aagcttgccg ccaccatgtc tgtgcctacc caggtgctgg gactgctgct gctgtggctg    60
acagacgccc gctgtgatgt tgtgatgacc caaactccac tctccctgcc tgtcagtctt   120
ggagatcaag cctccatctc ttgcacatct ggtcagagcc ttgtccacat taatggaaac   180
acctatttac attggtacct gcagaagcca ggccagtctc caaagctcct catctacaaa   240
gtttccaacc tattttctgg ggtcccagac aggttcagtg gcagtggatc agggacagat   300
ttcacactca agatcagcag agtggaggct gaggatctgg gagtttattt ctgctctcaa   360
agtacacatt ttccattcac gttcggcacg gggacaaaat tggaaataaa acgtacg      417
```

<210> SEQ ID NO 118
<211> LENGTH: 151
<212> TYPE: PRT
<213> ORGANISM: Artificial Sequence
<220> FEATURE:
<223> OTHER INFORMATION: Antibody variable domain with leader and cut site sequences added

<400> SEQUENCE: 118

```
Lys Leu Ala Ala Thr Met Glu Trp Ser Trp Val Phe Leu Phe Phe Leu
1               5                   10                  15

Ser Val Thr Thr Gly Val His Ser Gln Val Gln Leu Gln Gln Ser Gly
                20                  25                  30

Ala Glu Leu Val Arg Pro Gly Thr Ser Val Lys Val Ser Cys Lys Ala
            35                  40                  45

Ser Gly Tyr Gly Phe Ile Asn Tyr Leu Ile Glu Trp Ile Lys Gln Arg
        50                  55                  60

Pro Gly Gln Gly Leu Glu Trp Ile Gly Leu Ile Asn Pro Gly Ser Asp
65                  70                  75                  80

Tyr Thr Asn Tyr Asn Glu Asn Phe Lys Gly Lys Ala Thr Leu Thr Ala
                85                  90                  95

Asp Lys Ser Ser Ser Thr Ala Tyr Met His Leu Ser Ser Leu Thr Ser
            100                 105                 110

Glu Asp Ser Ala Val Tyr Phe Cys Ala Arg Arg Phe Gly Tyr Tyr Gly
        115                 120                 125

Ser Gly Asn Tyr Phe Asp Tyr Trp Gly Gln Gly Thr Thr Leu Thr Val
    130                 135                 140

Ser Ser Ala Ser Thr Lys Gly
145                 150
```

<210> SEQ ID NO 119
<211> LENGTH: 139
<212> TYPE: PRT
<213> ORGANISM: Artificial Sequence
<220> FEATURE:
<223> OTHER INFORMATION: Antibody variable domain with leader and cut site sequences added

<400> SEQUENCE: 119

```
Lys Leu Ala Ala Thr Met Ser Val Pro Thr Gln Val Leu Gly Leu Leu
1               5                   10                  15

Leu Leu Trp Leu Thr Asp Ala Arg Cys Asp Val Val Met Thr Gln Thr
                20                  25                  30

Pro Leu Ser Leu Pro Val Ser Leu Gly Asp Gln Ala Ser Ile Ser Cys
            35                  40                  45

Thr Ser Gly Gln Ser Leu Val His Ile Asn Gly Asn Thr Tyr Leu His
        50                  55                  60

Trp Tyr Leu Gln Lys Pro Gly Gln Ser Pro Lys Leu Leu Ile Tyr Lys
```

```
                65                  70                  75                  80
Val Ser Asn Leu Phe Ser Gly Val Pro Asp Arg Phe Ser Gly Ser Gly
                    85                  90                  95

Ser Gly Thr Asp Phe Thr Leu Lys Ile Ser Arg Val Glu Ala Glu Asp
            100                 105                 110

Leu Gly Val Tyr Phe Cys Ser Gln Ser Thr His Phe Pro Phe Thr Phe
        115                 120                 125

Gly Thr Gly Thr Lys Leu Glu Ile Lys Arg Thr
    130                 135

<210> SEQ ID NO 120
<211> LENGTH: 455
<212> TYPE: PRT
<213> ORGANISM: Artificial Sequence
<220> FEATURE:
<223> OTHER INFORMATION: Antibody variable domain with leader and cut
      site sequences added

<400> SEQUENCE: 120

Ala Ala Gly Cys Thr Thr Gly Cys Cys Gly Cys Ala Cys Cys Ala
1               5                   10                  15

Thr Gly Gly Ala Ala Thr Gly Gly Ala Gly Cys Thr Gly Gly Gly Thr
                20                  25                  30

Gly Thr Thr Cys Cys Thr Gly Thr Thr Cys Thr Thr Cys Thr Gly
            35                  40                  45

Thr Cys Cys Gly Thr Gly Ala Cys Cys Ala Cys Ala Gly Gly Cys Gly
        50                  55                  60

Thr Gly Cys Ala Thr Thr Cys Thr Cys Ala Gly Gly Thr Cys Cys Ala
65                  70                  75                  80

Gly Cys Thr Gly Cys Ala Gly Cys Ala Gly Thr Cys Thr Gly Gly Ala
                85                  90                  95

Gly Cys Thr Gly Ala Gly Cys Thr Gly Gly Thr Cys Ala Gly Gly Cys
            100                 105                 110

Cys Thr Gly Gly Gly Ala Cys Thr Thr Cys Ala Gly Thr Gly Ala Ala
        115                 120                 125

Gly Gly Thr Gly Thr Cys Cys Thr Gly Cys Ala Ala Gly Gly Cys Thr
    130                 135                 140

Thr Cys Thr Gly Gly Ala Gly Ala Cys Gly Cys Cys Thr Thr Cys Ala
145                 150                 155                 160

Cys Thr Ala Ala Thr Thr Ala Cys Thr Thr Gly Ala Thr Gly Ala
        165                 170                 175

Gly Thr Gly Gly Gly Thr Ala Ala Gly Cys Ala Gly Ala Gly Gly
            180                 185                 190

Cys Cys Thr Gly Gly Ala Cys Ala Gly Gly Gly Cys Cys Thr Thr Gly
        195                 200                 205

Ala Gly Thr Gly Gly Ala Thr Thr Gly Gly Ala Cys Thr Gly Ala Thr
    210                 215                 220

Thr Ala Thr Thr Cys Cys Thr Gly Gly Ala Ala Cys Thr Gly Gly Thr
225                 230                 235                 240

Thr Ala Thr Ala Cys Thr Ala Ala Cys Thr Ala Cys Ala Ala Thr Gly
        245                 250                 255

Ala Gly Ala Ala Cys Thr Thr Cys Ala Ala Gly Gly Gly Cys Ala Ala
            260                 265                 270

Gly Gly Cys Ala Ala Cys Ala Cys Thr Gly Ala Cys Thr Gly Cys Ala
        275                 280                 285
```

```
Gly Ala Cys Ala Ala Thr Cys Cys Thr Cys Ala Gly Cys Ala
    290                 295                 300

Cys Thr Gly Cys Cys Thr Ala Cys Ala Thr Gly Cys Ala Gly Cys Thr
305                 310                 315                 320

Cys Ala Gly Cys Ala Gly Cys Cys Thr Gly Ala Cys Ala Thr Cys Thr
                325                 330                 335

Gly Ala Gly Gly Ala Cys Thr Cys Gly Cys Gly Gly Thr Cys Thr
            340                 345                 350

Ala Thr Thr Thr Cys Thr Gly Thr Gly Cys Ala Ala Gly Ala Ala Gly
            355                 360                 365

Ala Thr Thr Thr Gly Gly Thr Thr Ala Cys Thr Ala Cys Gly Gly Thr
        370                 375                 380

Ala Gly Thr Ala Gly Cys Ala Ala Cys Thr Ala Cys Thr Thr Gly
385                 390                 395                 400

Ala Cys Thr Ala Cys Thr Gly Gly Gly Gly Cys Cys Ala Ala Gly Gly
                405                 410                 415

Cys Ala Cys Cys Ala Cys Thr Cys Thr Cys Ala Cys Ala Gly Thr Cys
            420                 425                 430

Thr Cys Cys Thr Cys Ala Gly Cys Cys Thr Cys Cys Ala Cys Cys Ala
        435                 440                 445

Ala Gly Gly Gly Cys Cys Cys
450                 455
```

<210> SEQ ID NO 121
<211> LENGTH: 417
<212> TYPE: DNA
<213> ORGANISM: Artificial Sequence
<220> FEATURE:
<223> OTHER INFORMATION: Antibody variable domain with leader and cut
      site sequences added

<400> SEQUENCE: 121

```
aagcttgccg ccaccatgtc tgtgcctacc caggtgctgg gactgctgct gctgtggctg      60
acagacgccc gctgtgatgt tgtgatgacc caaactccac tctccctgcc tgtcagtctt     120
ggagatcaag cctccatctc ttgcagatct agtcagagcc ttgtacacag taatggaaac     180
acctatttac attggtacct gcagaagcca ggccagtctc caaagctcct gatctacaaa     240
gtttccaacc gattttctgg ggtcccagac aggttcagtg gcagtggacc agggacagat     300
ttcacactca agatcagcag agtggaggct gaggatctgg gaatttattt ctgctctcaa     360
agtacacatt ttccattcac tttcggcacg gggacaaaat tggaaataaa acgtacg        417
```

<210> SEQ ID NO 122
<211> LENGTH: 151
<212> TYPE: PRT
<213> ORGANISM: Artificial Sequence
<220> FEATURE:
<223> OTHER INFORMATION: Antibody variable domain with leader and cut
      site sequences added

<400> SEQUENCE: 122

```
Lys Leu Ala Ala Thr Met Glu Trp Ser Trp Val Phe Leu Phe Phe Leu
1               5                   10                  15

Ser Val Thr Thr Gly Val His Ser Gln Val Gln Leu Gln Gln Ser Gly
            20                  25                  30

Ala Glu Leu Val Arg Pro Gly Thr Ser Val Lys Val Ser Cys Lys Ala
        35                  40                  45

Ser Gly Asp Ala Phe Thr Asn Tyr Leu Ile Glu Trp Val Lys Gln Arg
```

```
                 50                  55                  60
Pro Gly Gln Gly Leu Glu Trp Ile Gly Leu Ile Ile Pro Thr Gly
 65                  70                  75                  80

Tyr Thr Asn Tyr Asn Glu Asn Phe Lys Gly Lys Ala Thr Leu Thr Ala
                     85                  90                  95

Asp Lys Ser Ser Ser Thr Ala Tyr Met Gln Leu Ser Ser Leu Thr Ser
                100                 105                 110

Glu Asp Ser Ala Val Tyr Phe Cys Ala Arg Arg Phe Gly Tyr Tyr Gly
            115                 120                 125

Ser Ser Asn Tyr Phe Asp Tyr Trp Gly Gln Gly Thr Thr Leu Thr Val
        130                 135                 140

Ser Ser Ala Ser Thr Lys Gly
145                 150

<210> SEQ ID NO 123
<211> LENGTH: 139
<212> TYPE: PRT
<213> ORGANISM: Mus musculus

<400> SEQUENCE: 123

Lys Leu Ala Ala Thr Met Ser Val Pro Thr Gln Val Leu Gly Leu Leu
  1               5                  10                  15

Leu Leu Trp Leu Thr Asp Ala Arg Cys Asp Val Val Met Thr Gln Thr
                 20                  25                  30

Pro Leu Ser Leu Pro Val Ser Leu Gly Asp Gln Ala Ser Ile Ser Cys
             35                  40                  45

Arg Ser Ser Gln Ser Leu Val His Ser Asn Gly Asn Thr Tyr Leu His
         50                  55                  60

Trp Tyr Leu Gln Lys Pro Gly Gln Ser Pro Lys Leu Leu Ile Tyr Lys
 65                  70                  75                  80

Val Ser Asn Arg Phe Ser Gly Val Pro Asp Arg Phe Ser Gly Ser Gly
                 85                  90                  95

Pro Gly Thr Asp Phe Thr Leu Lys Ile Ser Arg Val Glu Ala Glu Asp
            100                 105                 110

Leu Gly Ile Tyr Phe Cys Ser Gln Ser Thr His Phe Pro Phe Thr Phe
        115                 120                 125

Gly Thr Gly Thr Lys Leu Glu Ile Lys Arg Thr
    130                 135

<210> SEQ ID NO 124
<211> LENGTH: 455
<212> TYPE: DNA
<213> ORGANISM: Artificial Sequence
<220> FEATURE:
<223> OTHER INFORMATION: Antibody variable domain with leader and cut
      site sequences added

<400> SEQUENCE: 124
aagcttgccg ccaccatgga atggagctgg gtgttcctgt tctttctgtc cgtgaccaca      60
ggcgtgcatt ctcaggtcca gctgcagcag tctggagctg agctggtcag gcctgggact     120
tcagtgaagt tgtcctgcaa ggcttctgga gacgccttca ctaattactt gatcgagtgg     180
gtaaagcaga ggcctggaca gggccttgag tggattggac tgattattcc tggaactggt     240
tatactaact acaatgagaa cttcaagggc aaggcaacac tgactgcaga caagtcctcc     300
agcactgcct acatgcagct cagcagcctg acatctgagg actctgcggt ctatttctgt     360
gcaagaagat ttggttacta cggtagtggc tactactttg actactgggg ccaaggcacc     420
```

```
actctcacag tctcctcagc ctccaccaag ggccc                               455
```

<210> SEQ ID NO 125
<211> LENGTH: 417
<212> TYPE: DNA
<213> ORGANISM: Artificial Sequence
<220> FEATURE:
<223> OTHER INFORMATION: Antibody variable domain with leader and cut
      site sequences added

<400> SEQUENCE: 125

```
aagcttgccg ccaccatgtc tgtgcctacc caggtgctgg gactgctgct gctgtggctg    60
acagacgccc gctgtgatgt tgtgatgacc caaactccac tctccctgcc tgtcagtctt   120
ggagatcaag cctccatctc ttgcagatct agtcagagcc ttgtacacag taatggaaac   180
acctatttac attggtacct gcagaagcca ggccagtctc caaagctcct gatctacaaa   240
gtttccaacc gattttctgg ggtcccagac aggttcagtg gcagtggacc agggacagat   300
ttcacactca agatcagcag agtggaggct gaggatctgg gagtttattt ctgctctcaa   360
agtacacatt ttccattcac gttcggcacg ggcacaaaat tggaaataaa acgtacg      417
```

<210> SEQ ID NO 126
<211> LENGTH: 151
<212> TYPE: PRT
<213> ORGANISM: Artificial Sequence
<220> FEATURE:
<223> OTHER INFORMATION: Antibody variable domain with leader and cut
 site sequences added

<400> SEQUENCE: 126

```
Lys Leu Ala Ala Thr Met Glu Trp Ser Trp Val Phe Leu Phe Phe Leu
1               5                   10                  15

Ser Val Thr Thr Gly Val His Ser Gln Val Gln Leu Gln Gln Ser Gly
            20                  25                  30

Ala Glu Leu Val Arg Pro Gly Thr Ser Val Lys Leu Ser Cys Lys Ala
        35                  40                  45

Ser Gly Asp Ala Phe Thr Asn Tyr Leu Ile Glu Trp Val Lys Gln Arg
    50                  55                  60

Pro Gly Gln Gly Leu Glu Trp Ile Gly Leu Ile Ile Pro Gly Thr Gly
65                  70                  75                  80

Tyr Thr Asn Tyr Asn Glu Asn Phe Lys Gly Lys Ala Thr Leu Thr Ala
                85                  90                  95

Asp Lys Ser Ser Ser Thr Ala Tyr Met Gln Leu Ser Ser Leu Thr Ser
            100                 105                 110

Glu Asp Ser Ala Val Tyr Phe Cys Ala Arg Arg Phe Gly Tyr Tyr Gly
        115                 120                 125

Ser Gly Tyr Tyr Phe Asp Tyr Trp Gly Gln Gly Thr Thr Leu Thr Val
    130                 135                 140

Ser Ser Ala Ser Thr Lys Gly
145                 150
```

<210> SEQ ID NO 127
<211> LENGTH: 139
<212> TYPE: PRT
<213> ORGANISM: Artificial Sequence
<220> FEATURE:
<223> OTHER INFORMATION: Antibody variable domain with leader and cut
      site sequences added

<400> SEQUENCE: 127

Lys Leu Ala Ala Thr Met Ser Val Pro Thr Gln Val Leu Gly Leu Leu
1               5                   10                  15

Leu Leu Trp Leu Thr Asp Ala Arg Cys Asp Val Val Met Thr Gln Thr
            20                  25                  30

Pro Leu Ser Leu Pro Val Ser Leu Gly Asp Gln Ala Ser Ile Ser Cys
        35                  40                  45

Arg Ser Ser Gln Ser Leu Val His Ser Asn Gly Asn Thr Tyr Leu His
    50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Pro Gly Thr Asp Phe Thr Leu Lys Ile Ser Arg Val Glu Ala Glu Asp
            100                 105                 110

Leu Gly Val Tyr Phe Cys Ser Gln Ser Thr His Phe Pro Phe Thr Phe
        115                 120                 125

Gly Thr Gly Thr Lys Leu Glu Ile Lys Arg Thr
    130                 135

<210> SEQ ID NO 128
<211> LENGTH: 443
<212> TYPE: DNA
<213> ORGANISM: Artificial Sequence
<220> FEATURE:
<223> OTHER INFORMATION: Antibody variable domain with leader and cut
      site sequences added

<400> SEQUENCE: 128
aagcttgccg ccaccatgga atggagctgg gtgttcctgt tctttctgtc cgtgaccaca      60
ggcgtgcatt ctgatataca gcttcaggag tcaggacctg gcctcgtgaa accttctcag     120
tctctgtctc tcacctgctc tgtcactggc ttctccatca ccagtggtta ttactggacc     180
tggatccggc agtttccagg aaacaaactg gagtgggtgg cctacatagg ctacgatggt     240
agcaatgact ccaacccatc tctcaaaaat cgaatctcca tcacccgtga cacatctaag     300
aaccagtttt tcctgaagtt gaattctgtg actactgagg acacagccac atattactgt     360
gcaagagcga tgttgcggcg aggatttgac tactggggcc aaggcaccac tctcacagtc     420
tcctcagcct ccaccaaggg ccc                                             443

<210> SEQ ID NO 129
<211> LENGTH: 393
<212> TYPE: DNA
<213> ORGANISM: Artificial Sequence
<220> FEATURE:
<223> OTHER INFORMATION: Antibody variable domain with leader and cut
      site sequences added

<400> SEQUENCE: 129
aagcttgccg ccaccatgtc tgtgcctacc caggtgctgg gactgctgct gctgtggctg      60
acagacgccc gctgtcaaat tgttctcacc cagtctccag caatcatgtc tgcatctcca     120
ggggagaagg tcaccatgac ctgcagtgcc agctcaagtt taagttacat gcactggtac     180
cagcagaagc caggcaccct ccccaaaaga tggatttatg acacatccaa actggcttct     240
ggagtccctg ctcgcttcag tggcagtggg tctgggacct cttattctct cacaatcagc     300
agcatggagg ctgaagatgc tgccacttat tactgccatc ggcggagtag ttacacgttc     360
ggagggggga ccaagctgga aataaaacgt acg                                  393

<210> SEQ ID NO 130
<211> LENGTH: 147
<212> TYPE: PRT
<213> ORGANISM: Artificial Sequence
<220> FEATURE:
<223> OTHER INFORMATION: Antibody variable domain with leader and cut
      site sequences added

<400> SEQUENCE: 130

```
Lys Leu Ala Ala Thr Met Glu Trp Ser Trp Val Phe Leu Phe Phe Leu
1               5                   10                  15

Ser Val Thr Thr Gly Val His Ser Asp Ile Gln Leu Gln Glu Ser Gly
            20                  25                  30

Pro Gly Leu Val Lys Pro Ser Gln Ser Leu Ser Leu Thr Cys Ser Val
        35                  40                  45

Thr Gly Phe Ser Ile Thr Ser Gly Tyr Tyr Trp Thr Trp Ile Arg Gln
    50                  55                  60

Phe Pro Gly Asn Lys Leu Glu Trp Val Ala Tyr Ile Gly Tyr Asp Gly
65                  70                  75                  80

Ser Asn Asp Ser Asn Pro Ser Leu Lys Asn Arg Ile Ser Ile Thr Arg
                85                  90                  95

Asp Thr Ser Lys Asn Gln Phe Phe Leu Lys Leu Asn Ser Val Thr Thr
            100                 105                 110

Glu Asp Thr Ala Thr Tyr Tyr Cys Ala Arg Ala Met Leu Arg Arg Gly
        115                 120                 125

Phe Asp Tyr Trp Gly Gln Gly Thr Thr Leu Thr Val Ser Ser Ala Ser
    130                 135                 140

Thr Lys Gly
145
```

<210> SEQ ID NO 131
<211> LENGTH: 131
<212> TYPE: PRT
<213> ORGANISM: Artificial Sequence
<220> FEATURE:
<223> OTHER INFORMATION: Antibody variable domain with leader and cut
      site sequences added

<400> SEQUENCE: 131

```
Lys Leu Ala Ala Thr Met Ser Val Pro Thr Gln Val Leu Gly Leu Leu
1               5                   10                  15

Leu Leu Trp Leu Thr Asp Ala Arg Cys Gln Ile Val Leu Thr Gln Ser
            20                  25                  30

Pro Ala Ile Met Ser Ala Ser Pro Gly Glu Lys Val Thr Met Thr Cys
        35                  40                  45

Ser Ala Ser Ser Ser Leu Ser Tyr Met His Trp Tyr Gln Gln Lys Pro
    50                  55                  60

Gly Thr Ser Pro Lys Arg Trp Ile Tyr Asp Thr Ser Lys Leu Ala Ser
65                  70                  75                  80

Gly Val Pro Ala Arg Phe Ser Gly Ser Gly Ser Gly Thr Ser Tyr Ser
                85                  90                  95

Leu Thr Ile Ser Ser Met Glu Ala Glu Asp Ala Ala Thr Tyr Tyr Cys
            100                 105                 110

His Arg Arg Ser Ser Tyr Thr Phe Gly Gly Gly Thr Lys Leu Glu Ile
        115                 120                 125

Lys Arg Thr
    130
```

<210> SEQ ID NO 132
<211> LENGTH: 122
<212> TYPE: PRT
<213> ORGANISM: Mus musculus

<400> SEQUENCE: 132

Gln Val Lys Leu Gln Gln Ser Gly Pro Glu Leu Val Arg Pro Gly Thr
1               5                   10                  15

Ser Val Lys Val Ser Cys Thr Ala Ser Gly Asp Ala Phe Thr Asn Tyr
            20                  25                  30

Leu Ile Glu Trp Val Lys Gln Arg Pro Gly Gln Gly Leu Glu Trp Ile
        35                  40                  45

Gly Leu Ile Tyr Pro Asp Ser Gly Tyr Ile Asn Tyr Asn Glu Asn Phe
    50                  55                  60

Lys Gly Lys Ala Thr Leu Thr Ala Asp Arg Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Phe Ala Tyr Tyr Gly Ser Gly Tyr Tyr Phe Asp Tyr Trp
            100                 105                 110

Gly Gln Gly Thr Thr Leu Thr Val Ser Ser
        115                 120

<210> SEQ ID NO 133
<211> LENGTH: 112
<212> TYPE: PRT
<213> ORGANISM: Mus musculus

<400> SEQUENCE: 133

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Thr
            20                  25                  30

Asn Gly Asn Thr Tyr Leu His Trp Tyr Leu Gln Lys Pro Gly Gln Ser
        35                  40                  45

Pro Lys Leu Leu Ile Phe Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Pro Phe Thr Phe Gly Thr Gly Thr Lys Leu Glu Ile Lys
            100                 105                 110

<210> SEQ ID NO 134
<211> LENGTH: 122
<212> TYPE: PRT
<213> ORGANISM: Mus musculus

<400> SEQUENCE: 134

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Gly Phe Ile Asn Tyr
            20                  25                  30

Leu Ile Glu Trp Ile Lys Gln Arg Pro Gly Gln Gly Leu Glu Trp Ile
        35                  40                  45

```
Gly Leu Ile Asn Pro Gly Ser Asp Tyr Thr Asn Tyr Asn Glu Asn Phe
        50                  55                  60

Lys Gly Lys Ala Thr Leu Thr Ala Asp Lys Ser Ser Thr Ala Tyr
 65                  70                  75                  80

Met His Leu Ser Ser Leu Thr Ser Glu Asp Ser Ala Val Tyr Phe Cys
                     85                  90                  95

Ala Arg Arg Phe Gly Tyr Tyr Gly Ser Gly Asn Tyr Phe Asp Tyr Trp
                100                 105                 110

Gly Gln Gly Thr Thr Leu Thr Val Ser Ser
            115                 120

<210> SEQ ID NO 135
<211> LENGTH: 112
<212> TYPE: PRT
<213> ORGANISM: Mus musculus

<400> SEQUENCE: 135

Asp Val Val Met Thr Gln Thr Pro Leu Ser Leu Pro Val Ser Leu Gly
 1               5                  10                  15

Asp Gln Ala Ser Ile Ser Cys Thr Ser Gly Gln Ser Leu Val His Ile
                20                  25                  30

Asn Gly Asn Thr Tyr Leu His Trp Tyr Leu Gln Lys Pro Gly Gln Ser
             35                  40                  45

Pro Lys Leu Leu Ile Tyr Lys Val Ser Asn Leu Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Phe Pro Phe Thr Phe Gly Thr Gly Thr Lys Leu Glu Ile Lys
                100                 105                 110

<210> SEQ ID NO 136
<211> LENGTH: 122
<212> TYPE: PRT
<213> ORGANISM: Mus musculus

<400> SEQUENCE: 136

Gln Val Gln Leu Gln Gln Ser Gly Ala Glu Leu Val Arg Pro Gly Thr
 1               5                  10                  15

Ser Val Lys Val Ser Cys Lys Ala Ser Gly Asp Ala Phe Thr Asn Tyr
                20                  25                  30

Leu Ile Glu Trp Val Lys Gln Arg Pro Gly Gln Gly Leu Glu Trp Ile
             35                  40                  45

Gly Leu Ile Ile Pro Gly Thr Gly Tyr Thr Asn Tyr Asn Glu Asn Phe
 50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Arg Phe Gly Tyr Tyr Gly Ser Ser Asn Tyr Phe Asp Tyr Trp
                100                 105                 110

Gly Gln Gly Thr Thr Leu Thr Val Ser Ser
            115                 120

<210> SEQ ID NO 137
<211> LENGTH: 112
```

<212> TYPE: PRT
<213> ORGANISM: Mus musculus

<400> SEQUENCE: 137

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Pro Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Phe Pro Phe Thr Phe Gly Thr Gly Thr Lys Leu Glu Ile Lys
            100                 105                 110

<210> SEQ ID NO 138
<211> LENGTH: 122
<212> TYPE: PRT
<213> ORGANISM: Mus musculus

<400> SEQUENCE: 138

Gln Val Gln Leu Gln Gln Ser Gly Ala Glu Leu Val Arg Pro Gly Thr
1               5                   10                  15

Ser Val Lys Leu Ser Cys Lys Ala Ser Gly Asp Ala Phe Thr Asn Tyr
            20                  25                  30

Leu Ile Glu Trp Val Lys Gln Arg Pro Gly Gln Gly Leu Glu Trp Ile
        35                  40                  45

Gly Leu Ile Ile Pro Gly Thr Gly Tyr Thr Asn Tyr Asn Glu Asn Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Phe Gly Tyr Tyr Gly Ser Gly Tyr Tyr Phe Asp Tyr Trp
            100                 105                 110

Gly Gln Gly Thr Thr Leu Thr Val Ser Ser
        115                 120

<210> SEQ ID NO 139
<211> LENGTH: 112
<212> TYPE: PRT
<213> ORGANISM: Mus musculus

<400> SEQUENCE: 139

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Pro Gly Thr Asp Phe Thr Leu Lys Ile

```
                65                  70                  75                  80
Ser Arg Val Glu Ala Glu Asp Leu Gly Val Tyr Phe Cys Ser Gln Ser
                85                  90                  95

Thr His Phe Pro Phe Thr Phe Gly Thr Gly Thr Lys Leu Glu Ile Lys
            100                 105                 110
```

<210> SEQ ID NO 140
<211> LENGTH: 118
<212> TYPE: PRT
<213> ORGANISM: Mus musculus

<400> SEQUENCE: 140

```
Asp Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Thr Ser Gly
                20                  25                  30

Tyr Tyr Trp Thr Trp Ile Arg Gln Phe Pro Gly Asn Lys Leu Glu Trp
            35                  40                  45

Val Ala Tyr Ile Gly Tyr Asp Gly Ser Asn Asp Ser Asn Pro Ser Leu
        50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Ala Met Leu Arg Arg Gly Phe Asp Tyr Trp Gly Gln Gly Thr
            100                 105                 110

Thr Leu Thr Val Ser Ser
        115
```

<210> SEQ ID NO 141
<211> LENGTH: 104
<212> TYPE: PRT
<213> ORGANISM: Mus musculus

<400> SEQUENCE: 141

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Leu Ser Tyr Met
                20                  25                  30

His Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Arg Arg Ser Ser Tyr Thr Phe Gly
                85                  90                  95

Gly Gly Thr Lys Leu Glu Ile Lys
            100
```

<210> SEQ ID NO 142
<211> LENGTH: 122
<212> TYPE: PRT
<213> ORGANISM: Artificial Sequence
<220> FEATURE:
<223> OTHER INFORMATION: Consensus sequence
<220> FEATURE:
<221> NAME/KEY: Xaa
<222> LOCATION: (1)..(122)

<223> OTHER INFORMATION: Xaa = any or other amino acid

<400> SEQUENCE: 142

```
Gln Val Xaa Leu Gln Gln Ser Gly Xaa Glu Leu Val Arg Pro Gly Thr
1               5                   10                  15

Ser Val Lys Xaa Ser Cys Xaa Ala Ser Gly Xaa Xaa Phe Xaa Asn Tyr
            20                  25                  30

Leu Ile Glu Trp Xaa Lys Gln Arg Pro Gly Gln Gly Leu Glu Trp Ile
            35                  40                  45

Gly Leu Ile Xaa Pro Xaa Xaa Xaa Tyr Xaa Asn Tyr Asn Glu Asn Phe
            50                  55                  60

Lys Gly Lys Ala Thr Leu Thr Ala Asp Xaa Ser Ser Thr Ala Tyr
65                  70                  75                  80

Met Xaa Leu Ser Ser Leu Thr Ser Glu Asp Ser Ala Val Tyr Phe Cys
            85                  90                  95

Ala Arg Arg Phe Xaa Tyr Tyr Gly Ser Xaa Xaa Tyr Phe Asp Tyr Trp
            100                 105                 110

Gly Gln Gly Thr Thr Leu Thr Val Ser Ser
            115                 120
```

<210> SEQ ID NO 143
<211> LENGTH: 112
<212> TYPE: PRT
<213> ORGANISM: Artificial Sequence
<220> FEATURE:
<223> OTHER INFORMATION: Consensus sequence
<220> FEATURE:
<221> NAME/KEY: Xaa
<222> LOCATION: (1)..(112)
<223> OTHER INFORMATION: Xaa= any or other

<400> SEQUENCE: 143

```
Asp Val Val Met Thr Gln Thr Pro Leu Ser Leu Pro Val Ser Leu Gly
1               5                   10                  15

Asp Gln Ala Ser Ile Ser Cys Xaa Ser Xaa Gln Ser Leu Xaa Xaa Xaa
            20                  25                  30

Asn Gly Asn Thr Tyr Leu His Trp Tyr Leu Gln Lys Pro Gly Gln Ser
            35                  40                  45

Pro Lys Leu Leu Ile Xaa Lys Val Ser Asn Xaa Phe Ser Gly Val Pro
            50                  55                  60

Asp Arg Phe Ser Gly Ser Gly Xaa Gly Thr Asp Phe Thr Leu Lys Ile
65                  70                  75                  80

Ser Arg Val Glu Ala Glu Asp Leu Gly Xaa Tyr Phe Cys Ser Gln Ser
            85                  90                  95

Thr His Phe Pro Phe Thr Phe Gly Thr Gly Thr Lys Leu Glu Ile Lys
            100                 105                 110
```